US012492386B2

(12) United States Patent
Linnemann et al.

(10) Patent No.: US 12,492,386 B2
(45) Date of Patent: Dec. 9, 2025

(54) METHODS TO ENRICH GENETICALLY ENGINEERED T CELLS

(71) Applicant: NEOGENE THERAPEUTICS B.V., Amsterdam (NL)

(72) Inventors: Carsten Linnemann, Amsterdam (NL); Thomas Kuilman, Amstelveen (NL); Gavin M. Bendle, Amsterdam (NL); Jeroen W.J. van Heijst, Amstelveen (NL); Xiangjun Kong, Amsterdam (NL)

(73) Assignee: NEOGENE THERAPEUTICS B.V., Amsterdam (NL)

( * ) Notice: Subject to any disclaimer, the term of this patent is extended or adjusted under 35 U.S.C. 154(b) by 881 days.

(21) Appl. No.: 17/395,132

(22) Filed: Aug. 5, 2021

(65) Prior Publication Data

US 2022/0041999 A1 Feb. 10, 2022

Related U.S. Application Data

(60) Provisional application No. 63/221,808, filed on Jul. 14, 2021, provisional application No. 63/170,269, filed on Apr. 2, 2021, provisional application No. 63/135,460, filed on Jan. 8, 2021, provisional application No. 63/062,854, filed on Aug. 7, 2020.

(51) Int. Cl.

| | |
|---|---|
| ***C12N 9/06*** | (2006.01) |
| ***A61K 35/17*** | (2025.01) |
| ***C07K 14/725*** | (2006.01) |
| ***C12N 5/0783*** | (2010.01) |
| ***C12N 15/90*** | (2006.01) |

(52) U.S. Cl.

CPC .............. *C12N 9/003* (2013.01); *A61K 35/17* (2013.01); *C07K 14/7051* (2013.01); *C12N 5/0636* (2013.01); *C12N 15/907* (2013.01); *C12Y 105/01003* (2013.01); *C12N 2310/20* (2017.05); *C12N 2510/00* (2013.01)

(58) Field of Classification Search

CPC .... C12N 9/003; C12N 5/0636; C12N 15/907; C12N 2310/20; C12N 2510/00; C12N 15/52; C07K 14/7051; C12Y 105/01003; A61K 35/17; Y02A 50/30

See application file for complete search history.

(56) References Cited

U.S. PATENT DOCUMENTS

| | | | | |
|---|---|---|---|---|
| 8,637,307 | B2 | 1/2014 | June et al. | |
| 10,246,752 | B2 | 4/2019 | Faham et al. | |
| 2006/0165668 | A1 | 7/2006 | Liu et al. | |
| 2017/0246277 | A1 | 8/2017 | Perica et al. | |
| 2018/0051089 | A1 | 2/2018 | Galetto et al. | |
| 2018/0325955 | A1 | 11/2018 | Terrett et al. | |
| 2018/0330055 | A1 | 11/2018 | Yelensky et al. | |
| 2018/0371410 | A1 | 12/2018 | Spits | |
| 2019/0034585 | A1 | 1/2019 | Yelensky et al. | |
| 2019/0065675 | A1 | 2/2019 | Yelensky et al. | |
| 2019/0279742 | A1 | 9/2019 | Bulik-Sullivan et al. | |
| 2019/0321403 | A1 | 10/2019 | Levitsky | |
| 2020/0000903 | A1 | 1/2020 | McGranahan et al. | |
| 2020/0224160 | A1 * | 7/2020 | Ding | A61K 39/464426 |
| 2020/0338125 | A1 | 10/2020 | Bobisse et al. | |
| 2021/0040558 | A1 | 2/2021 | Schumacher et al. | |
| 2022/0195006 | A1 | 6/2022 | Linnemann et al. | |
| 2022/0228164 | A1 | 7/2022 | Schumacher et al. | |
| 2022/0411753 | A1 * | 12/2022 | Sadelain | C12N 15/86 |

FOREIGN PATENT DOCUMENTS

| | | | | |
|---|---|---|---|---|
| CN | 107201365 A * | 9/2017 | | |
| CN | 110914289 A | 3/2020 | | |
| WO | WO 2015/187018 | 12/2015 | | |
| WO | WO 2016/073755 | 5/2016 | | |
| WO | WO-2017180989 A2 * | 10/2017 | | A61K 35/17 |
| WO | WO 2018/195357 A1 | 10/2018 | | |
| WO | WO-2019018553 A1 * | 1/2019 | | C07K 14/82 |
| WO | WO 2019/050994 A1 | 3/2019 | | |
| WO | WO 2019/086711 | 5/2019 | | |
| WO | WO 2019/168984 A1 | 9/2019 | | |
| WO | WO-2019199689 A1 * | 10/2019 | | A61K 35/17 |
| WO | WO 2022/032299 | 2/2022 | | |
| WO | WO 2022/140774 A1 | 6/2022 | | |
| WO | WO 2022/159460 | 7/2022 | | |

OTHER PUBLICATIONS

Sakuma T, Barry MA, Ikeda Y. Lentiviral vectors: basic to translational. Biochem J. May 1, 2012;443(3):603-18. doi: 10.1042/BJ20120146. PMID: 22507128. (Year: 2012).*

Liu X, Zhang Y, Cheng C, Cheng AW, Zhang X, Li N, Xia C, Wei X, Liu X, Wang H. CRISPR-Cas9-mediated multiplex gene editing in CAR-T cells. Cell Res. Jan. 2017;27(1):154-157. doi: 10.1038/cr.2016.142. Epub Dec. 2, 2016. PMID: 27910851; PMCID: PMC5223227. (Year: 2016) .*

Remy I, Campbell-Valois FX, Michnick SW. Detection of protein-protein interactions using a simple survival protein-fragment complementation assay based on the enzyme dihydrofolate reductase. Nat Protoc. 2007;2(9):2120-5. doi: 10.1038/nprot.2007.266. (Year: 2007).*

Kerppola TK, Curran T. Fos-Jun heterodimers and Jun homodimers bend DNA in opposite orientations: implications for transcription factor cooperativity. Cell. Jul. 26, 1991;66(2):317-26. doi: 10.1016/0092-8674(91)90621-5. PMID: 1906785. (Year: 1991).*

Levray YS, Berhe AD, Osborne AR. Use of split-dihydrofolate reductase for the detection of protein-protein interactions and simultaneous selection of multiple plasmids in Plasmodium falciparum. Mol Biochem Parasitol. Jul. 2020;238:111292. doi: 10.1016/j.molbiopara.2020.111292. (Year: 2020).*

(Continued)

*Primary Examiner* — Daniel C Gamett

(74) *Attorney, Agent, or Firm* — Knobbe, Martens, Olson & Bear, LLP

(57) ABSTRACT

Various embodiments are disclosed herein relate to methods for selection of a genetically engineered cell. Some embodiments relate to a cell that is produced with the methods disclosed herein.

16 Claims, 59 Drawing Sheets

Specification includes a Sequence Listing.

(56) References Cited

OTHER PUBLICATIONS

Barrero JJ, Papanikou E, Casler JC, Day KJ, Glick BS. An improved reversibly dimerizing mutant of the FK506-binding protein FKBP. Cell Logist. Jun. 24, 2016;6(3):e1204848. doi: 10.1080/21592799.2016.1204848. (Year: 2016).*
Lee JS, Kallehauge TB, Pedersen LE, Kildegaard HF. Site-specific integration in CHO cells mediated by CRISPR/Cas9 and homology-directed DNA repair pathway. Sci Rep. Feb. 25, 2015;5:8572. doi: 10.1038/srep08572. (Year: 2015).*
Li J, Zhang B, Bu J, Du J. Intron-based genomic editing: a highly efficient method for generating knockin zebrafish. Oncotarget. Jul. 20, 2015;6(20):17891-4. doi: 10.18632/oncotarget.4547. (Year: 2015).*
Wu L, Wei Q, Brzostek J, Gascoigne NRJ. Signaling from T cell receptors (TCRs) and chimeric antigen receptors (CARs) on T cells. Cell Mol Immunol. Jun. 2020;17(6):600-612. doi: 10.1038/s41423-020-0470-3. Epub May 25, 2020. (Year: 2020).*
Jonnalagadda et al., "Efficient selection of genetically modified human T cells using methotrexate-resistant human dihydrofolate reductase", Gene Therapy, vol. 20:853-860 (2013).
International Search Report and Written Opinion in International Application No. PCT/US2021/071122, mailed on Nov. 29, 2021, in 12 pages.
International Preliminary Report on Patentability and Written Opinion in International Application No. PCT/US2021/071122, dated Feb. 7, 2023, in 7 pages.
Butler et al., "Human cell-based artificial antigen-presenting cells for cancer immunotherapy", Immunol Rev. vol. 257(1):1-28 (2014).
Gros et al., "Prospective identification of neoantigen-specific lymphocytes in the peripheral blood of melanoma patients", Nat. Med. vol. 22(4):1-19 (2016).
Jin et al., "Simplified method of the growth of human tumor infiltrating lymphocytes in gas-permeable flasks to Nos. needed for patient treatment", J. Immunother. vol. 35(3):283-292 (2012).
Kula et al., "T-Scan: A genome-wide method for the systematic discovery of T cell epitopes", Cell vol. 178(4):1016-1028 (2019).
Kwakkenbos et al., "Generation of stable monoclonal antibody-producing BCR+ human memory B cells by genetic programming", Nat. Med. vol. 16(1):123-128 (2010).
Lapointe et al., "CD40-stimulated B lymphocytes pulsed with tumor antigens are effective antigen-presenting cells that can generate specific T cells", Cancer Research, vol. 63:2836-2843 (2003).
Linnemann et al., "High-throughput epitope discovery reveals frequent recognition of neo-antigens by CD4+ T cells in human melanoma", Nature Medicine, vol. 21(1):81-85 (2015).
Lizee et al., "Lentivirus vector-mediated expression of tumor-associated epitopes by human antigen presenting cells", Human Gene Therapy, vol. 15:393-404 (2004).
Lu et al., "Efficient identification of mutated cancer antigens recognized by T cells associated with durable tumor regressions", Clinical Cancer Research, vol. 20(13):3401-3410 (2014).
Peng et al., "Sensitive detection and analysis of neoantigen-specific T cell populations from tumors and blood", Cell Reports, vol. 28:2728-2738 (2019).
Robbins et al., "Mining exomic sequencing data to identify mutated antigens recognized by adoptively transferred tumor-reactive T cells", Nat Med vol. 19(6):747-752 (2013).
Scheeren et al., "Antigen-specific monoclonal antibodies isolated from B cells expressing constitutively active STAT5", PLoS One, vol. 6(4):1-7 (2011).
Shibahara et al., "Molecular basis for the heterogeneity of human tyrosinase", J. Exp. Med. vol. 156(4):403-14 (.
Spindler et al., "Massively parallel interrogation and mining of natively paired human TCRαβ repertoires", Nat Biotechnol vol. 38(5):609-619 (2020).
Thevenon et al., "Human germinal center reaction: Accessing T follicular helper-B cells interaction in vitro", Methods in Molecular Biology, vol. 2285:173-189 (2021).
Traggiai, "Immortalization of human B cells: Analysis of B cell repertoire and production of human monoclonal antibodies", Methods in Molecular Biology, vol. 901:161-170 (2012).
Tran et al., "Cancer immunotherapy based on mutation-specific CD4+ T cells in a patalent with epithelial cancer", Science, vol. 344(6184):641-645 (2014).
Tran et al., "Immunogenicity of somatic mutations in human gastrointestinal cancers", Science, vol. 350(6266:1387-1390 (2015).
Tsuji et al., "Rapid construction of antitumor T-cell receptor vectors from frozen tumors for engineered T-cell therapy", Cancer Immunology Research, vol. 6(5):594-604 (2018).
Yiwen et al., "Efficient generation of antigen-specific CTLs by the BAFF-activated human B Lymphocytes as APCs: a novel approach for immunotherapy", Oncotarget, vol. 7(47):77732-77748 (2016).
International Search Report and Written Opinion mailed on May 16, 2022, in International Application No. PCT/US2022/012935, in 10 pages.
International Preliminary Report on Patentability and Written Opinion in International Application No. PCT/US2022/012935, dated Jul. 20, 2023, in 6 pages.
Tawainese Office Action and Search Report, with English Translation, re TW Application No. 110129192, dated Mar. 20, 2025.

* cited by examiner

TIDE analysis of sgDHFR-1

TIDE analysis of sgDHFR-2

BC23

BC26

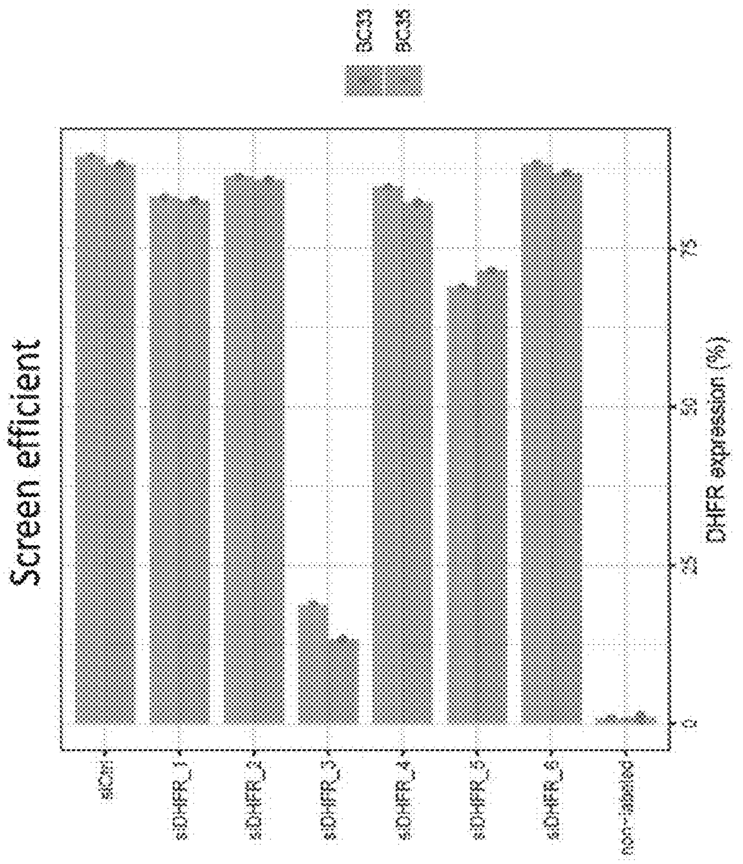
Fig. 12
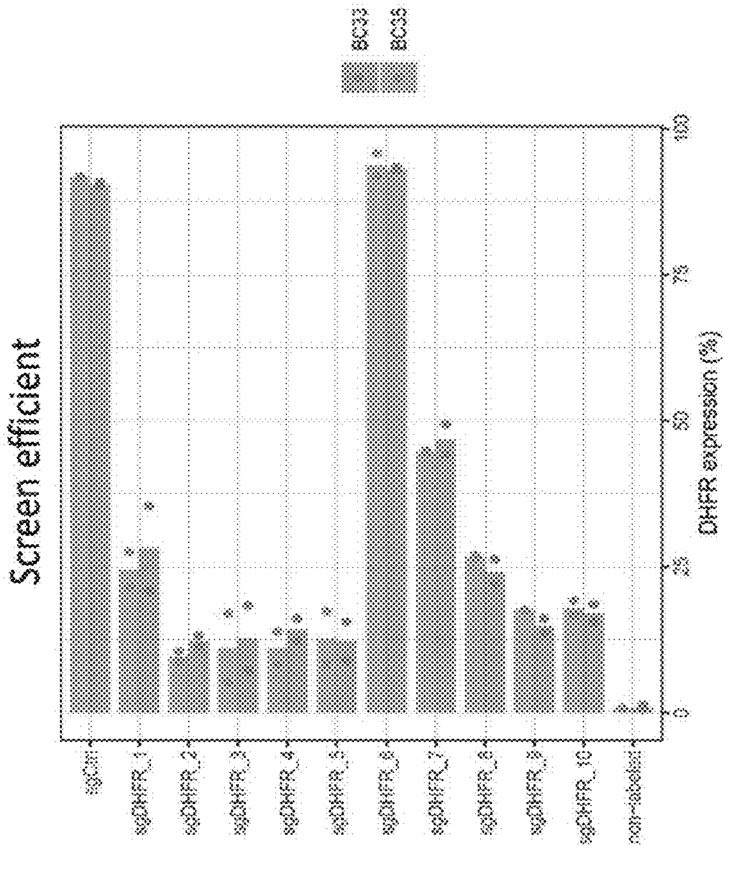

A. Knockout essential gene

B. Knockin altered essential gene into a gene locus of interest

MTX (nM)
-
25
50
untransduced
17.GCN4-mDHFRmt_A
18.GCN4-mDHFRmt_B
21.JUN-mDHFRmt_A
22.FOS-mDHFRmt_B
23.GCN4-mDHFRmt_A-2A
24.GCN4-mDHFRmt_B-2A
30.JUN-mDHFRmt_A-2A
31.FOS-mDHFRmt_B-2A
11%
41%
67%
0.12%
0.09%
0.53%
0.16%
0.39%
2.18%
6%
32%
63%
Comp-V_A-A :: LV6G-BV785
Comp-V_E-A :: CD90_2-BV510
Ly6G-BV785 (vector A)
CD90.2-BV510 (vector B)

Fig. 34. SEQ ID NO: 1 (human DHFR wildtype protein sequence)

MVGSLNCIVAVSQNMGIGKNGDLPWPPLRNEFRYFQRMTTTSSVEGKQNLVIMGKK
TWFSIPEKNRPLKGRINLVLSRELKEPPQGAHFLSRSLDDALKLTEQPELANKVDMV
WIVGGSSVYKEAMNHPGHLKLFVTRIMQDFESDTFFPEIDLEKYKLLPEYPGVLSDV
QEEKGIKYKFEVYEKND

Fig. 35. SEQ ID NO: 2 (human MTX-resistant DHFR mutant protein sequence)

MVGSLNCIVAVSQNMGIGKNGDFPWPPLRNESRYFQRMTTTSSVEGKQNLVIMGKK
TWFSIPEKNRPLKGRINLVLSRELKEPPQGAHFLSRSLDDALKLTEQPELANKVDMV
WIVGGSSVYKEAMNHPGHLKLFVTRIMQDFESDTFFPEIDLEKYKLLPEYPGVLSDV
QEEKGIKYKFEVYEKND

Fig. 36. SEQ ID NO: 3 (DNA sequence that encodes wildtype human DHFR)

ATGGTTGGTTCGCTAAACTGCATCGTCGCTGTGTCCCAGAACATGGGCATCGGCA
AGAACGGGGACCTGCCCTGGCCACCGCTCAGGAATGAATTCAGATATTTCCAGA
GAATGACCACAACCTCTTCAGTAGAAGGTAAACAGAATCTGGTGATTATGGGTA
AGAAGACCTGGTTCTCCATTCCTGAGAAGAATCGACCTTTAAAGGGTAGAATTA
ATTTAGTTCTCAGCAGAGAACTCAAGGAACCTCCACAAGGAGCTCATTTTCTTTC
CAGAAGTCTAGATGATGCCTTAAAACTTACTGAACAACCAGAATTAGCAAATAA
AGTAGACATGGTCTGGATAGTTGGTGGCAGTTCTGTTTATAAGGAAGCCATGAAT
CACCCAGGCCATCTTAAACTATTTGTGACAAGGATCATGCAAGACTTTGAAAGTG
ACACGTTTTTTCCAGAAATTGATTTGGAGAAATATAAACTTCTGCCAGAATACCC
AGGTGTTCTCTCTGATGTCCAGGAGGAGAAAGGCATTAAGTACAAATTTGAAGT
ATATGAGAAGAATGAT

Fig. 37. SEQ ID NO: 4 (codon-optimized and nuclease-resistant DNA sequence that encodes a wildtype human DHFR)

ATGGTAGGCTCCCTGAACTGTATAGTTGCGGTATCCCAAAATATGGGGATTGGA
AAGAACGGAGACCTTCCGTGGCCGCCCCTCCGAAATGAATTTCGATACTTTCAG
AGAATGACAACTACCTCATCTGTAGAGGGAAAGCAAAATCTGGTTATCATGGGA
AAGAAAACGTGGTTCTCTATCCCTGAAAAAAACAGACCTCTCAAAGGCAGGATA
AATTTGGTATTGTCAAGAGAATTGAAGGAACCGCCACAAGGAGCTCATTTTCTCA
GCAGATCTCTGGACGATGCACTCAAACTCACCGAACAACCAGAACTTGCTAATA
AGGTTGATATGGTCTGGATAGTTGGGGGCAGCAGTGTATATAAGGAAGCCATGA
ACCATCCTGGCCATCTGAAGCTGTTTGTTACGAGGATAATGCAGGACTTCGAGTC
CGACACTTTTTTCCCAGAGATTGACTTGGAAAAGTATAAACTCTTGCCTGAGTAT
CCTGGGGTTCTCTCCGATGTCCAAGAGGAGAAAGGTATTAAATATAAGTTTGAA
GTTTATGAAAAAAACGAT

Fig. 38. SEQ ID NO: 5 (codon-optimized DNA sequence that encodes a MTX-resistant human DHFR mutant)

ATGGTAGGCTCCCTGAACTGTATAGTTGCGGTATCCCAAAATATGGGGATTGGA
AAGAACGGAGACtTTCCGTGGCCGCCCCTCCGAAATGAATccCGATACTTTCAGAG
AATGACAACTACCTCATCTGTAGAGGGAAAGCAAAATCTGGTTATCATGGGAAA
GAAAACGTGGTTCTCTATCCCTGAAAAAAACAGACCTCTCAAAGGCAGGATAAA
TTTGGTATTGTCAAGAGAATTGAAGGAACCGCCACAAGGAGCTCATTTTCTCAGC
AGATCTCTGGACGATGCACTCAAACTCACCGAACAACCAGAACTTGCTAATAAG
GTTGATATGGTCTGGATAGTTGGGGGCAGCAGTGTATATAAGGAAGCCATGAAC
CATCCTGGCCATCTGAAGCTGTTTGTTACGAGGATAATGCAGGACTTCGAGTCCG
ACACTTTTTTCCCAGAGATTGACTTGGAAAAGTATAAACTCTTGCCTGAGTATCC
TGGGGTTCTCTCCGATGTCCAAGAGGAGAAAGGTATTAAATATAAGTTTGAAGTT
TATGAAAAAAACGAT

High efficacy selection of TCR-edited T cells with mDHFR-MTX technology strategy

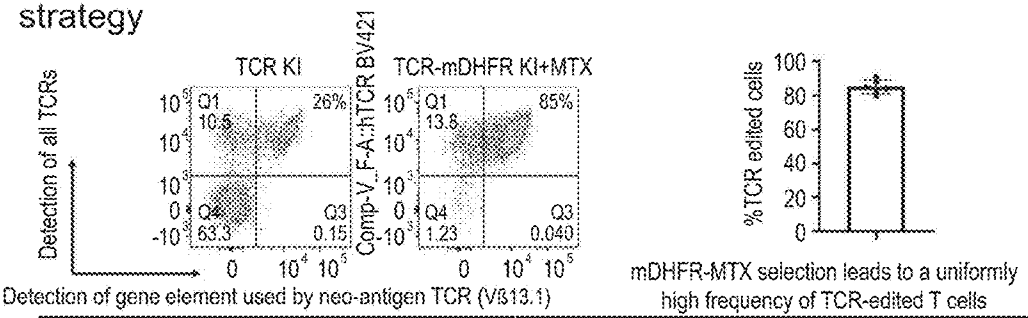

| Parameter | No selection vs. mDHFR-MTX based selection |
|---|---|
| Phenotype of TCR-edited T cells | Comparable |
| Functionality of TCR-edited T cells | Comparable |
| Proliferation capacity of TCR-edited T cells | Comparable |

Planning to progress with approach for clinical T cell production manufacturing in planned Phase I trail

Fig. 42

METHODS TO ENRICH GENETICALLY ENGINEERED T CELLS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority to U.S. Provisional Application Ser. No. 63/062,854, filed Aug. 7, 2020, Ser. No. 63/135,460, filed Jan. 8, 2021, Ser No. 63/170,269, filed Apr. 2, 2021, and Ser. No. 63/221,808, filed Jul. 14, 2021, hereby incorporated by reference in their entireties.

REFERENCE TO SEQUENCE LISTING

The present application is being filed along with a Sequence Listing in electronic format. The Sequence Listing is provided as a file entitled SEQUENCE_LISTING_NTBV024A.txt, created on Aug. 4, 2021, which is 70,429 bytes in size. The information in the electronic format of the Sequence Listing is incorporated herein by reference in its entirety.

BACKGROUND

Field of the Invention

The invention is in the cell therapy and/or gene therapy field. Some embodiments are also in the cell or gene engineering fields.

Description of the Related Art

Cell therapy is a therapy in which viable cells are injected, grafted or implanted into a patient in order to effectuate a medicinal effect, for example, by transplanting T-cells capable of fighting cancer cells via cell-mediated immunity in the course of immunotherapy, or grafting stem cells to regenerate diseased tissues.

SUMMARY

Some embodiments described herein relate to a method for selection of a genetically engineered cell. The method includes i) introducing into the cell at least one two-part nucleotide sequence that is operable for expression in a cell, wherein the cell has an essential protein for the survival and/or proliferation that is suppressed to a level that the cell cannot survive and/or proliferate in a normal cell culture medium, and wherein the at least one two-part nucleotide sequence comprises a first-part nucleotide sequence encoding the essential protein for the survival and/or proliferation and a second-part nucleotide sequence encoding a protein to be expressed, wherein the second-part nucleotide sequence is encoding a protein of interest (e.g., a protein that is exogenous to the cell); and ii) culturing the cell in the normal cell culture medium for selection of the cell that expresses both the first-part and second-part nucleotide sequences.

Some embodiments described herein relate to a method for selection of a genetically engineered cell. The method includes i) introducing at least one two-part nucleotide sequence that is operable for expression in a cell, wherein the cell has an essential protein for the survival and/or proliferation that is suppressed to a level that the cell cannot survive and/or proliferate under the selected culture conditions, and wherein the at least one two-part nucleotide sequence comprises a first-part nucleotide sequence encoding a protein allowing for the survival and/or proliferation and a second-part nucleotide sequence encoding a protein to be expressed, wherein the second-part nucleotide sequence is encoding a protein that is exogenous to the cell; and ii) culturing the cell under in vitro propagation conditions that allow enrichment of the cell that expresses both the first-part and second-part nucleotide sequences.

Some embodiments described herein relate to a method for enrichment of a genetically engineered cell. The method includes: i) decreasing activity of at least a first protein that is essential for the survival and/or proliferation of a cell to the level that the cell cannot survive and/or proliferate under normal in vitro propagation conditions; ii) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and iii) culturing the cell under normal in vitro propagation conditions for enrichment of the cell that expresses both the first protein and second protein.

Some embodiments described herein relate to a cell that includes i) endogenous dihydrofolate reductase (DHFR) being suppressed to a level that the cell cannot survive and/or proliferate in a normal cell culture medium, and ii) at least a two-part nucleotide sequence comprising a first-part nucleotide sequence encoding DHFR and a second-part nucleotide sequence encoding a neo-antigen T-cell receptor complex.

Some embodiments described herein relate to a method for enrichment of a genetically engineered cell. The method includes i) introducing at least a two-part nucleotide sequence that is operable for expression in the cell and comprises a first-part nucleotide sequence encoding the first protein providing the cell with resistance to selective pressure and a second-part nucleotide sequence encoding a second protein to be expressed, wherein the second-part protein is exogenous to the cell, and ii) culturing the cell in cell culture medium containing at least one supplement leading to enrichment of the cell that expresses both the first protein and the second protein.

Some embodiments described herein relate to a method for enrichment of a genetically engineered T cell. The method includes i) introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and ii) culturing the cell in cell culture medium containing methotrexate leading to enrichment of the cell that expresses both the first protein and the second protein.

Some embodiments described herein relate to a method for enrichment of a T cell engineered to express an exogenous T cell receptor gene. The method includes i) knocking-out an endogenous TRBC gene from its locus using a first CRISPR/Cas9 RNP; ii) knocking-in, using a second CRISPR/Cas9 RNP, into the endogenous TRBC locus a first-part nucleotide sequence encoding a methotrexate-resistant DHFR gene and a second-part nucleotide sequence comprising a therapeutic TCR gene, wherein both nucleotide sequences are operably linked allowing for expression from the endogenous TRBC promotor; and iii) culturing the cells in cell culture medium containing methotrexate leading to enrichment of T cells that express both the therapeutic TCR and the methotrexate-resistant DHFR gene.

Some embodiments described herein relate to a T cell, which include i) an endogenous dihydrofolate reductase (DHFR) being suppressed by the presence of methotrexate to a level that the cell cannot survive and/or proliferate, and ii) at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

Some embodiments described herein relate to a T cell, or a method for enrichment of a T cell engineered to express an exogenous gene, which include i) an endogenous DHFR being suppressed by the presence of methotrexate to a level that the cell cannot survive and/or proliferate, and ii) at least two nucleotide sequences, including a first nucleotide comprising a nucleotide sequence encoding a non-functional portion of a methotrexate-resistant DHFR protein fused to a first binding domain and a second nucleotide comprising a nucleotide sequence encoding a non-functional portion of a methotrexate-resistant DHFR protein fused to a second binding domain such that when both nucleotides are expressed, a functional methotrexate-resistant DHFR is present and is capable of facilitating selection of cells containing both the first and second nucleotides. Any of the nucleotide sequences may contain two or more parts such that a first part comprises a nucleotide sequence encoding a non-functional portion of a methotrexate-resistant DHFR protein fused to a binding domain and a second part comprises a nucleotide sequence encoding an exogenous gene. For certain methods of selection according to these embodiments, the T cell is then cultured in a cell culture medium containing methotrexate leading to enrichment of the cell that comprises the at least two nucleotide sequences.

Some embodiments described herein relate binding domains for restoring function to a DHFR protein split into multiple non-functional portions. The binding domains, when fused to complementary non-functional portions of a DHFR protein, can restore DHFR protein function. Binding domains can be native binding domains, engineered binding domains that do not interact with native proteins, or inducible binding domains.

Also disclosed herein is a method for the selection of a genetically engineered cell. In some embodiments, the method comprises introducing at least two, two-part nucleotide sequences that are operable for expression in a cell. In some embodiments, the cell has an essential protein for survival and/or proliferation that is suppressed to a level that the cell cannot survive and/or proliferate. In some embodiments, the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed. In some embodiments, the second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed. In some embodiments, when both the first and second fusion proteins are expressed together in a cell, the function of the essential protein for the survival and/or proliferation is restored. In some embodiments, the method further comprises culturing the cell under conditions leading to the selection of the cell that expresses both the first and second two-part nucleotide sequences.

In some embodiments, the essential protein is a DHFR protein. In some embodiments, the second-part nucleotide sequence of either the first or second two-part nucleotide sequences is exogenous to the cell. In some embodiments, the second-part nucleotide sequence of either the first or second two-part nucleotide sequence is a TCR. In some embodiments, the first and second binding domains are derived from GCN4. In some embodiments, the first and second binding domains are derived from FKBP12. In some embodiments, the FKBP12 has an F36V mutation. In some embodiments, the first binding domain is derived from JUN and the second binding domains is derived from FOS. In some embodiments, the first binding domain and second binding domain have complementary mutations that preserve binding to each other. In some embodiments, neither the first binding domain nor the second binding domain bind to a native binding partner. In some embodiments, each of the first binding domain and second binding domain have between 3 and 7 complementary mutations. In some embodiments, the first binding domain and second binding domain each have 3 complementary mutations. In some embodiments, the first binding domain and second binding domain each have 4 complementary mutations. In some embodiments, the restoration of the function of the essential protein is induced, optionally by AP1903. In some embodiments, the culturing step is done in the presence of methotrexate.

Also disclosed herein is a method for enrichment of a genetically engineered cell. In some embodiments, the method comprises decreasing activity of at least a first protein that is essential for the survival and/or proliferation of a cell to the level that the cell cannot survive and/or proliferate under normal in vitro propagation conditions. In some embodiments, the method further comprises introducing at least two two-part nucleotide sequences that are operable for expression in a cell. In some embodiments, the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed. In some embodiments, the second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed. In some embodiments, when both the first and second fusion proteins are expressed together in a cell, the function of the essential protein for the survival and/or proliferation is restored. In some embodiments, the method further comprises culturing the cell under in vitro propagation conditions that lead to the enrichment of the cell that expresses both the first fusion protein and second fusion protein.

In some embodiments, the essential protein is a DHFR protein. In some embodiments, the second-part nucleotide sequence of either the first or second two-part nucleotide sequences is exogenous to the cell. In some embodiments, the second-part nucleotide sequence of either the first or second two-part nucleotide sequence is a TCR. In some embodiments, the first and second binding domains are derived from GCN4. In some embodiments, the first and second binding domains are derived from FKBP12. In some embodiments, the FKBP12 has an F36V mutation. In some embodiments, the first binding domain is derived from JUN and the second binding domains is derived from FOS. In some embodiments, the first binding domain and second binding domain have complementary mutations that preserve binding to each other. In some embodiments, neither the first binding domain nor the second binding domain bind to a native binding partner. In some embodiments, each of the first binding domain and second binding domain have between 3 and 7 complementary mutations. In some embodiments, the first binding domain and second binding domain each have 3 complementary mutations. In some embodiments, the first binding domain and second binding domain each have 4 complementary mutations. In some embodiments, the restoration of the function of the essential protein is induced, optionally by AP1903. In some embodiments, the culturing step is done in the presence of methotrexate.

Some embodiments provided herein involve a method for selection or enrichment of a genetically engineered cell. In some embodiments, the method comprises introducing into a cell at least one two-part nucleotide sequence capable of expressing both the first-part and second-part nucleotide sequences in the cell. The cell has an essential protein for the survival and/or proliferation that is reduced to a level that the cell cannot survive and/or proliferate in a normal cell culture medium. The at least one two-part nucleotide sequence is operable for expression in the cell or becomes operable for expression when inserted into a pre-determined site in the target genome, and the at least one two-part nucleotide sequence comprises a first-part nucleotide sequence encoding the essential protein for the survival and/or proliferation, or a variant thereof, and a second-part nucleotide sequence encoding a protein to be expressed. The second-part nucleotide sequence encodes a protein of interest. The method further comprises culturing the cell in the normal cell culture medium without a pharmacologic exogenous selection pressure for selection or enrichment of the cell that expresses both the first-part and second-part nucleotide sequences.

In some embodiments, the method comprises reducing the level of at least a first protein that is essential for the survival and/or proliferation of a cell to the level that the cell cannot survive and/or proliferate under normal in vitro propagation conditions, introducing into the cell at least a two-part nucleotide sequence that is capable of expressing both the first-part and second-part nucleotide sequences in the cell and comprises a first-part nucleotide sequence encoding the first protein, or a variant thereof, and a second-part nucleotide sequence encoding a second protein to be expressed. The at least one two-part nucleotide sequence is operable for expression in the cell or becomes operable for expression when inserted into a pre-determined site in the target genome. The second-part protein is a protein of interest. The method further comprises culturing the cell under normal in vitro propagation conditions without a pharmacologic exogenous selection pressure for enrichment of the cell that expresses both the first protein and second protein.

In some embodiments, the method comprises introducing into a cell at least one two-part nucleotide sequence capable of expressing both the first-part and second-part nucleotide sequences in the cell. The cell has the functional activity of an essential protein for the survival and/or proliferation that is reduced such that the cell cannot survive and/or proliferate in a normal cell culture medium. The at least one two-part nucleotide sequence is operable for expression in the cell or becomes operable for expression when inserted into a pre-determined site in the target genome. The at least one two-part nucleotide sequence comprises a first-part nucleotide sequence encodes a first protein that provides a substantially equivalent function to the essential protein for the survival and/or proliferation and a second-part nucleotide sequence encodes a second protein to be expressed. The second protein that is a protein of interest. The method further comprises culturing the cell in cell culture medium containing at least one supplement leading to enrichment or selection of the cell that expresses both the first protein and the second protein.

In some embodiments, the method comprises reducing the functional activity of at least a first protein that is essential for the survival and/or proliferation of a cell to the level that the cell cannot survive and/or proliferate under normal in vitro propagation conditions; introducing into the cell at least a two-part nucleotide sequence that is capable of expressing both the first-part and second-part nucleotide sequences in the cell and comprises a first-part nucleotide sequence encodes a first protein that provides a substantially equivalent function to and a second-part nucleotide sequence encoding a second protein to be expressed. The at least one two-part nucleotide sequence is operable for expression in the cell or becomes operable for expression when inserted into a pre-determined site in the target genome, and the second protein is a protein of interest. The method further comprises culturing the cell in cell culture medium containing at least one supplement leading to selection or enrichment of the cell that expresses both the first protein and the second protein.

In some embodiments, the method comprises introducing into a cell at least two two-part nucleotide sequences capable of expressing both a first-part and a second-part nucleotide sequence in the cell. The cell has an essential protein for the survival and/or proliferation that is suppressed to a level that the cell cannot survive and/or proliferate. The first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest. The second two-part nucleotide sequence comprises a first-part nucleotide sequence encoding a second fusion protein comprising a non-functional portion of the essential protein for the survival and/or proliferation fused to a second binding domain and a second-part nucleotide sequence encoding a second protein of interest. When both the first and second fusion proteins are expressed together in a cell, the function of the essential protein for the survival and/or proliferation is restored. The method further comprises culturing the cell under conditions leading to the selection of the cell that expresses both the first and second two-part nucleotide sequences.

In some embodiments, the method comprises suppressing at least a first protein that is essential for the survival and/or proliferation of a cell to the level that the cell cannot survive and/or proliferate under normal in vitro propagation conditions, and introducing at least two two-part nucleotide sequences that are capable of being expressed in the cell. The first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest. The second two-part nucleotide sequence comprises a first-part nucleotide sequence encoding a second fusion protein comprising non-functional portion of the essential protein for the survival and/or proliferation fused to a second binding domain and a second-part nucleotide sequence encoding a second protein of interest. When both the first and second fusion proteins are expressed together in a cell, the function of the essential protein for the survival and/or proliferation is restored. The method further comprises culturing the cell under in vitro propagation conditions that lead to the enrichment of the cell that expresses both the first fusion protein and second fusion protein.

In some embodiments, the method comprises introducing at least one two-part nucleotide sequence that is operable for expression in a cell. The cell has an essential protein for the survival and/or proliferation that is suppressed to a level that the cell cannot survive and/or proliferate, and the at least one two-part nucleotide sequence comprises a first-part nucleotide sequence encoding the essential protein for the survival and/or proliferation and a second-part nucleotide sequence encoding a protein to be expressed. The second-part nucleotide sequence is encoding a protein that is exogenous to the cell. The method further comprises culturing the cell under conditions leading to the selection of the cell that expresses both the first-part and second-part nucleotide sequences.

In some embodiments, the method comprises decreasing activity of at least a first protein that is essential for the survival and/or proliferation of a cell to the level that the cell cannot survive and/or proliferate under normal in vitro propagation conditions, introducing at least a two-part nucleotide sequence that is operable for expression in the cell and comprises a first-part nucleotide sequence encoding the first protein and a second-part nucleotide sequence encoding a second protein to be expressed. The second-part protein is exogenous to the cell, and culturing the cell under in vitro propagation conditions that lead to the enrichment of the cell that expresses both the first protein and second protein.

Also disclosed herein is a cell that is made according to any of the methods of the present disclosure.

Also disclosed herein is a method for enrichment of a genetically engineered T cell. In some embodiments, the method comprises introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and culturing the cell in cell culture medium containing methotrexate leading to enrichment of the cell that expresses both the first protein and the second protein.

Also disclosed herein is a method for enrichment of a T cell engineered to express an exogenous T cell receptor gene. In some embodiments, the method comprises knocking-out an endogenous TRBC gene from its locus using a first CRISPR/Cas9 RNP, knocking-in, using a second CRISPR/Cas9 RNP, into the endogenous TRBC locus a first-part nucleotide sequence encoding a methotrexate-resistant DHFR gene and a second-part nucleotide sequence comprising a therapeutic TCR gene, wherein both nucleotide sequences are operably linked allowing for expression from the endogenous TRBC promotor, and culturing the cells in cell culture medium containing methotrexate leading to enrichment of T cells that express both the therapeutic TCR and the methotrexate-resistant DHFR gene.

Also disclosed herein is a T cell. In some embodiments, the T cell comprises an endogenous dihydrofolate reductase (DHFR) being suppressed by the presence of methotrexate to a level that the cell cannot survive and/or proliferate, and at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

In some embodiments, the T cell comprises a knock-out of endogenous dihydrofolate reductase (DHFR), and at least one two-part nucleotide sequence comprising a first-part nucleotide sequence encoding a DHFR protein, or variant thereof, and a second-part nucleotide sequence encoding a T-cell receptor operably expressed from the endogenous TRA or TRB promotor.

In some embodiments, the T cell comprises an endogenous dihydrofolate reductase (DHFR) being suppressed by the presence of methotrexate to a level that the cell cannot survive and/or proliferate, and at least two two-part nucleotide sequences. The first two-part nucleotide sequence comprises a first first-part nucleotide sequence encoding a non-functional or dysfunctional portion of a DHFR protein, or variant thereof, and a first second-part nucleotide sequence encoding a T-cell receptor operably expressed from the endogenous TRA or TRB promotor. The second two-part nucleotide sequence comprises a second first-part nucleotide sequence encoding a non-functional or dysfunctional portion of a DHFR protein, or variant thereof, and a second second-part nucleotide sequence encoding a protein of interest operably expressed from the endogenous B2M promotor, and the cell has DHFR activity.

These and other features, aspects, and advantages of the present invention will become better understood with reference to the following description and appended claims.

BRIEF DESCRIPTION OF THE DRAWINGS

FIG. 12 left panel shows the method described in FIG. 11 to screen for efficient guide RNAs which target DHFR; right panel, use of the method described in FIG. 11 to screen for efficient siRNAs which target DHFR.

FIG. 34 shows the sequence of SEQ ID NO: 1, which is a human DHFR wildtype protein sequence.

FIG. 35 shows the sequence of SEQ ID NO: 2, which is a human MTX-resistant DHFR mutant protein sequence.

FIG. 36 shows the sequence of SEQ ID NO: 3, which is a DNA sequence that encodes a wildtype human DHFR.

FIG. 37 shows the sequence of SEQ ID NO: 4, which is a codon-optimized and nuclease-resistant DNA sequence that encodes a wildtype human DHFR.

FIG. 38 shows the sequence of SEQ ID NO: 5, which is a codon-optimized DNA sequence that encodes a MTX-resistant human DHFR mutant.

FIG. 42 shows a summary comparison of TCR-edited T cells with and without use of an embodiment of an mDHFR-MTX selection strategy.

DETAILED DESCRIPTION

Figure 1:
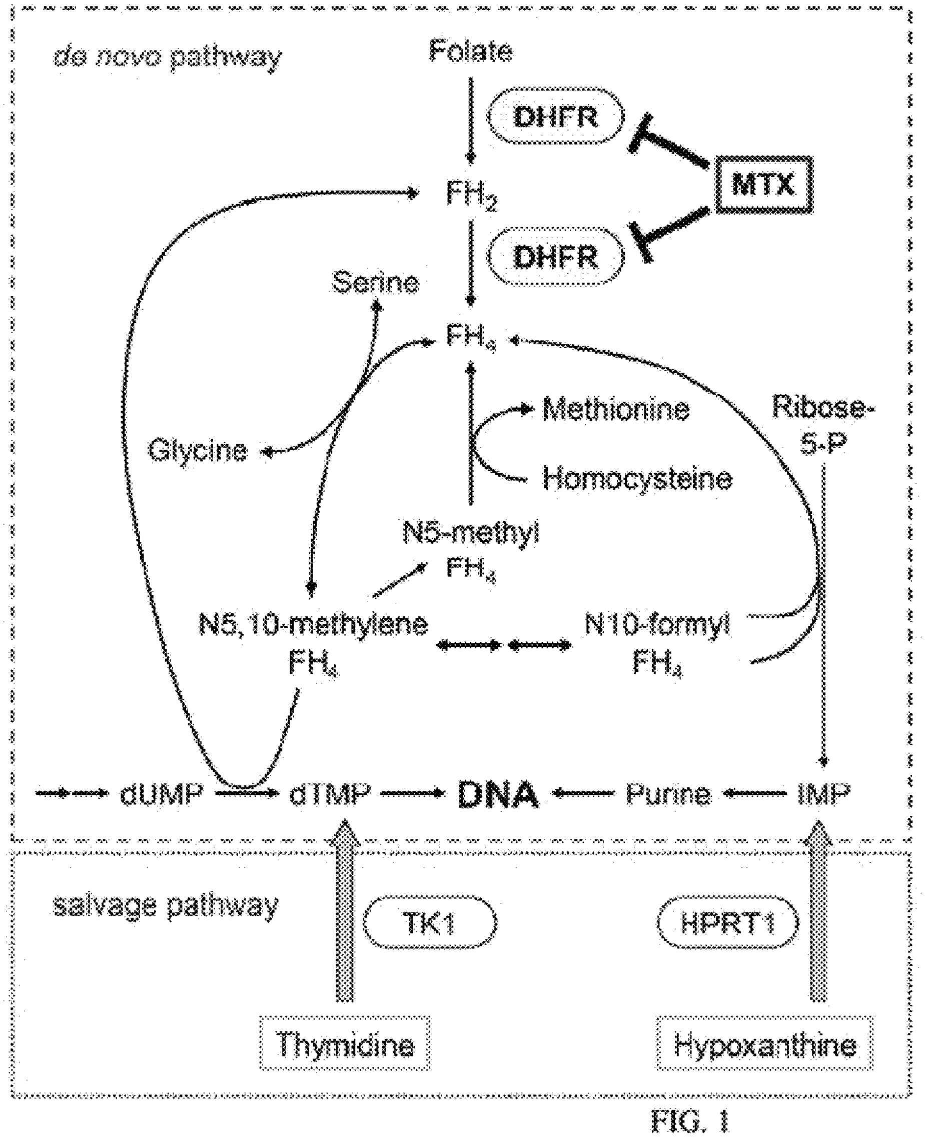
FIG. 1 shows some embodiments involving a DFHR involved pathway.

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The precise introduction of exogenous DNA sequences at a specific genomic site, also known as gene knock-in, generally requires two steps: (1) the introduction of a DNA double-strand break at the genomic site by a nuclease, and (2) the repair of that DNA break using a homologous repair template by the homology-directed repair (HDR) pathway. This process is generally inefficient because the enzymes that are required for HDR are only active during the S and G2 phases of the cell cycle. That is, gene knock-in is largely restricted to dividing cells. Given the overall low efficiency of the gene knock-in process, an approach that can select and enrich those cells that have successfully undergone the gene-editing procedure can be useful.

To allow for the enrichment of cells with successful knock-in of a therapeutic gene construct, a selective pressure is useful to ensure that primarily cells with the knock-in event can survive, while those without the knock-in event die.

Various embodiments described herein relate to methods for selection of a genetically engineered cell. In those methods, a genetically engineered cell is selected by the introduction of at least one two-part nucleotide sequence that encodes at least one protein that is exogenous to the cell (and for example is introduced for therapeutic purposes) and another protein that restores the function of an essential protein that is needed for the cell to survive and/or proliferate and has been suppressed.

The function of an essential protein that is needed for the cell to survive and/or proliferate may be suppressed by nucleases or protein inhibitors; the suppression can be permanent or transient, and the suppression can be at the nucleotide level or protein level.

The function of an essential protein that is needed for the cell to survive and/or proliferate may be suppressed by an exogenous selective pressure, for example induced by small molecule mediated inhibition.

The essential protein can be restored by encoding the essential protein in the two-part nucleotide sequence. The encoded essential protein may be genetically engineered so that its nucleotide sequence is nuclease resistant or the protein is protein inhibitor resistant. As such, cells with successful re-introduction of the essential protein will gain a strong survival advantage over the wild type cells and become enriched in time.

The essential protein may be introduced as one continuous sequence or split in distinct domains to allow genetic engineering of the cell with multiple exogenous proteins.

In addition, various embodiments described herein relate to a cell that is generated in the process using the methods described herein for selection of a genetically engineered cell.

Some embodiments described herein relate to a method for selection of a genetically engineered cell. The method includes i) introducing at least one two-part nucleotide sequence that is operable for expression in a cell, wherein the cell has an essential protein for the survival and/or proliferation that is suppressed to a level that the cell cannot survive and/or proliferate under the selected culture conditions, and wherein the at least one two-part nucleotide sequence comprises a first-part nucleotide sequence encoding a protein allowing for the survival and/or proliferation and a second-part nucleotide sequence encoding a protein to be expressed, wherein the second-part nucleotide sequence is encoding a protein that is exogenous to the cell; and ii) culturing the cell under in vitro propagation conditions that allow enrichment of the cell that expresses both the first-part and second-part nucleotide sequences.

Some embodiments described herein relate to a method for selection of a genetically engineered cell. The method includes i) suppressing an essential protein in a cell to a level that said cell cannot survive and/or proliferate in normal culture medium; ii) introducing at least one two-part nucleotide sequence that is operable for expression in a cell, wherein the at least one two-part nucleotide sequence comprises a first-part nucleotide sequence encoding a protein allowing for the survival and/or proliferation and a second-part nucleotide sequence encoding a protein to be expressed; iii) culturing the cell in normal culture medium allow enrichment of the cell that expresses both the first-part and second-part nucleotide sequences.

Some embodiments described herein relate to a method for selection of a genetically engineered cell. The method includes i) suppressing an essential protein in a cell to a level that said cell cannot survive and/or proliferate by supplementation of the cell culture medium with at least one compound; ii) introducing at least one two-part nucleotide sequence into the cell by targeted integration into a genomic locus to achieve operable expression in the cell from a cell-endogenous promotor, wherein the at least one two-part nucleotide sequence comprises a first-part nucleotide sequence encoding a protein allowing for the survival and/or proliferation of the cell in the supplemented medium and a second-part nucleotide sequence encoding a protein to be expressed; iii) culturing the cell in culture medium with at least one compound to allow enrichment of the cell that expresses both the first-part and second-part nucleotide sequences.

Some embodiments described herein relate to a method for selection of a genetically engineered cell. The method includes i) introducing at least two two-part nucleotide sequences that are operable for expression in a cell, wherein the cell has an essential protein for the survival and/or proliferation that is suppressed to a level that the cell cannot survive and/or proliferate under the selected culture conditions, wherein the first two-part nucleotide sequence comprises a first-part nucleotide sequence encoding a first portion of a protein allowing for the survival and/or proliferation and a second-part nucleotide sequence encoding a protein to be expressed, wherein the second two-part nucleotide sequence comprises a first-part nucleotide sequence encoding a second portion of a protein allowing for the survival and/or proliferation and a second-part nucleotide sequence encoding a protein to be expressed, wherein the portions of the protein can form a functional protein when co-expressed in the cell;

ii) culturing the cell under in vitro propagation conditions that allow enrichment of the cell that expresses both the first-part and second-part nucleotide sequences of the at least two two-part nucleotide sequences.

Figure 33:
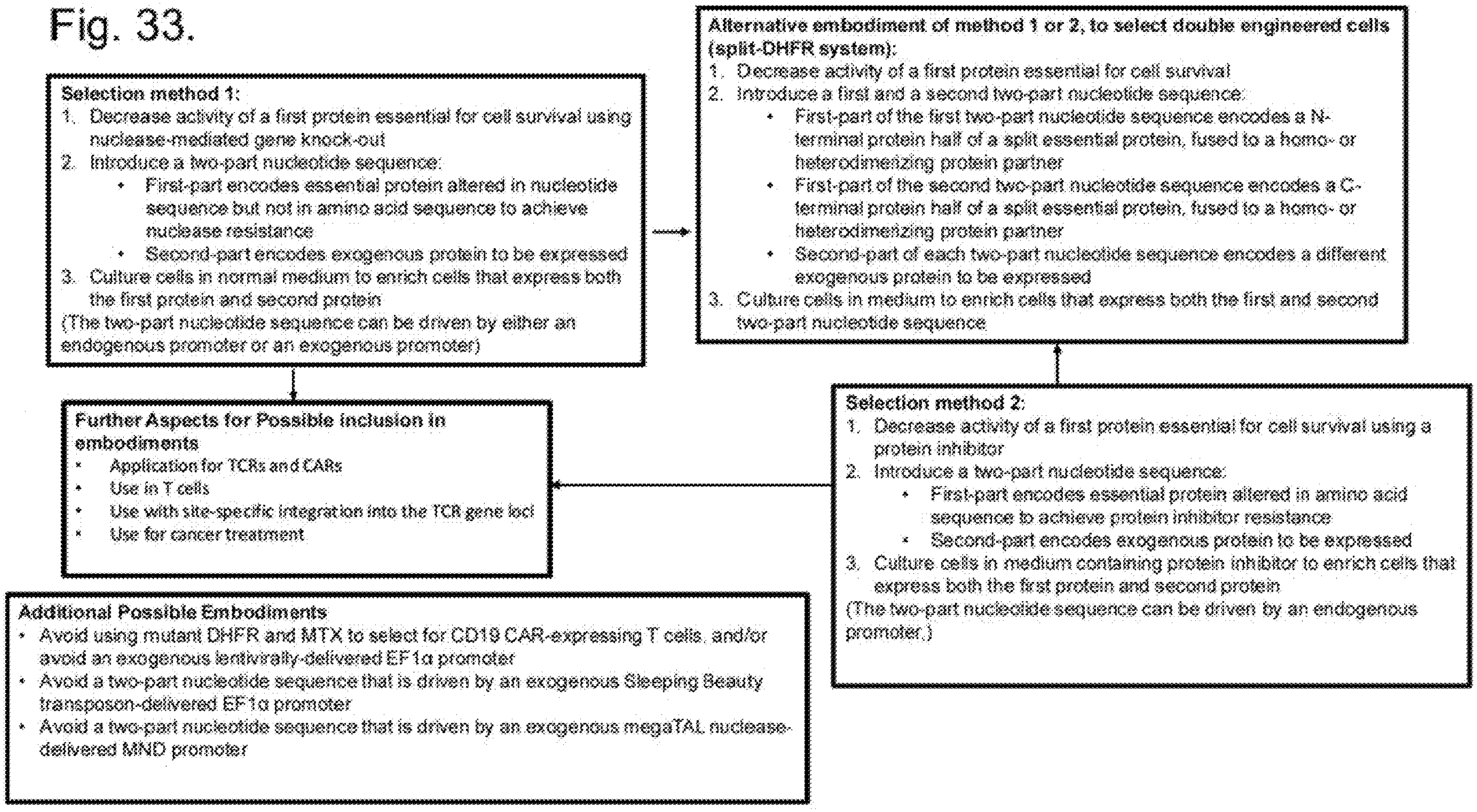
FIG. 33 shows some embodiments of selection methods for genetically engineered cells.
Figure 39:
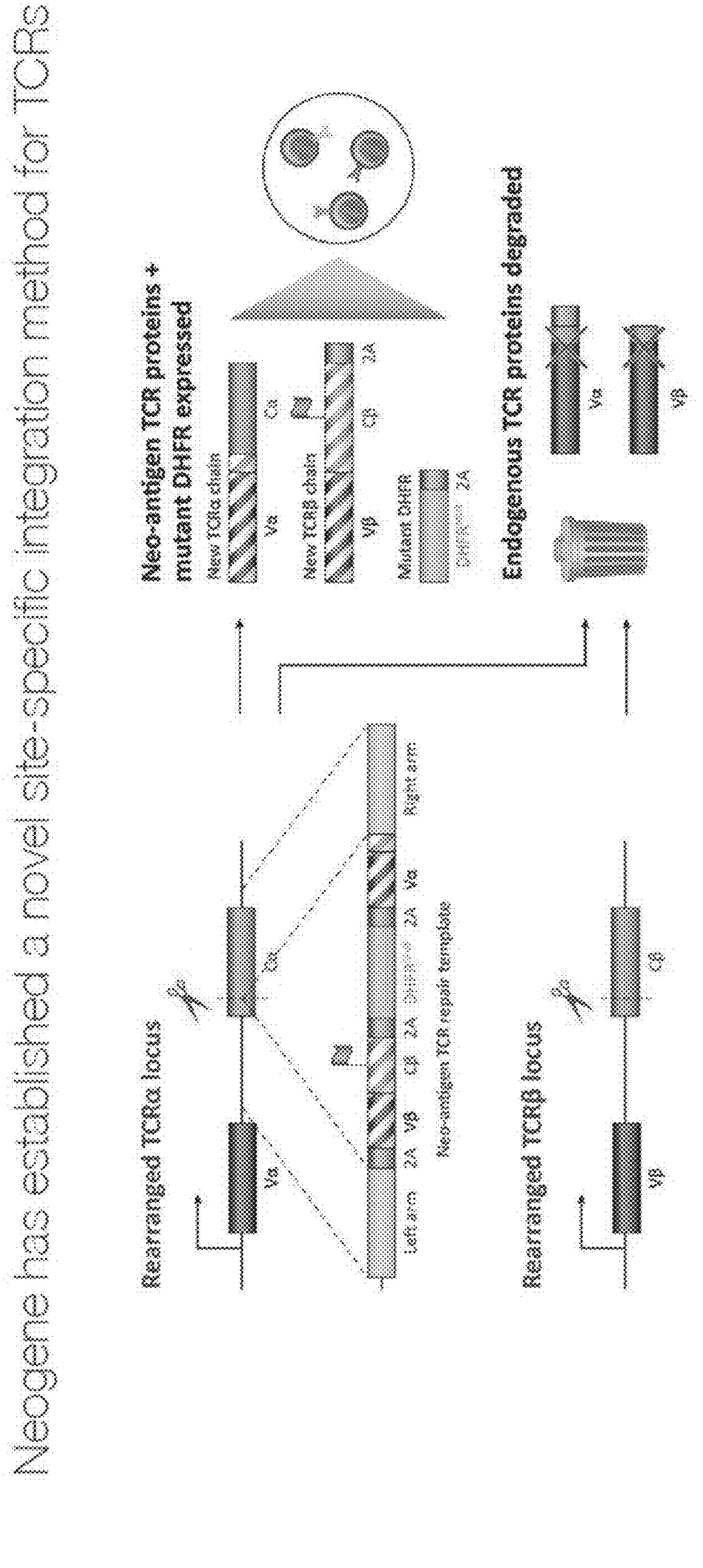
FIG. 39 shows a schematic for site-specific integration of TCRs.
Figure 40:
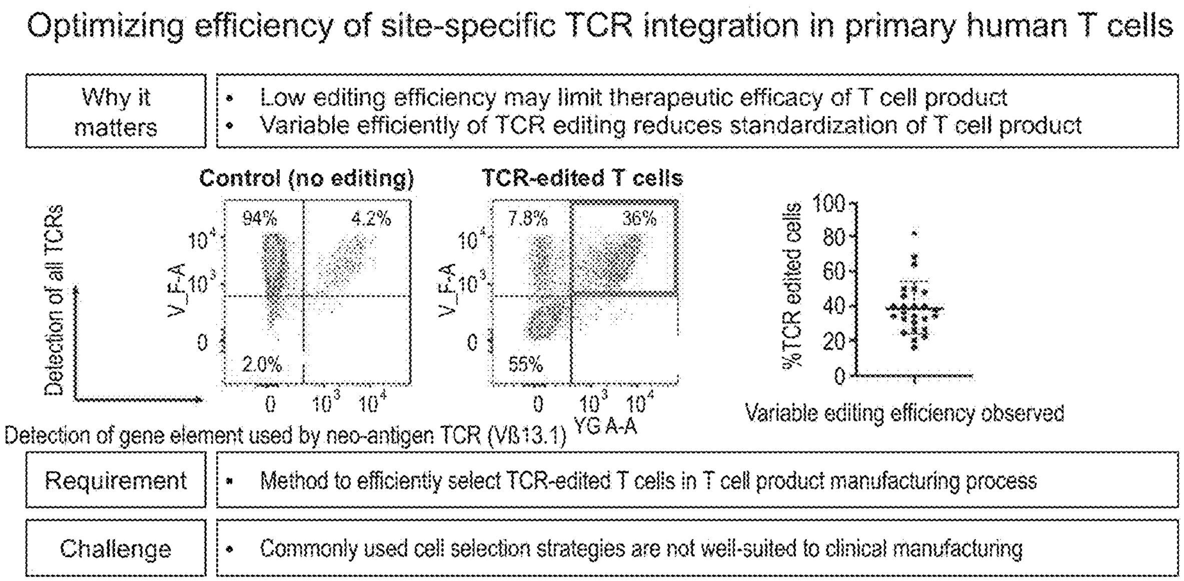
FIG. 40 shows sample data regarding the editing of T cells with a TCR in the absence of selection.
Figure 41:
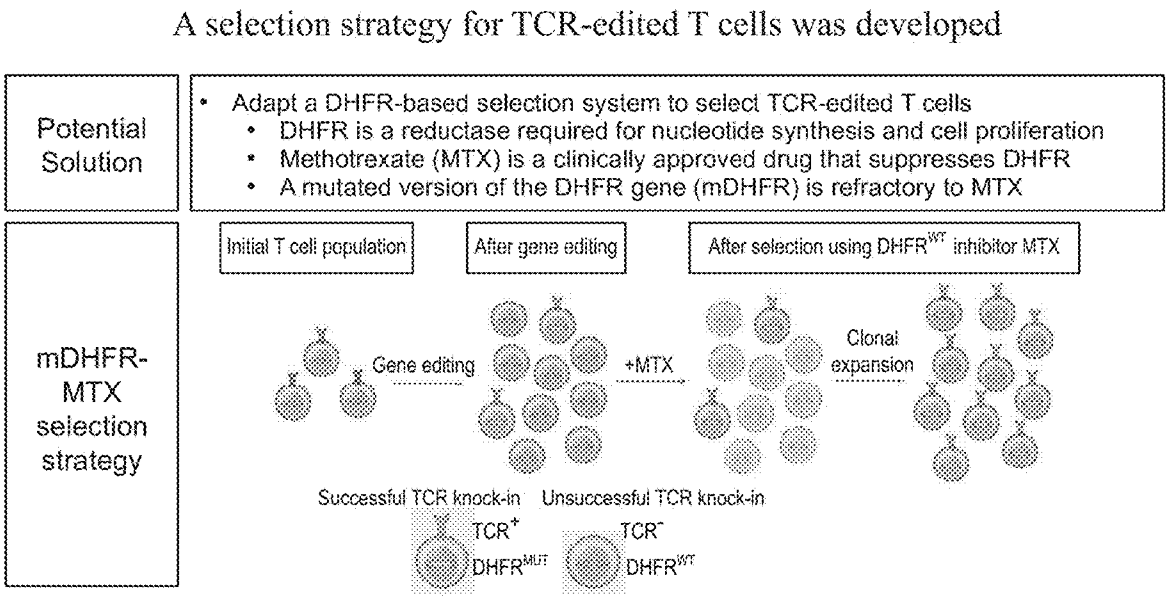
FIG. 41 shows a schematic of an embodiment of an mDHFR-MTX selection strategy.

Some embodiments are shown in FIG. 33. The novel aspect of these embodiments include:

Application for TCRs and CARs

Use in T cells

Use with site-specific integration into the TCR gene loci

Use for cancer treatment

Some embodiments described herein relate to a T cell which include i) an endogenous DHFR being suppressed by the presence of methotrexate to a level that the cell cannot survive and/or proliferate, and ii) at least two nucleotide sequences, including a first nucleotide comprising a nucleotide sequence encoding a non-functional portion of a methotrexate-resistant DHFR protein fused to a first binding domain and a second nucleotide comprising a nucleotide sequence encoding a non-functional portion of a methotrexate-resistant DHFR protein fused to a second binding domain such that when both nucleotides are expressed, a functional methotrexate-resistant DHFR is present and is capable of facilitating selection of cells containing both the first and second nucleotides.

Some embodiments described herein relate to a method for selection of a genetically engineered cell. The method includes i) introducing at least two two-part nucleotide sequences that are operable for expression in a cell, wherein the cell has an essential protein for the survival and/or proliferation that is suppressed to a level that the cell cannot survive and/or proliferate under the selected culture conditions, wherein the first two-part nucleotide sequence comprises a first-part nucleotide sequence encoding a fusion protein comprising a first binding domain fused to a first non-functional portion of a protein allowing for the survival and/or proliferation and a second-part nucleotide sequence encoding a protein to be expressed, wherein the second two-part nucleotide sequence comprises a first-part nucleotide sequence encoding a fusion protein comprising a second binding domain fused to a second non-functional portion of a protein allowing for the survival and/or proliferation and a second-part nucleotide sequence encoding a protein to be expressed, wherein the first and second binding domains are capable of binding to each other in the cell, wherein the first and second non-functional portions of the protein can form a functional protein when co-expressed in the cell;

ii) culturing the cell under in vitro propagation conditions that allow enrichment of the cell that expresses both the first-part and second-part nucleotide sequences of the at least two two-part nucleotide sequences.

Some embodiments described herein relate to binding domains for restoring function to a DHFR protein split into multiple non-functional portions. The binding domains, when fused to complementary non-functional portions of a DHFR protein, can restore DHFR protein function. Binding domains can be native binding domains, engineered binding domains that do not interact with native proteins, or inducible binding domains.

Some embodiments described herein relate to a method for selection or enrichment of a genetically engineered cell. It will be understood that the terms "selection" and "enrichment" refer to the overall increased ratio of a desirable genetically engineered cell in a population of cells. This therefore can include, for example, increasing the overall number of genetically engineered cells, decreasing the number of any other cells present in the population, purifying the genetically engineered cells, any combination thereof, and other similar approaches.

In some embodiments, the method comprises introducing into a cell at least one two-part nucleotide sequence capable of expressing both the first-part and second-part nucleotide sequences in the cell. In some embodiments, the cell has an essential protein for the survival and/or proliferation that is reduced to a level that the cell cannot survive and/or proliferate in a normal cell culture medium. The at least one two-part nucleotide sequence is operable for expression in the cell or becomes operable for expression when inserted into a pre-determined site in the target genome, and the at least one two-part nucleotide sequence comprises a first-part nucleotide sequence encoding the essential protein for the survival and/or proliferation, or a variant thereof, and a second-part nucleotide sequence encoding a protein to be expressed. The second-part nucleotide sequence encodes a protein of interest. The method further comprises culturing the cell in the normal cell culture medium without a pharmacologic exogenous selection pressure for selection or enrichment of the cell that expresses both the first-part and second-part nucleotide sequences.

In some embodiments, the method comprises reducing the level of at least a first protein that functions and/or is essential the survival and/or proliferation of a cell to the level that the cell cannot survive and/or proliferate under normal in vitro propagation conditions, introducing into the cell at least a two-part nucleotide sequence that is capable of expressing both the first-part and second-part nucleotide sequences in the cell and comprises a first-part nucleotide sequence encoding the first protein, or a variant thereof, and a second-part nucleotide sequence encoding a second protein to be expressed.

It will be understood by those skilled in the art that an "essential" protein may be any protein that influences growth, replication, cell cycle, gene regulation (including DNA repair, transcription, translation, and replication), stress response, metabolism, apoptosis, nutrient acquisition, protein turnover, cell surface integrity, essential enzyme activity, survival, or any combination thereof in a given cell.

In some embodiments, the reduction in level of the essential protein is permanent. In some embodiments, the reduction in level of the essential protein is transient, or non-permanent. In some embodiments, the reduction in level of the essential protein is inducible. In some embodiments, the reduction in level of the essential protein influences the survival and/or proliferation of a cell through a single cell cycle time period. In some embodiments, the reduction in level of the essential protein influences the survival and/or proliferation of a cell for a period of at least about 1 minute, at least about 10 minutes, at least about 30 minutes, at least about 60 minutes, at least about 2 hours, at least about 5 hours, at least about 10 hours, at least about 20 hours, at least about 1 day, at least about 2 days, at least about 4 days, at least about 1 week, at least about 2 weeks, at least about 1 month, or at least about 2 months. In some embodiments, the reduction in level of the essential protein results in a complete halt of proliferation. the reduction in level of the essential protein results in a partial halt of proliferation. In some embodiments, proliferation is halted by at least about 5%, at least about 10%, at least about 20%, at least about 30%, at least about 50%, at least about 75%, at least about 80%, at least about 90%, at least about 95%, at least about 99%, or at least about 100%. In some embodiments, the reduction in level of the essential protein results in complete cell death. In some embodiments, the reduction in level of the essential protein initiates cell death in all cells in a population. the reduction in level of the essential protein initiates cell death in some cells within a population. In some embodiments, cell death (or the reduced rate of survival) is increased by at least about 5%, at least about 10%, at least about 20%, at least about 30%, at least about 50%, at least about 75%, at least about 80%, at least about 90%, at least about 95%, at least about 99%, or at least about 100% in a population of cells. In some embodiments, the reduction in level of the essential protein comprises a knock-out of the gene encoding the essential protein. In some embodiments, the reduction in level of the essential protein comprises a knock-down of the gene encoding the essential protein. In some embodiments, the reduction in level of the essential protein comprises a knock-in of a gene capable of inhibiting the essential protein. In some embodiments, the knock-out and/or knock-down is mediated by CRISPR Ribonucleoprotein (RNP), TALEN, MegaTAL, or any other nucleases. In some embodiments, the transient suppression is through siRNA, miRNA, or CRISPR interference (CRISPRi). It will be understood to those skilled in the art that knock-outs, knock-downs, and other methods of protein level reduction may be performed using any conventional method, including restriction enzymes and selection cassettes, selective transcription inhibition, selective translation inhibition, and driving protein targeting for degradation. In some embodiments, the reduction in level of the essential protein comprises transient reduction in the level of the essential protein at the RNA level. In some embodiments, the RNA of the essential protein is reduced by at least about 5%, at least about 10%, at least about 20%, at least about 30%, at least about 50%, at least about 75%, at least about 80%, at least about 90%, at least about 95%, at least about 99%, or at least about 100%. In some embodiments, the cell is a T cell, NK cell, NKT cell, iNKT cell, hematopoietic stem cell, mesenchymal stem cell, iPSC, neural precursor cell, a cell type in retinal gene therapy, or any other cell.

In some embodiments, the at least one two-part nucleotide sequence is operable for expression in the cell or becomes operable for expression when inserted into a pre-determined site in the target genome, and the second-part protein is a protein of interest. In some embodiments, the first-part nucleotide sequence is altered in nucleotide sequence to achieve nuclease, siRNA, miRNA, or CRISPRi resistance. In some embodiments, the first-part nucleotide sequence is altered in nucleotide sequence to achieve at least about 5%, at least about 10%, at least about 20%, at least about 30%, at least about 50%, at least about 75%, at least about 80%, at least about 90%, at least about 95%, at least about 99%, or at least about 100% nuclease, siRNA, miRNA, or CRISPRi resistance. In some embodiments, the first part nucleotide sequence encodes a protein having an identical amino acid sequence to the essential first protein. In some embodiments, the first part nucleotide sequence encodes a protein having an amino acid sequence that is at least about 5%, at least about 10%, at least about 20%, at least about 30%, at least about 50%, at least about 75%, at least about 80%, at least about 90%, at least about 95%, at least about 99%, or at least about 100% identical to the essential first protein. In some embodiments, the first-part nucleotide sequence is altered to encode an altered protein that does not have an identical amino acid sequence to the first protein. In some embodiments, the altered protein has specific features that the first protein does not have. In some embodiments, specific features include, but are not limited to, one or more of the following: reduced activity, increased activity, and altered half-life. In some embodiments, activity of the altered protein is altered by at least about 5%, at least about 10%, at least about 20%, at least about 30%, at least about 50%, at least about 75%, at least about 80%, at least about 90%, at least about 95%, at least about 99%, or at least about 100% compared to the first protein. In some embodiments, the half-life of the altered protein is reduced compared to the first protein. In some embodiments, the half-life of the altered protein is extended compared to the first protein. In some embodiments, the half-life of the altered protein is extended or reduced at least about 1.5-fold, at least about 2-fold, at least about 5-fold, at least about 10-fold, at least about 20-fold, at least about 50-fold, or at least about 100-fold compared to the first protein. In some embodiments, both the first-part and the second-part nucleotide sequences are driven by a same promoter. In some embodiments, the first-part and the second-part nucleotide sequences are driven by different promoters. the second-part nucleotide sequence comprises at least a therapeutic gene.

It will be understood to those skilled in the art that a "therapeutic" gene or protein can be any gene or protein that is useful in the treatment, prevention, prophylaxis, palliation, amelioration, or cure of any disease or disorder.

In some embodiments, the second-part nucleotide sequence encodes a neo-antigen T-cell receptor complex (TCR) containing a TCR alpha chain and a TCR beta chain. In some embodiments, the essential or first protein is dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC). In some embodiments, the first-part nucleotide sequence comprises a nuclease-resistant or siRNA-resistant DHFR gene, and the second-part nucleotide sequence comprises a TRA gene and a TRB gene. In some embodiments, the first-part nucleotide sequence comprises a nuclease-resistant or siRNA-resistant DHFR gene, and the second-part nucleotide sequence comprises a TRA gene and a TRB gene. In some embodiments, the TRA, TRB, and DHFR genes are separated by an at least one linker. In some embodiments, the at least one linker is an at least one self-cleaving 2A peptide and/or an at least one IRES element. In some embodiments, the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1. In some embodiments, the two-part nucleotide sequence is integrated into the genome of the cell. In some embodiments, the at least one two part nucleotide sequence becomes operable for expression when inserted into the pre-determined site in the target genome and both the first-part and second-part nucleotide sequences are driven by a promoter in the target genome. In some embodiments, the integration is through nuclease-mediated site-specific integration, transposon-mediated gene delivery, or virus-mediate gene delivery. In some embodiments, the nuclease-mediated site-specific integration is through CRISPR RNP, optionally a CRISPR/Cas9 RNP. In some embodiments, the method further comprises culturing the cell under normal in vitro propagation conditions without a pharmacologic exogenous selection pressure for enrichment of the cell that expresses both the first protein and second protein.

It will be understood to those skilled in the art that "normal in vitro propagation conditions" encompass typical conditions in which a cell, cell line, or tissue sample can be maintained, but which do not include a variable (e.g., process or ingredient) that has intentionally been left out or added to drive the methods as provided herein.

In some embodiments, the method further comprises using the Split intein system. In some embodiments, the introduced two-part nucleotide sequence is not integrated into the genome of the cell. In some embodiments, a CRISPR RNP that targets an endogenous TCR Constant locus, the first-part nucleotide sequence encoding a nuclease-resistant DHFR gene, and the second-part nucleotide sequence encoding a neo-antigen TCR are delivered to the cell. In some embodiments, the endogenous TCR constant locus can be a TCR alpha Constant (TRAC) locus or a TCR beta Constant (TRBC) locus. In some embodiments, the endogenous TCR constant locus can be a TCR alpha Constant (TRAC) locus or a TCR beta Constant (TRBC) locus. In some embodiments, the endogenous TCR constant locus can be a TCR alpha Constant (TRAC) locus or a TCR beta Constant (TRBC) locus. In some embodiments, the second CRISPR RNP is a TRAC RNP that cuts the TRAC locus for knock-in. In some embodiments, the CRISPR RNP is a CRISPR/Cas9 RNP. In some embodiments, the normal cell culture medium is one that is suitable for non-modified cell's growth and/or proliferation. In some embodiments, the normal cell culture medium is without any exogenous selection pressure. In some embodiments, a CRISPR RNP is used to knock-in into a pre-determined site in the target genome a second two-part nucleotide, optionally wherein the pre-determined site in the target genome is the B2M gene.

In some embodiments, the method comprises introducing into a cell at least one two-part nucleotide sequence capable of expressing both the first-part and second-part nucleotide sequences in the cell. The cell has the functional activity of an essential protein for the survival and/or proliferation that is reduced such that the cell cannot survive and/or proliferate in a normal cell culture medium. The at least one two-part nucleotide sequence is operable for expression in the cell or becomes operable for expression when inserted into a pre-determined site in the target genome, and the at least one two-part nucleotide sequence comprises a first-part nucleotide sequence encodes a first protein that provides a substantially equivalent function to the essential protein for the survival and/or proliferation and a second-part nucleotide sequence encodes a second protein to be expressed. The second protein is a protein of interest. The method further comprises culturing the cell in cell culture medium containing at least one supplement leading to enrichment or selection of the cell that expresses both the first protein and the second protein.

In some embodiments, the method comprises reducing the functional activity of at least a first protein that is essential for the survival and/or proliferation of a cell to the level that the cell cannot survive and/or proliferate under normal in vitro propagation conditions and introducing into the cell at least a two-part nucleotide sequence that is capable of expressing both the first-part and second-part nucleotide sequences in the cell and comprises a first-part nucleotide sequence encodes a first protein that provides a substantially equivalent function to and a second-part nucleotide sequence encoding a second protein to be expressed. The at least one two-part nucleotide sequence is operable for expression in the cell or becomes operable for expression when inserted into a pre-determined site in the target genome, and the second protein is a protein of interest. The method further comprises culturing the cell in cell culture medium containing at least one supplement leading to selection or enrichment of the cell that expresses both the first protein and the second protein.

In some embodiments, the cell is a T cell, NK cell, NKT cell, iNKT cell, hematopoietic stem cell, mesenchymal stem cell, iPSC, neural precursor cell, a cell type in retinal gene therapy, or any other cell. In some embodiments, the cell is mammalian. In some embodiments, the cell is rat or mouse. In some embodiments, the cell is human. In some embodiments, the cell is from an established or standard cell line. In some embodiments, the cell is from primary tissue or primary cells. In some embodiments, the first-part nucleotide sequence is altered in nucleotide sequence to achieve nuclease, siRNA, miRNA, or CRISPRi resistance, and either a) encodes a protein having an identical amino acid sequence to the first protein or b) encodes a protein having an adjusted functionality to the first protein. In some embodiments, the first-part nucleotide sequence is altered to encode an altered protein that does not have an identical amino acid sequence to the first protein. In some embodiments, the first part nucleotide sequence encodes a protein having an amino acid sequence that is at least about 5%, at least about 10%, at least about 20%, at least about 30%, at least about 50%, at least about 75%, at least about 80%, at least about 90%, at least about 95%, at least about 99%, or at least about 100% identical to the first protein. In some embodiments, the altered protein has specific features that the first protein does not have. the specific features include, but are not limited to, one or more of the following: reduced activity, increased activity, altered half-life resistance to small molecule inhibition, and increased activity after small molecule binding. In some embodiments, activity of the altered protein is altered by at least about 5%, at least about 10%, at least about 20%, at least about 30%, at least about 50%, at least about 75%, at least about 80%, at least about 90%, at least about 95%, at least about 99%, or at least about 100% compared to the first protein. In some embodiments, the half-life of the altered protein is reduced compared to the first protein. In some embodiments, the half-life of the altered protein is extended compared to the first protein. In some embodiments, the half-life of the altered protein is extended or reduced at least about 1.5-fold, at least about 2-fold, at least about 5-fold, at least about 10-fold, at least about 20-fold, at least about 50-fold, or at least about 100-fold compared to the first protein. In some embodiments, both the first-part and the second-part nucleotide sequences are driven by a same promoter. In some embodiments, the first-part and the second-part nucleotide sequences are driven by different promoters. In some embodiments, the second-part nucleotide sequence comprises at least a therapeutic gene. In some embodiments, the second-part nucleotide sequence encodes a neo-antigen T-cell receptor complex (TCR) containing a TCR alpha chain and a TCR beta chain. In some embodiments, the essential or first protein is dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC). In some embodiments, the first-part nucleotide sequence comprises a protein inhibitor-resistant DHFR gene, and the second-part nucleotide sequence comprises a TRA gene and a TRB gene. In some embodiments, the TRA, TRB, and DHFR genes are operably configured to be expressed from a single open reading frame. the TRA, TRB, and DHFR genes are expressed two or three open reading frames. In some embodiments, the TRA, TRB, and DHFR genes are separated by an at least one linker. In some embodiments, the TRA, TRB, and DHFR genes are separated by two linkers. In some embodiments, the order of the at least one linker, TRA, TRB, and DHFR genes is the following: TRA-linker-TRB-linker-DHFR, TRA-linker-DHFR-linker-TRB, TRB-linker-TRA-linker-DHFR, TRB-linker-DHFR-linker-TRA, DHFR-linker-TRA-linker-TRB, or DHFR-linker-TRB-linker-TRA. In some embodiments, the at least one linker is an at least one self-cleaving 2A peptide and/or an at least one IRES element. In some embodiments, the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1. In some embodiments, the two-part nucleotide sequence is integrated into the genome of the cell. In some embodiments, the two-part nucleotide sequence is not integrated into the genome of the cell. In some embodiments, the two-part nucleotide sequence is not integrated into the genome of the cell, but is expressed by the cell through an at least one plasmid. In some embodiments, the two-part nucleotide sequence is integrated into the nuclear genome of the cell. the two-part nucleotide sequence is integrated into the mitochondrial genome of the cell. In some embodiments, the at least one two part nucleotide sequence becomes operable for expression when inserted into the pre-determined site in the target genome and both the first-part and second-part nucleotide sequences are driven by a promoter in the target genome. In some embodiments, the integration is through nuclease-mediated site-specific integration, transposon-mediated gene delivery, or virus-mediate gene delivery. In some embodiments, the nuclease-mediated site-specific integration is through CRISPR RNP, optionally a CRISPR/Cas9 RNP. In some embodiments, the method further comprises using the Split intein system. In some embodiments, a CRISPR RNP that targets an endogenous TCR Constant locus, the first-part nucleotide sequence encoding a protein inhibitor-resistant DHFR gene, and the second-part nucleotide sequence encoding a neo-antigen TCR are delivered to the cell. In some embodiments, the endogenous TCR constant locus can be a TCR alpha Constant (TRAC) locus or a TCR beta Constant (TRBC) locus. In some embodiments, the delivery is by electroporation, or methods based on mechanical or chemical membrane permeabilization. In some embodiments, the CRISPR RNP is a TRAC RNP that cuts the TRAC locus for knock-in. In some embodiments, the CRISPR RNP is a CRISPR/Cas9 RNP. In some embodiments, wherein the supplement leading to enrichment or selection of the cell is an antibody that allows enrichment of the cells by flow cytometry or magnetic bead enrichment. In some embodiments, the supplement leading to enrichment or selection of the cell is an antibody that allows enrichment of the cells by flow cytometry or magnetic bead enrichment. In some embodiments, the first protein mediates resistance of the cell to the supplement mediated impairment of survival and/or proliferation of cells. In some embodiments, the supplement is methotrexate. In some embodiments, the first protein is a methotrexate-resistant DHFR mutant protein.

In some embodiments, the method comprises introducing into a cell at least two, two-part nucleotide sequences capable of expressing both a first-part and a second-part nucleotide sequence in the cell. The cell has an essential protein for the survival and/or proliferation that is suppressed to a level that the cell cannot survive and/or proliferate, and the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest. The second two-part nucleotide sequence comprises a first-part nucleotide sequence encoding a second fusion protein comprising a non-functional portion of the essential protein for the survival and/or proliferation fused to a second binding domain and a second-part nucleotide sequence encoding a second protein of interest. When both the first and second fusion proteins are expressed together in a cell, the function of the essential protein for the survival and/or proliferation is restored. The method further comprises culturing the cell under conditions leading to the selection of the cell that expresses both the first and second two-part nucleotide sequences.

In some embodiments, the method comprises suppressing at least a first protein that is essential for the survival and/or proliferation of a cell to the level that the cell cannot survive and/or proliferate under normal in vitro propagation conditions and introducing at least two two-part nucleotide sequences that are capable of being expressed in the cell. The first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest. The second two-part nucleotide sequence comprises a first-part nucleotide sequence encoding a second fusion protein comprising non-functional portion of the essential protein for the survival and/or proliferation fused to a second binding domain and a second-part nucleotide sequence encoding a second protein of interest, and when both the first and second fusion proteins are expressed together in a cell, the function of the essential protein for the survival and/or proliferation is restored. The method further comprises culturing the cell under in vitro propagation conditions that lead to the enrichment of the cell that expresses both the first fusion protein and second fusion protein.

In some embodiments, the method comprises introducing at least one two-part nucleotide sequence that is operable for expression in a cell. The cell has an essential protein for the survival and/or proliferation that is suppressed to a level that the cell cannot survive and/or proliferate, and the at least one two-part nucleotide sequence comprises a first-part nucleotide sequence encoding the essential protein for the survival and/or proliferation and a second-part nucleotide sequence encoding a protein to be expressed. The second-part nucleotide sequence is encoding a protein that is exogenous to the cell; and culturing the cell under conditions leading to the selection of the cell that expresses both the first-part and second-part nucleotide sequences.

In some embodiments, the method comprises decreasing activity of at least a first protein that is essential for the survival and/or proliferation of a cell to the level that the cell cannot survive and/or proliferate under normal in vitro propagation conditions, introducing at least a two-part nucleotide sequence that is operable for expression in the cell and comprises a first-part nucleotide sequence encoding the first protein and a second-part nucleotide sequence encoding a second protein to be expressed. The second-part protein is exogenous to the cell, and culturing the cell under in vitro propagation conditions that lead to the enrichment of the cell that expresses both the first protein and second protein.

In some embodiments, cell survival and/or proliferation are measured after at least about 1 minute, at least about 10 minutes, at least about 30 minutes, at least about 60 minutes, at least about 2 hours, at least about 5 hours, at least about 10 hours, at least about 20 hours, at least about 1 day, at least about 2 days, at least about 3 days, at least about 4 days, at least about 5 days, at least about 6 days, at least about 1 week, at least about 2 weeks, at least about 1 month, or at least about 2 months. In some embodiments, decreasing activity of at least a first protein that is essential for the survival and/or proliferation lasts for at least about 1 minute, at least about 10 minutes, at least about 30 minutes, at least about 60 minutes, at least about 2 hours, at least about 5 hours, at least about 10 hours, at least about 20 hours, at least about 1 day, at least about 2 days, at least about 3 days, at least about 4 days, at least about 5 days, at least about 6 days, at least about 1 week, at least about 2 weeks, at least about 1 month, or at least about 2 months. In some embodiments, decreasing activity of at least a first protein that is essential for the survival and/or proliferation is permanent.

Some embodiments described herein relate to a cell that is made according to any of the methods of the present disclosure.

Some embodiments described herein relate to a method for enrichment of a genetically engineered T cell. In some embodiments, the method comprises introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and culturing the cell in cell culture medium containing methotrexate leading to enrichment of the cell that expresses both the first protein and the second protein.

Some embodiments described herein relate to a method for enrichment of a T cell engineered to express an exogenous T cell receptor gene. In some embodiments, the method comprises knocking-out an endogenous TRBC gene from its locus using a first CRISPR/Cas9 RNP, knocking-in, using a second CRISPR/Cas9 RNP, into the endogenous TRBC locus a first-part nucleotide sequence encoding a methotrexate-resistant DHFR gene and a second-part nucleotide sequence comprising a therapeutic TCR gene. Both nucleotide sequences are operably linked allowing for expression from the endogenous TRBC promotor, and culturing the cells in cell culture medium containing methotrexate leading to enrichment of T cells that express both the therapeutic TCR and the methotrexate-resistant DHFR gene.

In some embodiments, the essential protein is a DHFR protein. In some embodiments, the essential protein is a DHFR mimic or analog. In some embodiments, the essential protein is at least about 50%, at least about 75%, at least about 80%, at least about 90%, at least about 95%, at least about 99%, or at least about 100% identical to a DHFR protein or portion thereof. In some embodiments, the second-part nucleotide sequence of either the first or second two-part nucleotide sequences is exogenous to the cell. In some embodiments, the second-part nucleotide sequence of either the first or second two-part nucleotide sequence is a TCR. In some embodiments, the first and/or second binding domains are derived from GCN4. In some embodiments, the first and/or second binding domains are derived from a GCN4 mimic or analog. In some embodiments, the first and/or second binding domains are derived from a sequence that is at least about 50%, at least about 75%, at least about 80%, at least about 90%, at least about 95%, at least about 99%, or at least about 100% identical to GCN4. In some embodiments, the first and/or second binding domains comprise SEQ ID NO: 24. In some embodiments, the first and/or second binding domains comprise a sequence that at least about 50%, at least about 75%, at least about 80%, at least about 90%, at least about 95%, at least about 99%, or at least about 100% identical to SEQ ID NO: 24. In some embodiments, the first fusion protein and/or second fusion protein comprise SEQ ID NO: 39 and/or SEQ ID NO: 40. In some embodiments, the first fusion protein and/or second fusion protein comprise a sequence that is at least about 50%, at least about 75%, at least about 80%, at least about 90%, at least about 95%, at least about 99%, or at least about 100% identical to SEQ ID NO: 39 and/or SEQ ID NO: 40. In some embodiments, the first fusion protein and/or second fusion protein comprise SEQ ID NO: 35 and/or SEQ ID NO: 36. In some embodiments, the first fusion protein and/or second fusion protein comprise a sequence that is at least about 50%, at least about 75%, at least about 80%, at least about 90%, at least about 95%, at least about 99%, or at least about 100% identical to SEQ ID NO: 35 and/or SEQ ID NO: 36. In some embodiments, the first fusion protein and/or second fusion protein comprise SEQ ID NO: 37 and/or SEQ ID NO: 38. In some embodiments, the first fusion protein and/or second fusion protein comprise a sequence that is at least about 50%, at least about 75%, at least about 80%, at least about 90%, at least about 95%, at least about 99%, or at least about 100% identical to SEQ ID NO: 37 and/or SEQ ID NO: 38. In some embodiments, the first fusion protein and/or second fusion protein comprise SEQ ID NO:62 and/or SEQ ID NO: 63. In some embodiments, the first fusion protein and/or second fusion protein comprise a sequence that is at least about 50%, at least about 75%, at least about 80%, at least about 90%, at least about 95%, at least about 99%, or at least about 100% identical to SEQ ID NO: 62 and/or SEQ ID NO: 63. In some embodiments, the first and second binding domains are derived from FKBP12. In some embodiments, the first and second binding domains are derived from a FKBP12 analog or mimic. In some embodiments, the FKBP12 has an F36V mutation. In some embodiments, the first and second binding domains are derived from a sequence that is at least about 50%, at least about 75%, at least about 80%, at least about 90%, at least about 95%, at least about 99%, or at least about 100% identical to FKBP12. In some embodiments, the first and/or second binding domains comprise SEQ ID NO: 31. In some embodiments, the first and/or second binding domains comprise a sequence that is at least about 50%, at least about 75%, at least about 80%, at least about 90%, at least about 95%, at least about 99%, or at least about 100% identical to SEQ ID NO: 31. In some embodiments, the first and/or second binding domains are derived from JUN and/or FOS. In some embodiments, the first and/or second binding domains are derived from a JUN and/or FOS analog or mimic. In some embodiments, the first and/or second binding domains are derived from a sequence that is at least about 50%, at least about 75%, at least about 80%, at least about 90%, at least about 95%, at least about 99%, or at least about 100% identical to JUN and/or FOS. In some embodiments, the first and/or second binding domains are derived from SEQ ID NO: 26 and/or SEQ ID NO: 29. In some embodiments, the first and/or second binding domains are derived from a sequence that is at least about 50%, at least about 75%, at least about 80%, at least about 90%, at least about 95%, at least about 99%, or at least about 100% identical to SEQ ID NO: 26 and/or SEQ ID NO: 29. In some embodiments, the first and/or second binding domains are derived from SEQ ID NO: 27 and/or SEQ ID NO: 30. In some embodiments, the first and/or second binding domains are derived from a sequence that is at least about 50%, at least about 75%, at least about 80%, at least about 90%, at least about 95%, at least about 99%, or at least about 100% identical to SEQ ID NO: 27 and/or SEQ ID NO: 30. In some embodiments, the first binding domain and second binding domain have complementary mutations that preserve binding to each other. In some embodiments, neither the first binding domain nor the second binding domain bind to a native binding partner. In some embodiments, wherein each of the first binding domain and second binding domain have between 3 and 7 complementary mutations. In some embodiments, the first binding domain and second binding domain each have 3 complementary mutations. In some embodiments, the first binding domain and second binding domain each have 4 complementary mutations. In some embodiments, the at least two two-part nucleotide sequences are integrated into the genome of the cell. In some embodiments, the at least two two-part nucleotide sequences are not integrated into the genome of the cell. In some embodiments, the at least two two-part nucleotide sequences are integrated into the nuclear genome of the cell. In some embodiments, the at least two two-part nucleotide sequences are integrated into the mitochondrial genome of the cell. In some embodiments, the at least two two-part nucleotide sequences are not integrated into the genome of the cell but are expressed by the cell through an at least one plasmid. In some embodiments, the at least two two-part nucleotide sequences become operable for expression when inserted into pre-determined sites in the target genome and both the first-part and second-part nucleotide sequences are driven by a promoters in the target genome. In some embodiments, the integration is through nuclease-mediated site-specific integration, transposon-mediated gene delivery, or virus-mediate gene delivery. In some embodiments, the nuclease-mediated site-specific integration is through CRISPR RNP. In some embodiments, the first two-part nucleotide sequence is delivered to the cell by a CRISPR RNP that targets an endogenous TCR Constant locus, the first first-part nucleotide sequence encodes a non-functional portion of a DHFR protein, and the first second-part nucleotide sequence encodes a neo-antigen TCR. In some embodiments, the first two-part nucleotide sequence is delivered to the cell by a CRISPR RNP that targets an endogenous TCR Constant locus, the first first-part nucleotide sequence encodes a non-functional portion of a DHFR protein, and the first second-part nucleotide sequence encodes a neo-antigen TCR. In some embodiments, the first first-part nucleotide sequence and the second first-part nucleotide sequences encode fusion proteins comprising non-functional portions of a DHFR protein that have DHFR activity when the fusion proteins are co-expressed. In some embodiments, the endogenous TCR Constant locus can be a TCR alpha Constant (TRAC) locus or a TCR beta Constant (TRBC) locus. In some embodiments, the endogenous locus other than a TCR Constant locus is a B2M locus. In some embodiments, the delivery is by electroporation, or methods based on mechanical or chemical membrane permeabilization. In some embodiments, the CRISPR RNP is a CRISPR/Cas9 RNP.

In some embodiments, the nuclease allows for in-frame exonic integration into a gene locus to enable expression from the endogenous promotor, the endogenous splice sites, and the endogenous termination signal. In some embodiments, the nuclease allows for in-frame exonic integration into a gene locus to allow for expression from the endogenous promotor, the endogenous splice sites, and an exogenous termination signal. In some embodiments, these embodiments can be part of any of the embodiments provided herein.

In some embodiments, the nuclease allows for intronic integration into a gene locus to allow for expression from the endogenous promotor, an exogenous splice acceptor site, and an exogenous termination signal. In some embodiments, the essential or first protein is split into at least two individually dysfunctional protein portions, wherein each of the at least two portions is fused to multimerization domain and wherein each of the at least two portions is integrated into distinct two-part nucleotide sequences to allow for selection of cells in which all distinct two-part nucleotide sequences are expressed, optionally wherein the function of the essential or first protein is restored. In some embodiments, the essential or first protein is split into at least two individually dysfunctional protein portions, wherein each of the at least two portions is fused to multimerization domain and wherein each of the at least two portions is integrated into distinct two-part nucleotide sequences to allow for selection of cells in which all distinct two-part nucleotide sequences are expressed, optionally wherein the function of the essential or first protein is partially restored. the essential or first protein is split into at least two individually dysfunctional protein portions, wherein each of the at least two portions is fused to multimerization domain and wherein each of the at least two portions is integrated into distinct two-part nucleotide sequences to allow for selection of cells in which all distinct two-part nucleotide sequences are expressed, optionally wherein the function of the essential or first protein is restored at least about 10%, at least about 20%, at least about 50%, at least about 75%, at least about 80%, at least about 95%, at least about 99%, or at least about 100% to its normal level. In some embodiments, the essential or first protein is split into a dysfunctional N-terminal and C-terminal protein half, each half fused to a homo- or heterodimerizing protein partner or to a split intein. In some embodiments, the essential or first protein is a DHFR protein. In some embodiments, the essential or first protein is a DHFR protein analog or mimic. In some embodiments, the essential or first protein is at least about 50%, at least about 75%, at least about 80%, at least about 95%, at least about 99%, or at least about 100% identical to a DHFR protein. In some embodiments, the homodimerizing protein is GCN4, FKBP12, or a variant thereof. In some embodiments, the heterodimerizing proteins are Jun/Fos, or variants thereof. In some embodiments, restoration of the function of the essential protein is induced. In some embodiments, restoration of the function of the essential protein is induced by AP1903. In some embodiments, restoration of the function of the essential protein is induced by at least about 5%, at least about 10%, at least about 20%, at least about 50%, at least about 75%, at least about 80%, at least about 95%, at least about 99%, or at least about 100%. In some embodiments, the culturing step is done in the presence of methotrexate. In some embodiments, the protein of interest is a T cell receptor. In some embodiments, the T cell receptor is specific for a viral or a tumor antigen. In some embodiments, the tumor antigen is a tumor neo-antigen. In some embodiments, the genetically engineered cell is a primary human T cell.

Some embodiments described herein relate to a T cell. In some embodiments, the T cell comprises an endogenous dihydrofolate reductase (DHFR) being suppressed by the presence of methotrexate to a level that the cell cannot survive and/or proliferate, and at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

In some embodiments, the T cell comprises a knock-out of endogenous dihydrofolate reductase (DHFR), and at least one two-part nucleotide sequence comprising a first-part nucleotide sequence encoding a DHFR protein, or variant thereof, and a second-part nucleotide sequence encoding a T-cell receptor operably expressed from the endogenous TRA or TRB promotor.

In some embodiments, the T cell comprises an endogenous dihydrofolate reductase (DHFR) being suppressed by the presence of methotrexate to a level that the cell cannot survive and/or proliferate, and at least two two-part nucleotide sequences. The first two-part nucleotide sequence comprises a first first-part nucleotide sequence encoding a non-functional or dysfunctional portion of a DHFR protein, or variant thereof, and a first second-part nucleotide sequence encoding a T-cell receptor operably expressed from the endogenous TRA or TRB promotor. The second two-part nucleotide sequence comprises a second first-part nucleotide sequence encoding a non-functional or dysfunctional portion of a DHFR protein, or variant thereof, and a second second-part nucleotide sequence encoding a protein of interest operably expressed from the endogenous B2M promotor, and wherein the cell has DHFR activity.

Definitions

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Unless otherwise specified, the definitions provided herein control when the present definitions may be different from other possible definitions.

Unless explained otherwise, all technical and scientific terms used herein have the same meaning as commonly understood to one of ordinary skill in the art to which this disclosure belongs. All HUGO Gene Nomenclature Committee (HGNC) identifiers (IDs) mentioned herein are incorporated by reference in their entirety. Although methods and materials similar or equivalent to those described herein can be used in the practice or testing of the present disclosure, suitable methods and materials are described below. The materials, methods, and examples are illustrative only and not intended to be limiting.

"T cell receptor" or "TCR" denotes a molecule found on the surface of T cells or T lymphocytes that recognizes antigen bound as peptides to major histocompatibility complex (MHC) molecules. The TCR is composed of two different protein chains (that is, it is a hetero dimer). In humans, in 95% of T cells the TCR consists of an alpha ($\alpha$) chain and a beta ($\beta$) chain (encoded by TRA and TRB, respectively), whereas in 5% of T cells the TCR consists of gamma and delta ($\gamma/\delta$) chains (encoded by TRG and TRD, respectively). This ratio changes during ontogeny and in diseased states (such as leukemia). It also differs between species. Each TCR chain is composed of two extracellular domains: Variable (V) region and a Constant (C) region. The Constant region is proximal to the cell membrane, followed by a transmembrane region and a short cytoplasmic tail, while the Variable region binds to the peptide/MHC complex. The variable domain of both the TCR$\alpha$ and TCR$\beta$ chains has three hypervariable complementarity determining regions (CDRs), denoted CDR1, CDR2, and CDR3. In some embodiments, CDR3 is the main antigen-recognizing region. In some embodiments, TCR$\alpha$ chain genes comprise V and J, and TCR$\beta$ chain genes comprise V, D and J gene segments that contribute to TCR diversity. The constant domain of the TCR consists of short connecting sequences in which a cysteine residue forms disulfide bonds, which form a link between the two chains.

In addition to other features, T Cells can be characterized by the expression of markers that indicate functionality or activation state, including but not limited to CD4, CD8, CD25, and CD69. In some embodiments, the cells are a specific subset of T cells, such as CD4+ or CD8+ T cells. In some embodiments, the methods are used on a specific subset of T cells, such as CD4+ or CD8+ T cells. In some embodiments, the methods are used in the process of generating a specific subset of T cells, such as CD4+ or CD8+ T cells. In some embodiments, the cells are activated, for example, expressing CD25 or CD69. In some embodiments, the methods are used on cells that are activated, for example, expressing CD25 or CD69. In some embodiments, the methods are used in the process of generating cells that are activated, for example, expressing CD25 or CD69.

The term "therapeutic TCRs" or "therapeutic TCR genes" can refer to specific combinations of TCRα and TCRβ chains that mediate a desired functionality, for example, being able to facilitate a host's immune system to fight against a disease. Therapeutic TCR genes can be selected from in vitro mutated TCR chains expressed as recombinant TCR libraries by phage-, yeast- or T cell-display systems. Therapeutic TCR genes can be autologous or allogeneic.

The term "protein of interest" can refer to any protein that is to be expressed in addition to the protein that is essential for the survival and/or proliferation of a cell according to some embodiments described herein. A protein of interest may be exogenous to the cell. A protein of interest may be a protein that is natively expressed by the cell but that is to be overexpressed. Proteins may be of interest for therapeutic, diagnostic, research, or any other purpose. Examples of proteins of interest include TCRs, chimeric-antigen receptors, switch receptors, cytokines, enzymes, growth factors, antibodies, and modified versions thereof.

"Genetically engineered cells" are cells that have changes in their genetic makeup using biotechnology. Such changes include transfer of genes within and across species boundaries, the introduction of new natural or synthetic genes, or the removal of native genes, to produce improved or novel organisms or improved or novel functionality within an organism. New DNA is obtained by either isolating and copying the genetic material of interest using recombinant DNA methods or by artificially synthesizing the DNA. Isolated or synthesized DNA may be modified prior to introduction into the genetically engineered cell.

"Genetically engineered T cells" are T cells that have changes in their genetic makeup using biotechnology.

A "linker," when used in the context of a protein or polypeptide, refers to an amino acid sequence that connects two proteins, polypeptides, peptides, domains, regions, or motifs and may provide a spacer function compatible with interaction of the two sub-binding domains so that the resulting polypeptide retains a specific function or activity. In certain embodiments, a linker is comprised of about two to about 35 amino acids or 2-35 amino acids, for instance, about four to about 20 amino acids or 4-20 amino acids, about eight to about 15 amino acids or 8-15 amino acids, about 15 to about 25 amino acids or 15-25 amino acids. In some embodiments, linkers can be rich in glycines and/or serine amino acids.

An "intein," also known as a "protein intron," is a protein segment or segments capable of joining adjacent residues. In some embodiments, the intein is able to excise itself and/or join the remaining portions of a precursor polypeptide during protein splicing. In some embodiments, an intein joins together with other residues through a peptide bond. A "Split intein" refers to a case in which the intein of the precursor protein comes from at least two genes.

The term "nonfunctional" refers to a molecule, amino acid, amino acids, nucleotide, nucleotides, domain, protein segment, protein, RNA, RNA segment, DNA, or DNA segment that has no or severely reduced activity.

The term "dysfunctional" refers to a molecule, amino acid, amino acids, nucleotide, nucleotides, domain, protein segment, protein, RNA, RNA segment, DNA, or DNA segment that cannot function in the expected or complete manner and may or may not have aberrant activity.

As used herein, the term "neo-antigen" refers to an antigen derived from a tumor-specific genomic mutation. For example, a neo-antigen can result from the expression of a mutated protein in a tumor sample due to a non-synonymous single nucleotide mutation or from the expression of alternative open reading frames due to mutation induced frame-shifts. Thus, a neo-antigen may be associated with a pathological condition. In some embodiments, "mutated protein" refers to a protein comprising at least one amino acid that is different from the amino acid in the same position of the canonical amino acid sequence. In some embodiments, a mutated protein comprises insertions, deletions, substitutions, inclusion of amino acids resulting from reading frame shifts, or any combination thereof, relative to the canonical amino acid sequence. "PTM neo-antigens" refers to antigens that are tumor specific but are not based on genomic mutations. Examples of PTM neo-antigens include phospho-neo-antigens and glycan-neo-antigens.

"CRISPR/Cas9" is a technology that enables geneticists and medical researchers to edit parts of the genome by removing, adding or altering sections of the DNA sequence. The CRISPR/Cas9 system consists of two key molecules that introduce a change into the DNA: an enzyme called Cas9, which acts as a pair of "molecular scissors" that can cut the two strands of DNA at a specific location in the genome so that bits of DNA can then be added or removed; a piece of RNA called guide RNA (gRNA), which consists of a small piece of pre-designed RNA sequence (about 20 bases long) located within a longer RNA scaffold. The scaffold part binds to DNA and the pre-designed sequence "guides" Cas9 to the right part of the genome. This makes sure that the Cas9 enzyme cuts at the right point in the genome. A ribonucleoprotein (RNP) is a complex of ribonucleic acid and RNA-binding protein. Persons having skill in the art will recognize that CRISPR systems other than Cas9 may equivalently be used in various embodiments described herein and the term "CRISPR" refers to the genus of such systems when the term is used to refer to a technology, system, or method.

CRISPR interference (CRISPRi) is a genetic perturbation technique that allows for sequence-specific repression of gene expression in prokaryotic and eukaryotic cells.

"TALEN," or Transcription activator-like effector nucleases, are restriction enzymes that can be engineered to cut specific sequences of DNA. They are made by fusing a TAL effector DNA-binding domain to a DNA cleavage domain (a nuclease which cuts DNA strands). Transcription activator-like effectors (TALEs) can be engineered to bind to practically any desired DNA sequence, so when combined with a nuclease, DNA can be cut at specific locations.

"MegaTAL" is a single-chain rare-cleaving nuclease system, in which the DNA binding region of a transcription activator-like (TAL) effector is used to address a site-specific meganuclease adjacent to a single desired genomic target site. This system allows the generation of extremely active and hyper-specific compact nucleases.

"siRNA," Small interfering RNA, sometimes known as short interfering RNA or silencing RNA, is a class of double-stranded RNA non-coding RNA molecules, typically 20-27 base pairs in length, similar to miRNA, and operating within the RNA interference (RNAi) pathway. It interferes with the expression of specific genes with complementary nucleotide sequences by degrading mRNA after transcription, preventing translation.

"miRNA" (microRNA) is a small non-coding RNA molecule (containing about 22 nucleotides) found in plants, animals and some viruses, that functions in RNA silencing and post-transcriptional regulation of gene expression. miRNAs function via base-pairing with complementary sequences within mRNA molecules. As a result, these mRNA molecules are silenced.

Various Embodiments

Figure 27A:
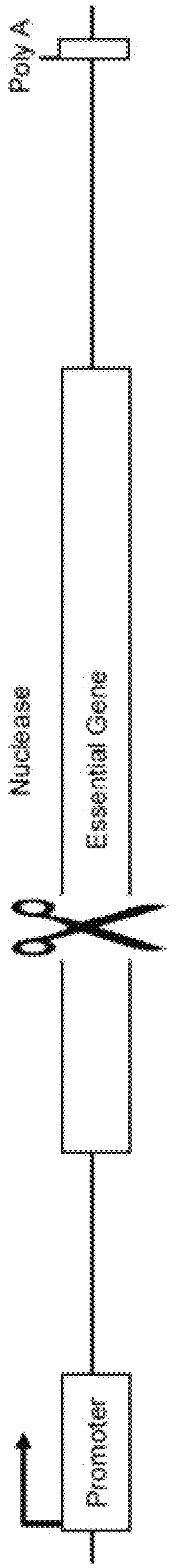
FIG. 27A shows a diagram of knocking out of an essential gene.

In some embodiments, a method provided herein is a selection method for the enrichment of a genetically engineered cell. The method can comprise: introducing a genomic knock-out at, at least, one genomic locus encoding a protein essential for the survival and/or proliferation of a cell. See FIG. 27A "knockout essential gene." The method may also include introducing at least one nucleotide sequence that is operable for expression in the cell and encodes, at least, the protein essential for the survival and/or proliferation of the cell.

In some embodiments, the selection is achieved without an exogenous selection pressure. An "exogenous selection pressure" is a supplement added to a normal culture media that allows for selection of the cell. Exogenous selection pressures can be molecules that inhibit or activate a protein or cellular process (e.g., a drug molecule such as methotrexate), molecules that bind to a component of the cell to allow for physical, optical, or magnetic sorting of cells having the component from cells that do not have the component (e.g., an antibody that allows enrichment by flow cytometry or magnetic bead enrichment), or molecules that can be added to a cell culture media to differentially promote the proliferation of a cell having a modification from one that does not have a modification. In some preferred embodiments, the exogenous selection pressure is a pharmacological exogenous selection pressure (e.g., methotrexate). In some embodiments, the re-introduced gene is identical in amino acid sequence to the endogenous gene that is genetically knocked-out but altered in nucleotide sequence to achieve nuclease resistance, thereby allowing to avoid the use of a mutant protein, such as a DHFR protein. In some embodiments, the introduced nucleotide sequence needs to be integrated into the genome of the cell (i.e. requirement for stable expression of the transgene). The gene encoding the essential protein can be integrated into a gene locus of interest. See FIG. 27B "Knockin altered essential gene into locus of interest."

In some embodiments, the method is for the enrichment of a genetically engineered T cell. The method comprises introducing a nuclease-mediated knock-out of the endogenous DHFR gene of the T cell, and introducing into the T cell genome a nucleotide sequence encoding a T cell receptor alpha chain, a T cell receptor beta chain and DHFR, in which the T cell receptor alpha chain, a T cell receptor beta chain and DHFR are all operably linked to be expressed simultaneously. See FIG. 2.

In some embodiments, any of the selection methods provided herein can be employed for the enrichment of genetically engineered T cells of which the antigen specificity has been redirected for cell therapy. In some embodiments, this can be used for fully personalized engineered TCR therapy for the treatment of solid cancer. To allow for this, this method can be included in larger methods that allow for the identification of neo-antigen specific TCR genes from tumor biopsies on an individual patient basis. Following their identification, such neo-antigen TCR genes can then be introduced into patient T cells via any technique, including, but not limited to, CRISPR nuclease-mediated gene knock-in, thereby redirecting the antigen specificity of the T cells towards tumor neo-antigens. Finally, the genetically engineered T cells can be administered back to the patient via intravenous infusion.

To allow for maximal therapeutic efficacy, it is useful that a large fraction of the genetically engineered T cells that are administered back to the patient express the neo-antigen specific TCR genes of interest. Since the efficiency of TCR gene knock-in generally ranges between 10-30%, a selection method is useful that can enrich successfully engineered cells prior to cell infusion. In some embodiments, such a selection method can make use of the same molecular components that are needed for the TCR knock-in, meaning that no additional experimental procedures are required for the T cell manufacturing process. This can be achieved by some of the various embodiments provided herein.

Figure 2:
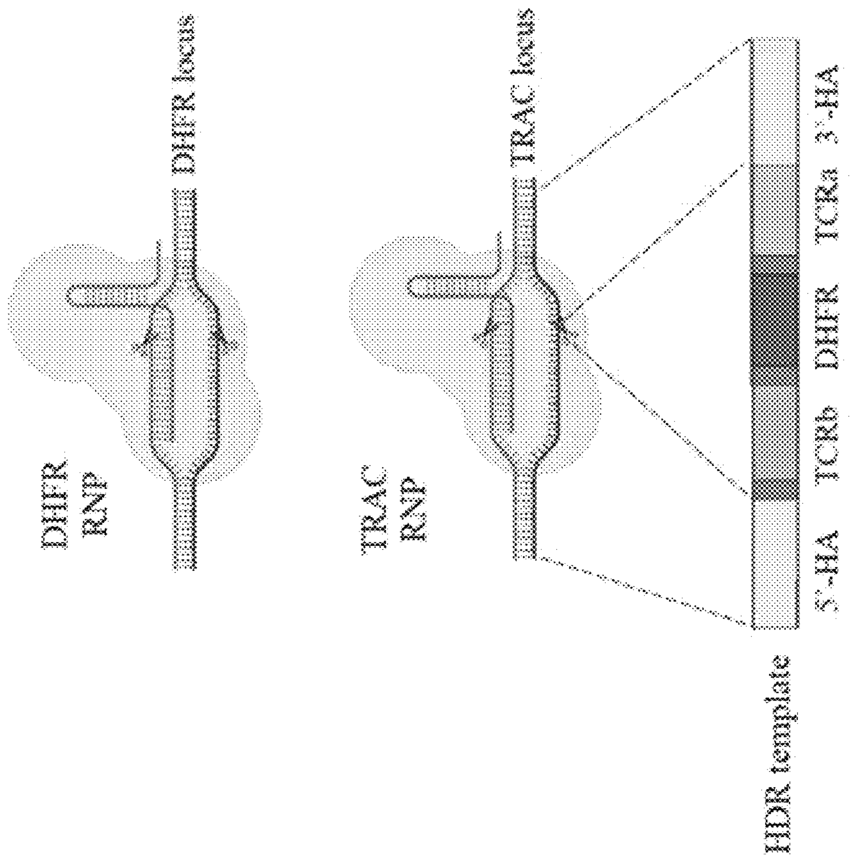
FIG. 2 shows the genetic construct of some embodiments.

In some embodiments, the strategy is also applicable to enrich cells with a genetic knockout for a particular gene, provided the endogenous gene used as the selection marker (e.g. DHFR) is introduced as a knock-in. In some embodiments, CRISPR/Cas9 Ribonucleoprotein (RNP) (or any other nuclease, including other CRISPR systems) can be used to knock-out the essential endogenous dihydrofolate reductase (DHFR) gene. See FIG. 2 upper panel. A second CRISPR/Cas9 RNP can be used to knock-in a construct containing a therapeutic TCR gene and a CRISPR/Cas9 nuclease-resistant DHFR gene into the endogenous TCR locus. See FIG. 2 lower panel. As such, cells with successful knock-in of the TCR gene construct will gain a strong survival advantage over the other DHFR knock-out cells and become enriched in time. Some embodiments provided herein can be used to enrich genetically modified cells independent of (1) the gene delivery method, (2) the nature of the transgene and (3) the target cell type. The DFHR involved pathway is shown in FIG. 1. DHFR/methotrexate (MTX) selection is used for multiple amplification to isolate high recombinant protein producing clones. DHFR is a reductase that coverts folate to tetrahydrofolate, an essential precursor in the de novo nucleotide synthesis pathway for cell proliferation. When DHFR is suppressed, the cells cannot proliferate without extra supplements (hypoxanthine and thymidine (HT)). Thus, a DHFR selection system provides a point at which one can select knockin cells. An embodiment of a genetic construct is shown in FIG. 2. In some embodiments, for this enrichment strategy, one can knockout endogenous DHFR and reintroduce it together with the therapeutic transgenes (TCRβ and TCRα). The cells with DHFR knockout will stop proliferating and/or die and only the cells that have re-introduced DHFR (together with transgenes TCRβ and TCRα) can continue to proliferate and/or survive and therefore will be enriched; the reintroduced DHFR is nuclease-resistant but has the same amino acid sequence as wild-type DHFR. For the embodiments in FIG. 2, it allows one to co-deliver 3 components during electroporation:

1. TRAC RNP to cut TRAC locus for knockin
2. DHFR RNP to knockout endogenous DHFR
3. Linear dsDNA template including 1G4-TCR and sgRNA-resistant DHFR. For the DHFR knockout cells, only cells with concomitant sgRNA-resistant DHFR knockin can proliferate in normal medium.

As noted above, DHFR is an essential enzyme that converts dihydrofolate to tetrahydrofolate during the synthesis of purine nucleotides (see, e.g., FIG. 1). As such, knock-out of DHFR inhibits DNA synthesis and repair, and preferentially impairs growth of highly proliferative cells such as T cells. Based on this, the present gene-editing enrichment strategy has been provided in which, for example, cells can be electroporated with a CRISPR/Cas9 RNP complex (or, in the alternative, any other relevant system) that knocks out/suppresses the endogenous DHFR gene. Simultaneously, the cells are electroporated with an RNP complex that targets the endogenous TCRalpha Constant (TRAC) gene together with a DNA repair template that encodes a neo-antigen TCR and a nuclease-resistant DHFR gene, which contains silent mutations to which the RNP complex cannot bind. To ensure that the nuclease-resistant DHFR gene is always co-expressed with the introduced TCR, the DNA repair template can be designed in the following order: TCRbeta-2A-nuclease-resistant DHFR-2A-TCRalpha, as such that three proteins can be expressed from a single open reading frame using self-cleaving 2A peptides.

In some embodiments, at 10 days post electroporation of the TRAC RNP and the DNA repair template, 20%±10% of T cells can display successful knock-in of the introduced TCR gene. Notably, this can increase, for example, to 73%±12% of T cells when the DHFR RNP are electroporated simultaneously. This shows that functional DHFR is useful for T cell survival and that knock-in of a nuclease-resistant DHFR gene can be used to enrich the frequency of T cells with successful TCR knock-in by, for example, ~5 fold during a culture period of 10 days.

As shown in the examples herein, the DHFR selection strategy can efficiently enrich knockin cells. However, knocking out DHFR with sgRNA can permanently alter the endogenous DHFR locus. Furthermore, it can introduce unspecific off-target editing. In some embodiments, sgRNA can be replaced with siRNA to transiently suppress endogenous DHFR expression, or with methotrexate, a clinically approved DHFR inhibitor during T cell expansion.

Several selection systems based on current technologies can be used for the enrichment of gene-modified cells. Most systems rely on the selection of modified cells based on antibody binding to the introduced transgene or an introduced marker (e.g. truncated mutants of surface molecules such as EGFR and LNGFR). Such systems are fundamentally different from the presented options because they require dedicated process steps, reagents and/or equipment to enrich for genetically modified cells.

Compared to the selection systems based on current technologies for genetically modified cells, some of the present embodiments offer significant advantages, including, one or more of the following:

1. No required introduction of an exogenous genetic sequence to allow for selection: unlike alternative systems based on surface marker (e.g., truncated EGFR), drug resistance (e.g., methotrexate) or antibiotic resistance (e.g., puromycin or blasticidin) mediated selection, no exogenous gene sequence is introduced into the cell other than the transgene. In some embodiments, selection is solely based on genetic knockout of an essential endogenous gene that is re-introduced with unaltered amino acid sequence in conjunction with a transgene.
2. No requirement for physical selection of genetically engineered cells: unlike other methods in the art, the invention does not require antibody-mediated enrichment (e.g. by flow cytometry sorting or magnetic bead enrichment). Selection is achieved by loss of expression or suppression of function of an essential gene in cells that do not express the transgene cassette while function in genetically engineered cells is restored by the transgene cassette.
3. No requirement for mutants of the cell endogenous protein: previously described selection systems based on DHFR are based on the generation and introduction of a methotrexate-resistant DHFR mutant. The modified amino acid sequence of the DHFR mutant is potentially immunogenic and may facilitate cell rejection after adoptive transfer. Furthermore, in the context of T cells, genetically engineered T cells will become resistant to methotrexate. This is undesirable because methotrexate is commonly used to treat autoimmune disease. The lack of a requirement for a mutant protein version greatly facilitates the use of the system with other essential genes than DHFR. In principle, the relevant various embodiments provided here can be applied to any gene that is essential for the survival of the gene-modified cell.
4. Reduced risk for transgene loss: due to the selective pressure to maintain transgene expression for cell survival because expression of the transgene is required to achieve expression of an essential protein or of a resistance protein, it is conceivable that loss of transgene expression, e.g. through promotor silencing, is likely reduced.
5. Compatible with complex genetic payloads: the disclosed invention enables the enrichment of cells expressing three exogenously introduced proteins (TCRalpha, TCRbeta and DHFR) from a single genetic locus. Notably, it is understood that the expression of even more proteins could be co-enriched by using additional 2A peptide sequences or IRES elements. Furthermore, the invention allows to select for genetically engineered cells modified with co-occurring genetic engineering events, e.g. expression of two two-part nucleotide sequences (each of which may encode for multiple exogenously introduced proteins.)

As noted herein, some embodiments may have fewer than all five of these described advantages (e.g., one, two, three, or four of these advantages). For example, (1) in an embodiment where the endogenous DHFR is knocked out, the knock-in DHFR may be a wild-type DHFR (2) in an embodiment where the endogenous DHFR is suppressed by methotrexate, a methotrextate-resistant DHFR or split-DHFR may be used while maintaining selection pressure with the exogenously expressed elements from the same locus. Each of these embodiments and collections of advantages are consistent with and reflected in various embodiments of the present disclosure. It will be appreciated by those of skill in the art that the present disclosure provides multiple and varied inventions and not all of the elements of one invention are required for the other inventions. Thus, not all (or necessarily any) of the inventions disclosed herein will necessarily have one or more of the above embodiments. One of skill in the art will be able to determine which inventions will have the above advantages given the present disclosure, and their knowledge, and/or the specific elements provided for the invention itself.

In some embodiments, knock-down of endogenous DHFR using siRNA, shRNA, miRNA, or CRISPR interference (CRISPRi) technology in combination with expressing a TCR gene construct containing an siRNA, shRNA, miRNA, or CRISPRi-resistant DHFR gene variant may be used instead of permanent genetic knock-out of the endogenous genomic loci.

In some embodiments, inhibition of endogenous DHFR using Methotrexate (MTX) in combination with expressing of transgene cassette containing an MTX-resistant DHFR gene and that is integrated in-frame into an exon of a gene locus to enable expression from the endogenous promotor, the endogenous splice sites, and the endogenous termination signal can be employed.

In some embodiments, inhibition of endogenous DHFR using Methotrexate (MTX) in combination with expressing a TCR gene construct containing an MTX-resistant DHFR gene variant can be employed.

In some embodiments, the selection principle is applicable to other genes than DHFR, provided that the gene is essential for the survival and/or proliferation of the cell.

In some embodiments, endogenous DHFR is knocked out or knocked down by a nuclease; the selection principle is applicable to any other therapeutic gene as provided that the therapeutic gene is coupled to re-introducing a nuclease-resistant DHFR variant.

In some embodiments, the selection principle is applicable in other cell types as well, e.g. hematopoietic stem cells, mesenchymal stem cells, iPSCs, neural precursor cells, fibroblasts, B cells, NK cells, monocytes, macrophages, dendritic cells, and cell types in retinal gene therapy etc.

In some embodiments, the transgene can be delivered in other ways than nuclease-mediated site-specific integration by HDR, namely transposon-mediated gene delivery, micro-injection, liposome/nanoparticle-mediate gene transfer, virus-mediated gene delivery, electroporation, or methods based on mechanical or chemical membrane permeabilization.

In some embodiments, the protein restoring a suppressed function or providing resistance for a selective pressure may be i) split into two or more portions which can be operably combined within the cell and ii) each portion linked to a transgene cassette in order to allow selection for cells that have successfully been engineered simultaneously with all transgene cassettes. In some embodiments, the protein restoring a suppressed function may be fused to dimerization domains. In some embodiments, the dimerization domains may be derived from GCN4, Fos, Jun, or FKBP12 proteins. In some embodiments, dimerization may be achieved using leucine-zipper motifs. In some embodiments, dimerization may be achieved by using Split intein proteins. In some embodiments, the dimerization domain can be modified (e.g., have alterations to the amino acid sequences) that reduce or prevent dimerization with an endogenous protein, that promote dimerization and/or binding with an exogenous protein. In some embodiments, the dimerization domain can be modified (e.g., have alterations to the amino acid sequences) to add, remove, and/or modify a feature of the dimerization domain (e.g., inducible dimerization).

In some embodiments, different designs of the transgene cassette can be employed, for example, six different orientations:

Exogenous Protein 1-2A-Exogenous protein 2-2A-Selection advantage protein
Exogenous Protein 1-2A-Selection advantage protein-2A-Exogenous protein 2
Exogenous protein 2-2A-Exogenous Protein 1-2A-Selection advantage protein
Exogenous protein 2-2A-Selection advantage protein-2A-Exogenous Protein 1
Selection advantage protein-2A-Exogenous Protein 1-2A-Exogenous protein 2
Selection advantage protein-2A-Exogenous protein 2-2A-Exogenous Protein 1
(Based on any 2A element)

In some embodiments, different designs of the transgene cassette can be employed, for example 6 different orientations of TCRa, TCRb and DHFR:

TCRa-2A-TCRb-2A-DHFR
TCRa-2A-DHFR-2A-TCRb
TCRb-2A-TCRa-2A-DHFR
TCRb-2A-DHFR-2A-TCRa
DHFR-2A-TCRa-2A-TCRb
DHFR-2A-TCRb-2A-TCRa
(Based on any 2A element)

In some embodiments, the two-part nucleotide sequence is integrated in-frame into an exon of a gene locus to enable expression from the endogenous promotor, the endogenous splice sites, and the endogenous termination signal.

In some embodiments, the two-part nucleotide sequence is integrated together with its own exogenous promotor that enables expression of the first protein, the second protein or both.

In some embodiments, the TCRa- and TCRb-chains will be driven by endogenous TCR promoter while a DHFR protein will be driven from an exogenously induced promotor and the transgene cassette has one of the following designs:

TCRa-2A-TCRb-pA-promoter-DHFR-pA
TCRb-2A-TCRa-pA-promoter-DHFR-pA
TCRa-2A-TCRb-pA-promoter-DHFR-2A (use endogenous TRAC pA)
TCRb-2A-TCRa-pA-promoter-DHFR-2A (use endogenous TRAC pA)

Elements of the at least two-part nucleotide sequences can be expressed from the same or different promoters. In some embodiments, the elements are expressed from the same promoter and are linked by either genetic linkers (such that each element is separately expressed as a protein) or by protein linkers (such that the linked elements are expressed as a single protein, which may or may not be cleaved after translation). An example of a genetic linker is an IRES element. Examples of protein linkers include 2A or gly-ser linkers. Proteins can also be expressed as a fusion protein without any linker between elements.

In some embodiments, any of the methods provided herein can include the use for the enrichment of genetically modified T cells. In those T cells, an essential protein is suppressed so that the cells cannot survive or proliferate unless a genetically engineered nucleotide encoding the same essential protein or a variant thereof is re-introduced into those cells. The T cells with successful re-introduction of the essential protein will gain a strong survival advantage over the other knock-out cells and become enriched in time. This includes (1) the introduction of any transgene, including T cell receptors and Chimeric Antigen Receptors as well as exogenous genes to modify the phenotype and/or function of the T cell (e.g. dominant negative TGFbeta receptors, switch receptors, etc.) and/or (2) the use of any T cell subset (naïve T cells, memory T cells, tumor-infiltrating lymphocytes (TIL), etc.).

In some embodiments, the method is generically applicable to deliver a wide range of transgenes into different cell types. It is applicable to enrich a wide range of genetic-modifications (gene knockout, knock-in, etc.) provided the endogenous gene used as a selection marker is re-introduced into the cells.

In some embodiments, the methods provided herein provide one or more of the following:

a solution for the enrichment of CRISPR nuclease gene-edited T cells expressing therapeutic TCR or CAR genes,
a solution for the enrichment of genetically engineered T cells,
a method that allows selection without use of an antibody,
a method that allows to deliver complex and multiple transgenes.

In some embodiments, any of the methods provided herein can be applied for the enrichment of genetically engineered cells in all therapeutic areas besides oncology, such as Barth syndrome, β-Thalassemia, Cystic fibrosis, Duchenne muscular dystrophy, hemophilia, Sickle cell disease, autoimmunity and infectious disease.

In some embodiments, the present method does not require one to use a vector to express nuclease and sgRNAs. In some embodiments, a ribonucleoprotein complex (nuclease protein+guide RNA) instead of a DNA vector can be used.

In some embodiments, this approach may only lead to a temporary expression of nuclease and sgRNAs. This can allow for one to avoid permanent integration in the genome, which allows one to avoid 1) random integration, which can lead to gene disruption and 2) continuous expression of nuclease, which can be immunogenic or toxic to the cells.

In some embodiments, the two-part nucleotide sequence is expressed in the cell by genomic integration mediated by plasmid-, transposon- or virus-mediated random genomic integration. In some embodiments, the two-part nucleotide sequence is expressed by targeted site-specific integration into the genome of the cell. In some embodiments, targeted site-specific integration is achieved by homology-directed repair of DNA breaks. This can be desirable as the plasmid or virus can randomly integrate into the genome of the target cell. In some embodiments, the two-part nucleotide sequence is linear double-stranded DNA, single-stranded DNA, nano-plasmid, adeno-associated virus (AAV) or any other viral, circular, linear template suitable for Homology-directed repair. Linear double-stranded DNA may be either open-ended or closed-ended.

In some embodiments, the methods do not use a separate promoter to drive transgene and cargo expression as the present repair template will be integrated into the specific site of the genome and therefore, an endogenous promoter will drive their expressions.

In some embodiments, the present methods do not necessarily require a nuclease or a base editor. Instead, a siRNA, shRNA, miRNA, or CRISPRi will work.

In some embodiments, the present methods use a two-vector system which avoids permanent integration of the nuclease. This can be useful as continuous expression of the nuclease may be toxic.

In some embodiments, two promotors need not be used, and one can couple expression of transgene and rescue gene. In some embodiments, this can be beneficial because it makes transgene loss less likely.

In some embodiments, the various embodiments herein can overcome one or more of the following: addressing T cell donors where gene knockin efficiency is low (e.g., less than 20%), allows for selecting knockin cells. An approach more amenable to cGMP-manufacturing requirements. Avoiding adding antibiotic selection markers to the cells or exposing the cells to additional antibody selection methods.

Some embodiments described herein relate to a method for enrichment of a genetically engineered cell. The method can include: i) decreasing activity of at least a first protein that is essential for the survival and/or proliferation of a cell to the level that the cell cannot survive and/or proliferate under normal in vitro propagation conditions. The method can further include ii) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and iii) culturing the cell under normal in vitro propagation conditions for enrichment of the cell that expresses both the first protein and second protein. In some embodiments, step iii) can be culturing the cell in vitro propagation conditions leading to enrichment of the cell that expresses both the first protein and second protein.

In these embodiments, the first protein is essential for the survival and/or proliferation of a cell. The essential or first protein can be dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC). The activity of the essential protein can be suppressed at nucleotide or protein levels. If the activity of the essential protein is suppressed, the cell can no longer survive or proliferate under normal in vitro propagation conditions unless a substance is added to the culture medium or a genetically engineered nucleotide encoding the same essential protein is re-introduced into those cells. For example, when DHFR is suppressed, the cells cannot proliferate without extra supplements (hypoxanthine and thymidine (HT)) or re-introduced into those cells a functional DHFR.

Figure 27B:
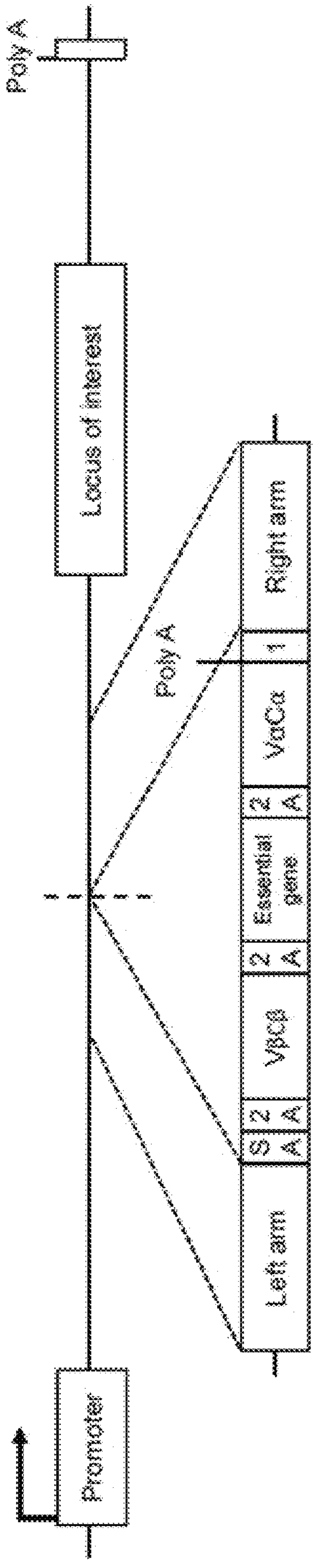
FIG. 27B shows a diagram of knocking in a two-part nucleotide sequence that encodes an altered essential protein and a second protein.

The first part of the two-part nucleotide sequence encodes an essential protein, which not only has an altered nucleotide or protein sequence so that it can be resistant to the matter that was used to suppress the activity of the endogenous essential protein, but also has the ability to restore the cells' ability to survive or proliferate under the selected in vitro propagation conditions. The second part of the two-part nucleotide sequence encodes a second protein, which is exogenous to the cell and can have therapeutic functions. For example, the second protein can be a TCR complex containing a TCR alpha chain and a TCR beta chain. FIG. 27B shows an example of the two-part nucleotide sequence.

The cells with successful re-introduction of the two-part nucleotide sequence will express the essential protein and restore the cells' ability to survive or proliferate under the selected in vitro propagation conditions, thus gain a strong survival advantage over the other cells and become enriched in time. In some embodiments, the first part and the second part of the nucleotides are configured to be expressed from a single open reading frame so that they are co-expressed in the cells. Therefore, the enriched cells can be used for downstream applications, such as T cell therapy.

Some embodiments described herein relate to a method for selection of a genetically engineered cell when the cell has an essential protein for the survival and/or proliferation that is being suppressed. The method can include i) introducing at least one two-part nucleotide sequence that is operable for expression in a cell, wherein the cell has an essential protein for the survival and/or proliferation that is suppressed to a level that the cell cannot survive and/or proliferate under selected culture conditions, and wherein the at least one two-part nucleotide sequence comprises a first-part nucleotide sequence encoding the essential protein for the survival and/or proliferation and a second-part nucleotide sequence encoding a protein to be expressed, and the second-part nucleotide sequence is encoding a protein that is exogenous to the cell; The method can further include ii) culturing the cell under cell culture conditions leading to the selection of the cell that expresses both the first-part and second-part nucleotide sequences.

In these embodiments, the cells with successful re-introduction of the two-part nucleotide sequence will gain a strong survival advantage over the other cells and become enriched in time. In some embodiments, the selection of engineered cells is possible in normal cell culture medium. In some embodiments, the normal cell culture medium is one that is suitable for non-modified cell's growth and/or proliferation. For example, a normal culture medium for T cells is RPMI 1640 from Thermo Fisher Scientific.

In some embodiments, the normal cell culture medium is without an exogenous selection pressure, such as a drug molecule, an antibody, or any specific supplements that allows enrichment of the cells by flow cytometry or magnetic bead enrichment. In some embodiments, the selection of engineered cells is possible based on addition of components to the cell culture medium that lead to an exogenous selective pressure. In some embodiments, the exogenous selective pressure leads to suppression of a protein essential for the survival and/or proliferation of a cell. In some embodiments, the exogenous selective pressure is based on addition of methotrexate to the cell culture medium.

In some embodiments, the decreasing activity can be permanently or transiently. In some embodiments, the decreasing activity or suppression is accomplished by a permanent or transient reduction in the amount or level of the essential protein in the cell. In some embodiments, the level of protein remains the same, but the functionality of the protein is decreased or suppressed. In some embodiments, the decreasing activity or suppression is accomplished by a permanent or transient reduction in the functional activity of the cell with or without reducing the level of the protein in the cell. In some embodiments, the decreasing activity or suppression is accomplished by a permanent or transient reduction in the functional activity of the cell without separately altering the level of the protein in the cell. In permanent embodiments, the gene encoding the essential protein can be knocked out, which permanently removes the essential gene from the cell's genome. In some embodiments, the knock-out is mediated by CRISPR/Cas9 Ribonucleoprotein (RNP), TALEN, MegaTAL, or any other nucleases.

In transient embodiments, the activity of the essential protein can be suppressed transiently. In some embodiments, the transient suppression is through siRNA, miRNA, or CRISPR interference (CRISPRi), where the activity of the essential protein is suppressed at RNA level. In some embodiments, the transient suppression is through a protein inhibitor, which suppress the activity of the essential protein at protein level. The activity of the essential protein will restore once the siRNA, miRNA, CRISPR interference (CRISPRi), or protein inhibitor are removed from the cell growth/culture environment.

In some embodiments, the essential protein is DHFR and the transient suppression is by methotrexate. Methotrexate is a protein inhibitor that competitively inhibits DHFR, an enzyme that participates in the synthesis of tetrahydrofolate, which is thought to be required in the synthesis of DNA, RNA, thymidylates, and proteins. Thus, cells with DHFR suppressed will not be able to survive or proliferate.

In some embodiments, the cell is a T cell, NK cell, NKT cell, iNKT cell, hematopoietic stem cell, mesenchymal stem cell, iPSC, neural precursor cell, a cell type in retinal gene therapy, or any other cell.

In some embodiments, the first-part nucleotide sequence is altered in nucleotide sequence to achieve nuclease, siRNA, miRNA, or CRISPRi resistance, but encodes a protein having an identical amino acid sequence to the first protein. For example, SEQ ID NO: 1 (FIG. 34) is a first-part nucleotide sequence that has altered nucleotide sequence than endogenous DHFR gene. SEQ ID NO: 1 is created by point mutating certain nucleotides in the endogenous DHFR gene. The altered nucleotide sequence renders SEQ ID NO: 1 nuclease resistant. However, the DHFR protein encoded by SEQ ID NO: 1 has an identical amino acid sequence to the endogenous DHFR protein, thus has an identical function.

In some embodiments, the first-part nucleotide sequence is altered in nucleotide sequence to encode an altered protein that does not have an identical amino acid sequence to the first protein. The altered protein can have an adjusted functionality to the first protein. In some embodiments, the altered protein has specific features that the first protein does not have. In some embodiments, the specific features include, but are not limited to, one or more of the following: reduced activity, increased activity, altered half-life, resistance to small molecule inhibition, and increased activity after small molecule binding. For example, SEQ ID NO: 2 (FIG. 35) is created by point mutating certain nucleotides in the endogenous DHFR gene and SEQ ID NO: 2 encodes an altered DHFR protein with an amino acid sequence different than that of the endogenous DHFR. The altered DHFR protein has similar activity to the endogenous DHFR but is resistant to MTX, a protein inhibitor.

In some embodiments, the at least one nucleotide sequence is operable for expressing both the first-part and second-part nucleotide sequences. A nucleotide sequence is operable for expression when it has all the elements for gene transcription. The elements include, but are not limited to, a promoter, an enhancer, a TATA box, and a poly(A) termination signal. In some embodiments, one or more of these is optional. In some embodiments, both the first-part and second-part nucleotide sequences can be driven by a same promoter or different promoters.

In some embodiments, the two part nucleotide sequence is capable of expressing both the first-part and second-part nucleotide sequences in the cell. A nucleotide sequence is capable of expression if (i) it is operable for expression in a cell or (ii) will become operable for expression in the cell when inserted at a pre-determined site in the target genome because it will have or be operably linked with all the elements for gene transcription. The elements include, but are not limited to, a promoter, an enhancer, a TATA box, and a poly(A) termination signal. Not all elements may be necessary in all circumstances for expression. In some embodiments, both the first-part and second-part nucleotide sequences can be driven by a same promoter and/or upstream sequences (e.g., an enhancer) or different promoters and/or upstream sequences (e.g., an enhancer).

In some embodiments, the second-part nucleotide sequence comprises at least a therapeutic gene. A therapeutic gene is a gene that is used as a drug to treat a disease. For example, genes encoding T cell receptors that target specific cancer antigens can be used as a therapeutic gene. In some embodiments, the second-part nucleotide sequence encodes a neo-antigen T-cell receptor complex (TCR) containing a TCR alpha chain and a TCR beta chain.

In some embodiments, the first-part nucleotide sequence comprises a nuclease-resistant, siRNA-resistant, or protein inhibitor-resistant DHFR gene, and the second-part nucleotide sequence comprises a TRA gene and a TRB gene. For example, SEQ ID NO: 3 (FIG. 36) is a DNA sequence that encodes a wildtype human DHFR; SEQ ID NO: 4 (FIG. 37) is a codon-optimized and nuclease-resistant DNA sequence that encodes a wildtype human DHFR; SEQ ID NO: 5 (FIG.

38) is a codon-optimized DNA sequence that encodes a MTX-resistant human DHFR mutant. In some embodiments, the protein inhibitor-resistant DHFR gene is a methotrexate-resistant DHFR gene.

In some embodiments, the TRA, TRB, and DHFR genes are operably configured to be expressed from a single open reading frame. One advantage of this arrangement is that if the cells express DHFR and survive in the normal cell culture medium, the cells also express TRA and TRB genes and can be used for downstream applications, such as TCR therapy.

In some embodiments, the TRA, TRB, and DHFR genes are separated by linkers. These linkers allow multiple genes under a single open reading frame to be expressed. In some embodiments, the order of the linkers, TRA, TRB, and DHFR genes is in the following order:

TRA-linker-TRB-linker-DHFR,
TRA-linker-DHFR-linker-TRB,
TRB-linker-TRA-linker-DHFR,
TRB-linker-DHFR-linker-TRA,
DHFR-linker-TRA-linker-TRB, or
DHFR-linker-TRB-linker-TRA.

In some embodiments, the linkers are self-cleaving 2A peptides or IRES elements. Both self-cleaving 2A peptides and IRES elements allow multiple genes under a single open reading frame to be expressed.

In some embodiments, the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1.

In some embodiments, the two-part nucleotide sequence is integrated into the genome of the cell. In some embodiments, the integration is through nuclease-mediated site-specific integration, transposon-mediated gene delivery, or virus-mediate gene delivery. In some embodiments, the nuclease-mediated site-specific integration is through CRISPR/Cas9 RNP. Some embodiments further include using the split intein system, where the essential protein or first protein can be split into a dysfunctional N-terminal and C-terminal protein half, each fused to a homo- or heterodimerizing protein partner or to a split intein. Functional reconstitution of the essential protein or the first protein is then only possible when both protein halves are co-expressed in the same cell. In some embodiments, the essential or first protein is a DHFR protein. (Pelletier J N, Campbell-Valois F X, Michnick S W. Oligomerization domain-directed reassembly of active dihydrofolate reductase from rationally designed fragments. Proc. Natl. Acad. Sci. USA. 1998 Oct. 13; 95(21):12141-6; and Remy I, Michnick S W. Clonal selection and in vivo quantitation of protein interactions with protein-fragment complementation assays. Proc. Natl. Acad. Sci. USA. 1999 May 11; 96(10):5394-9, both of which are hereby expressly incorporated by reference in their entireties for any purpose.)

In some embodiments, the introduced two-part nucleotide sequence is not integrated into the genome of the cell.

In some embodiments, a CRISPR/Cas9 RNP that targets the endogenous TCR Constant locus, the first-part nucleotide sequence encoding a nuclease-resistant DHFR gene, and the second-part nucleotide sequence encoding a neo-antigen TCR are delivered to the cell. In some embodiments, the endogenous TCR constant locus can be a TCR alpha Constant (TRAC) locus or a TCR beta Constant (TRBC) locus. In some embodiments, the delivery is by electroporation, or methods based on mechanical or chemical membrane permeabilization.

In some embodiments, a first CRISPR/Cas9 RNP is used to knock-out endogenous dihydrofolate reductase (DHFR) gene, and a second CRISPR/Cas9 RNP is used to knock-in into an endogenous TCR constant locus the first-part nucleotide sequence comprising the CRISPR/Cas9 nuclease-resistant DHFR gene and the second-part nucleotide sequence encoding a therapeutic TCR gene. In these embodiments, the endogenous dihydrofolate reductase (DHFR) is no longer being expressed, the introduced nuclease-resistant DHFR gene has alteration in the nucleotide sequence but not in the corresponding protein sequence. In some embodiments, the second CRISPR/Cas9 RNP is a TRAC RNP that cuts the TRAC locus for knock-in.

In some embodiments, methotrexate is used to inhibit the first protein, and a CRISPR/Cas9 RNP is used to knock-in into an endogenous TCR constant locus the first-part nucleotide sequence encoding a methotrexate-resistant DHFR protein and the second-part nucleotide sequence comprising a therapeutic TCR gene. In these embodiments, the endogenous first protein is still being expressed, but its activity has been inhibited by methotrexate; and the introduced nucleotide sequence encodes a DHFR protein that is methotrexate-resistant.

Some embodiments described herein relate to a cell that is made according to any of the methods disclosed herein.

In some embodiments, a cell includes i) endogenous dihydrofolate reductase (DHFR) being suppressed to a level that the cell cannot survive and/or proliferate in a normal cell culture medium, and ii) at least a two-part nucleotide sequence comprising a first-part nucleotide sequence encoding DHFR and a second-part nucleotide sequence encoding a neo-antigen T-cell receptor complex.

Some embodiments described herein relate to a method for enrichment of a genetically engineered cell. The method can include i) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and ii) culturing the cell in cell culture medium containing at least one supplement leading to enrichment of the cell that expresses both the first protein and the second protein.

In some embodiments, the genetically engineered cell is a primary human T cell. In some embodiments, the supplement impairs survival and/or proliferation of cells without expressing both the first protein and the second protein. In some embodiments, at least one protein mediates resistance of the cell to the supplement mediated impairment of survival and/or proliferation of cells. In some embodiments, the supplement is methotrexate. In some embodiments, the first protein is a methotrexate-resistant DHFR mutant protein.

In some embodiments, the second protein is a T cell receptor. In some embodiments, the T cell receptor is specific for a viral or a tumor antigen. In some embodiments, the first-part nucleotide sequence is altered in nucleotide sequence to achieve nuclease, siRNA, miRNA, or CRISPRi resistance.

In some embodiments, expression of the at least a two-part nucleotide sequence is achieved by site-specific integration into an endogenous gene locus of the cell. In some embodiments, site-specific integration into an endogenous gene locus of the cell is achieved by using CRISPR/Cas9, TALEN, MegaTAL or any other nuclease that allows for traceless integration into a gene locus to enable expression from the endogenous promotor of the gene locus.

Figure 24:
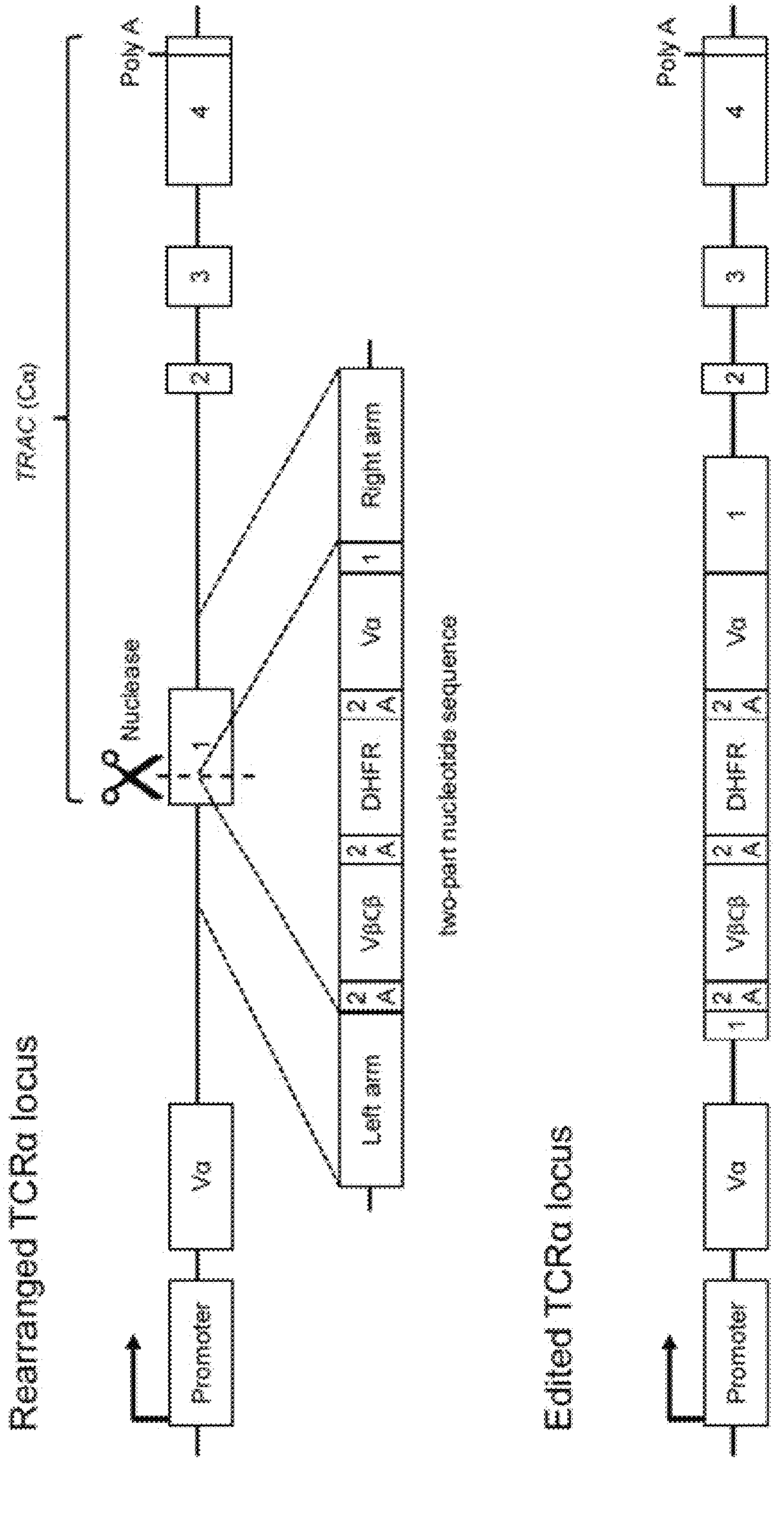
FIG. 24 is a diagram of in-frame exonic integration into a gene locus to enable expression from the endogenous promotor, the endogenous splice sites, and the endogenous termination signal.

In some embodiments, the nuclease allows for in-frame exonic integration of the two-part nucleotide sequence into a gene locus to enable expression from the endogenous promotor, the endogenous splice sites, and the endogenous transcription termination signal. In this configuration, the elements controlling the expression of the two-part nucleotide sequence are all endogenous elements. Exonic integration refers to the situation where the two-part nucleotide sequence is integrated into an exon of the gene locus. The diagram of some of these embodiments can be found in FIG. 24.

Figure 25:
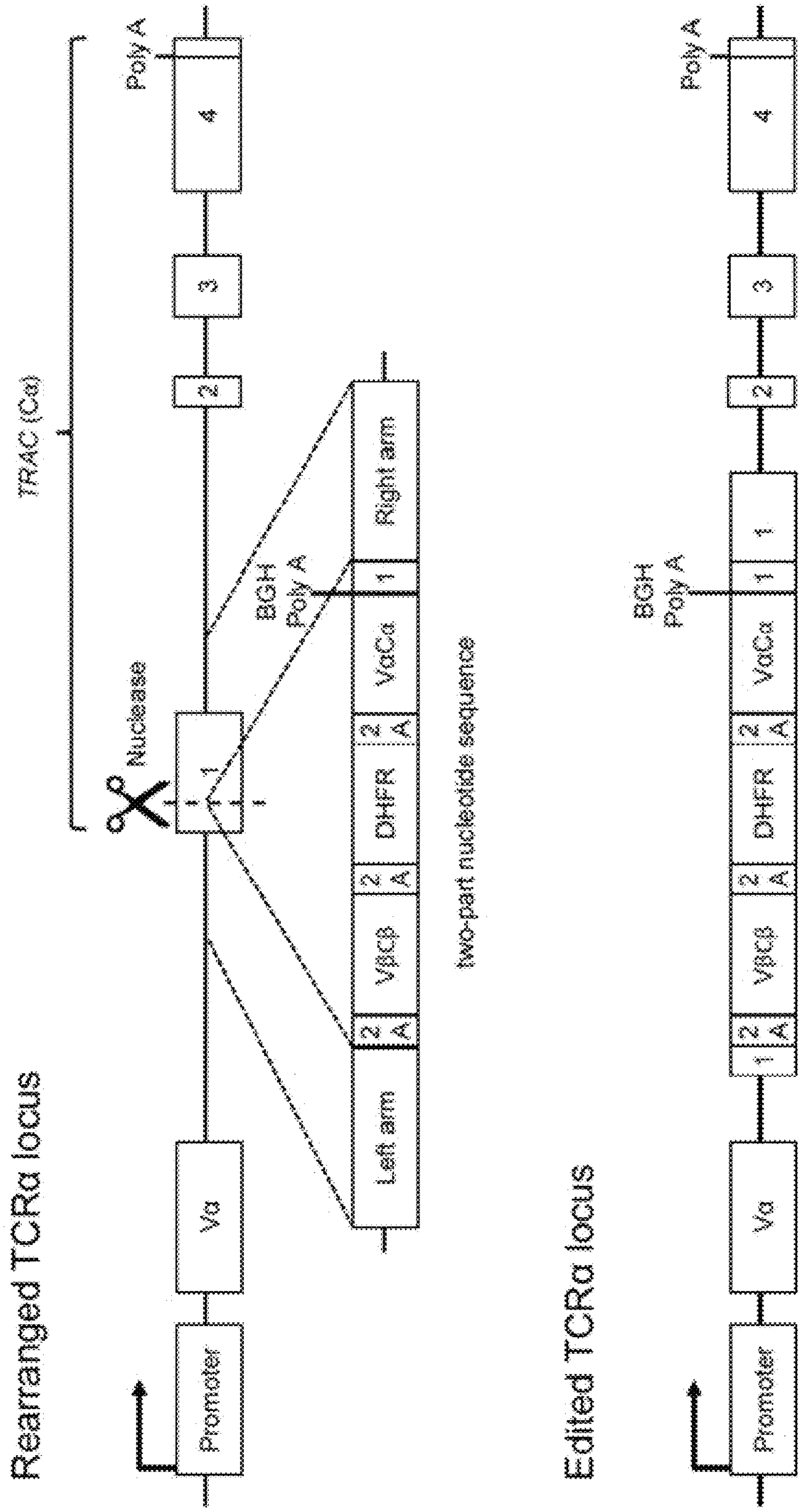
FIG. 25 is a diagram of in-frame exonic integration into a gene locus to enable expression from the endogenous promotor, the endogenous splice sites, and an exogenous termination signal.

In some embodiments, the nuclease allows for in-frame exonic integration of the two-part nucleotide sequence into a gene locus to enable expression from the endogenous promotor, the endogenous splice sites, and an exogenous transcription termination signal. In this configuration, the elements controlling the expression of the two-part nucleotide sequence are a mixture of endogenous and exogenous elements. The diagram of some of these embodiments can be found in FIG. 25.

Figure 26:
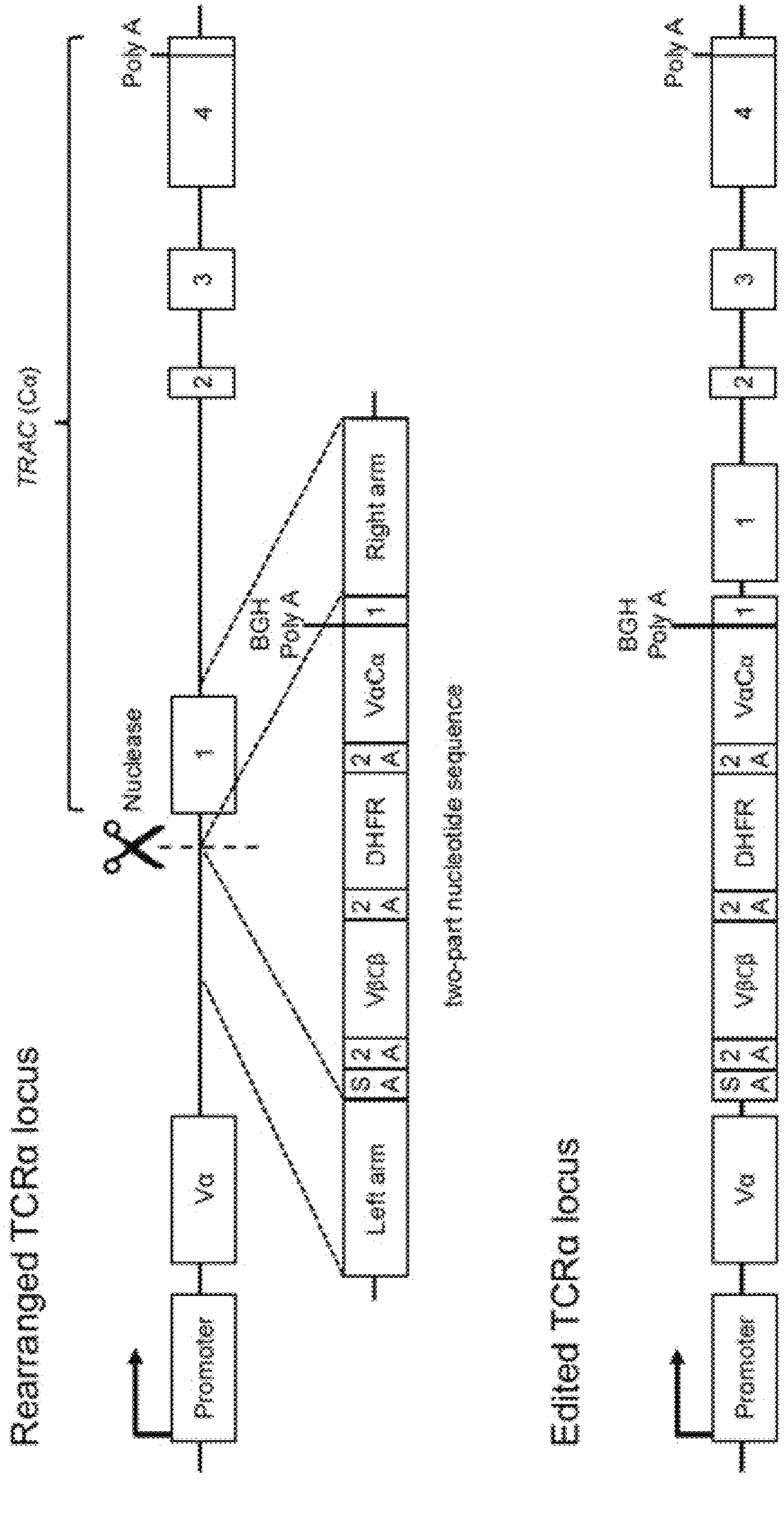
FIG. 26 is a diagram of intronic integration into a gene locus to enable expression from the endogenous promotor, an exogenous splice acceptor site, and an exogenous termination signal.

In some embodiments, the nuclease allows for intronic integration of the two-part nucleotide sequence into a gene locus to enable expression from the endogenous promotor, an exogenous splice acceptor site, and an exogenous transcription termination signal. In this configuration, the elements controlling the expression of the two-part nucleotide sequence are a mixture of endogenous and exogenous elements. Intronic integration refers to the situation where the two-part nucleotide sequence is integrated into an intron of the gene locus. The diagram of these embodiments can be found in FIG. 26.

In some embodiments, a CRISPR/Cas9 RNP is used to knock-in into an endogenous TCR constant locus the first-part nucleotide sequence encoding a methotrexate-resistant DHFR mutant protein and the second-part nucleotide sequence comprising a therapeutic TCR gene.

Some embodiments further include a second CRISPR/Cas9 RNP that is used to knock-out the endogenous TRAC or TRBC gene.

Some embodiments described herein relate to a method for enrichment of a genetically engineered T cell. The method includes i) introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and ii) culturing the cell in cell culture medium containing methotrexate (25 nM to 100 nM) leading to enrichment of the cell that expresses both the first protein and the second protein.

Some embodiments described herein relate to a method for enrichment of a T cell engineered to express an exogenous T cell receptor gene. The method includes i) knocking-out an endogenous TRBC gene from its locus using a first CRISPR/Cas9 RNP; ii) knocking-in, using a second CRISPR/Cas9 RNP, into the endogenous TRAC locus a first-part nucleotide sequence encoding a methotrexate-resistant DHFR gene and the second-part nucleotide sequence comprising a therapeutic TCR gene, wherein both nucleotide sequences are operably linked allowing for expression from the endogenous TRAC promotor; and iii) culturing the cells in cell culture medium containing methotrexate leading to enrichment of T cells that express both the therapeutic TCR and the methotrexate-resistant DHFR gene.

Some embodiments described herein relate to a T cell, which include i) an endogenous dihydrofolate reductase (DHFR) being suppressed by the presence of methotrexate to a level that the cell cannot survive and/or proliferate, and ii) at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

In some embodiments, a method for selection of a genetically engineered cell comprises i) introducing at least two two-part nucleotide sequences that are operable for expression in a cell. The cell has an essential protein for the survival and/or proliferation that is suppressed to a level that the cell cannot survive and/or proliferate. The first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed. The second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed. Both the first and second fusion proteins can be expressed together in a cell, and the function of the essential protein for the survival and/or proliferation is restored by that co-expression. The method further comprises ii) culturing the cell under conditions leading to the selection of the cell that expresses both the first and second two-part nucleotide sequences. In some embodiments, one or more of the above processes can be repeated and/or omitted and/or modified with any of the other embodiments provided herein.

In some embodiments, a method for enrichment of a genetically engineered cell comprises: i) decreasing activity of at least a first protein that is essential for the survival and/or proliferation of a cell to the level that the cell cannot survive and/or proliferate under normal in vitro propagation conditions; and ii) introducing at least two two-part nucleotide sequences that are operable for expression in a cell. The first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed. The second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed. Both the first and second fusion proteins can be expressed together in a cell, and the function of the essential protein for the survival and/or proliferation is restored by that co-expression. The method can further comprise iii) culturing the cell under in vitro propagation conditions that lead to the enrichment of the cell that expresses both the first fusion protein and second fusion protein. In some embodiments, one or more of the above processes can be repeated and/or omitted and/or modified with any of the other embodiments provided herein.

Some embodiments described herein relate to a method for the selection of a genetically engineered cell. The term "cell" as used herein can refer to any single cell, multiple cells, or cell line from any organism. In some embodiments, the cell is eukaryotic. In some embodiments, the cell is mammalian. In some embodiments, the cell is a primary cell or from a primary tissue. In some embodiments, the cell is derived from an established cell line. In some embodiments, the cell is mouse, rat, non-human primate, or human. It will be understood that the cell may be from any cell, tissue, organ, or organ system type. Non-limiting examples of a cell include a T cell, CD4+ T cell, CD8+ T cell, CAR T Cell, B cell, immune cell, nerve cell, muscle cell, epithelial cell, connective tissue cell, stem cell, bone cell, blood cell, endothelial cell, fat cell, sex cell, kidney cell, lung cell, brain cell, heart cell, root hair cell, pancreatic cell, and cancer cell.

In some embodiments, the method comprises introducing at least one nucleotide sequence that is operable for expression in a cell. In some embodiments, the method comprises introducing at least two, at least three, at least four, at least five, at least ten sequences, or at least twenty nucleotide sequences.

In some embodiments, the at least one nucleotide sequence comprises a single part. In some embodiments, the at least one nucleotide sequence comprises at least two parts. In some embodiments, the nucleotide sequences comprises at least three parts. In some embodiments, the nucleotide sequences comprises at least four parts. In some embodiments, the nucleotide sequences comprises at least five parts. In some embodiments, the nucleotide sequences comprises ten parts. In some embodiments, the nucleotide sequences comprises twenty parts.

In some embodiments, an at least one protein and/or cellular process essential for survival and/or proliferation of the cell is otherwise suppressed in the cell to a level that the cell cannot survive and/or proliferate independently. It will be understood by those skilled in the art that an "essential" protein or cellular system may be any protein or cellular system that influences growth, replication, cell cycle, gene regulation (including DNA repair, transcription, translation, and replication), stress response, metabolism, apoptosis, nutrient acquisition, protein turnover, cell surface integrity, essential enzyme activity, survival, or any combination thereof in a given cell. It will also be understood that the term "suppression" may apply to any phenotype from a significant increase in one or more occurrence of cell death, metabolic arrest, cell cycle arrest, stress induction, protein turnover arrest, DNA stress, and/or growth arrest compared to a control, to complete cell death, metabolic arrest, cell cycle arrest, stress induction, protein turnover arrest, DNA stress, and/or growth arrest compared to a control. In some embodiments, suppression can be partial or complete (e.g., a protein may be reduced in level or have its functional activity reduced by at least about some detectable amount, including, but not limited to 50%, 75%, 85%, 90%, 95%, 96%, 97%, 98%, 99%, or 100%). In some embodiments, suppression is accomplished by reducing the level or amount of a protein in the cell (e.g., knock-out, gene silencing, siRNA, CRISPRi, miRNA, shRNA). In some embodiments, suppression is accomplished by reducing the functional activity of a protein (e.g., small molecule inhibitors of protein function, antibodies that block binding, mutations that reduce the function of a protein) with or without altering the level of protein in the cell.

In some embodiments, the nucleotide sequence comprises an at least one sequence encoding a fusion protein comprising a non-functional portion of the essential protein for the survival and/or proliferation fused to a binding domain. In some embodiments, the first part of a nucleotide sequence comprises an at least one sequence encoding a fusion protein comprising a non-functional portion of the essential protein for the survival and/or proliferation fused to a binding domain. In some embodiments, the second-part of the nucleotide sequence comprises an at least one sequence encoding an at least one protein to be expressed.

In some embodiments, the nucleotide sequence comprises an at least one sequence encoding a second fusion protein comprising a second non-functional portion of the essential protein for the survival and/or proliferation fused to a second binding domain and a second nucleotide sequence encoding the at least one protein to be expressed. In some embodiments, the second part of the nucleotide sequence comprises an at least one sequence encoding a second fusion protein comprising a second non-functional portion of the essential protein for the survival and/or proliferation fused to a second binding domain and a second nucleotide sequence encoding the at least one protein to be expressed. In some embodiments, the fusion proteins, when expressed together in a cell, result in the successful expression of an at least one essential protein. This returns the functionality of the essential protein to the cell, allowing the cell to survive. While many of the examples disclosed herein relate to two fusion proteins combining, it will be understood to those skilled in the art that the same method disclosed herein can be used under a multitude of various fusion proteins that can successfully combine into an at least one essential protein.

As disclosed herein, in some embodiments, when the first and second fusion proteins are expressed together in a cell, the function of the at least one essential protein for the survival and/or proliferation is restored. In some embodiments, when the first and second fusion proteins are expressed together in a cell, the function of the at least one essential cellular process for the survival and/or proliferation is restored. In some embodiments, the at least one essential protein or cellular process is the same essential protein or cellular process as the suppressed protein or cellular process. In some embodiments, the at least one essential protein comprises similar activity as the suppressed protein. In some embodiments, the at least one essential protein functions in the at least one suppressed cellular pathway or process. In some embodiments, the at least one essential protein functions in at least two essential cellular pathways or processes. In some embodiments, the expression of the at least one essential protein alleviates, activates, restores, or diminishes the suppression phenotype of the suppressed protein and/or cellular process. In some embodiments, the survival and/or proliferation of the cell is increased upon expression of the at least one essential protein. In some embodiments, the survival and/or proliferation of the cell is fully restored upon expression of the at least one essential protein.

In some embodiments, the method further comprises culturing the cell under conditions leading to the selection of the cell. In some embodiments, the selection comprises the expression of the at least one essential protein encoded on the nucleotide sequence. In some embodiments, the selection comprises the expression of both the first and second two-part nucleotide sequences encoded on the nucleotide sequence.

In some embodiments, the essential protein is a DHFR protein. In some embodiments, the essential protein is a protein that has at least about 75%, at least about 80%, at least about 85%, at least about 90%, at least about 95%, at least about 99%, or about 100% identity to DHFR. In some embodiments, the protein is mammalian DHFR. In some embodiments, the protein is human DHFR. In some embodiments, the protein is a DHFR analog.

In some embodiments, the nucleotide sequence is exogenous to the cell. In some embodiments, the nucleotide sequence of either the first and/or second two-part nucleotide sequences is exogenous to the cell. In some embodiments, the first-part nucleotide sequence of either the first and/or second two-part nucleotide sequences is exogenous to the cell. In some embodiments, the second-part nucleotide sequence of either the first or second two-part nucleotide sequences is exogenous to the cell. In some embodiments, the nucleotide sequence of the first and/or second two-part nucleotide sequence is a TCR. In some embodiments, the first-part nucleotide sequence of the first and/or second two-part nucleotide sequence is a TCR. In some embodiments, the second-part nucleotide sequence of the first and/or second two-part nucleotide sequence is a TCR.

In some embodiments, at least one of the first and/or second binding domains is derived from GCN4. In some embodiments, the binding domain is derived from a protein that has at least about 75%, at least about 80%, at least about 85%, at least about 90%, at least about 95%, at least about 99%, or about 100% identity to GCN4. In some embodiments, the binding domain is derived from a protein that is mammalian GCN4. In some embodiments, the binding domain is derived from a protein that is human GCN4. In some embodiments, the binding domain is derived from a protein that is a GCN4 analog.

In some embodiments, at least one of the first and/or second binding domains is derived from FKBP12. In some embodiments, the binding domain is derived from a protein that has at least about 75%, at least about 80%, at least about 85%, at least about 90%, at least about 95%, at least about 99%, or about 100% identity to FKBP12. In some embodiments, the binding domain is derived from a protein that is mammalian FKBP12. In some embodiments, the binding domain is derived from a protein that is human FKBP12. In some embodiments, the binding domain is derived from a protein that is a FKBP12 analog. In some embodiments, the FKBP12 has an F36V mutation. In some embodiments, FKBP12 binding is induced. (Straathof K C, Pule` M A, Yotnda P, Dotti G, Vanin E F, Brenner M K, Heslop H E, Spencer D M, Rooney C M. An inducible caspase 9 safety switch for T-cell therapy. Blood. 2005 Jun. 1; 105(11):4247-54, hereby expressly incorporated by reference in its entirety for any purpose.)

In some embodiments, at least one of the first and/or second binding domains is derived from JUN. In some embodiments, the binding domain is derived from a protein that has at least about 75%, at least about 80%, at least about 85%, at least about 90%, at least about 95%, at least about 99%, or about 100% identity to JUN. In some embodiments, the binding domain is derived from a protein that is mammalian JUN. In some embodiments, the binding domain is derived from a protein that is human JUN. In some embodiments, the binding domain is derived from a protein that is a JUN analog.

In some embodiments, at least one of the first and/or second binding domains is derived from FOS. In some embodiments, the binding domain is derived from a protein that has at least about 75%, at least about 80%, at least about 85%, at least about 90%, at least about 95%, at least about 99%, or about 100% identity to FOS. In some embodiments, the binding domain is derived from a protein that is mammalian FOS. In some embodiments, the binding domain is derived from a protein that is human FOS. In some embodiments, the binding domain is derived from a protein that is a FOS analog. In some embodiments, the first binding domain is derived from JUN and the second binding domains is derived from FOS. In some embodiments, JUN and FOS have complementary changes that promote binding to each other relative to wild-type JUN and FOS. (Glover J N, Harrison S C. Crystal structure of the heterodimeric bZIP transcription factor c-Fos-c-Jun bound to DNA. Nature. 1995 Jan. 19; 373(6511):257-61, and Glover and Harrison, Nature 1995. Jerome and Muller, Gene Ther 2001, and Jérôme V, Müller R. A synthetic leucine zipper-based dimerization system for combining multiple promoter specificities. Gene Ther. 2001 May; 8(9):725-9 both of which are hereby expressly incorporated by reference in their entireties for any purpose)

In some embodiments, the first binding domain and second binding domain have complementary mutations that preserve binding to each other. In some embodiments, the first binding domain does not bind to a native binding partner. In some embodiments, the second binding domain does not bind to a native binding partner. In some embodiments, neither the first binding domain nor the second binding domain bind to a native binding partner. In some embodiments, at least one of the first binding domain and/or second binding domain have between 3 and 7 complementary mutations. In some embodiments, at least one of the first binding domain and/or second binding domain have 3 or more complementary mutations. In some embodiments, at least one of the first binding domain and/or second binding domain have 4 or more complementary mutations. In some embodiments, at least one of the first binding domain and/or second binding domain have 5 or more complementary mutations. In some embodiments, at least one of the first binding domain and/or second binding domain have 6 complementary mutations. In some embodiments, at least one of the first binding domain and/or second binding domain have 7 complementary mutations. In some embodiments, the first binding domain has a different number of complementary mutations than the second binding domain. In some embodiments, the complementary mutations are one or more charge pair (or charge switch) mutations, such that paired charges are maintained in the structure, but the positions charges are reversed between the pairs of residues. For example, in a situation where there are a first residue associated with a second residue via a charge interaction, and where the first residue is a positively charged residue and the second residue is a negatively charged residue, the charge can be switched such that the first residue is a negatively charged residue and the second residue is a positively charged residue. In some embodiments, the first residue and second residue may reside on the same protein. In some embodiments, the first residue and second residue reside on different proteins.

In some embodiments, the restoration of the function of the essential protein is induced. In some embodiments, the restoration of the function of the essential protein is induced by a dimerizer agent. The term "dimerizer agent" as used herein has its ordinary meaning as commonly understood to one of ordinary skill in the art, and includes any small molecule or protein that cross-links two or more domains. A non-limiting example of a dimerizer agent is AP1903. As understood to one of skill in the art given the present disclosure, when restoration of the function of the essential protein is induced by a dimerizer agent, the dimerizer agent or inducer is not considered an exogenous selection pressure.

In some embodiments, the culturing step is done in the presence of at least one of a cell cycle inhibitor, growth inhibitor, DNA replication inhibitor, metabolic inhibitor, gene expression inhibitor, or stress inhibitor. In some embodiments, the culturing step is done in the presence of methotrexate.

Some embodiments described herein relate to a method for enrichment of a genetically engineered cell. The term "enrichment" as used herein has its ordinary meaning as commonly understood to one of ordinary skill in the art, and includes enhancing the ratio of a desired cell type within a population of cells. Nonlimiting examples of enrichment include purifying a desired cell type out of a population, increasing the numbers of a desired cell type, and decreasing the numbers of an undesired cell type. In some embodiments, the method comprises decreasing activity of an at least first protein or cellular process that is essential for the survival and/or proliferation of a cell to the level such that the cell cannot survive and/or proliferate under normal in vitro propagation conditions. For example, a cell that has the activity of DHFR decreased by methotrexate cannot survive and/or proliferate under normal in vitro propagation conditions as extra supplements to the in vitro propagation conditions (e.g., hypoxanthine and thymidine (HT) may be required. Thus, as will be appreciated by one of skill in the art given the disclosure herein, in this context, normal conditions (or similar phrases) denote conditions that do not provide specific components that compensate for the specifically denoted alteration(s). As noted herein, this may be any protein or cellular system that influences growth, replication, cell cycle, gene regulation (including DNA repair, transcription, translation, and replication), stress response, metabolism, apoptosis, nutrient acquisition, protein turnover, cell surface integrity, essential enzyme activity, or any combination thereof in a given cell. It will also be understood that the term "suppression" can apply to any phenotype from a significant increase in one or more occurrence of cell death, metabolic arrest, cell cycle arrest, stress induction, protein turnover arrest, DNA stress, and/or growth arrest compared to a control, to complete cell death, metabolic arrest, cell cycle arrest, stress induction, protein turnover arrest, DNA stress, and/or growth arrest compared to a control.

In some embodiments, the method further comprises introducing the at least one nucleotide sequence disclosed herein that is operable for expression in a cell. In some embodiments, the nucleotide sequence comprises at least two parts. As noted herein, these parts function together towards the expression of an at least one essential protein. It will be understood that there can be any number of parts that will work together for the expression of an at least one essential protein.

In some embodiments, the nucleotide sequence comprises an at least one sequence encoding a fusion protein comprising a non-functional portion of the essential protein for the survival and/or proliferation fused to a binding domain. In some embodiments, the first part of a nucleotide sequence comprises an at least one sequence encoding a fusion protein comprising a non-functional portion of the essential protein for the survival and/or proliferation fused to a binding domain. In some embodiments, the second-part of the nucleotide sequence comprises an at least one sequence encoding an at least one protein to be expressed.

In some embodiments, the nucleotide sequence comprises an at least one sequence encoding a second fusion protein comprising a second non-functional portion of the essential protein for the survival and/or proliferation fused to a second binding domain and a second nucleotide sequence encoding the at least one protein to be expressed. In some embodiments, the second part of the nucleotide sequence comprises an at least one sequence encoding a second fusion protein comprising a second non-functional portion of the essential protein for the survival and/or proliferation fused to a second binding domain and a second nucleotide sequence encoding the at least one protein to be expressed. In some embodiments, the fusion proteins expressed together in a cell result in the successful expression of an at least one essential protein. While many of the examples disclosed herein relate to two fusion proteins combining, it will be understood to those skilled in the art that the same method disclosed herein can be used under any number of fusion proteins that can successfully combine into an at least one essential protein.

In some embodiments, when the first and second fusion proteins are expressed together in a cell, the function of the at least one essential protein for the survival and/or proliferation is restored. As disclosed herein, in some embodiments, when the first and second fusion proteins are expressed together in a cell, the function of the at least one essential cellular process for the survival and/or proliferation is restored. In some embodiments, the at least one essential protein or cellular process is the same essential protein or cellular process as the suppressed protein or cellular process. In some embodiments, the at least one essential protein comprises similar activity as the suppressed protein. In some embodiments, the at least one essential protein functions in the at least one suppressed cellular pathway or process. In some embodiments, the at least one essential protein functions in at least two essential cellular pathways or processes. In some embodiments, the expression of the at least one essential protein alleviates, activates, restores, or diminishes the suppression phenotype of the suppressed protein and/or cellular process. In some embodiments, the survival and/or proliferation of the cell is increased upon expression of the at least one essential protein. In some embodiments, the survival and/or proliferation of the cell is fully restored upon expression of the at least one essential protein.

In some embodiments, the method further comprises culturing the cell under in vitro propagation conditions that lead to the enrichment of the cell that expresses both the first fusion protein and second fusion protein.

In some embodiments one or more of the constructs, sequences, or subsequences within any one or more of Tables 1-5 can be employed in the present embodiments and/or arrangements and/or methods and/or compositions provided herein.

TABLE 1

Target sequences for gRNAs

| Description | Sequence targeted | SEQ ID NO: |
|---|---|---|
| DHFR sgRNA-1 | tgattatgggtaagaagacc | 10 |
| DHFR sgRNA-2 | AACCTTAGGGAACCTCCACA | 11 |
| DHFR sgRNA-3 | Cggcccggcagatacctgag | 12 |
| DHFR sgRNA-4 | Gacatggtctggatagttgg | 13 |
| DHFR sgRNA-5 | gtcgctgtgtcccagaacat | 14 |
| DHFR sgRNA-6 | cagatacctgagcggtggcc | 15 |
| DHFR sgRNA-7 | cacattaccttctactgaag | 16 |
| DHFR sgRNA-8 | cgtcgctgtgtcccagaaca | 17 |

TABLE 1-continued

| Target sequences for gRNAs | | |
|---|---|---|
| Description | Sequence targeted | SEQ ID NO: |
| DHFR sgRNA-9 | accacaacctcttcagtaga | 18 |
| DHFR sgRNA-10 | aaattaattctaccctttaa | 19 |
| TRAC sgRNA | GAGAATCAAAATCGGTGAAT | 20 |
| B2M | GAGTAGCGCGAGCACAGCTA | 21 |

TABLE 2

| Fusion proteins and related elements | | |
|---|---|---|
| Description | Sequence | SEQ ID NO: |
| mDHFRmt-A (N-term) | MVRPLNCIVAVSQNMGIGKNGDFPWPPLRNESKYFQR MTTTSSVEGKQNLVIMGRKTWFSIPEKNRPLKDRINIVL SRELKEPPRGAHFLAKSLDDALRLIEQPEL | 22 |
| mDHFRmt-B (C-term) | ASKVDMVWIVGGSSVYQEAMNQPGHLRLFVTRIMQEF ESDTFFPEIDLGKYKLLPEYPGVLSEVQEEKGIKYKFEV YEKKD | 23 |
| GCN4 | NTEAARRSRARKLQRMKQLEDKVEELLSKNYHLENEV ARLKKLVGER | 24 |
| JUN | RIARLEEKVKTLKAQNSELASTANMLREQVAQLKQKV MNH | 25 |
| $JUN^{MUT3AA}$ | RIARLEEEVKTLEAQNSELASTANMLEEQVAQLKQKV MNH | 26 |
| $JUN^{MUT4AA}$ | RIARLEEEVKTLEAQNSELASTANMLEEQVAQLEQKV | 27 |
| FOS | LTDTLQAETDQLEDEKSALQTEIANLLKEKEKLEFILAA H | 28 |
| $FOS^{MUT3AA}$ | LTDTLQAKTDQLKDEKSALQTRIANLLKEKEKLEFILAA H | 29 |
| $FOS^{MUT4AA}$ | LTDTLQAKTDQLKDEKSALQTRIANLLKKKEKLEFIL | 30 |
| $FKBP12^{F36V}$ | GVQVETISPGDGRTFPKRGQTCVVHYTGMLEDGKKVD SSRDRNKPFKFMLGKQEVIRGWEEGVAQMSVGQRAKL TISPDYAYGATGHPGIIPPHATLVFDVELLKLE | 31 |
| dn-TGFBR2 | MGRGLLRGLWPLHIVLWTRIASTIPPHVQKSVNNDMIV TDNNGAVKFPQLCKFCDVRFSTCDNQKSCMSNCSITSIC EKPQEVCVAVWRKNDENITLETVCHDPKLPYHDFILED AASPKCIMKEKKKPGETFFMCSCSSDECNDNIIFSEEYN TSNPDLLLVIFQVTGISLLPPLGVAISVIIIFYCYRV | 32 |
| Linker 1 | GGGGSGGGGS | 33 |
| Linker 2 | SGGGS | 34 |
| $JUN^{MUT3AA}$-mDHFR_A | RIARLEEEVKTLEAQNSELASTANMLEEQVAQLKQKVG GGGSGGGGSMVRPLNCIVAVSQNMGIGKNGDFPWPPL RNESKYFQRMTTTSSVEGKQNLVIMGRKTWFSIPEKNR PLKDRINIVLSRELKEPPRGAHFLAKSLDDALRLIEQPEL | 35 |
| $FOS^{MUT3AA}$-mDHFR_B | LTDTLQAKTDQLKDEKSALQTRIANLLKEKEKLEFILGG GGSGGGGSASKVDMVWIVGGSSVYQEAMNQPGHLRLF VTRIMQEFESDTFFPEIDLGKYKLLPEYPGVLSEVQEEK GIKYKFEVYEKKD | 36 |
| $JUN^{MUT4AA}$-mDHFR_A | RIARLEEEVKTLEAQNSELASTANMLEEQVAQLEQKVG GGGSGGGGSMVRPLNCIVAVSQNMGIGKNGDFPWPPL RNESKYFQRMTTTSSVEGKQNLVIMGRKTWFSIPEKNR PLKDRINIVLSRELKEPPRGAHFLAKSLDDALRLIEQPEL | 37 |

TABLE 2-continued

| Fusion proteins and related elements | | |
|---|---|---|
| Description | Sequence | SEQ ID NO: |
| FOS$^{MUT4AA}$_ mDHFR_B | LTDTLQAKTDQLKDEKSALQTRIANLLKKKEKLEFILGG GGSGGGGSASKVDMVWIVGGSSVYQEAMNQPGHLRLF VTRIMQEFESDTFFPEIDLGKYKLLPEYPGVLSEVQEEK GIKYKFEVYEKKD | 38 |
| GCN4-mDHFRmt_A | NTEAARRSRARKLQRMKQLEDKVEELLSKNYHLENEV ARLKKLVGERGGGGSGGGGSMVRPLNCIVAVSQNMGI GKNGDFPWPPLRNESKYFQRMTTTSSVEGKQNLVIMGR KTWFSIPEKNRPLKDRINIVLSRELKEPPRGAHFLAKSLD DALRLIEQPEL | 39 |
| GCN4-mDHFRmt_B | NTEAARRSRARKLQRMKQLEDKVEELLSKNYHLENEV ARLKKLVGERGGGGSGGGGSASKVDMVWIVGGSSVY QEAMNQPGHLRLFVTRIMQEFESDTFFPEIDLGKYKLLP EYPGVLSEVQEEKGIKYKFEVYEKKD | 40 |
| JUN-mDHFRmt_A-2A | RIARLEEKVKTLKAQNSELASTANMLREQVAQLKQKV MNHGGGGSGGGGSMVRPLNCIVAVSQNMGIGKNGDFP WPPLRNESKYFQRMTTTSSVEGKQNLVIMGRKTWFSIP EKNRPLKDRINIVLSRELKEPPRGAHFLAKSLDDALRLIE QPELGSGATNFSLLKQAGDVEENPGP | 41 |
| FOS-mDHFRmt_B-2A | LTDTLQAETDQLEDEKSALQTEIANLLKEKEKLEFILAA HGGGGSGGGGSASKVDMVWIVGGSSVYQEAMNQPGH LRLFVTRIMQEFESDTFFPEIDLGKYKLLPEYPGVLSEVQ EEKGIKYKFEVYEKKDGSGATNFSLLKQAGDVEENPGP | 42 |
| JUN-mDHFRmt_A | RIARLEEKVKTLKAQNSELASTANMLREQVAQLKQKV MNHGGGGSGGGGSMVRPLNCIVAVSQNMGIGKNGDFP WPPLRNESKYFQRMTTTSSVEGKQNLVIMGRKTWFSIP EKNRPLKDRINIVLSRELKEPPRGAHFLAKSLDDALRLIE QPEL | 43 |
| FOS-mDHFRmt_B | LTDTLQAETDQLEDEKSALQTEIANLLKEKEKLEFILAA HGGGGSGGGGSASKVDMVWIVGGSSVYQEAMNQPGH LRLFVTRIMQEFESDTFFPEIDLGKYKLLPEYPGVLSEVQ EEKGIKYKFEVYEKKD | 44 |
| GCN4-mDHFRmt_A-2A | NTEAARRSRARKLQRMKQLEDKVEELLSKNYHLENEV ARLKKLVGERGGGGSGGGGSMVRPLNCIVAVSQNMGI GKNGDFPWPPLRNESKYFQRMTTTSSVEGKQNLVIMGR KTWFSIPEKNRPLKDRINIVLSRELKEPPRGAHFLAKSLD DALRLIEQPELGSGATNFSLLKQAGDVEENPGP | 45 |
| GCN4-mDHFRmt_B-2A | NTEAARRSRARKLQRMKQLEDKVEELLSKNYHLENEV ARLKKLVGERGGGGSGGGGSASKVDMVWIVGGSSVY QEAMNQPGHLRLFVTRIMQEFESDTFFPEIDLGKYKLLP EYPGVLSEVQEEKGIKYKFEVYEKKDGSGATNFSLLKQ AGDVEENPGP | 46 |
| FKBP12$^{F36V}$-mDHFR$^{MUT}$-A | GVQVETISPGDGRTFPKRGQTCVVHYTGMLEDGKKVD SSRDRNKPFKFMLGKQEVIRGWEEGVAQMSVGQRAKL TISPDYAYGATGHPGIIPPHATLVFDVELLKLESGGGSM VRPLNCIVAVSQNMGIGKNGDFPWPPLRNESKYFQRMT TTSSVEGKQNLVIMGRKTWFSIPEKNRPLKDRINIVLSRE LKEPPRGAHFLAKSLDDALRLIEQPEL | 62 |
| FKBP12$^{F36V}$-mDHFR$^{MUT}$-B | GVQVETISPGDGRTFPKRGQTCVVHYTGMLEDGKKVD SSRDRNKPFKFMLGKQEVIRGWEEGVAQMSVGQRAKL TISPDYAYGATGHPGIIPPHATLVFDVELLKLESGGGSAS KVDMVWIVGGSSVYQEAMNQPGHLRLFVTRIMQEFES DTFFPEIDLGKYKLLPEYPGVLSEVQEEKGIKYKFEVYE KKD | 63 |

TABLE 3

| Knockin templates | | |
|---|---|---|
| Description | Sequence | SEQ ID NO: |
| NY-ESO-1<br>1G4 TCR | GCCAGAGTTATATTGCTGGGGTTTTGAAGAAGATCCT<br>ATTAAATAAAAGAATAAGCAGTATTATTAAGTAGCCC<br>TGCATTTCAGGTTTCCTTGAGTGGCAGGCCAGGCCTGG<br>CCGTGAACGTTCACTGAAATCATGGCCTCTTGGCCAA<br>GATTGATAGCTTGTGCCTGTCCCTGAGTCCCAGTCCAT<br>CACGAGCAGCTGGTTTCTAAGATGCTATTTCCCGTATA<br>AAGCATGAGACCGTGACTTGCCAGCCCCACAGAGCCC<br>CGCCCTTGTCCATCACTGGCATCTGGACTCCAGCCTGG<br>GTTGGGGCAAAGAGGGAAATGAGATCATGTCCTAACC<br>CTGATCCTCTTGTCCCACAGATATCCAGAACCCTGACC<br>CTGCCGTGTACCAGCTGAGAGACTCTAAATCCAGTGA<br>CAAGTCTGTCTGCCTATTCGGATCTGGCGCCACCAATT<br>TCAGCCTGCTGAAACAGGCTGGCGACGTGGAAGAGAA<br>CCCCGGACCTATGTCTATCGGCCTGCTGTGTTGTGCCG<br>CTCTGTCTCTGCTTTGGGCCGGACCTGTTAATGCCGGC<br>GTGACCCAGACACCTAAGTTCCAGGTGCTGAAAACCG<br>GCCAGAGCATGACCCTGCAGTGCGCCCAGGATATGAA<br>CCACGAGTACATGAGCTGGTACAGACAGGACCCTGGC<br>ATGGGCCTGAGACTGATCCACTATTCTGTCGGAGCCG<br>GCATCACCGACCAGGGCGAAGTTCCTAATGGCTACAA<br>CGTGTCCAGAAGCACCACCGAGGACTTCCCACTGAGA<br>CTGCTGTCTGCCGCTCCTAGCCAGACCAGCGTGTACTT<br>TTGTGCCAGCAGCTACGTGGGCAACACCGGCGAGCTG<br>TTTTTTGGCGAGGGCAGCAGACTGACCGTGCTGGAGG<br>ACCTGAAGAACGTGTTCCCTCCAAAGGTGGCCGTGTT<br>CGAGCCTTCTGAGGCCGAGATCAGCCACACACAGAAA<br>GCCACACTCGTGTGTCTGGCCACCGGCTTCTACCCCGA<br>TCACGTGGAACTGTCTTGGTGGGTCAACGGCAAAGAG<br>GTGCACAGCGGCGTCAGCACAGATCCCCAGCCTCTGA<br>AAGAACAGCCCGCTCTGAACGACAGCCGGTACTGTCT<br>GAGCAGCAGACTGAGAGTGTCCGCCACCTTCTGGCAG<br>AACCCCAGAAACCACTTCAGATGCCAGGTGCAGTTCT<br>ACGGCCTGAGCGAAAACGACGAGTGGACCCAGGACA<br>GGGCCAAGCCTGTGACACAGATCGTGTCTGCCGAAGC<br>CTGGGGCAGAGCCGATTGTGGCTTTACCAGCGAGAGC<br>TACCAGCAGGGCGTGCTGTCTGCCACAATCCTGTACG<br>AGATCCTGCTGGGCAAAGCCACTCTGTACGCCGTGCT<br>GGTGTCTGCCCTGGTGCTGATGGCCATGGTCAAGCGG<br>AAGGATAGCAGAGGCGGCAGCGGCGAAGGCAGAGGC<br>TCTCTTCTTACATGCGGCGACGTCGAAGAAAATCCTG<br>GGCCTATGAAGTCCCTGCGGGTGCTGCTGGTTATCCTG<br>TGGCTGCAGCTGAGCTGGGTCTGGTCCCAGAAACAAG<br>AAGTGACTCAGATCCCAGCCGCTCTGAGTGTGCCTGA<br>GGGCGAAAACCTGGTCCTGAACTGCAGCTTCACCGAC<br>AGCGCCATCTACAACCTGCAGTGGTTCAGGCAGGATC<br>CCGGCAAGGGACTGACAAGCCTGCTGCTGATTCAGAG<br>CAGCCAGAGAGAGCAGACCTCCGGCAGACTGAATGCC<br>AGCCTGGATAAGAGCAGCGGCCGCAGCACACTGTATA<br>TCGCCGCTTCTCAGCCTGGCGATAGCGCCACATATCTG<br>TGTGCCGTGCGACCTCTGTACGGCGGCAGCTACATCC<br>CTACATTTGGCAGAGGCACCAGCCTGATCGTGCACCC<br>CTACATTCAGAACCCCGATCCTGCCGTGTATCAGCTGA<br>GAGACAGCAAGTCCAGCGACAAGAGCGTGTGTTTGTT<br>CACCGATTTTGATTCTCAAACAAATGTGTCACAAAGT<br>AAGGATTCTGATGTGTATATCACAGACAAAACTGTGC<br>TAGACATGAGGTCTATGGACTTCAAGAGCAACAGTGC<br>TGTGGCCTGGAGCAACAAATCTGACTTTGCATGTGCA<br>AACGCCTTCAACAACAGCATTATTCCAGAAGACACCT<br>TCTTCCCCAGCCCAGGTAAGGGCAGCTTTGGTGCCTTC<br>GCAGGCTGTTTCCTTGCTTCAGGAATGGCCAGGTTCTG<br>CCCAGAGCTCTGGTCAATGATGTCTAAAACTCCTCTGA<br>TTGGTGGTCTCGG | 47 |
| NY-ESO-1<br>1G4 TCR and<br>DHFR | GCCAGAGTTATATTGCTGGGGTTTTGAAGAAGATCCT<br>ATTAAATAAAAGAATAAGCAGTATTATTAAGTAGCCC<br>TGCATTTCAGGTTTCCTTGAGTGGCAGGCCAGGCCTGG<br>CCGTGAACGTTCACTGAAATCATGGCCTCTTGGCCAA<br>GATTGATAGCTTGTGCCTGTCCCTGAGTCCCAGTCCAT<br>CACGAGCAGCTGGTTTCTAAGATGCTATTTCCCGTATA<br>AAGCATGAGACCGTGACTTGCCAGCCCCACAGAGCCC<br>CGCCCTTGTCCATCACTGGCATCTGGACTCCAGCCTGG<br>GTTGGGGCAAAGAGGGAAATGAGATCATGTCCTAACC<br>CTGATCCTCTTGTCCCACAGATATCCAGAACCCTGACC<br>CTGCCGTGTACCAGCTGAGAGACTCTAAATCCAGTGA<br>CAAGTCTGTCTGCCTATTCGGATCTGGCGCCACCAATT | 48 |

TABLE 3-continued

| Knockin templates | | |
|---|---|---|
| Description | Sequence | SEQ ID NO: |
| | TCAGCCTGCTGAAACAGGCTGGCGACGTGGAAGAGAA | |
| | CCCCGGACCTATGTCTATCGGCCTGCTGTGTTGTGCCG | |
| | CTCTGTCTCTGCTTTGGGCCGGACCTGTTAATGCCGGC | |
| | GTGACCCAGACACCTAAGTTCCAGGTGCTGAAAACCG | |
| | GCCAGAGCATGACCCTGCAGTGCGCCCAGGATATGAA | |
| | CCACGAGTACATGAGCTGGTACAGACAGGACCCTGGC | |
| | ATGGGCCTGAGACTGATCCACTATTCTGTCGGAGCCG | |
| | GCATCACCGACCAGGGCGAAGTTCCTAATGGCTACAA | |
| | CGTGTCCAGAAGCACCACCGAGGACTTCCCACTGAGA | |
| | CTGCTGTCTGCCGCTCCTAGCCAGACCAGCGTGTACTT | |
| | TTGTGCCAGCAGCTACGTGGGCAACACCGGCGAGCTG | |
| | TTTTTTGGCGAGGGCAGCAGACTGACCGTGCTGGAAG | |
| | ATCTGAACAAGGTGTTCCCTCCAGAGGTGGCCGTGTT | |
| | CGAGCCTTCTGAGGCCGAGATCAGCCACACACAGAAA | |
| | GCCACACTCGTGTGCCTGGCCACCGGCTTTTTTCCCGA | |
| | TCACGTGGAACTGTCTTGGTGGGTCAACGGCAAAGAG | |
| | GTGCACAGCGGCGTCAGCACAGATCCCCAGCCTCTGA | |
| | AAGAACAGCCCGCTCTGAACGACAGCCGGTACTGTCT | |
| | GTCCTCCAGACTGAGAGTGTCCGCCACCTTCTGGCAG | |
| | AACCCCAGAAACCACTTCAGATGCCAGGTGCAGTTCT | |
| | ACGGCCTGAGCGAGAACGATGAGTGGACCCAGGATA | |
| | GAGCCAAGCCTGTGACACAGATCGTGTCTGCCGAAGC | |
| | CTGGGGCAGAGCCGATTGTGGCTTTACCTCCGTGTCCT | |
| | ATCAGCAGGGCGTGCTGAGCGCCACAATCCTGTATGA | |
| | GATCCTGCTGGGCAAAGCCACTCTGTACGCCGTGCTG | |
| | GTGTCTGCCCTGGTGCTGATGGCCATGGTCAAGAGAA | |
| | AGGACTTCGGCAGCGGCGAAGGCAGAGGCTCTCTTCT | |
| | TACATGCGGCGACGTCGAAGAAAATCCTGGGCCTATG | |
| | GTAGGCTCCCTGAACTGTATAGTTGCGGTATCCCAAA | |
| | ATATGGGGATTGGAAAGAACGGAGACCTTCCGTGGCC | |
| | GCCCCTCCGAAATGAATTTCGATACTTTCAGAGAATG | |
| | ACAACTACCTCATCTGTAGAGGGAAAGCAAAATCTGG | |
| | TTATCATGGGAAAGAAAACGTGGTTCTCTATCCCTGA | |
| | AAAAAACAGACCTCTCAAAGGCAGGATAAATTTGGTA | |
| | TTGTCAAGAGAATTGAAGGAACCGCCACAAGGAGCTC | |
| | ATTTTCTCAGCAGATCTCTGGACGATGCACTCAAACTC | |
| | ACCGAACAACCAGAACTTGCTAATAAGGTTGATATGG | |
| | TCTGGATAGTTGGGGGCAGCAGTGTATATAAGGAAGC | |
| | CATGAACCATCCTGGCCATCTGAAGCTGTTTGTTACGA | |
| | GGATAATGCAGGACTTCGAGTCCGACACTTTTTTCCCA | |
| | GAGATTGACTTGGAAAAGTATAAACTCTTGCCTGAGT | |
| | ATCCTGGGGTTCTCTCCGATGTCCAAGAGGAGAAAGG | |
| | TATTAAATATAAGTTTGAAGTTTATGAAAAAAACGAT | |
| | GGATCTGGCGCCACCAATTTCAGCCTGCTGAAACAGG | |
| | CTGGCGACGTGGAAGAGAACCCCGGACCTATGAAGTC | |
| | CCTGCGGGTGCTGCTGGTTATCCTGTGGCTGCAGCTGA | |
| | GCTGGGTCTGGTCCCAGAAACAAGAAGTGACTCAGAT | |
| | CCCAGCCGCTCTGAGTGTGCCTGAGGGCGAAAACCTG | |
| | GTCCTGAACTGCAGCTTCACCGACAGCGCCATCTACA | |
| | ACCTGCAGTGGTTCAGGCAGGATCCCGGCAAGGGACT | |
| | GACAAGCCTGCTGCTGATTCAGAGCAGCCAGAGAGAG | |
| | CAGACCTCCGGCAGACTGAATGCCAGCCTGGATAAGA | |
| | GCAGCGGCCGCAGCACACTGTATATCGCCGCTTCTCA | |
| | GCCTGGCGATAGCGCCACATATCTGTGTGCCGTGCGA | |
| | CCTCTGTACGGCGGCAGCTACATCCCTACATTTGGCAG | |
| | AGGCACCAGCCTGATCGTGCACCCCTACATTCAGAAC | |
| | CCCGATCCTGCCGTGTATCAGCTGAGAGACAGCAAGT | |
| | CCAGCGACAAGAGCGTGTGTTTGTTCACCGATTTTGAT | |
| | TCTCAAACAAATGTGTCACAAAGTAAGGATTCTGATG | |
| | TGTATATCACAGACAAAACTGTGCTAGACATGAGGTC | |
| | TATGGACTTCAAGAGCAACAGTGCTGTGGCCTGGAGC | |
| | AACAAATCTGACTTTGCATGTGCAAACGCCTTCAACA | |
| | ACAGCATTATTCCAGAAGACACCTTCTTCCCCAGCCCA | |
| | GGTAAGGGCAGCTTTGGTGCCTTCGCAGGCTGTTTCCT | |
| | TGCTTCAGGAATGGCCAGGTTCTGCCCAGAGCTCTGG | |
| | TCAATGATGTCTAAAACTCCTCTGATTGGTGGTCTCGG | |
| NY-ESO-1 | GCCAGAGTTATATTGCTGGGGTTTTGAAGAAGATCCT | 49 |
| 1G4 TCR and | ATTAAATAAAAGAATAAGCAGTATTATTAAGTAGCCC | |
| DHFRm | TGCATTTCAGGTTTCCTTGAGTGGCAGGCCAGGCCTGG | |
| (methotrexate- | CCGTGAACGTTCACTGAAATCATGGCCTCTTGGCCAA | |
| resistant) | GATTGATAGCTTGTGCCTGTCCCTGAGTCCCAGTCCAT | |
| | CACGAGCAGCTGGTTTCTAAGATGCTATTTCCCGTATA | |
| | AAGCATGAGACCGTGACTTGCCAGCCCCACAGAGCCC | |
| | CGCCCTTGTCCATCACTGGCATCTGGACTCCAGCCTGG | |

TABLE 3-continued

| Knockin templates | | |
|---|---|---|
| Description | Sequence | SEQ ID NO: |
| | GTTGGGGCAAAGAGGGAAATGAGATCATGTCCTAACC | |
| | CTGATCCTCTTGTCCCACAGATATCCAGAACCCTGACC | |
| | CTGCCGTGTACCAGCTGAGAGACTCTAAATCCAGTGA | |
| | CAAGTCTGTCTGCCTATTCGGATCTGGCGCCACCAATT | |
| | TCAGCCTGCTGAAACAGGCTGGCGACGTGGAAGAGAA | |
| | CCCCGGACCTATGTCTATCGGCCTGCTGTGTTGTGCCG | |
| | CTCTGTCTCTGCTTTGGGCCGGACCTGTTAATGCCGGC | |
| | GTGACCCAGACACCTAAGTTCCAGGTGCTGAAAACCG | |
| | GCCAGAGCATGACCCTGCAGTGCGCCCAGGATATGAA | |
| | CCACGAGTACATGAGCTGGTACAGACAGGACCCTGGC | |
| | ATGGGCCTGAGACTGATCCACTATTCTGTCGGAGCCG | |
| | GCATCACCGACCAGGGCGAAGTTCCTAATGGCTACAA | |
| | CGTGTCCAGAAGCACCACCGAGGACTTCCCACTGAGA | |
| | CTGCTGTCTGCCGCTCCTAGCCAGACCAGCGTGTACTT | |
| | TTGTGCCAGCAGCTACGTGGGCAACACCGGCGAGCTG | |
| | TTTTTTGGCGAGGGCAGCAGACTGACCGTGCTGGAAG | |
| | ATCTGAACAAGGTGTTCCCTCCAGAGGTGGCCGTGTT | |
| | CGAGCCTTCTGAGGCCGAGATCAGCCACACACAGAAA | |
| | GCCACACTCGTGTGCCTGGCCACCGGCTTTTTTCCCGA | |
| | TCACGTGGAACTGTCTTGGTGGGTCAACGGCAAAGAG | |
| | GTGCACAGCGGCGTCAGCACAGATCCCCAGCCTCTGA | |
| | AAGAACAGCCCGCTCTGAACGACAGCCGGTACTGTCT | |
| | GTCCTCCAGACTGAGAGTGTCCGCCACCTTCTGGCAG | |
| | AACCCCAGAAACCACTTCAGATGCCAGGTGCAGTTCT | |
| | ACGGCCTGAGCGAGAACGATGAGTGGACCCAGGATA | |
| | GAGCCAAGCCTGTGACACAGATCGTGTCTGCCGAAGC | |
| | CTGGGGCAGAGCCGATTGTGGCTTTACCTCCGTGTCCT | |
| | ATCAGCAGGGCGTGCTGAGCGCCACAATCCTGTATGA | |
| | GATCCTGCTGGGCAAAGCCACTCTGTACGCCGTGCTG | |
| | GTGTCTGCCCTGGTGCTGATGGCCATGGTCAAGAGAA | |
| | AGGACTTCGGCAGCGGCGAAGGCAGAGGCTCTCTTCT | |
| | TACATGCGGCGACGTCGAAGAAAATCCTGGGCCTATG | |
| | GTAGGCTCCCTGAACTGTATAGTTGCGGTATCCCAAA | |
| | ATATGGGGATTGGAAAGAACGGAGACtTTCCGTGGCC | |
| | GCCCCTCCGAAATGAATccCGATACTTTCAGAGAATGA | |
| | CAACTACCTCATCTGTAGAGGGAAAGCAAAATCTGGT | |
| | TATCATGGGAAAGAAAACGTGGTTCTCTATCCCTGAA | |
| | AAAAACAGACCTCTCAAAGGCAGGATAAATTTGGTAT | |
| | TGTCAAGAGAATTGAAGGAACCGCCACAAGGAGCTCA | |
| | TTTTCTCAGCAGATCTCTGGACGATGCACTCAAACTCA | |
| | CCGAACAACCAGAACTTGCTAATAAGGTTGATATGGT | |
| | CTGGATAGTTGGGGGCAGCAGTGTATATAAGGAAGCC | |
| | ATGAACCATCCTGGCCATCTGAAGCTGTTTGTTACGAG | |
| | GATAATGCAGGACTTCGAGTCCGACACTTTTTTCCCAG | |
| | AGATTGACTTGGAAAAGTATAAACTCTTGCCTGAGTA | |
| | TCCTGGGGTTCTCTCCGATGTCCAAGAGGAGAAAGGT | |
| | ATTAAATATAAGTTTGAAGTTTATGAAAAAAACGATG | |
| | GATCTGGCGCCACCAATTTCAGCCTGCTGAAACAGGC | |
| | TGGCGACGTGGAAGAGAACCCCGGACCTATGAAGTCC | |
| | CTGCGGGTGCTGCTGGTTATCCTGTGGCTGCAGCTGAG | |
| | CTGGGTCTGGTCCCAGAAACAAGAAGTGACTCAGATC | |
| | CCAGCCGCTCTGAGTGTGCCTGAGGGCGAAAACCTGG | |
| | TCCTGAACTGCAGCTTCACCGACAGCGCCATCTACAA | |
| | CCTGCAGTGGTTCAGGCAGGATCCCGGCAAGGGACTG | |
| | ACAAGCCTGCTGCTGATTCAGAGCAGCCAGAGAGAGC | |
| | AGACCTCCGGCAGACTGAATGCCAGCCTGGATAAGAG | |
| | CAGCGGCCGCAGCACACTGTATATCGCCGCTTCTCAG | |
| | CCTGGCGATAGCGCCACATATCTGTGTGCCGTGCGAC | |
| | CTCTGTACGGCGGCAGCTACATCCCTACATTTGGCAG | |
| | AGGCACCAGCCTGATCGTGCACCCCTACATTCAGAAC | |
| | CCCGATCCTGCCGTGTATCAGCTGAGAGACAGCAAGT | |
| | CCAGCGACAAGAGCGTGTGTTTGTTCACCGATTTTGAT | |
| | TCTCAAACAAATGTGTCACAAAGTAAGGATTCTGATG | |
| | TGTATATCACAGACAAAACTGTGCTAGACATGAGGTC | |
| | TATGGACTTCAAGAGCAACAGTGCTGTGGCCTGGAGC | |
| | AACAAATCTGACTTTGCATGTGCAAACGCCTTCAACA | |
| | ACAGCATTATTCCAGAAGACACCTTCTTCCCCAGCCCA | |
| | GGTAAGGGCAGCTTTGGTGCCTTCGCAGGCTGTTTCCT | |
| | TGCTTCAGGAATGGCCAGGTTCTGCCCAGAGCTCTGG | |
| | TCAATGATGTCTAAAACTCCTCTGATTGGTGGTCTCGG | |
| JUN$^{MUTAAA}$ - | gccagagttatattgctggggttttgaagaagatcctattaaataaaagaataagcagtatta | 50 |
| mDHFR_A_1G4_ | ttaagtagccctgcatttcaggtttccttgagtggcaggccaggcctggccgtgaacgttca | |
| TRAC | ctgaaatcatggcctcttggccaagattgatagcttgtgcctgtccctgagtcccagtccat | |
| | cacgagcagctggtttctaagatgctatttcccgtataaagcatgagaccgtgacttgccag | |

TABLE 3-continued

| Knockin templates | | |
|---|---|---|
| Description | Sequence | SEQ ID NO: |
| | ccccacagagccccgcccttgtccatcactggcatctggactccagcctgggttggggca<br>aagagggaaatgagatcatgtcctaaccctgatcctcttgtcccacagatatccagaaccc<br>tgaccctgccgtgtaccagctgagagactctaaatccagtgacaagtctgtctgcctattcg<br>gatctggcgccaccaatttcagcctgctgaaacaggctggcgacgtggaagagaacccc<br>ggacctATGTCTATCGGCCTGCTGTGTTGTGCCGCTCTGT<br>CTCTGCTTTGGGCCGGACCTGTTAATGCCGGCGTGACC<br>CAGACACCTAAGTTCCAGGTGCTGAAAACCGGCCAGA<br>GCATGACCCTGCAGTGCGCCCAGGATATGAACCACGA<br>GTACATGAGCTGGTACAGACAGGACCCTGGCATGGGC<br>CTGAGACTGATCCACTATTCTGTCGGAGCCGGCATCA<br>CCGACCAGGGCGAAGTTCCTAATGGCTACAACGTGTC<br>CAGAAGCACCACCGAGGACTTCCCACTGAGACTGCTG<br>TCTGCCGCTCCTAGCCAGACCAGCGTGTACTTTTGTGC<br>CAGCAGCTACGTGGGCAACACCGGCGAGCTGTTTTTT<br>GGCGAGGGCAGCAGACTGACCGTGCTGGAAGATCTGC<br>GGAACGTGTTCCCTCCAAAGGTGGCCGTGTTTGAGCC<br>TAGCGAGGCCGAGATCAGCCACACACAGAAAGCCAC<br>ACTCGTGTGTCTGGCCACCGGCTTCTATCCCGATCACG<br>TGGAACTGTCTTGGTGGGTCAACGGCAAAGAGGTGCA<br>CAGCGGCGTCAGCACAGATCCCCAGCCTCTGAAAGAA<br>CAGCCCGCTCTGAACGACAGCCGGTACTGTCTGTCCTC<br>CAGACTGAGAGTGTCCGCCACCTTCTGGCAGAACCCC<br>AGAAACCACTTCAGATGCCAGGTGCAGTTCTACGGCC<br>TGAGCGAGAACGACAAGTGGCCTGAGGGATCTGCCAA<br>GCCTGTGACACAGATCGTGTCTGCCGAAGCTTGGGGC<br>AGAGCCGATTGTGGCTTTACCAGCGAGAGCTACCAGC<br>AGGGCGTTCTGTCTGCCACCATCCTGTACGAGATCCTG<br>CTGGGCAAAGCCACTCTGTACGCCGTGCTGGTGTCTG<br>CCCTGGTGCTGATGGCCATGGTCAAGCGGAAGGATAG<br>CAGAGGCGGAAGCGGAGAAGGCAGAGGCTCTCTGCTT<br>ACATGCGGAGATGTGGAAGAAAATCCTGGACCAAGA<br>ATCGCCCGCCTGGAAGAAgAgGTCAAGACCCTGgAGGC<br>CCAGAACAGCGAGCTGGCCTCTACCGCCAACATGCTG<br>gaAGAACAGGTCGCCCAGCTGgAGCAGAAAGTCGGCG<br>GCGGAGGATCTGGCGGAGGCGGATCTATGGTTCGACC<br>CCTGAATTGCATCGTGGCCGTGTCTCAGAACATGGGC<br>ATCGGCAAGAACGGCGACTTCCCTTGGCCTCCTCTGC<br>GGAACGAGAGCAAGTACTTCCAGAGAATGACCACCAC<br>CAGCAGCGTGGAAGGCAAGCAGAACCTGGTCATCATG<br>GGCAGAAAGACCTGGTTCAGCATCCCCGAGAAGAACA<br>GGCCCCTGAAGGACCGGATCAACATCGTGCTGAGCAG<br>AGAGCTGAAAGAGCCTCCTAGAGGCGCCCACTTTCTG<br>GCCAAGTCTCTGGACGATGCCCTGCGGCTGATTGAGC<br>AGCCTGAACTTGGCAGCGGCGCCACAAACTTTTCACT<br>GCTGAAGCAAGCCGGGGATGTCGAAGAGAATCCAGG<br>GCCTATGAAGTCCCTGCGGGTGCTGCTGGTTATCCTGT<br>GGCTGCAGCTGAGCTGGGTCTGGTCCCAGAAACAAGA<br>AGTGACTCAGATCCCAGCCGCTCTGAGTGTGCCTGAG<br>GGCGAAAACCTGGTCCTGAACTGCAGCTTCACCGACA<br>GCGCCATCTACAACCTGCAGTGGTTCAGGCAGGATCC<br>CGGCAAGGGACTGACAAGCCTGCTGCTGATTCAGAGC<br>AGCCAGAGAGAGCAGACCTCCGGCAGACTGAATGCC<br>AGCCTGGATAAGAGCAGCGGCCGCAGCACACTGTATA<br>TCGCCGCTTCTCAGCCTGGCGATAGCGCCACATATCTG<br>TGTGCCGTGCGACCTCTGTACGGCGGCAGCTACATCC<br>CTACATTTGGCAGAGGCACCAGCCTGATCGTGCACCC<br>Ctacattcagaaccccgatcctgccgtgtatcagctgagagacagcaagtccagcgaca<br>agagcgtgtgtttgttcaccgattttgattctcaaacaaatgtgtcacaaagtaaggattctga<br>tgtgtatatcacagacaaaactgtgctagacatgaggtctatggacttcaagagcaacagt<br>gctgtggcctggagcaacaaatctgactttgcatgtgcaaacgccttcaacaacagcatta<br>ttccagaagacaccttcttccccagcccaggtaagggcagctttggtgccttcgcaggctg<br>tttccttgcttcaggaatggccaggttctgcccagagctctggtcaatgatgtctaaaactcc<br>tctgattggtggtctcgg | |
| FOS$^{MUT4AA}$-<br>mDHFR_B_<br>TGFBR2_B2M<br>(crB2M-4) | gaagttctccttctgctaggtagcattcaaagatcttaatcttctgggtttccgttttctcgaatg<br>aaaaatgcaggtccgagcagttaactggctggggcaccattagcaagtcacttagcatct<br>ctggggccagtctgcaaagcgagggggcagccttaatgtgcctccagcctgaagtccta<br>gaatgagcgcccggtgtcccaagctggggcgcgcaccccagatcggagggcgccgat<br>gtacagacagcaaactcacccagtctagtgcatgccttcttaaacatcacgagactctaag<br>aaaaggaaactgaaaacgggaaagtccctctctctaacctggcactgcgtcgctggcttg<br>gagacaggtgacggtccctgcgggccttgtcctgattggctgggcacgcgtttaatataa<br>gtggaggcgtcgcgctggcgggcattcctgaagctgacagcattcgggccgagatgtct<br>cgctccgtggccttagctGGAtctGGAGAAGGCAGAGGCagcCTGC<br>TTACATGCGGAGATGTGGAAGAAAATCCTGGACCAAT<br>GGGAAGAGGCCTGCTGAGAGGACTGTGGCCTCTGCAC | 51 |

TABLE 3-continued

| Knockin templates | | |
|---|---|---|
| Description | Sequence | SEQ ID NO: |
| | ATTGTGCTGTGGACCAGAATCGCCAGCACAATCCCTC<br>CACACGTGCAGAAAAGCGTGAACAACGACATGATCGT<br>GACCGACAACAATGGCGCCGTGAAGTTCCCTCAGCTG<br>TGCAAGTTCTGCGACGTGCGGTTCAGCACCTGTGACA<br>ACCAGAAAAGCTGCATGAGCAACTGCAGCATCACCAG<br>CATCTGCGAGAAGCCCCAAGAAGTGTGCGTCGCCGTC<br>TGGCGGAAGAACGACGAGAACATCACCCTGGAAACC<br>GTGTGTCACGACCCCAAGCTGCCCTACCACGACTTCAT<br>CCTGGAAGATGCCGCCTCTCCTAAGTGCATCATGAAG<br>GAAAAGAAGAAGCCCGGCGAGACATTCTTCATGTGCA<br>GCTGCTCCAGCGACGAGTGCAACGACAACATCATCTT<br>CAGCGAAGAGTACAACACCAGCAATCCCGACCTGCTG<br>CTGGTCATCTTCCAGGTGACCGGCATCAGCCTGCTGCC<br>TCCACTGGGAGTTGCCATCAGCGTGATCATCATCTTTT<br>ACTGCTACCGCGTGggatctggcgccaccaatttcagcctgctgaaacagg<br>ctggcgacgtggaagagaaccccggacctCTGACCGACACACTGCAG<br>GCCaAGACAGACCAACTGaAAGATGAGAAGTCTGCCC<br>TGCAGACCagGATCGCTAACCTGCTGAAAaAGAAAGAG<br>AAGCTCGAGTTCATCCTGGGTGGCGGAGGATCTGGCG<br>GAGGCGGATCTGCCAGCAAGGTGGACATGGTCTGGAT<br>CGTCGGCGGCTCCTCTGTGTACCAAGAGGCCATGAAT<br>CAGCCCGGACACCTGAGGCTGTTCGTGACCAGAATCA<br>TGCAAGAGTTCGAGAGCGACACATTCTTCCCAGAGAT<br>CGACCTGGGCAAGTACAAGCTGCTGCCTGAGTATCCC<br>GGCGTGCTGTCTGAGGTGCAAGAGGAAAAGGGCATCA<br>AGTATAAGTTCGAGGTGTACGAGAAAAAGGATGGATC<br>CGGCGAAGGCAGAGGATCTCTGCTGACATGTGGCGAC<br>GTGGAAGAGAACCCTGGACCTATGGATACCTGCCACA<br>TTGCCAAGAGCTGCGTGCTGATCCTGCTGGTCGTTCTG<br>CTGTGTGCCGAGCGAGCACAGGGCCTCGAGTGCTACA<br>ATTGCATTGGCGTGCCACCTGAGACAAGCTGCAACAC<br>CACCACCTGTCCTTTCAGCGACGGCTTCTGTGTGGCCC<br>TGGAAATCGAAGTGATCGTGGACAGCCACCGGTCCAA<br>AGTGAAGTCCAACCTGTGCCTGCCTATCTGCCCCACCA<br>CACTGGACAACACCGAGATCACAGGCAACGCCGTGAA<br>CGTGAAAACCTACTGCTGCAAAGAGGACCTCTGCAAC<br>GCCGCTGTTCCAACAGGTGGAAGCTCTTGGACTATGG<br>CCGGCGTGCTGCTGTTTAGCCTGGTGTCTGTTCTGCTG<br>CAGACCTTCCTGGGATCAGGCGCCACGAATTTTAGCC<br>TGCTCAAACAGGCGGGCGACGTAGAAGAGAACCCaGG<br>ACCTgtgctcgcgctactctctctttctggcctggaggctatccagcgtgagtctctcct<br>accctcccgctctggtccttcctctcccgctctgcaccctctgtggccctcgctgtgctctct<br>cgctccgtgacttcccttctccaagttctccttggtggcccgccgtggggctagtccaggg<br>ctggatctcggggaagcggcggggtggcctgggagtggggaaggggtgcgcaccc<br>gggacgcgcgctacttgccccttttcggcggggagcaggggagacctttggcctacggc<br>gacgggagggtcgggacaaagtttagggcgtcgataagcgtcagagcgccgaggttgg<br>gggagggtttctcttccgctctttcgcggggcctctggctcccccagcgcagctggagtg<br>ggggacgggtaggctcgtcccaaaggcgcggcgctgaggtttgtgaacgcgtggagg<br>ggcgcttggggtctgggggaggcgtcgcccg | |
| FOS$^{MUTAA}$-<br>mDHFR_B_<br>TGFBR2_B2M<br>(crB2M-5) | agtatcttggggccaaatcatgtagactcttgagtgatgtgttaaggaatgctatgagtgctg<br>agagggcatcagaagtccttgagagcctccagagaaaggctcttaaaaatgcagcgcaa<br>tctccagtgacagaagatactgctagaaatctgctagaaaaaaaacaaaaaaggcatgtat<br>agaggaattatgagggaaagataccaagtcacggtttattcttcaaaatggaggtggcttgt<br>tgggaaggtggaagctcatttggccagagtggaaatggaattgggagaaatcgatgacc<br>aaatgtaaacacttggtgcctgatatagcttgacaccaagttagccccaagtgaaataccct<br>ggcaatattaatgtgtcttttcccgatattcctcaggtactccaaagattcaggtttactcacgt<br>catccagcagagaatggaaagtcaaatttcctgaattgctatgtgtctgggtttcatccatcc<br>gacattGGAtctGGAGAAGGCAGAGGCagcCTGCTTACATGC<br>GGAGATGTGGAAGAAAATCCTGGACCAATGGGAAGA<br>GGCCTGCTGAGAGGACTGTGGCCTCTGCACATTGTGC<br>TGTGGACCAGAATCGCCAGCACAATCCCTCCACACGT<br>GCAGAAAAGCGTGAACAACGACATGATCGTGACCGA<br>CAACAATGGCGCCGTGAAGTTCCCTCAGCTGTGCAAG<br>TTCTGCGACGTGCGGTTCAGCACCTGTGACAACCAGA<br>AAAGCTGCATGAGCAACTGCAGCATCACCAGCATCTG<br>CGAGAAGCCCCAAGAAGTGTGCGTCGCCGTCTGGCGG<br>AAGAACGACGAGAACATCACCCTGGAAACCGTGTGTC<br>ACGACCCCAAGCTGCCCTACCACGACTTCATCCTGGA<br>AGATGCCGCCTCTCCTAAGTGCATCATGAAGGAAAAG<br>AAGAAGCCCGGCGAGACATTCTTCATGTGCAGCTGCT<br>CCAGCGACGAGTGCAACGACAACATCATCTTCAGCGA<br>AGAGTACAACACCAGCAATCCCGACCTGCTGCTGGTC<br>ATCTTCCAGGTGACCGGCATCAGCCTGCTGCCTCCACT<br>GGGAGTTGCCATCAGCGTGATCATCATCTTTTACTGCT | 52 |

TABLE 3-continued

Knockin templates

| Description | Sequence | SEQ ID NO: |
|---|---|---|
| | ACCGCGTGggatctggcgccaccaatttcagcctgctgaaacaggctggcgacgt<br>ggaagagaaccccggacctCTGACCGACACACTGCAGGCCaAGA<br>CAGACCAACTGaAAGATGAGAAGTCTGCCCTGCAGAC<br>CagGATCGCTAACCTGCTGAAAaAGAAAGAGAAGCTCG<br>AGTTCATCCTGGGTGGCGGAGGATCTGGCGGAGGCGG<br>ATCTGCCAGCAAGGTGGACATGGTCTGGATCGTCGGC<br>GGCTCCTCTGTGTACCAAGAGGCCATGAATCAGCCCG<br>GACACCTGAGGCTGTTCGTGACCAGAATCATGCAAGA<br>GTTCGAGAGCGACACATTCTTCCCAGAGATCGACCTG<br>GGCAAGTACAAGCTGCTGCCTGAGTATCCCGGCGTGC<br>TGTCTGAGGTGCAAGAGGAAAAGGGCATCAAGTATAA<br>GTTCGAGGTGTACGAGAAAAAGGATGGATCCGGCGA<br>AGGCAGAGGATCTCTGCTGACATGTGGCGACGTGGAA<br>GAGAACCCTGGACCTATGGATACCTGCCACATTGCCA<br>AGAGCTGCGTGCTGATCCTGCTGGTCGTTCTGCTGTGT<br>GCCGAGCGAGCACAGGGCCTCGAGTGCTACAATTGCA<br>TTGGCGTGCCACCTGAGACAAGCTGCAACACCACCAC<br>CTGTCCTTTCAGCGACGGCTTCTGTGTGGCCCTGGAAA<br>TCGAAGTGATCGTGGACAGCCACCGGTCCAAAGTGAA<br>GTCCAACCTGTGCCTGCCTATCTGCCCCACCACACTGG<br>ACAACACCGAGATCACAGGCAACGCCGTGAACGTGA<br>AAACCTACTGCTGCAAAGAGGACCTCTGCAACGCCGC<br>TGTTCCAACAGGTGGAAGCTCTTGGACTATGGCCGGC<br>GTGCTGCTGTTTAGCCTGGTGTCTGTTCTGCTGCAGAC<br>CTTCCTGGGATCAGGCGCCACGAATTTTAGCCTGCTCA<br>AACAGGCGGGCGACGTAGAAGAGAACCCaGGACCTgaa<br>gttgacttactgaagaatggagagagaattgaaaaagtggagcattcagacttgtctttcag<br>caaggactggtctttctatctcttgtactacactgaattcacccccactgaaaaagatgagta<br>tgcctgccgtgtgaaccatgtgactttgtcacagcccaagatagttaagtggggtaagtctt<br>acattcttttgtaagctgctgaaagttgtgtatgagtagtcatatcataaagctgctttgatata<br>aaaaaggtctatggccatactaccctgaatgagtcccatcccatctgatataaacaatctgc<br>atattgggattgtcagggaatgttcttaaagatcagattagtggcacctgctgagatactgat<br>gcacagcatggtttctgaaccagtagtttccctgcagttgagcagggagcagcagcagca<br>cttgcacaaatacatatacactcttaacacttcttacctactggcttcctctagcttttg | |
| FKBP12$^{F36V}$-<br>mDHFR_A_1G4_<br>TRAC<br>repair<br>template | gccagagttatattgctggggttttgaagaagatcctattaaataaaagaataagcagtatta<br>ttaagtagccctgcatttcaggtttccttgagtggcaggccaggcctggccgtgaacgttca<br>ctgaaatcatggcctcttggccaagattgatagcttgtgcctgtccctgagtcccagtccat<br>cacgagcagctggtttctaagatgctatttcccgtataaagcatgagaccgtgacttgccag<br>ccccacagagccccgcccttgtccatcactggcatctggactccagcctgggttggggca<br>aagagggaaatgagatcatgtcctaaccctgatcctcttgtcccacagatatccagaaccc<br>tgaccctgccgtgtaccagctgagagactctaaatccagtgacaagtctgtctgcctattcg<br>gatctggcgccaccaatttcagcctgctgaaacaggctggcgacgtggaagagaacccc<br>ggacctATGTCTATCGGCCTGCTGTGTTGTGCCGCTCTGT<br>CTCTGCTTTGGGCCGGACCTGTTAATGCCGGCGTGACC<br>CAGACACCTAAGTTCCAGGTGCTGAAAACCGGCCAGA<br>GCATGACCCTGCAGTGCGCCCAGGATATGAACCACGA<br>GTACATGAGCTGGTACAGACAGGACCCTGGCATGGGC<br>CTGAGACTGATCCACTATTCTGTCGGAGCCGGCATCA<br>CCGACCAGGGCGAAGTTCCTAATGGCTACAACGTGTC<br>CAGAAGCACCACCGAGGACTTCCCACTGAGACTGCTG<br>TCTGCCGCTCCTAGCCAGACCAGCGTGTACTTTTGTGC<br>CAGCAGCTACGTGGGCAACACCGGCGAGCTGTTTTTT<br>GGCGAGGGCAGCAGACTGACCGTGCTGGAAGATCTGC<br>GGAACGTGTTCCCTCCAAAGGTGGCCGTGTTTGAGCC<br>TAGCGAGGCCGAGATCAGCCACACACAGAAAGCCAC<br>ACTCGTGTGTCTGGCCACCGGCTTCTATCCCGATCACG<br>TGGAACTGTCTTGGTGGGTCAACGGCAAAGAGGTGCA<br>CAGCGGCGTCAGCACAGATCCCCAGCCTCTGAAAGAA<br>CAGCCCGCTCTGAACGACAGCCGGTACTGTCTGTCCTC<br>CAGACTGAGAGTGTCCGCCACCTTCTGGCAGAACCCC<br>AGAAACCACTTCAGATGCCAGGTGCAGTTCTACGGCC<br>TGAGCGAGAACGACAAGTGGCCTGAGGGATCTGCCAA<br>GCCTGTGACACAGATCGTGTCTGCCGAAGCTTGGGGC<br>AGAGCCGATTGTGGCTTTACCAGCGAGAGCTACCAGC<br>AGGGCGTTCTGTCTGCCACCATCCTGTACGAGATCCTG<br>CTGGGCAAAGCCACTCTGTACGCCGTGCTGGTGTCTG<br>CCCTGGTGCTGATGGCCATGGTCAAGCGGAAGGATAG<br>CAGAGGCGGAAGCGGAGAAGGCAGAGGCTCTCTGCTT<br>ACATGCGGAGATGTGGAAGAAAATCCTGGACCAATGG<br>GAGTTCAAGTGGAGACAATATCACCAGGCGATGGAAG<br>GACATTCCCCAAGCGAGGGCAAACGTGTGTGGTACAC<br>TACACTGGCATGTTGGAGGACGGAAAGAAAGTCGACA<br>GTTCCCGCGACCGGAATAAGCCTTTCAAATTCATGCTC<br>GGCAAGCAGGAGGTCATTCGGGGTTGGGAGGAAGGG | 53 |

TABLE 3-continued

| Knockin templates | | |
|---|---|---|
| Description | Sequence | SEQ ID NO: |
| | GTCGCGCAAATGAGTGTCGGACAACGCGCAAAACTTA<br>CTATTTCCCCAGATTACGCCTACGGAGCCACAGGTCA<br>CCCTGGTATCATACCACCCCACGCGACTCTGGTTTTTG<br>ATGTCGAATTGCTGAAATTGGAATCTGGCGGAGGCTC<br>TATGGTTCGACCCCTGAATTGCATCGTGGCCGTGTCTC<br>AGAACATGGGCATCGGCAAGAACGGCGACTTCCCTTG<br>GCCTCCTCTGCGGAACGAGAGCAAGTACTTCCAGAGA<br>ATGACCACCACCAGCAGCGTGGAAGGCAAGCAGAAC<br>CTGGTCATCATGGGCAGAAAGACCTGGTTCAGCATCC<br>CCGAGAAGAACAGGCCCCTGAAGGACCGGATCAACA<br>TCGTGCTGAGCAGAGAGCTGAAAGAGCCTCCTAGAGG<br>CGCCCACTTTCTGGCCAAGTCTCTGGACGATGCCCTGC<br>GGCTGATTGAGCAGCCTGAACTTGGCAGCGGCGCCAC<br>AAACTTTTCACTGCTGAAGCAAGCCGGGGATGTCGAA<br>GAGAATCCAGGGCCTATGAAGTCCCTGCGGGTGCTGC<br>TGGTTATCCTGTGGCTGCAGCTGAGCTGGGTCTGGTCC<br>CAGAAACAAGAAGTGACTCAGATCCCAGCCGCTCTGA<br>GTGTGCCTGAGGGCGAAAACCTGGTCCTGAACTGCAG<br>CTTCACCGACAGCGCCATCTACAACCTGCAGTGGTTC<br>AGGCAGGATCCCGGCAAGGGACTGACAAGCCTGCTGC<br>TGATTCAGAGCAGCCAGAGAGAGCAGACCTCCGGCAG<br>ACTGAATGCCAGCCTGGATAAGAGCAGCGGCCGCAGC<br>ACACTGTATATCGCCGCTTCTCAGCCTGGCGATAGCGC<br>CACATATCTGTGTGCCGTGCGACCTCTGTACGGCGGC<br>AGCTACATCCCTACATTTGGCAGAGGCACCAGCCTGA<br>TCGTGCACCCCtacattcagaaccccgatcctgccgtgtatcagctgagagaca<br>gcaagtccagcgacaagagcgtgtgtttgttcaccgattttgattctcaaacaaatgtgtca<br>caaagtaaggattctgatgtgtatatcacagacaaaactgtgctagacatgaggtctatgga<br>cttcaagagcaacagtgctgtggcctggagcaacaaatctgactttgcatgtgcaaacgc<br>cttcaacaacagcattattccagaagacaccttcttccccagcccaggtaagggcagcttt<br>ggtgccttcgcaggctgtttccttgcttcaggaatggccaggttctgcccagagctctggtc<br>aatgatgtctaaaactcctctgattggtggtctcgg | |
| FKBP12$^{F36V}$ -<br>mDHFR_B_<br>TGFBR2_B2M<br>(crB2M-4) | gaagttctccttctgctaggtagcattcaaagatcttaatcttctgggtttccgttttctcgaatg<br>aaaaatgcaggtccgagcagttaactggctggggcaccattagcaagtcacttagcatct<br>ctggggccagtctgcaaagcgagggggcagccttaatgtgcctccagcctgaagtccta<br>gaatgagcgcccggtgtcccaagctggggcgcgcaccccagatcggagggcgccgat<br>gtacagacagcaaactcacccagtctagtgcatgccttcttaaacatcacgagactctaag<br>aaaaggaaactgaaaacgggaaagtccctctctctaacctggcactgcgtcgctggcttg<br>gagacaggtgacggtccctgcgggccttgtcctgattggctgggcacgcgtttaatataa<br>gtggaggcgtcgcgctggcgggcattcctgaagctgacagcattcgggccgagatgtct<br>cgctccgtggccttagctGGAtctGGAGAAGGCAGAGGCagcCTGC<br>TTACATGCGGAGATGTGGAAGAAAATCCTGGACCAAT<br>GGGAAGAGGCCTGCTGAGAGGACTGTGGCCTCTGCAC<br>ATTGTGCTGTGGACCAGAATCGCCAGCACAATCCCTC<br>CACACGTGCAGAAAAGCGTGAACAACGACATGATCGT<br>GACCGACAACAATGGCGCCGTGAAGTTCCCTCAGCTG<br>TGCAAGTTCTGCGACGTGCGGTTCAGCACCTGTGACA<br>ACCAGAAAAGCTGCATGAGCAACTGCAGCATCACCAG<br>CATCTGCGAGAAGCCCCAAGAAGTGTGCGTCGCCGTC<br>TGGCGGAAGAACGACGAGAACATCACCCTGGAAACC<br>GTGTGTCACGACCCCAAGCTGCCCTACCACGACTTCAT<br>CCTGGAAGATGCCGCCTCTCCTAAGTGCATCATGAAG<br>GAAAAGAAGAAGCCCGGCGAGACATTCTTCATGTGCA<br>GCTGCTCCAGCGACGAGTGCAACGACAACATCATCTT<br>CAGCGAAGAGTACAACACCAGCAATCCCGACCTGCTG<br>CTGGTCATCTTCCAGGTGACCGGCATCAGCCTGCTGCC<br>TCCACTGGGAGTTGCCATCAGCGTGATCATCATCTTTT<br>ACTGCTACCGCGTGggatctggcgccaccaatttcagcctgctgaaacagg<br>ctggcgacgtggaagagaaccccggacctATGGGTGTGCAGGTGGAA<br>ACAATCTCTCCGGGAGACGGTCGCACTTTCCCGAAGC<br>GCGGGCAAACCTGTGTCGTACATTACACTGGCATGTT<br>GGAAGATGGAAAAAAGGTCGATAGTTCTCGCGACCGC<br>AATAAGCCATTCAAATTCATGCTGGGGAAGCAGGAGG<br>TTATTCGCGGATGGGAGGAAGGAGTTGCCCAAATGTC<br>TGTGGGACAAAGGGCCAAGTTGACTATTAGTCCCGAC<br>TACGCATACGGGGCGACCGGACACCCCGGTATAATAC<br>CCCCTCACGCCACTCTGGTCTTCGACGTAGAGCTTTTG<br>AAACTCGAGTCAGGGGGCGGATCTGCCAGCAAGGTGG<br>ACATGGTCTGGATCGTCGGCGGCTCCTCTGTGTACCAA<br>GAGGCCATGAATCAGCCCGGACACCTGAGGCTGTTCG<br>TGACCAGAATCATGCAAGAGTTCGAGAGCGACACATT<br>CTTCCCAGAGATCGACCTGGGCAAGTACAAGCTGCTG<br>CCTGAGTATCCCGGCGTGCTGTCTGAGGTGCAAGAGG<br>AAAAGGGCATCAAGTATAAGTTCGAGGTGTACGAGAA | 54 |

TABLE 3-continued

Knockin templates

| Description | Sequence | SEQ ID NO: |
|---|---|---|
| | AAAGGATGGATCCGGCGAAGGCAGAGGATCTCTGCTG | |
| | ACATGTGGCGACGTGGAAGAGAACCCTGGACCTATGG | |
| | ATACCTGCCACATTGCCAAGAGCTGCGTGCTGATCCT | |
| | GCTGGTCGTTCTGCTGTGTGCCGAGCGAGCACAGGGC | |
| | CTCGAGTGCTACAATTGCATTGGCGTGCCACCTGAGA | |
| | CAAGCTGCAACACCACCACCTGTCCTTTCAGCGACGG | |
| | CTTCTGTGTGGCCCTGGAAATCGAAGTGATCGTGGAC | |
| | AGCCACCGGTCCAAAGTGAAGTCCAACCTGTGCCTGC | |
| | CTATCTGCCCCACCACACTGGACAACACCGAGATCAC | |
| | AGGCAACGCCGTGAACGTGAAAACCTACTGCTGCAAA | |
| | GAGGACCTCTGCAACGCCGCTGTTCCAACAGGTGGAA | |
| | GCTCTTGGACTATGGCCGGCGTGCTGCTGTTTAGCCTG | |
| | GTGTCTGTTCTGCTGCAGACCTTCCTGGGATCAGGCGC | |
| | CACGAATTTTAGCCTGCTCAAACAGGCGGGCGACGTA | |
| | GAAGAGAACCCaGGACCTgtgctcgcgctactctctctttctggcctggag | |
| | gctatccagcgtgagtctctcctaccctcccgctctggtccttcctctcccgctctgcaccct | |
| | ctgtggccctcgctgtgctctctcgctccgtgacttcccttctccaagttctccttggtggccc | |
| | gccgtggggctagtccagggctggatctcggggaagcggcggggtggcctgggagtg | |
| | gggaagggggtgcgcacccgggacgcgcgctacttgcccctttcggcggggagcagg | |
| | ggagacctttggcctacggcgacgggagggtcgggacaaagtttagggcgtcgataag | |
| | cgtcagagcgccgaggttgggggagggtttctcttccgctctttcgcggggcctctggctc | |
| | ccccagcgcagctggagtgggggacgggtaggctcgtcccaaaggcgcggcgctgag | |
| | gtttgtgaacgcgtggaggggcgcttggggtctgggggaggcgtcgcccg | |
| FKBP12$^{F36V}$ - | agtatcttggggccaaatcatgtagactcttgagtgatgtgttaaggaatgctatgagtgctg | 55 |
| mDHFR_B_ | agagggcatcagaagtccttgagagcctccagagaaaggctcttaaaaatgcagcgcaa | |
| TGFBR2_B2M | tctccagtgacagaagatactgctagaaatctgctagaaaaaaaacaaaaaaggcatgtat | |
| (crB2M-5) | agaggaattatgagggaaagataccaagtcacggtttattcttcaaaatggaggtggcttgt | |
| | tgggaaggtggaagctcatttggccagagtggaaatggaattgggagaaatcgatgacc | |
| | aaatgtaaacacttggtgcctgatatagcttgacaccaagttagccccaagtgaaataccct | |
| | ggcaatattaatgtgtcttttcccgatattcctcaggtactccaaagattcaggtttactcacgt | |
| | catccagcagagaatggaaagtcaaatttcctgaattgctatgtgtctgggtttcatccatcc | |
| | gacattGGAtctGGAGAAGGCAGAGGCagcCTGCTTACATGC | |
| | GGAGATGTGGAAGAAAATCCTGGACCAATGGGAAGA | |
| | GGCCTGCTGAGAGGACTGTGGCCTCTGCACATTGTGC | |
| | TGTGGACCAGAATCGCCAGCACAATCCCTCCACACGT | |
| | GCAGAAAAGCGTGAACAACGACATGATCGTGACCGA | |
| | CAACAATGGCGCCGTGAAGTTCCCTCAGCTGTGCAAG | |
| | TTCTGCGACGTGCGGTTCAGCACCTGTGACAACCAGA | |
| | AAAGCTGCATGAGCAACTGCAGCATCACCAGCATCTG | |
| | CGAGAAGCCCCAAGAAGTGTGCGTCGCCGTCTGGCGG | |
| | AAGAACGACGAGAACATCACCCTGGAAACCGTGTGTC | |
| | ACGACCCCAAGCTGCCCTACCACGACTTCATCCTGGA | |
| | AGATGCCGCCTCTCCTAAGTGCATCATGAAGGAAAAG | |
| | AAGAAGCCCGGCGAGACATTCTTCATGTGCAGCTGCT | |
| | CCAGCGACGAGTGCAACGACAACATCATCTTCAGCGA | |
| | AGAGTACAACACCAGCAATCCCGACCTGCTGCTGGTC | |
| | ATCTTCCAGGTGACCGGCATCAGCCTGCTGCCTCCACT | |
| | GGGAGTTGCCATCAGCGTGATCATCATCTTTTACTGCT | |
| | ACCGCGTGGgatctggcgccaccaatttcagcctgctgaaacaggctggcgacgt | |
| | ggaagagaaccccggacctATGGGTGTGCAGGTGGAAACAATC | |
| | TCTCCGGGAGACGGTCGCACTTTCCCGAAGCGCGGGC | |
| | AAACCTGTGTCGTACATTACACTGGCATGTTGGAAGA | |
| | TGGAAAAAAGGTCGATAGTTCTCGCGACCGCAATAAG | |
| | CCATTCAAATTCATGCTGGGGAAGCAGGAGGTTATTC | |
| | GCGGATGGGAGGAAGGAGTTGCCCAAATGTCTGTGGG | |
| | ACAAAGGGCCAAGTTGACTATTAGTCCCGACTACGCA | |
| | TACGGGGCGACCGGACACCCCGGTATAATACCCCCTC | |
| | ACGCCACTCTGGTCTTCGACGTAGAGCTTTTGAAACTC | |
| | GAGTCAGGGGGCGGATCTGCCAGCAAGGTGGACATG | |
| | GTCTGGATCGTCGGCGGCTCCTCTGTGTACCAAGAGG | |
| | CCATGAATCAGCCCGGACACCTGAGGCTGTTCGTGAC | |
| | CAGAATCATGCAAGAGTTCGAGAGCGACACATTCTTC | |
| | CCAGAGATCGACCTGGGCAAGTACAAGCTGCTGCCTG | |
| | AGTATCCCGGCGTGCTGTCTGAGGTGCAAGAGGAAAA | |
| | GGGCATCAAGTATAAGTTCGAGGTGTACGAGAAAAAG | |
| | GATGGATCCGGCGAAGGCAGAGGATCTCTGCTGACAT | |
| | GTGGCGACGTGGAAGAGAACCCTGGACCTATGGATAC | |
| | CTGCCACATTGCCAAGAGCTGCGTGCTGATCCTGCTG | |
| | GTCGTTCTGCTGTGTGCCGAGCGAGCACAGGGCCTCG | |
| | AGTGCTACAATTGCATTGGCGTGCCACCTGAGACAAG | |
| | CTGCAACACCACCACCTGTCCTTTCAGCGACGGCTTCT | |
| | GTGTGGCCCTGGAAATCGAAGTGATCGTGGACAGCCA | |
| | CCGGTCCAAAGTGAAGTCCAACCTGTGCCTGCCTATCT | |
| | GCCCCACCACACTGGACAACACCGAGATCACAGGCAA | |
| | CGCCGTGAACGTGAAAACCTACTGCTGCAAAGAGGAC | |

TABLE 3-continued

| Knockin templates | | |
|---|---|---|
| Description | Sequence | SEQ ID NO: |
| | CTCTGCAACGCCGCTGTTCCAACAGGTGGAAGCTCTT GGACTATGGCCGGCGTGCTGCTGTTTAGCCTGGTGTCT GTTCTGCTGCAGACCTTCCTGGGATCAGGCGCCACGA ATTTTAGCCTGCTCAAACAGGCGGGCGACGTAGAAGA GAACCCaGGACCTgaagttgacttactgaagaatggagagagaattgaaaaa gtggagcattcagacttgtctttcagcaaggactggtctttctatctcttgtactacactgaatt cacccccactgaaaaagatgagtatgcctgccgtgtgaaccatgtgactttgtcacagccc aagatagttaagtggggtaagtcttacattcttttgtaagctgctgaaagttgtgtatgagtag tcatatcataaagctgctttgatataaaaaaggtctatggccatactaccctgaatgagtccc atcccatctgatataaacaatctgcatattgggattgtcagggaatgttcttaaagatcagatt agtggcacctgctgagatactgatgcacagcatggtttctgaaccagtagtttccctgcagt tgagcagggagcagcagcagcacttgcacaaatacatatacactcttaacacttcttacct actggcttcctctagcttttg | |

TABLE 4

| Target sequences for siRNAs | | |
|---|---|---|
| Description | Sequence targeted | SEQ ID NO: |
| DHFR siRNA-1 | GAGCAGGTTCTCATTGATAACAAGC | 56 |
| DHFR siRNA-2 | ATCAATTGAGGTACGGAGAAACTGA | 57 |
| DHFR siRNA-3 | GTCATGGTTGGTTCGCTAAACTGCA | 58 |
| DHFR siRNA-4 | GCAGGTTCTCATTGATAACAAGCTC | 59 |
| DHFR siRNA-5 | GTTGACTTTAGATCTATAATTATTT | 60 |
| DHFR siRNA-6 | AAATCATCAATTGAGGTACGGAGAA | 61 |

TABLE 5

| Novel sequences | | |
|---|---|---|
| Description | Sequence | SEQ ID NO: |
| $JUN^{MUT8AA}$ | TIARLEEEVKTLEAKESELASTANMLEEKVAQLEQKV | 6 |
| $FOS^{MUT8AA}$ | LRDTLQAKTDQLKDNQSALQTRIANLLKKQEKLEFIL | 7 |
| $JUN^{MUT8AA}$-mDHFR_A | TIARLEEEVKTLEAKESELASTANMLEEKVAQLEQKVGGGGSGGGGSMVRPLNCIVAVSQNMGIGKNGDFPWPPLRNESKYFQRMTTTSSVEGKQNLVIMGRKTWFSIPEKNRPLKDRINIVLSRELKEPPRGAHFLAKSLDDALRLIEQPEL | 8 |
| $FOS^{MUT8AA}$-mDHFR_B | LRDTLQAKTDQLKDNQSALQTRIANLLKKQEKLEFILGGGGSGGGGSASKVDMVWIVGGSSVYQEAMNQPGHLRLFVTRIMQEFESDTFFPEIDLGKYKLLPEYPGVLSEVQEEKGIKYKFEVYEKKD | 9 |

Example 1

This Example demonstrates that simultaneous knock-out of DHFR and knock-in of a TCR gene construct containing a nuclease-resistant DHFR gene leads to a 5-fold enrichment of T cells with successful TCR knock-in.

Materials and Methods for FIG. 3-FIG. 7

Figure 3:
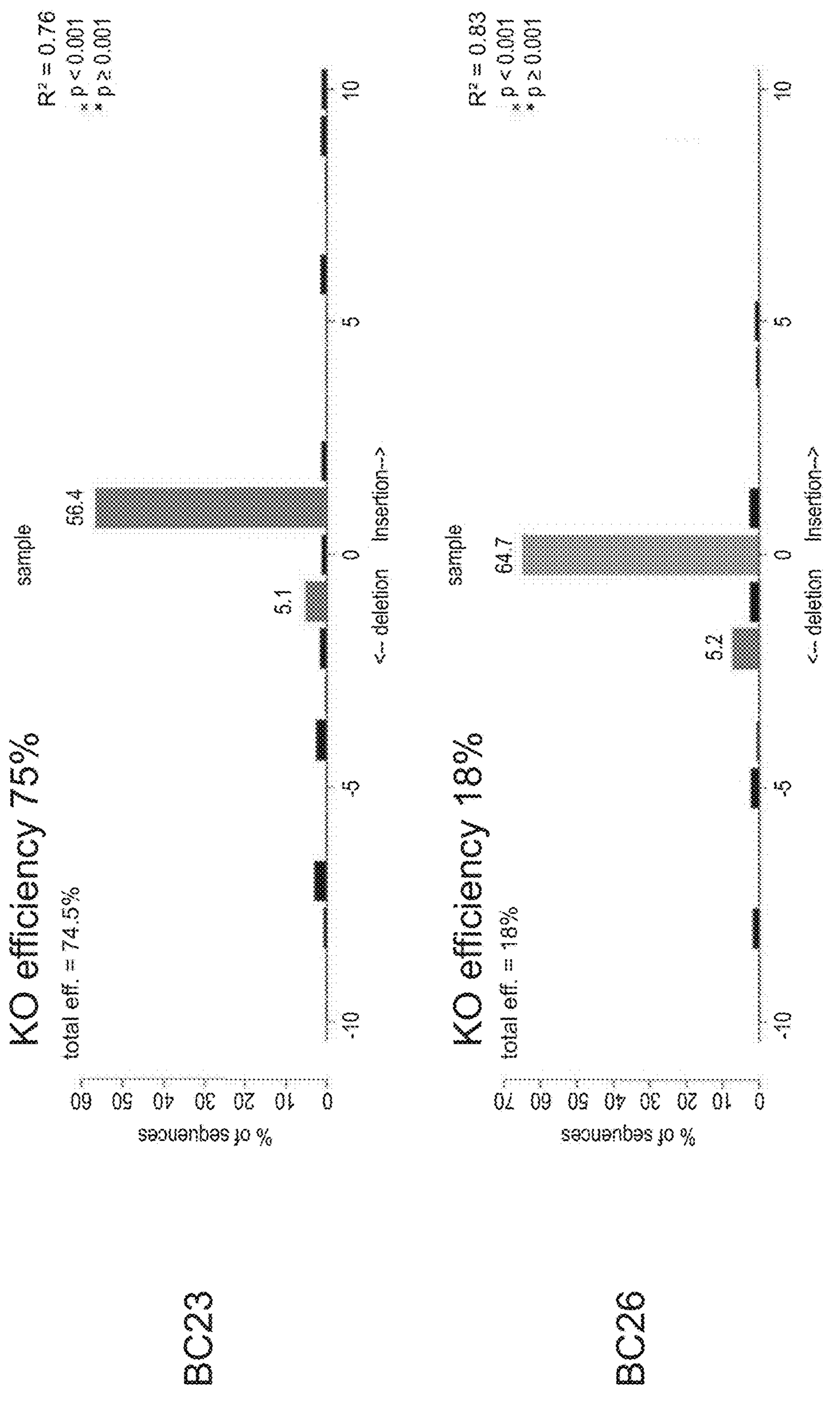
FIG. 3 depicts the results of a TIDE (Tracking of Indels by Decomposition) analysis to determine the knockout efficiency of sgRNA sgDHFR-1 in human T cells from two donors (75% and 18% for BC23 and BC26, respectively).
Figure 4:
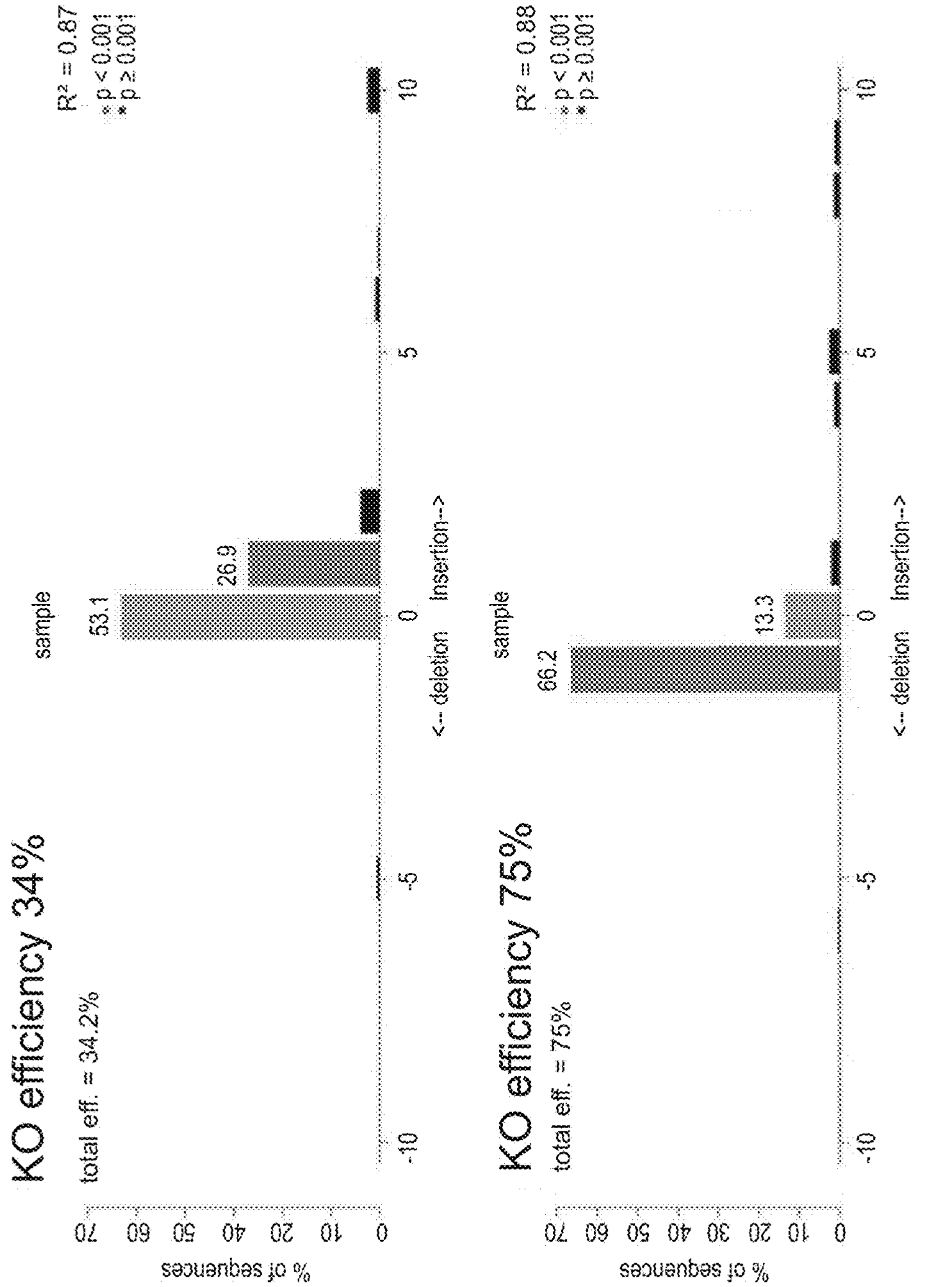
FIG. 4 depicts the results of a TIDE analysis to determine the knockout efficiency of sgRNA sgDHFR-2 in human T cells from two donors (34% and 75% for BC23 and BC26, respectively).
Figure 6:
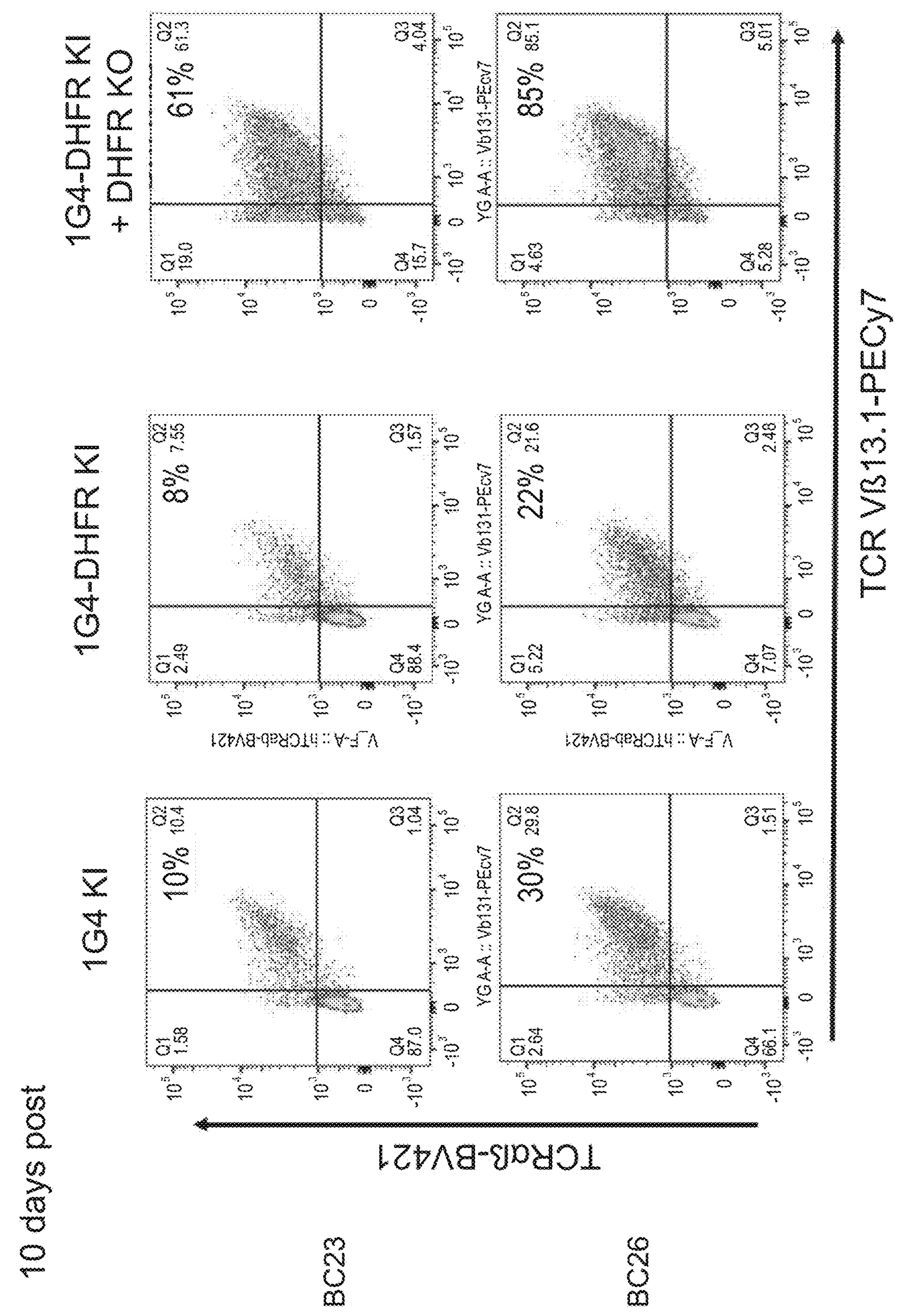
FIG. 6 depicts the results of a FACS analysis to check NY-ESO-1 1G4 TCR knockin efficiency in T cells from two donors at day 10 post-electroporation.
Figure 7:
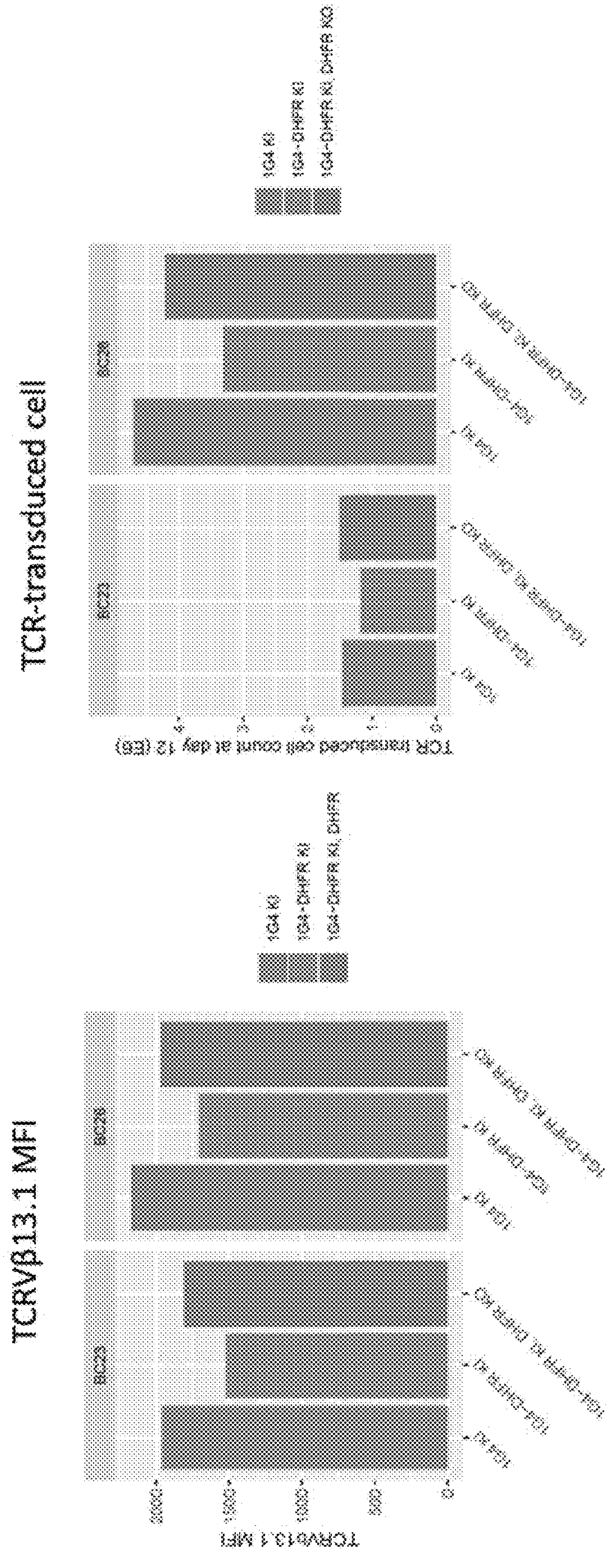
FIG. 7 provides a left panel that shows that TCR expression levels are comparable between 1G4-TCR KI (knockin) T cells and 1G4-TCR-DHFR KI+DHFR KO T cells; right panel shows that the total number of TCR knockin cells are comparable between 1G4-TCR knockin and 1G4-TCR-DHFR KI+DHFR KO T cells in both donor T cells at day 12 post electroporation.

Human primary T cells were isolated and activated by anti-CD3/CD28 beads (ThermoFisher, Cat. #: 111.32D, 3:1 beads:T cells ratio) from two buffy coats isolated from different donors BC23 and BC26. Two days after activation, cells were harvested, and electroporation was performed with cells together with the following components: (1) DHFR sgRNA-1/Cas9 RNP, (2) DHFR sgRNA-2/Cas9 RNP, (3) TRAC sgRNA/Cas9 RNP+knockin template encoding NY-ESO-1 1G4 TCR, (4) TRAC sgRNA/Cas9 RNP+knockin template encoding NY-ESO-1 1G4 TCR and DHFR, (5) TRAC sgRNA/Cas9 RNP+knockin template encoding NY-ESO-1 1G4 TCR and DHFR+DHFR sgRNA-1/Cas9 RNP. The RNP complex was prepared by first annealing crRNA (32 pmol) with TracrRNA (32 pmol) at 95° C. for 5 min, after incubation at room temperature for 10 min, 16 pmol of Cas9 nuclease was added and incubated for 15 min at room temperature. The RNP complex was left on ice until use or at −80° C. for long term storage. The electroporation were performed by mixing 1 million activated T cells (in 20 μl P3 buffer) with 16 pmol RNP complex and 1 μg repair template, electroporation was subsequently started with a Lonza 4D-Nucleofector device with pulse code EH-115. For cells electroporated in conditions (1) and (2), they were harvested at day 5 post electroporation, genomic DNA was isolated, DHFR locus was amplified by PCR and TIDE analysis was performed (FIG. 3 and FIG. 4). For cells electroporated in conditions (3), (4) and (5), cells were harvested for FACS analysis of TCR expression at day 6 (FIG. 5) and day 10 post electroporation (FIG. 6 and FIG. 7 left). At day 12 post electroporation, total cell number was also counted and TCR knockin cells were calculated and plotted (FIG. 7 right).

FIG. 3 depicts the results of a TIDE analysis to determine the knockout efficiency of sgRNA sgDHFR-1 in human T cells from two donors (75% and 18% for BC23 and BC26, respectively) providing evidence that the endogenous DHFR gene can be genetically inactivated within human primary T cells. TIDE stands for "Tracking of Indels by Decomposition," which is a method to measure insertions and deletions (indels) generated in a pool of cells by genome editing tools such as CRISPR/Cas9.

FIG. 4 depicts the results of a TIDE analysis to determine the knockout efficiency of sgRNA sgDHFR-2 in human T cells from two donors (34% and 75% for BC23 and BC26, respectively) providing evidence that the endogenous DHFR gene can be genetically inactivated within human primary T cells.

Figure 5:
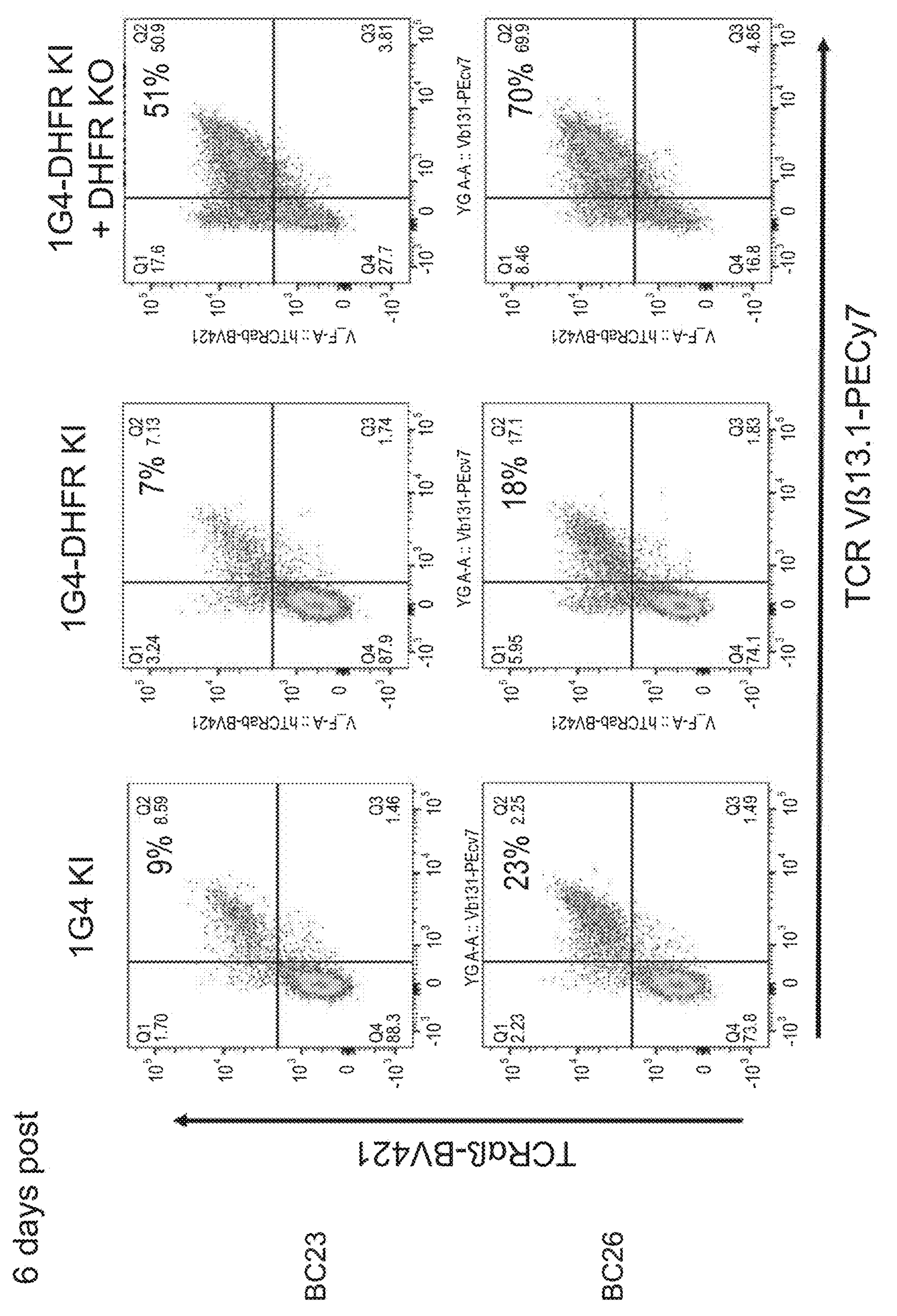
FIG. 5 depicts the results of a FACS analysis to check NY-ESO-1 1G4 TCR knockin efficiency in T cells from two donors at day 6 post-electroporation.

FIG. 5 depicts the results of a FACS analysis to check NY-ESO-1 1G4 TCR knockin efficiency in T cells from two donors (BC23 and BC 26) by staining with an anti-Vβ13.1 (Biolegend, cat #362406) antibody that binds to the β-chain of the 1G4 TCR. The T cells have been electroporated with a TRAC RNP (to generate a DNA double strand break at the TRAC locus) and various repair templates (all containing the NY-ESO-1 1G4 TCR sequence) which repair the double strand DNA break and are therefore incorporated at this site.

Left columns show knockin of a repair template only encoding the NY-ESO-1 1G4 TCR, middle columns show knockin of a repair template encoding the 1G4 TCR linked with the nuclease-resistant DHFR gene (IG4 TCR-DHFR KI), right columns show knockin of 1G4 TCR-DHFR repair template combined with simultaneous knockout of endogenous DHFR using DHFR specific sgRNA. Simultaneous knockout of endogenous DHFR leads to efficient selection of T cells with delivery of the 1G4-DHFR repair template at day 6 post-electroporation as the frequency of T cells with the knockin increased from 9% to 51% (5.7 fold enrichment) and 23% to 70% (3 fold enrichment) for BC23 and BC26, respectively. The data indicate the method described in the invention can enrich genetically-modified cells without requiring physical or drug-mediated selection and without the introduction of a genetic sequence encoding an exogenous gene to enable selection.

FIG. 6 depicts the results of a FACS analysis to check NY-E50-1 1G4 TCR knockin efficiency in T cells from two donors (BC23 and BC 26) when the nuclease resistant DHFR transgene is included in the TCRα/β-encoding DNA repair template in combination with knockout of endogenous DHFR. Left columns show knockin of NY-E50-1 1G4 TCR only, middle columns show knockin of 1G4 TCR-DHFR, right columns show knockin of 1G4 TCR-DHFR with simultaneous knockout of endogenous DHFR. The data demonstrate that simultaneous knockout of endogenous DHFR leads to efficient selection of T cells with the 1G4-DHFR KI at day 10 post-electroporation as the frequency of T cells with the knockin increased from 10% to 61% (6.1 fold enrichment) and 30% to 85% (2.8 fold enrichment) for BC23 and BC26, respectively. The data indicate the method described in the invention can enrich genetically-modified cells without requiring physical or drug-mediated selection and without the introduction of a genetic sequence encoding an exogenous gene to allow for selection.

The above data indicate that the method can enrich genetically-engineered cells without requiring physical or drug-mediated selection and without the introduction of a genetic sequence encoding an exogenous gene to enable selection.

There are various strategies to achieve enrichment of gene-edited T cells by knockin of a DNA repair template encoding the therapeutic gene(s) of interest (e.g. TCRα and TCRβ) and an siRNA- or inhibitor-resistant DHFR gene and using an siRNA or an inhibitor (Methotrexate) to suppress endogenous DHFR function rather than knocking it out.

FIG. 7 provides a left panel that shows that TCR expression levels were comparable between 1G4-TCR KI (knockin) T cells and 1G4-TCR-DHFR KI+DHFR KO T cells based on the FACS analysis of TCRVβ13.1 antibody fluorescence intensity in human T cells from two donors (BC23 and BC26). The anti-Vβ13.1 antibody binds to the β-chain of the 1G4 TCR. This data demonstrates that TCR expression achieved with the invention is comparable to site-specific integration of unmodified TCR transgenes.

Right panel shows that the total number of TCR knockin cells are comparable between 1G4-TCR knockin and 1G4-TCR-DHFR KI+DHFR KO T cells in both donor T cells at day 12 post electroporation, demonstrating that T cells modified using the method proliferate after genetic engineering.

Figure 8:
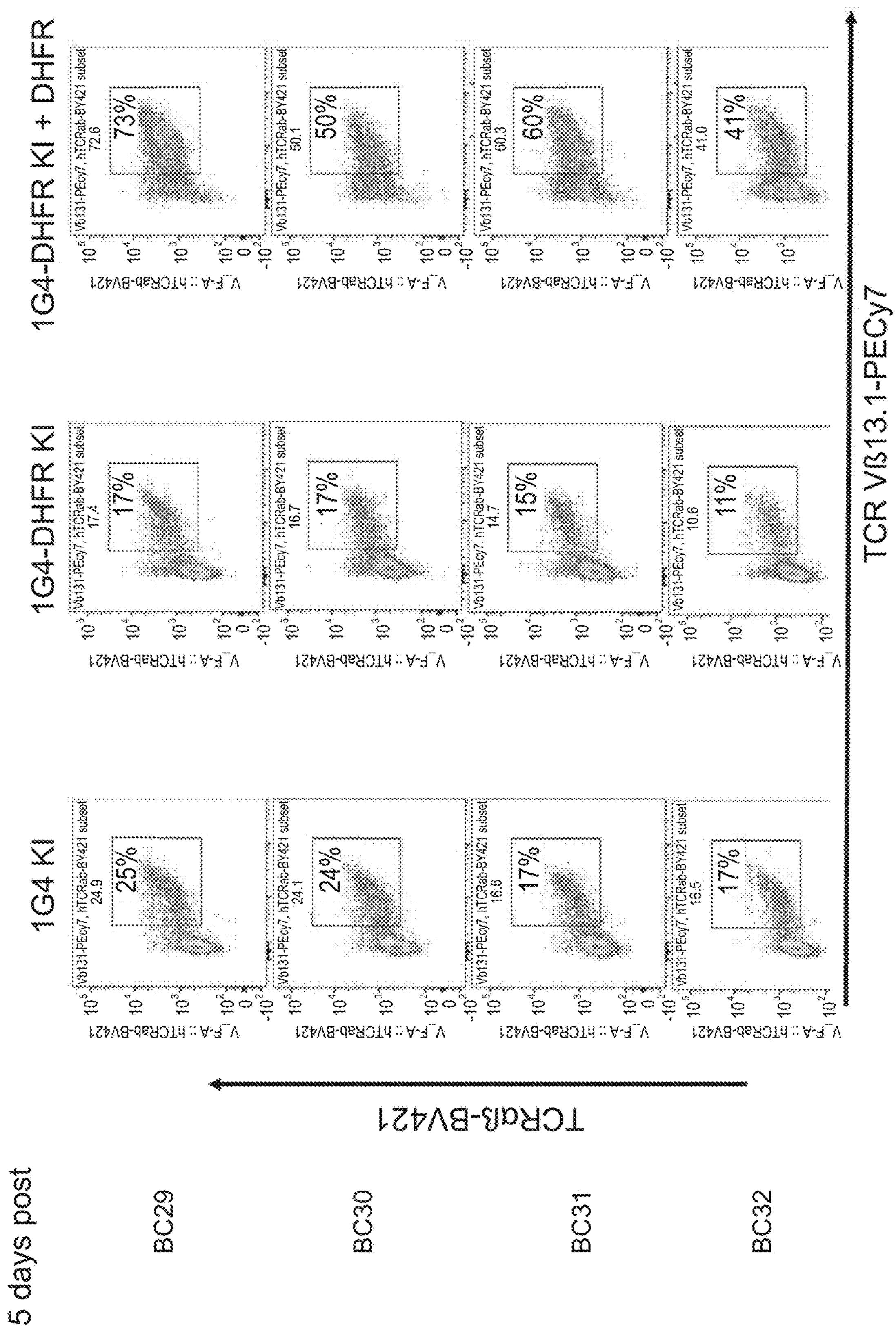
FIG. 8 depicts the results of a FACS analysis to check NY-ESO-1 1G4 TCR knockin efficiency in T cells from four donors (BC29, BC30, BC31, and BC32) at day 5 post electroporation.
Figure 9:
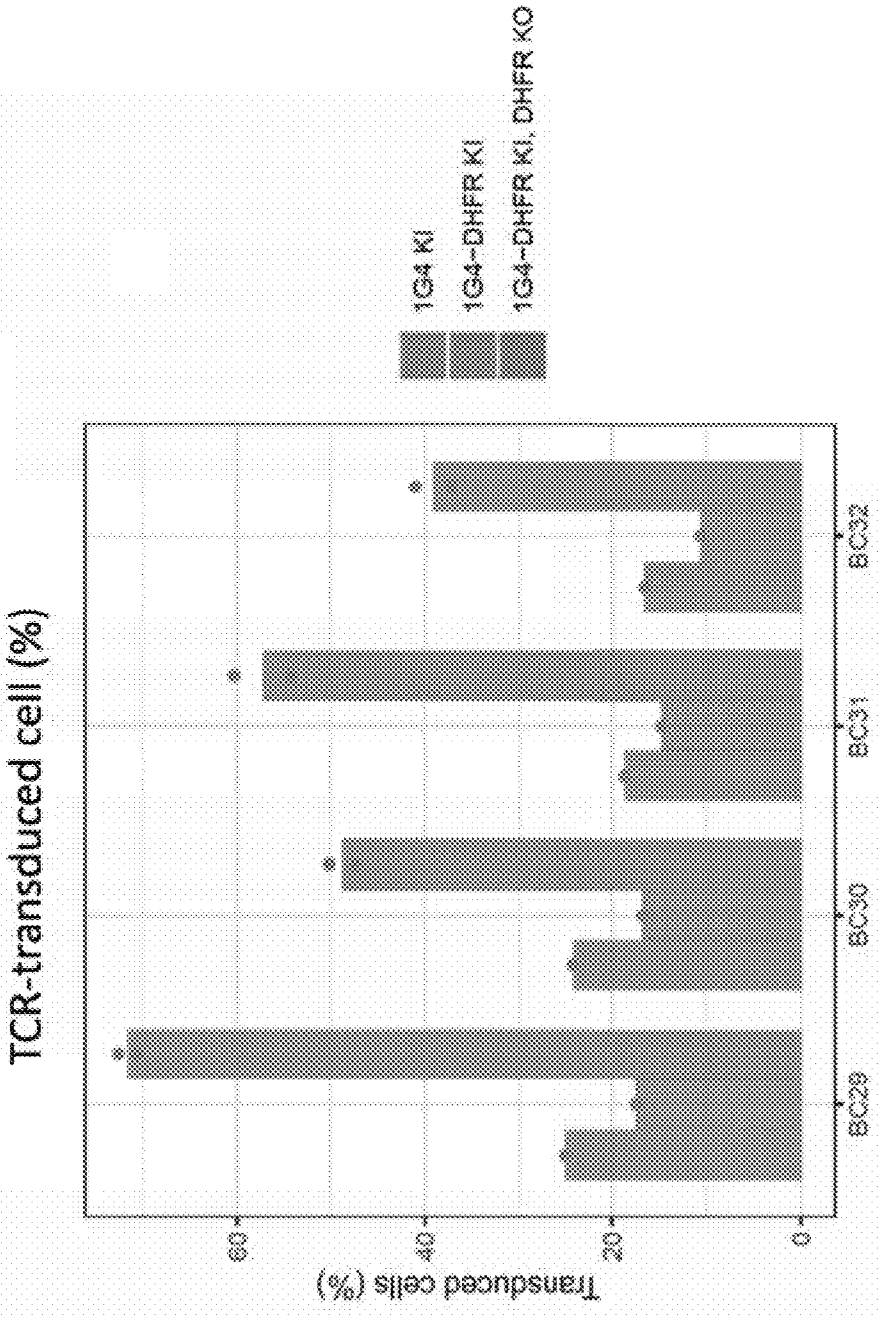
FIG. 9 provides the quantification data of FIG. 8.
Figure 10:
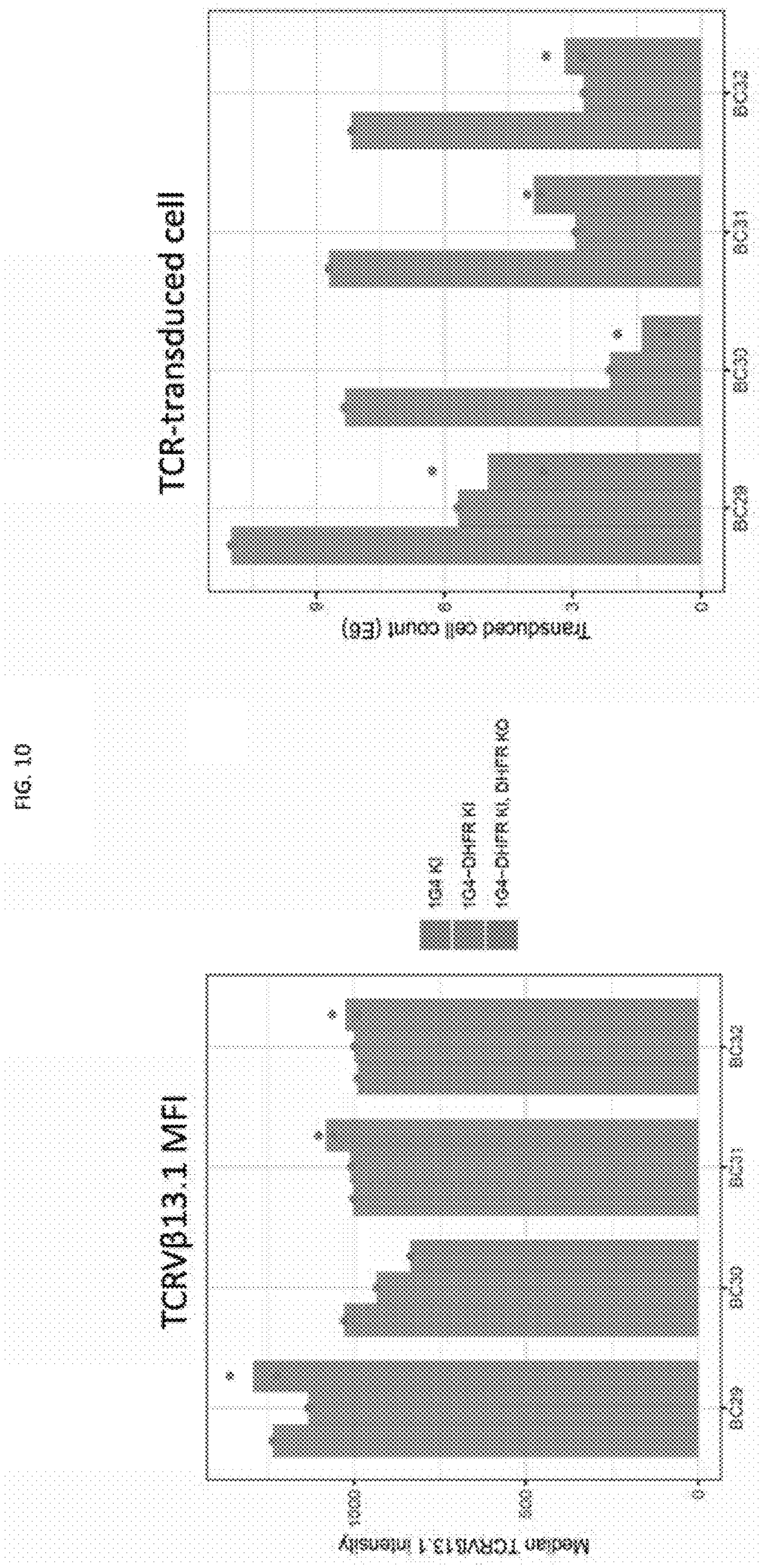
FIG. 10 provides a left panel showing that TCR expression levels are comparable between 1G4-TCR KI and 1G4-TCR-DHFR KI+DHFR KO cells; right panel shows that the total number of TCR knockin cells for the 1G4-TCR knockin condition is higher compared to either the 1G4-DHFR-KI T cells or 1G4-TCR-DHFR KI+DHFR KO T cells in four donor T cells.

Materials and Methods for FIG. 8-FIG. 10

Human primary T cells were isolated and activated by anti-CD3/CD28 beads from four buffy coats from different donors BC29, BC30, BC31 and BC32. Two days after activation, cells were harvested, and electroporation was performed with cells together with the following components: (1) TRAC sgRNA/Cas9 RNP+knockin template encoding NY-ESO-1 1G4 TCR, (2) TRAC sgRNA/Cas9 RNP+knockin template encoding NY-ESO-1 1G4 TCR and DHFR, (3) TRAC sgRNA/Cas9 RNP+knockin template encoding NY-ESO-1 1G4 TCR and DHFR+DHFR sgRNA-1/Cas9 RNP. Electroporation and transduction parameters were the same as above. Cells were harvested for FACS analysis of TCR expression at day 5 (FIG. 8, FIG. 9 and FIG. 10 left). At day 12 post electroporation, total cell number was also counted and TCR knockin cells were calculated and plotted (FIG. 10 right).

FIG. 8 depicts the results of a FACS analysis to check NY-ESO-1 1G4 TCR knockin efficiency in T cells from four donors (BC29, BC30, BC31, and BC32) at day 5 post electroporation when the nuclease resistant DHFR transgene is included in the TCRα/β-encoding DNA repair template in combination with knockout of endogenous DHFR. Left columns show knockin of NY-ESO-1 1G4 TCR, middle columns show knockin of 1G4 TCR-DHFR, right columns show knockin of 1G4 TCR-DHFR with simultaneous knockout of endogenous DHFR; The anti-Vβ13.1 antibody binds to the β-chain of the 1G4 TCR. The data shows that the knockin efficiency for BC23 increased from 25% to 73%; from 24% to 50% for BC30; from 17% to 60% for BC31 and from 17% to 41% for BC32 at day 5 post electroporation. This indicates that the method described in the invention can enrich genetically-modified cells without requiring physical or drug-mediated selection and without the introduction of a genetic sequence encoding an exogenous gene to enable selection.

FIG. 9 provides the quantification data of FIG. 8 indicating that the method can enrich genetically-modified cells without requiring physical or drug-mediated selection and without the introduction of a genetic sequence encoding an exogenous gene to enable selection.

FIG. 10 provides a left panel showing that TCR expression levels are comparable between 1G4-TCR KI and 1G4-TCR-DHFR KI+DHFR KO cells based on the FACS analysis of TCRVβ13.1 fluorescence intensity in human T cells from four donors (BC29, BC30, BC31, and BC32), the anti-Vβ13.1 antibody binds to the β-chain of the 1G4 TCR. Right panel shows that the total number of TCR knockin cells for 1G4-TCR knockin condition is higher compared to either the 1G4-DHFR-KI T cells or 1G4-TCR-DHFR KI+DHFR KO T cells in four donor T cells.

Figure 11:
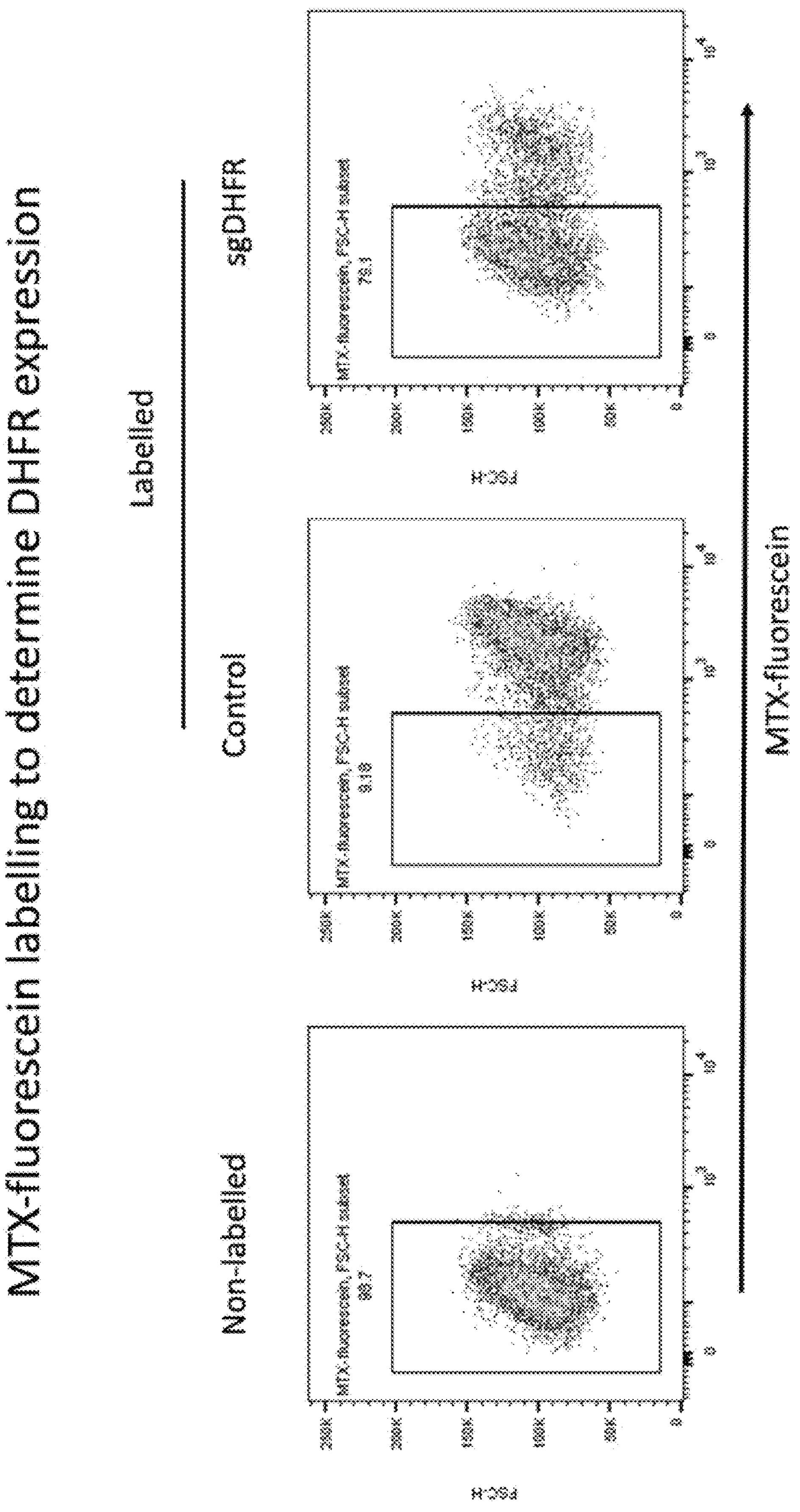
FIG. 11 provides the results of using MTX-fluorescein labeling to determine DHFR expression.

Materials and Methods for FIG. 11-FIG. 12

Human primary T cells were isolated and activated by anti-CD3/CD28 beads from buffy coats BC33 and BC35. Two days after activation, cells were harvested, and electroporation was performed with cells together with the following components: (1) DHFR sgRNA/Cas9 RNP targeting 10 different sites in the DHFR locus, (2) DHFR siRNA targeting 6 different sites in the DHFR mRNA. Three days post electroporation, cells were incubated with MTX-fluorescein overnight and then were harvested for FACS analysis of fluorescein expression (FIG. 12).

FIG. 11 provides the results of using MTX-fluorescein labeling to determine DHFR expression, left panel shows cells without labeling are largely negative for the fluorescein staining; the middle and right figures are cells that have been labeled with MTX-fluorescein; the middle figure shows that control cells (wild-type) are largely positive for the fluorescein staining; the right panel shows that cells that have been electroporated with a DHFR sgRNA are predominantly negative for the MTX-fluorescein staining. This data suggests that fluorescein-labelled MTX can be used to identify DHFR-knockout cells.

FIG. 12, left panel shows the method described in FIG. 11 to screen for efficient guide RNAs which target DHFR; right panel, use of the method described in FIG. 11 to screen for efficient siRNAs which target DHFR.

The results above demonstrate that: 1) DHFR selection strategy can enrich TCR knockin cells robustly, and 2) MTX labelling is able to quantify DHFR expression.

Example 2

This example shows that a method according to some embodiments could efficiently enrich genetically-modified T cells by introducing a mutant DHFR gene and subsequently selecting with the clinically-approved drug methotrexate (MTX).

T cells from three donors (BC37, BC38, and BC39) were either knocked in using CRISPR/Cas9 with a control repair template encoding the NY-ESO-1 1G4 TCR (1G4 KI) or a repair template encoding the 1G4 TCR linked with the methotrexate (MTX)-resistant DHFR mutant gene (1G4-DHFRm KI). The T cells were then stained with an anti-Vβ13.1 (Biolegend, cat #362406) antibody that binds to the β-chain of the 1G4 TCR. For cells that were repaired with 1G4-DHFRm KI templates, they were treated with 0.1 μM MTX at day 3 post electroporation for 4 days. For cells that were repaired with 1G4 KI templates, they were left untreated until FACS analysis was performed. FACS analysis was performed on day 11 post electroporation.

Figures 13A, 13B, 13C:
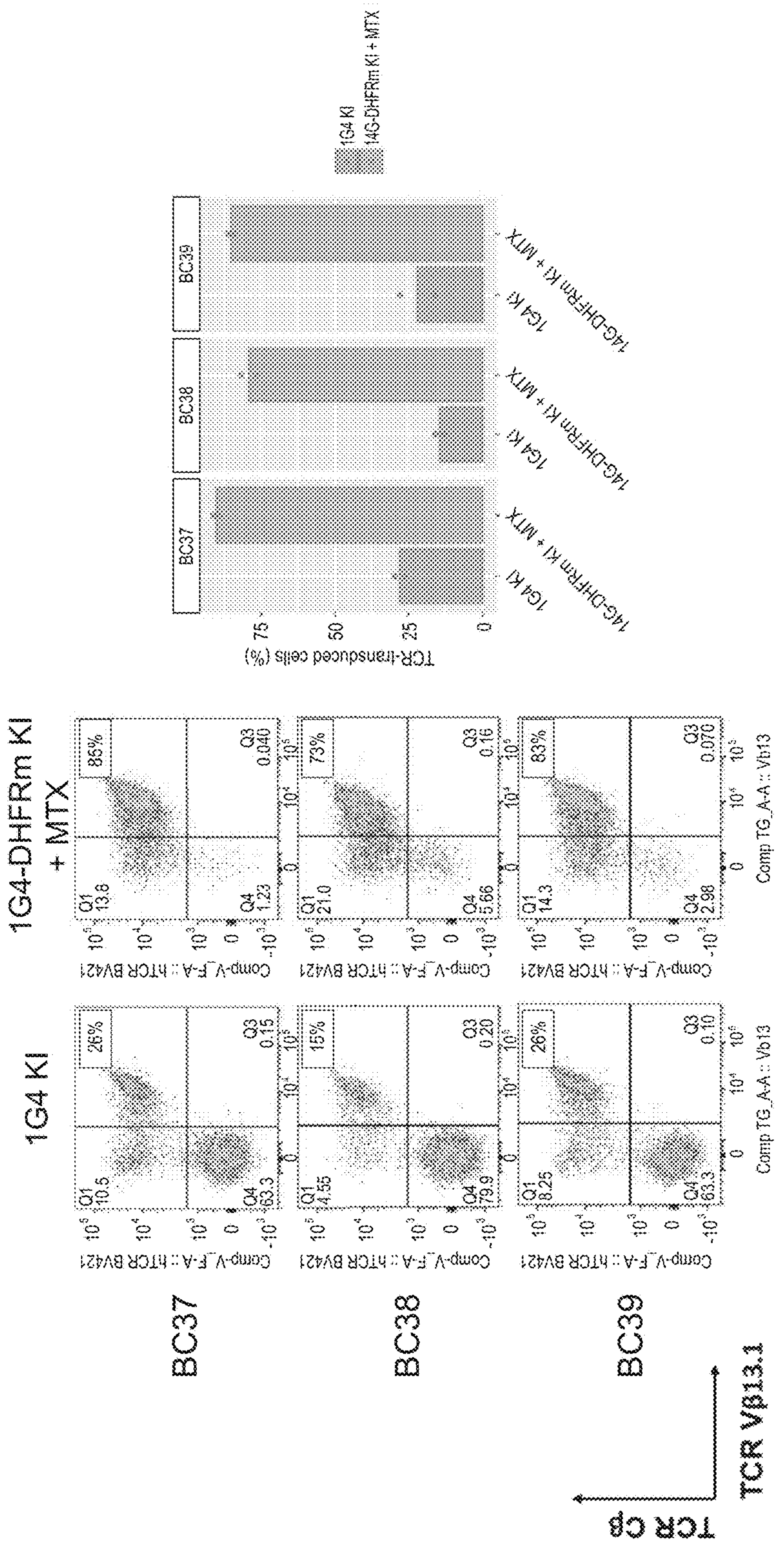
FIG. 13A are FACS plots showing T cells with knockin of the control repair template 1G4 KI, FIG. 13B are FACS plots showing T cells with knockin of the repair template 1G4-DHFRm KI, and FIG. 13C are bar charts showing the quantification of FIG. 13A and FIG. 13B with three donors (BC37, BC38, and BC39) and two technical replicates.

FIG. 13A are FACS plots showing the T cells with knockin of the control repair template 1G4 KI, FIG. 13B are FACS plots showing the T cells with knockin of the repair template 1G4-DHFRm KI, and FIG. 13C are bar charts showing the quantification of FIG. 13A and FIG. 13B with two technical replicates.

The data in FIG. 13A-C shows that introduction of MTX-resistant DHFRm and subsequent treatment of the cells with MTX leads to an efficient selection of knockin T cells, as the frequency of T cells with successful knockin increased from 26% to 85% (3.3 fold enrichment), 15% to 73% (4.9 fold enrichment) and 26% to 83% (3.2 fold enrichment) for BC37, BC38, and BC39, respectively. The data indicates that the method described in the invention can efficiently enrich genetically-modified cells by introducing a mutant DHFR gene and subsequently selecting with the clinically-approved drug MTX.

Figure 14:
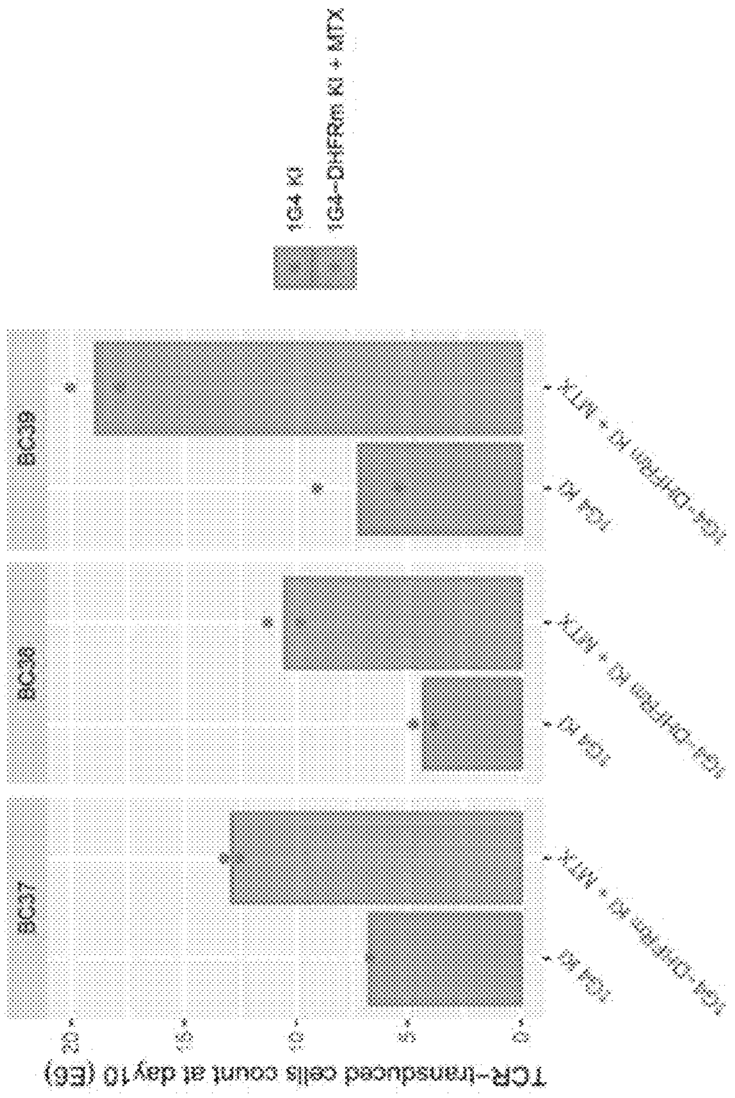
FIG. 14 are bar plots showing the T cell expansion of the two knockin conditions described on FIG. 13.

FIG. 14 are bar plots showing the T cell expansion of the two knockin conditions described in FIG. 13. Total cell numbers were counted at day 10 post electroporation and TCR knockin cell numbers were calculated based on the FACS analysis of the knockin efficiency. The data indicated that by applying the MTX selection strategy, the yield of TCR knockin cells is 2-3-fold higher compared with the conventional non-selected method, in three donors.

Example 3

This example shows that a method according to some embodiments that efficiently enriched genetically-modified T cells did not significantly alter the proportion of CD4+ cells. CD4+ cells are one of the two main subsets of human T cells (the other being CD8+ T cells). An abnormal proportion of CD4+ cells would indicate impaired immune function.

Figure 15:
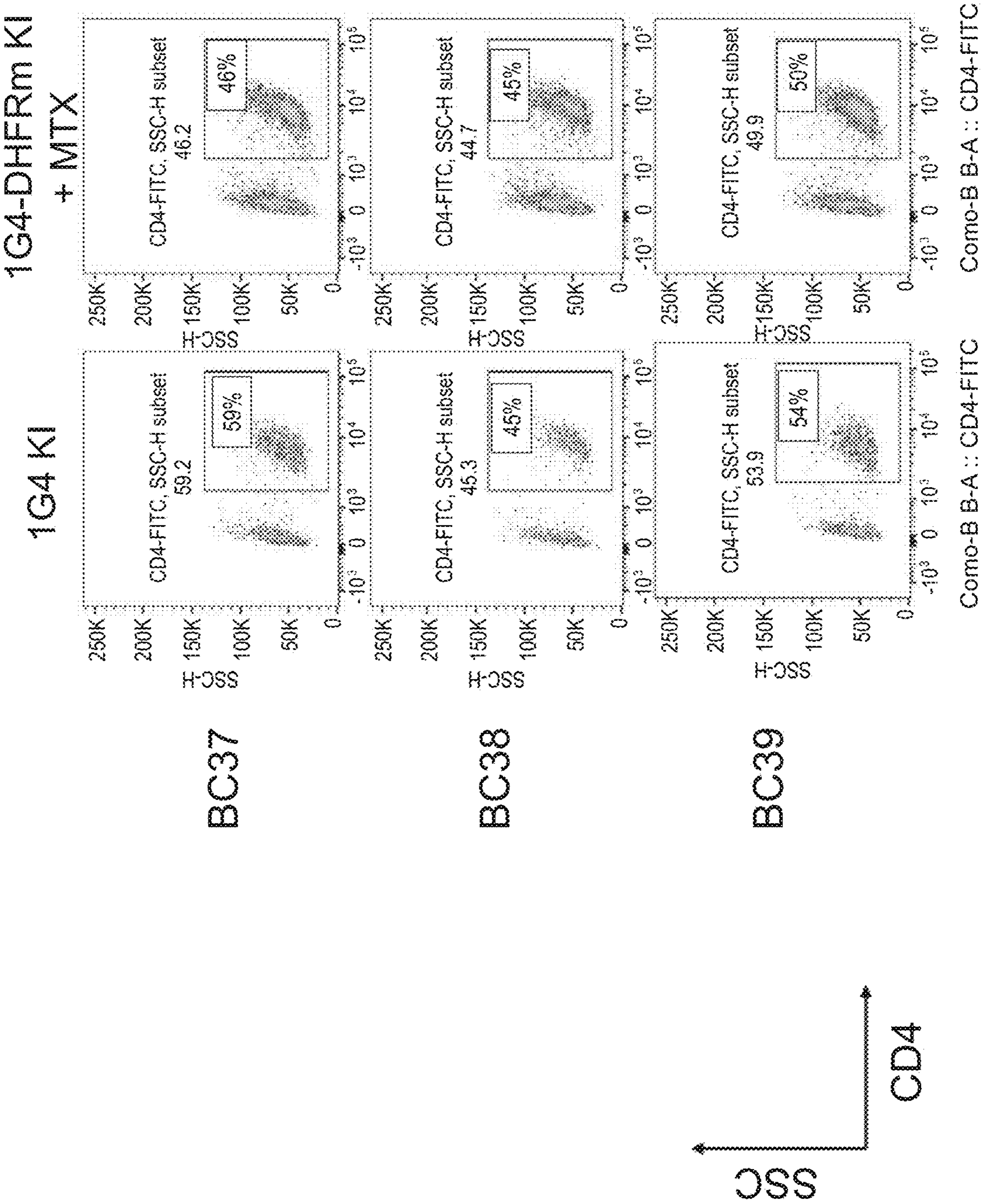
FIG. 15 shows FACS analysis of the proportion of $CD4^+$ cells in the two knockin conditions described on FIG. 13 by staining with an anti-CD4 antibody.

FIG. 15 shows FACS analysis of the proportion of CD4+ cells in the two knockin conditions described in FIG. 13 by staining with an anti-CD4 antibody (BD Bioscience, cat #: 345768). The data indicated that the proportion of CD4+ cells was comparable between the two conditions, and therefore the MTX-selection strategy did not significantly alter the proportion of CD4+ cells.

Example 4

This example shows that a method according to some embodiments did not significantly alter the phenotype of the enriched genetically-modified T cells.

Figure 16:
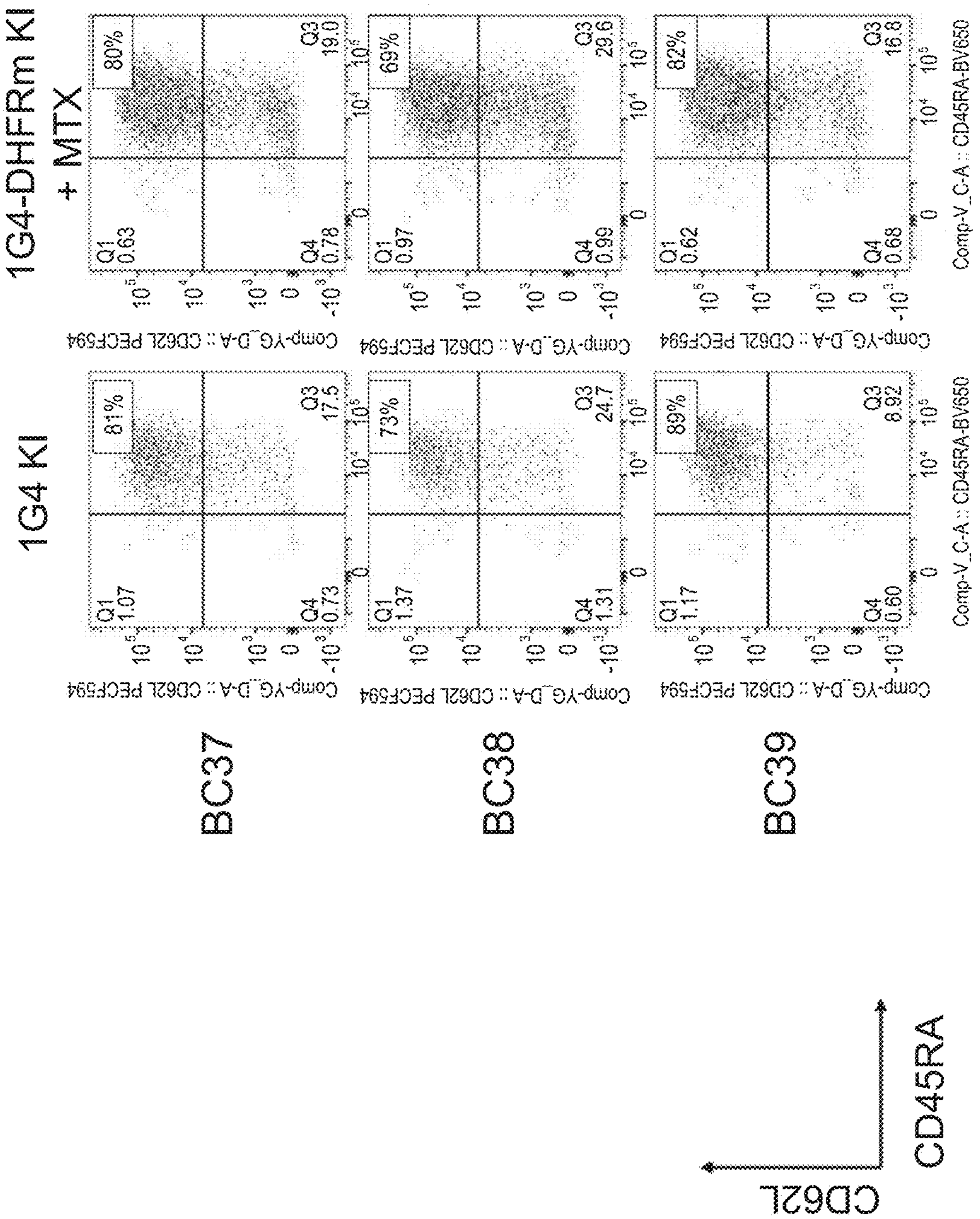
FIG. 16 shows FACS analysis of the phenotype of TCR knockin cells by staining with an anti-CD45RA and an anti-CD62L antibody.

FIG. 16 shows FACS analysis of the phenotype of TCR knockin cells in the two knockin conditions described in FIG. 13 by staining with an anti-CD45RA (BD Biosciences, cat #: 563963) and an anti-CD62L antibody (BD Biosciences, cat #: 562330). The CD45RA+CD62L+ population reflects a naïve stem cell-like phenotype, which is highly functional. The data indicated that the proportion of CD45RA+CD62L+ cells was comparable between the two knockin conditions, and therefore the MTX-selection strategy did not significantly alter the phenotype of the cells.

Figure 17:
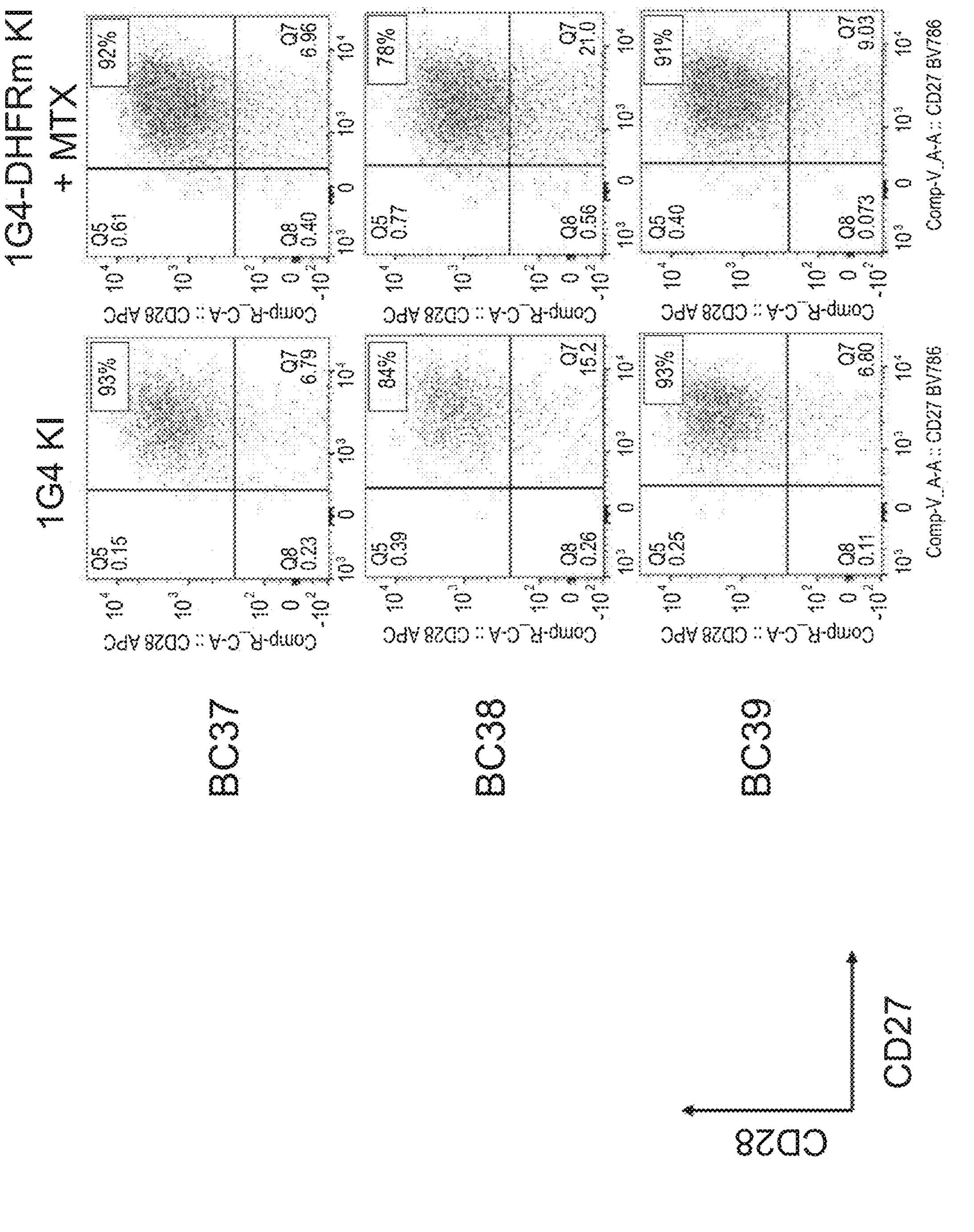
FIG. 17 shows FACS analysis of the phenotype of TCR knockin cells by staining with an anti-CD27 and an anti-CD28 antibody.

FIG. 17 shows FACS analysis of the phenotype of TCR knockin cells in the two knockin conditions described in FIG. 13 by staining with an anti-CD27 (BD Biosciences, cat #: 740972) and an anti-CD28 antibody (BD Biosciences, cat #: 559770). The co-receptors CD27 and CD28 are T cell costimulatory molecules and therefore, the double-positive cells are considered highly functional T cells. The data indicated that the proportion of CD27+CD28+ cells was comparable between the two knockin conditions, and therefore the MTX-selection strategy did not significantly alter the phenotype of the cells.

Example 5

This example shows the enriched genetically-modified T cells generated by a method according to some embodiments have similar cytolytic capacity as T cells generated without selection.

Figure 18:
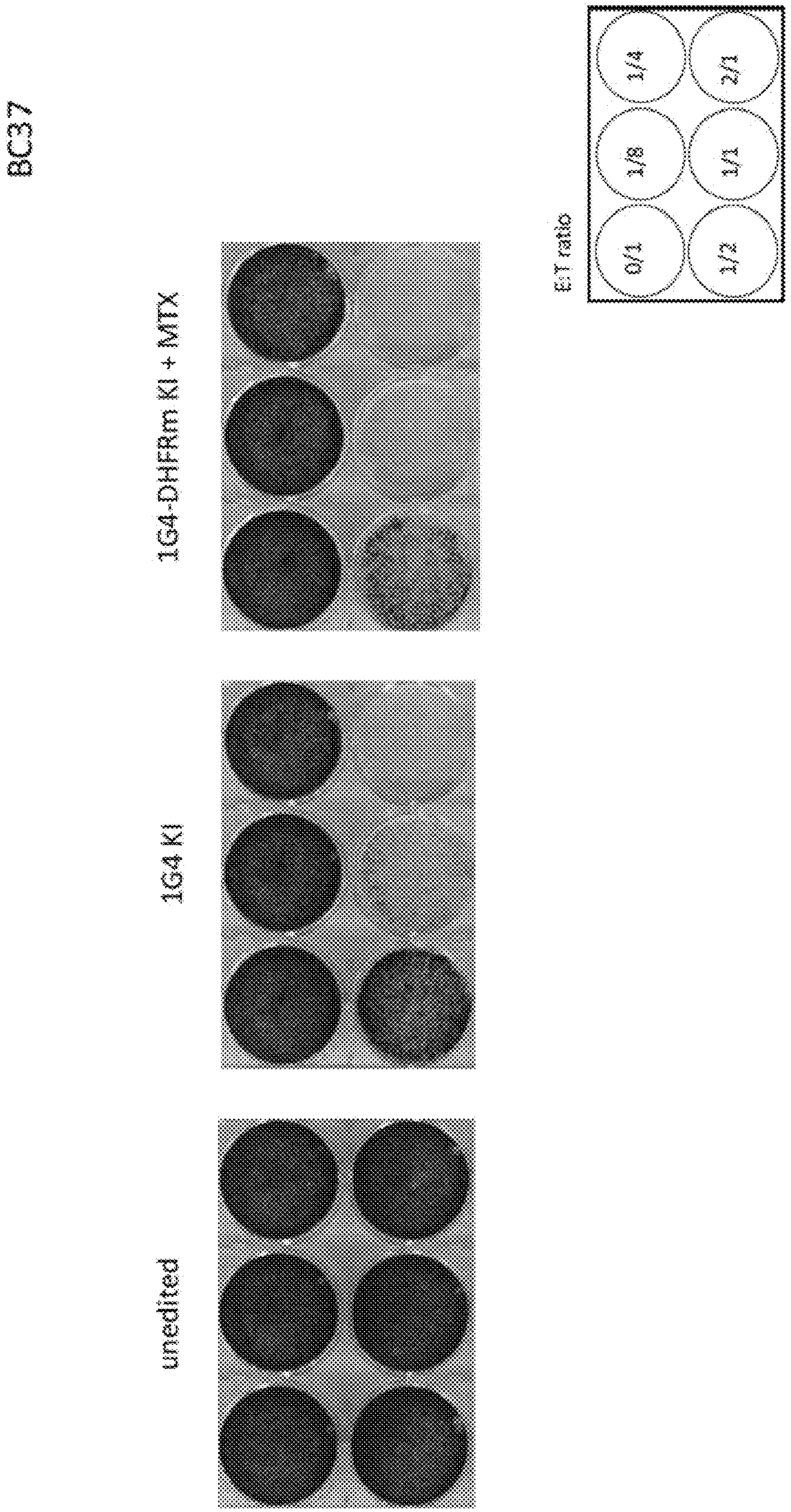
FIG. 18 shows colony formation assay to determine the cytolytic capacity of T cells by co-culturing with tumor cells (donor BC37).

Human melanoma A375 cells (HLA-A*02:01+NY-ESO-1+) were plated in a six-well plate and different numbers of NY-ESO-1 1G4 TCR knockin T cells as generated in Example 2 (from Donor BC37) were added (E:T ratio from 0:1 to 2:1). After 5 days, the remaining tumor cells were fixed with formaldehyde and stained with crystal violet solution. As shown in FIG. 18, the left plate was co-cultured with unedited T cells, the middle plate was co-cultured with 1G4-knockin T cells (1G4 KI) and the right plate was with MTX-selected 1G4-DHFRm-knockin T cells (1G4-DHFRm KI+MTX). The results indicated that this co-culture assay can demonstrate TCR-specific tumor cell killing, as unedited T cells that do not have NY-ESO-1 1G4 TCR expression cannot kill the tumor cells, while 1G4 TCR knockin T cells (middle and right plates) can efficiently eliminate tumor cells at medium to high E:T ratios. The results also demonstrated that T cells generated by the MTX-selection method (right plate) have similar cytolytic capacity as T cells generated without selection (middle plate).

Figure 19:
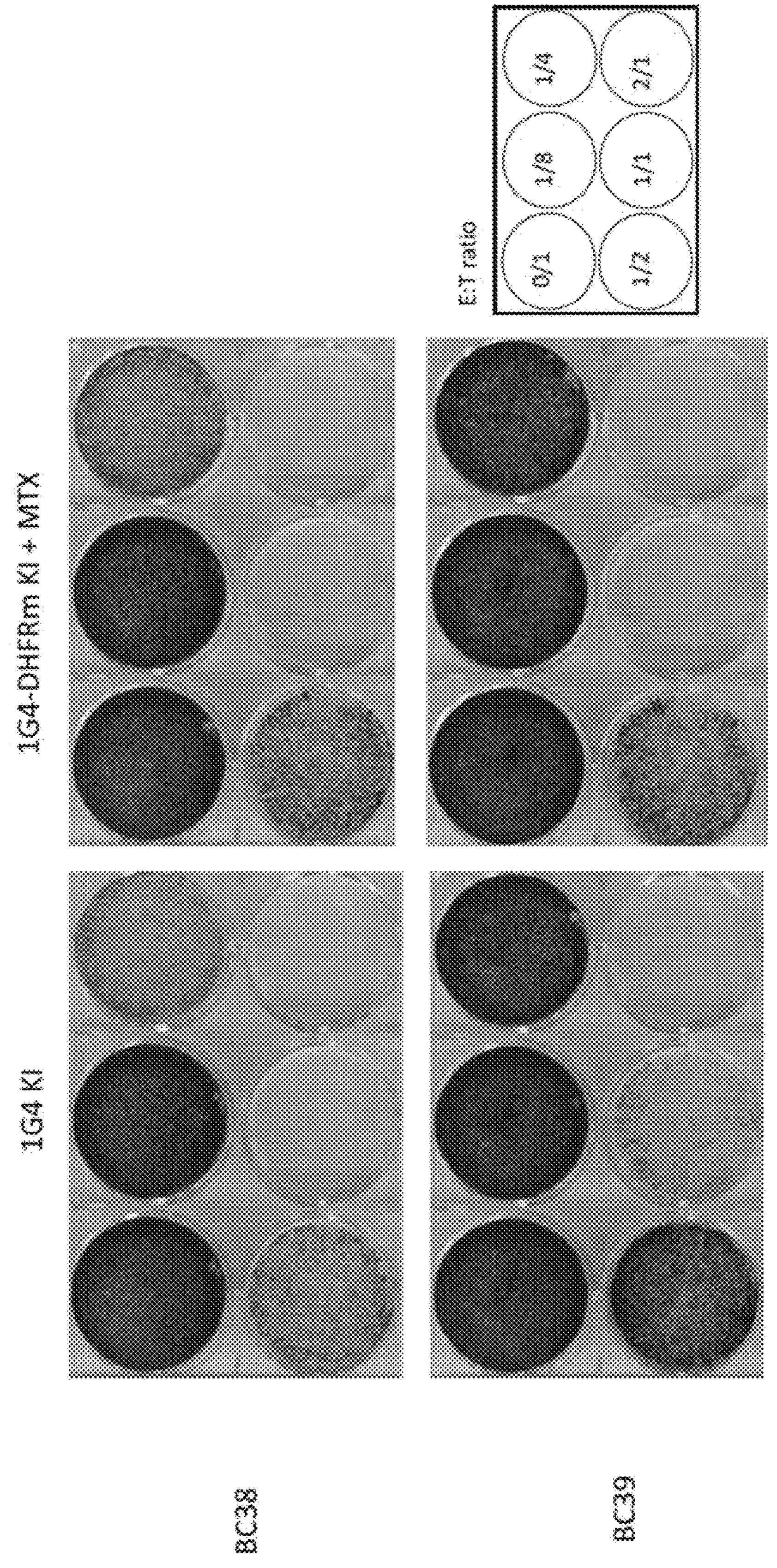
FIG. 19 shows tumor-T cell co-culture assay with T cells derived from two additional donors (BC38 and BC39).

FIG. 19 shows tumor-T cell co-culture assay with T cells derived from two additional donors (BC38 and BC39). The results confirmed that T cells generated by the MTX-selection method (right column) have similar cytolytic capacity as T cells generated without selection (left column).

Example 6

This example shows the enriched genetically-modified T cells generated by a method according to some embodiments have similar IFNγ and IL2 production capacity as T cells generated without selection.

Figure 20:
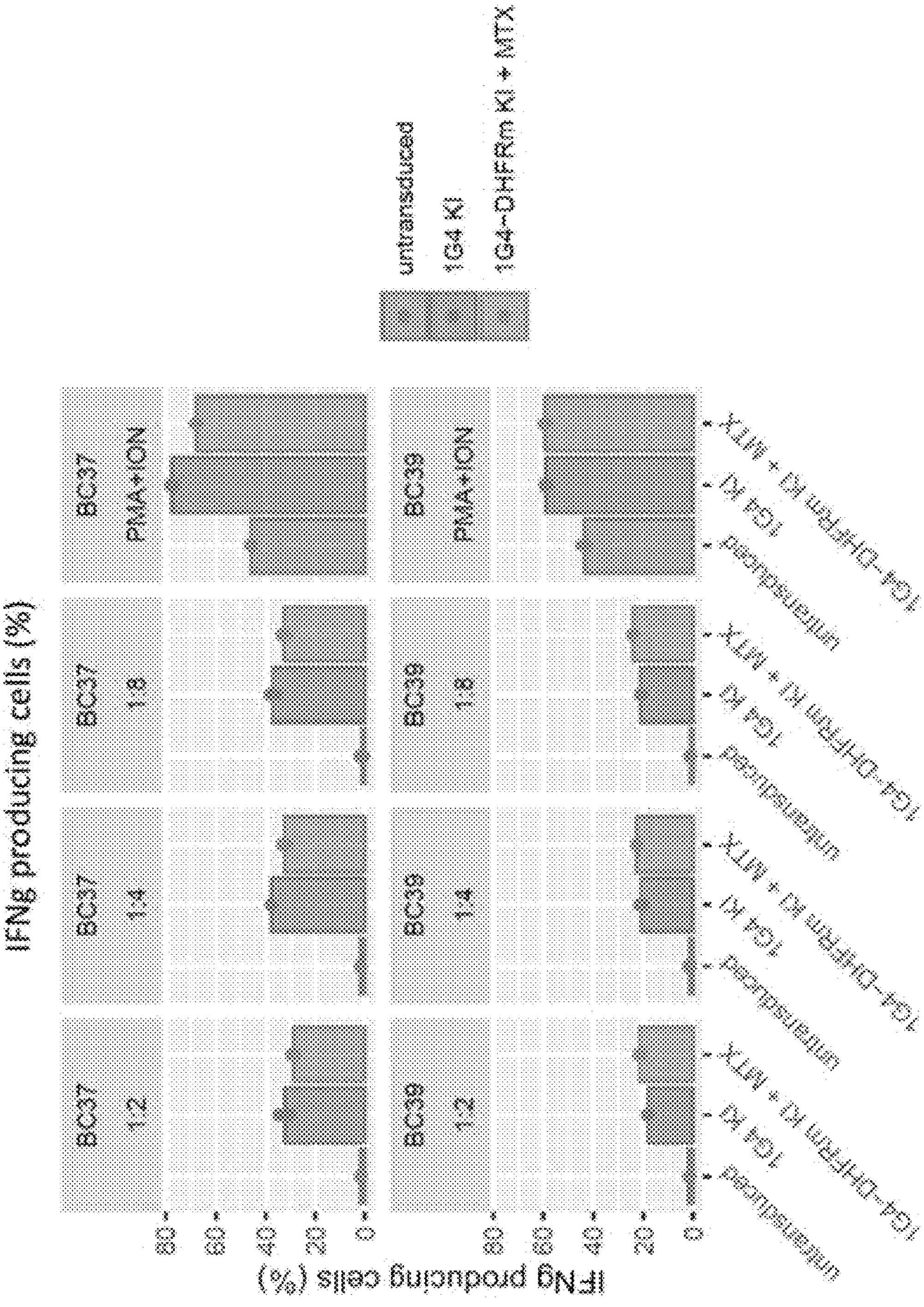
FIG. 20 are bar plots showing the IFNγ production capacity of T cells when stimulated with tumor cells.

IFNγ is a cytokine that plays a central role in immune responses, and it is considered one of the key features of activated T cells. To study the IFNγ production capacity of the enriched genetically-modified T cells (as generated in Example 2), human melanoma A375 (HLA-A*02:01+NY-ESO-1+) cells were plated in 96-well plates and different numbers of NY-ESO-1 1G4 TCR knockin T cells (from two donors, FIG. 20, first row: donor BC37, second row: donor BC39) were added (E:T ratio of 1:2 to 1:8, first three columns). As a positive control for stimulation, PMA and Ionomycin (PMA+ION, right column) were added. The T cells were stimulated overnight in the presence of brefeldin A (Golgi-plug BD Biosciences, cat #: 554724) to prevent the cytokine secretion and collected for FACS analysis of IFNγ production by intracellular staining with an anti-IFNγ antibody (BD Biosciences, cat #: 340452) and an anti-IL2 antibody (BD Biosciences, cat #: 340448). The proportion of IFNγ-producing T cells were plotted as shown in FIG. 20. The data indicated that the T cells generated by the MTX-selection method (1G4-DHFRm KI+MTX) have similar IFNγ production capacity as T cells generated without selection (1G4 KI).

Figure 21:
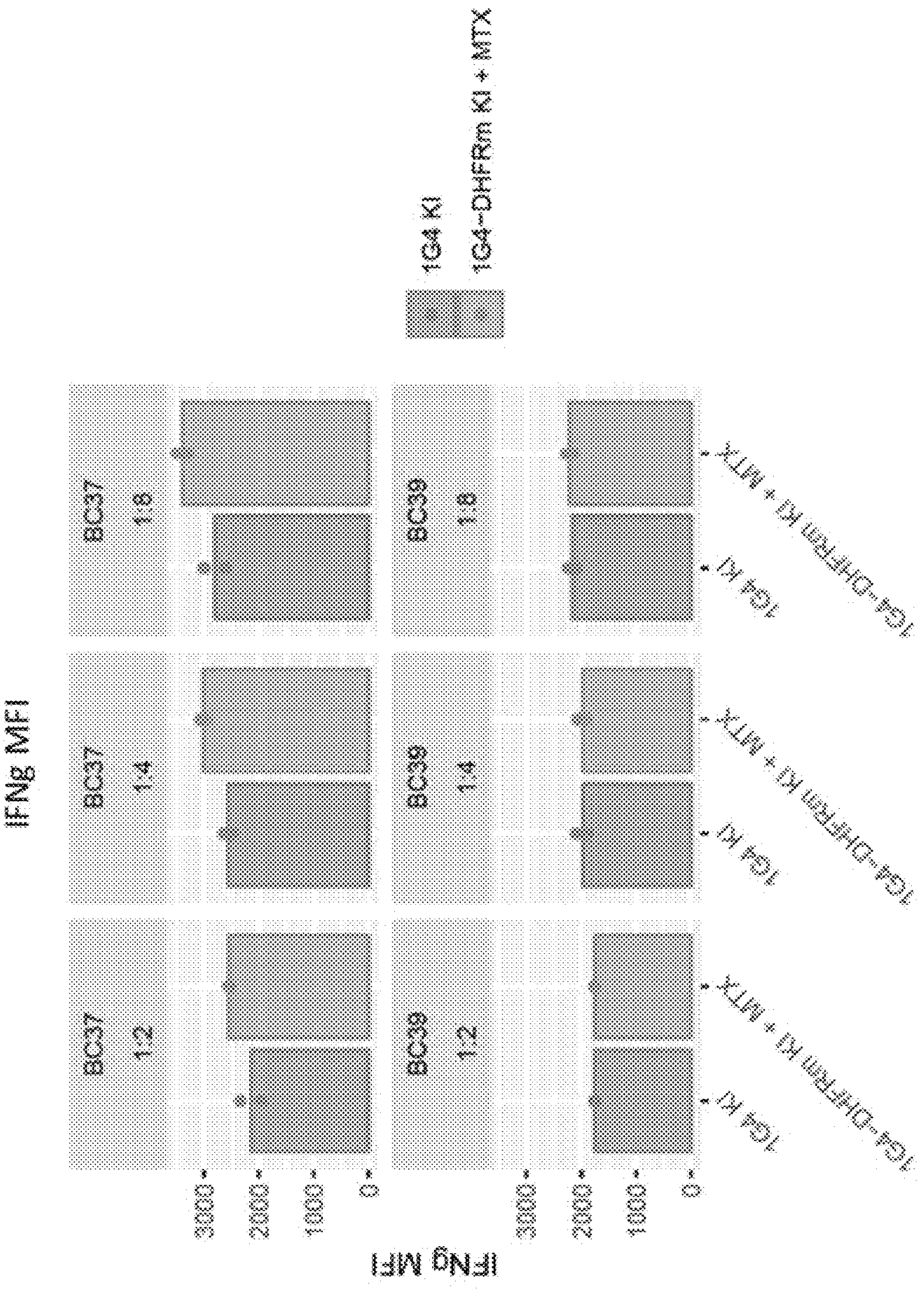
FIG. 21 are bar plots showing the IFNγ expression levels (determined by Mean Fluorescence Intensity, MFI) of T cells when stimulated with tumor cells.

FIG. 21 are bar plots showing the IFNγ production capacity of T cells when stimulated with tumor cells. As in FIG. 20, T cells were stimulated with A375 cells at different E:T ratios, and IFNγ expression levels (determined by Mean Fluorescence Intensity, MFI) were plotted here. The data indicated that the T cells generated by the MTX-selection method (1G4-DHFRm KI+MTX) produce a similar amount of IFNγ compared with T cells generated without selection (1G4 KI).

Figure 22:
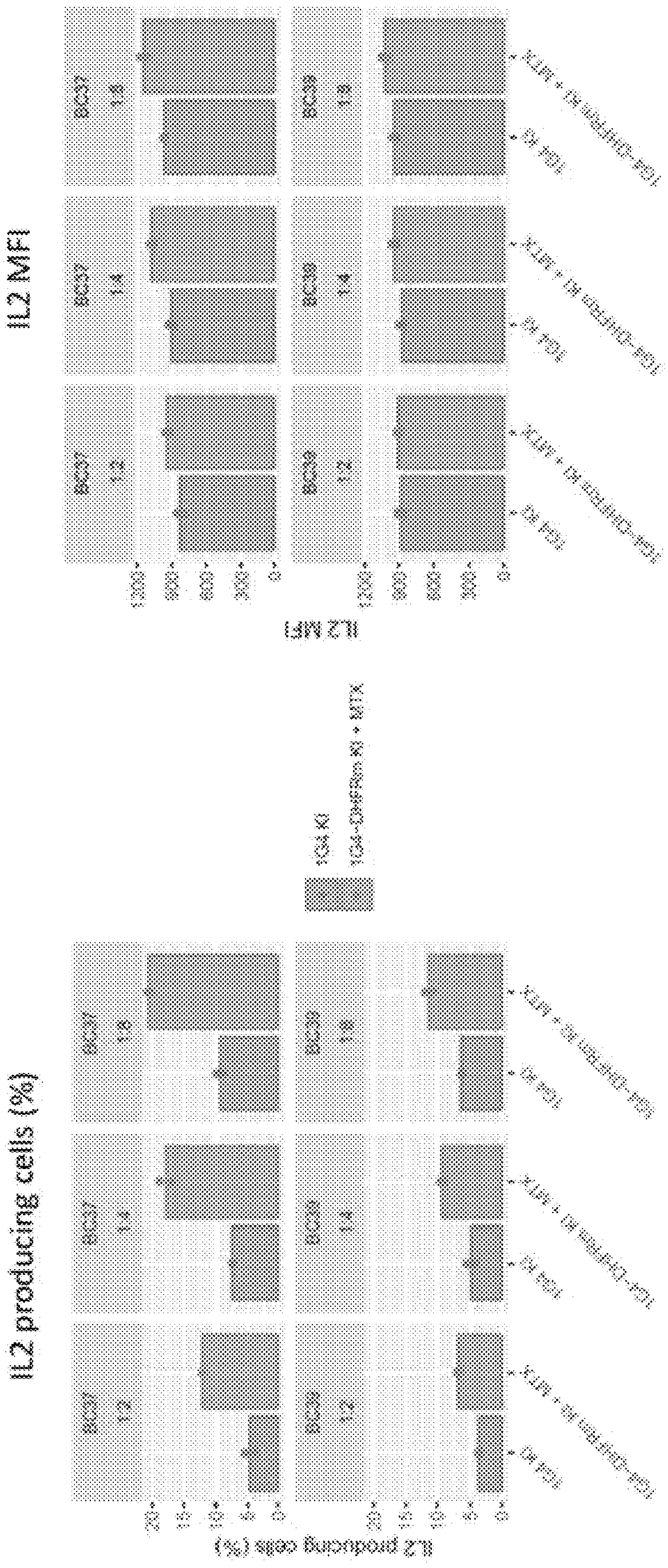
FIG. 22 are bar plots showing the IL2 production capacity of T cells when stimulated with tumor cells. Left panel: the proportion of IL2-producing cells. Right panel: expression levels of IL2-producing cells.

FIG. 22 are bar plots showing the IL2 production capacity of T cells when stimulated with tumor cells. As in FIG. 20 and FIG. 21, T cells were stimulated with A375 cells at different E:T ratios. The proportion of IL2-producing cells (left panel) and their expression levels (MFI, right panel) were plotted here. The left panel indicated that the T cells generated by the MTX-selection method (1G4-DHFRm KI+MTX) have a higher proportion of IL2-producing cells as T cells generated without selection (1G4 KI), while the right panel indicated that the T cells generated by the MTX-selection method (1G4-DHFRm KI+MTX) produce a similar amount of IL2 compared with T cells generated without selection (1G4 KI).

Example 7

This example shows the enriched genetically-modified T cells generated by a method according to some embodiments have similar proliferation capacity as T cells generated without selection.

Figure 23:
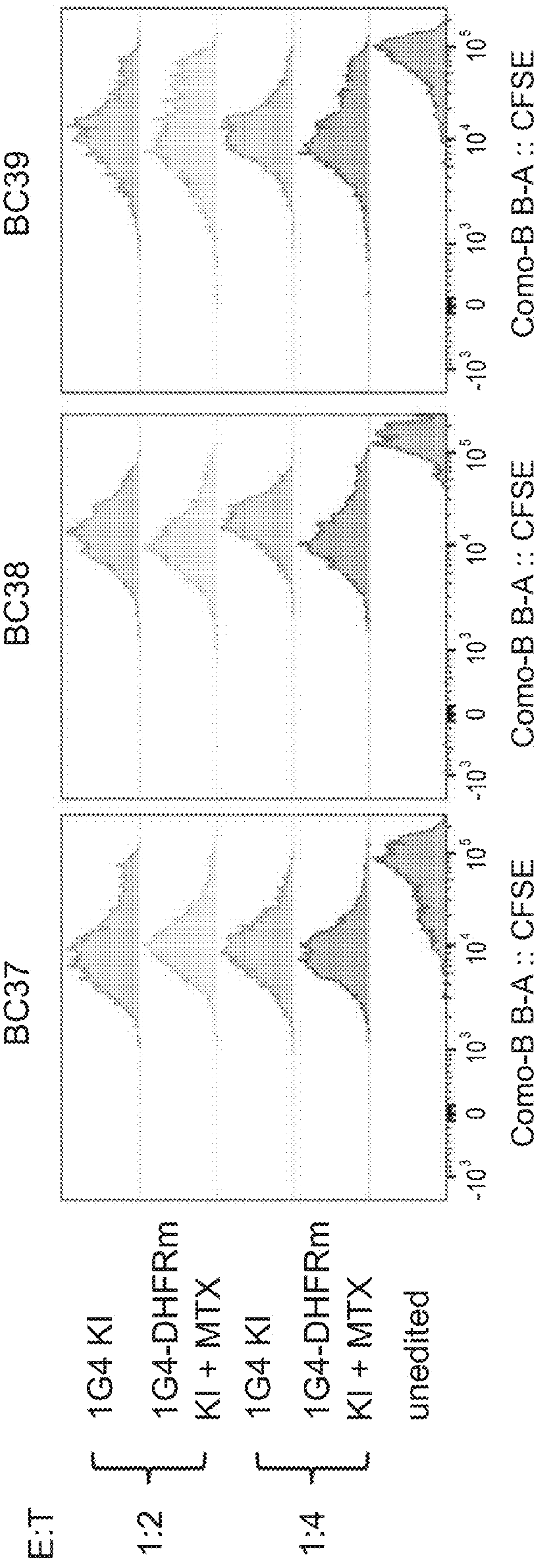
FIG. 23 are histograms showing the T cell proliferation capacity when stimulated with tumor cells.

FIG. 23 are histograms showing the T cell proliferation capacity when stimulated with tumor cells. A375 cells were plated on 24 well plates, and different ratios of CFSE-labeled T cells (E:T of 1:2 and 1:4) were added to the plate. T cells were harvested 3 days later for FACS analysis of CFSE dilution. The data indicated that the proliferation capacity of T cells generated by the MTX-selection method (1G4-DHFRm KI+MTX) upon stimulation with tumor cells was comparable with T cells generated without selection (1G4 KI).

Example 8

This example shows that the split-DHFR strategy can efficiently enrich double engineered T cells, and that this enrichment operates in a MTX dose-dependent manner.

Figure 28:
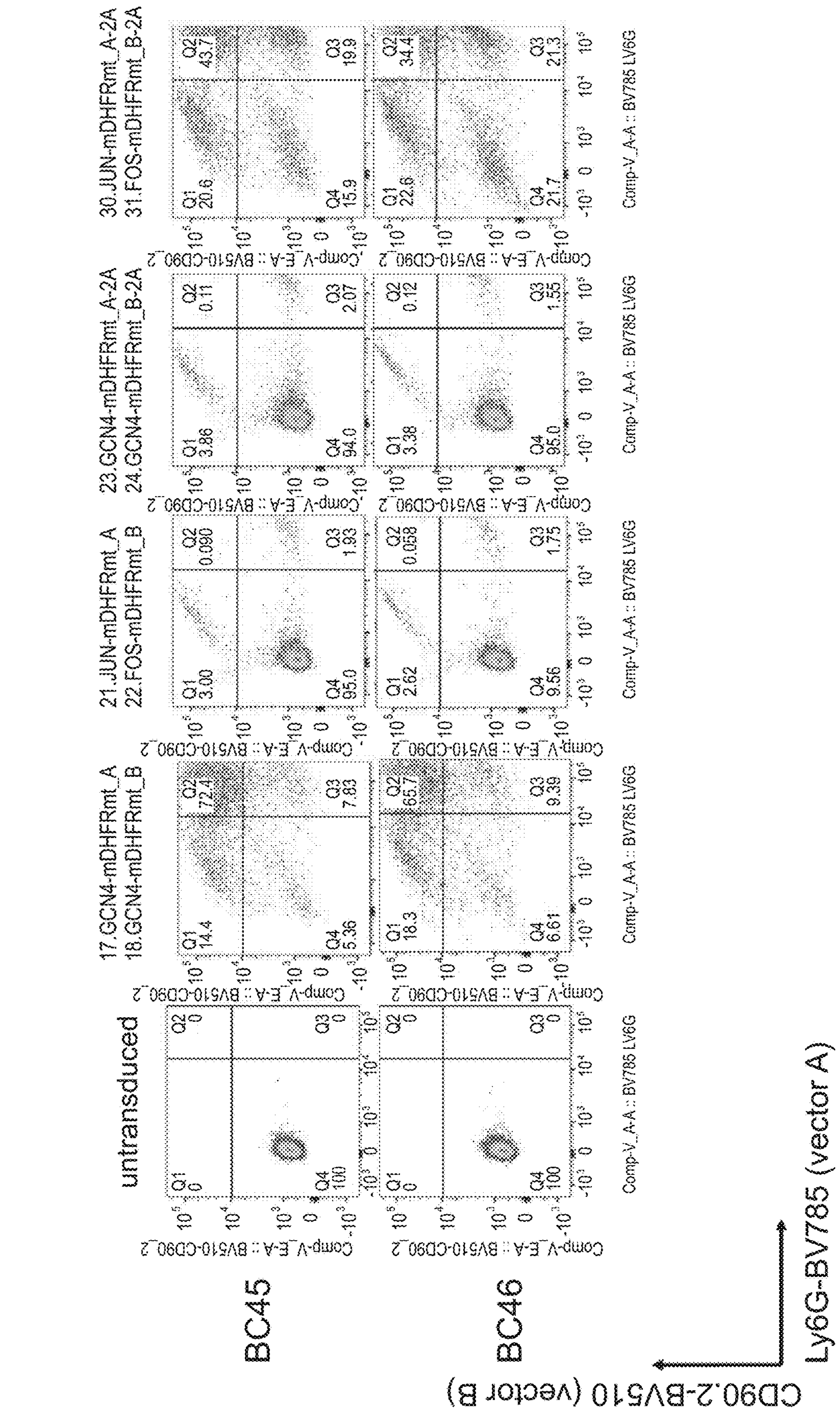
FIG. 28 shows the FACS results of BC45 and BC46 double transduction.

FIG. 28 shows the FACS results of BC45 and BC46 double transduction. Activated human primary T cells isolated from two buffy coats, BC45 and BC46, were double-infected with BEAV retroviral vectors encoding an MTX-resistant murine DHFR$^{FS}$ mutant (mDHFRmt) split into a N-terminal and C-terminal protein half (vector A and B) fused to homodimerizing (GCN4) or heterodimerizing (JUN-FOS) leucine zippers. Vector A and B also encoded a Ly6G or CD90.2 transduction marker, respectively. FACS analysis of transduction efficiency was performed at day 3 post virus infection. The data indicated that cells were efficiently transduced with vector pair 17-18 (GCN4-mDHFRmt_A and GCN4-mDHFRmt_B) and vector pair 30-31 (JUN-mDHFRmt_A-2A and FOS-mDHFRmt_B-2A). The double transduction efficiency for these vector pairs varied from 34.4% to 72.4%. In contrast, the double transduction efficiency for vector pair 21-22 (JUN-mDHFRmt_A and FOS-mDHFRmt_B) and vector pair 23-24 (GCN4-mDHFRmt_A-2A and GCN4-mDHFRmt_B-2A) was relatively low (from 0.058% to 0.12%). To determine whether the double transduced cells could be enriched, cells of pair 17-18 and pair 30-31 were mixed with a large amount of untransduced cells to mimic a low transduction efficiency setting.

Figure 29:
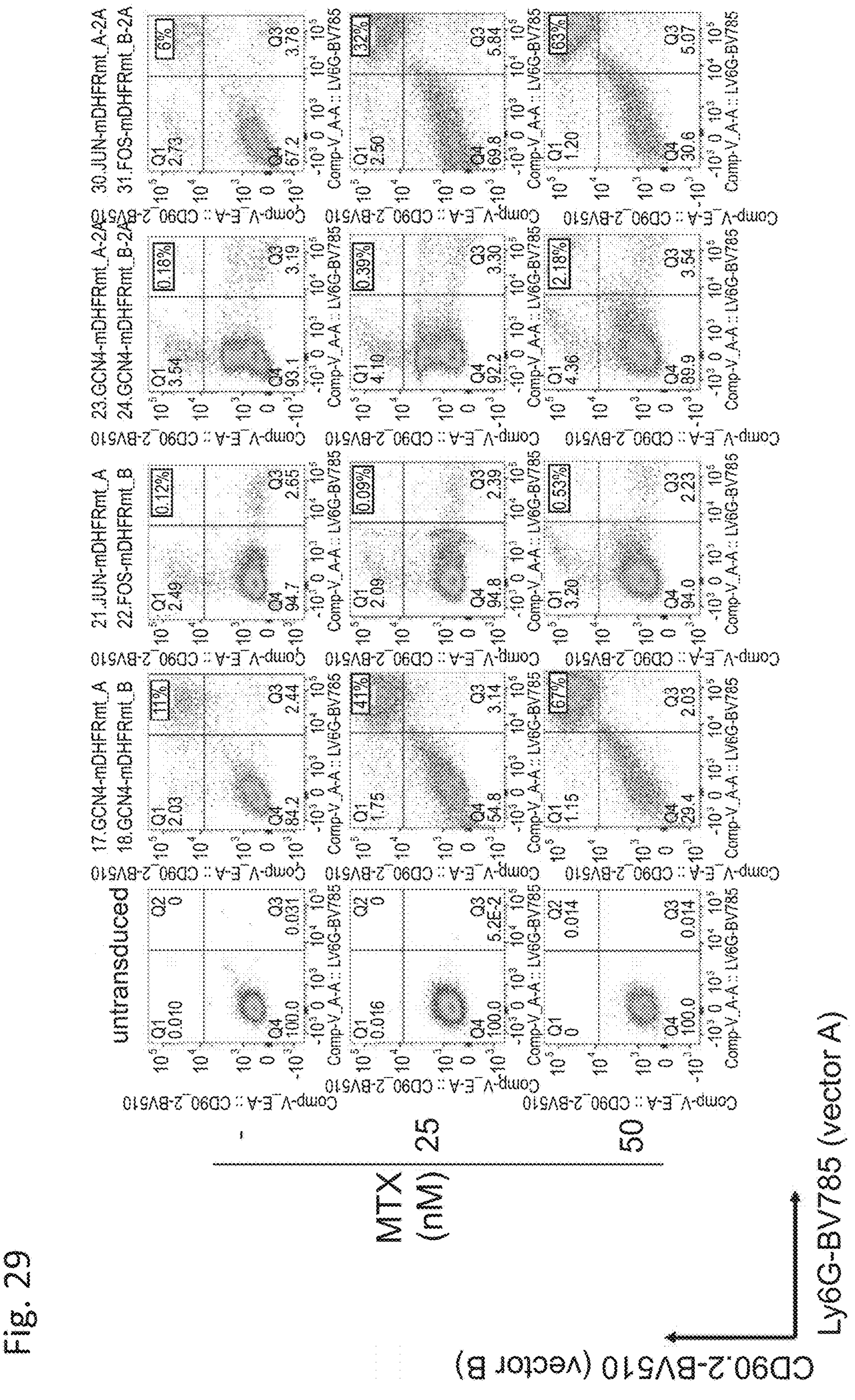
FIG. 29 shows the results of MTX selection of BC 45 cells.

FIG. 29 shows the results of MTX selection of BC 45 cells. BC45 cells from FIG. 28 were left untreated (row 1), or were treated with 25 nM (row 2) or 50 nM (row 3) MTX for 4 days (after determination of transduction efficiency), after which enrichment of double transduced cells was measured by FACS analysis. The data indicated that cells infected with vector pair 17-18 were enriched from 11% to 41% (25 nM MTX; 3.7 fold) and 67% (50 nM MTX; 6.1 fold), that cells infected with vector pair 21-22 were enriched from 0.12% to 0.53% (50 nM MTX; 4.4 fold), that cells infected with vector pair 23-24 were enriched from 0.18% to 2.18% (50 nM MTX; 12 fold), and that cells infected with vector pair 30-31 were enriched from 6% to 32% (25 nM MTX; 5.3 fold) and 63% (50 nM MTX; 10.5 fold). Together, these data showed that the split-DHFR strategy can efficiently enrich double engineered T cells, and that this enrichment operates in a MTX dose-dependent manner.

Figure 30:
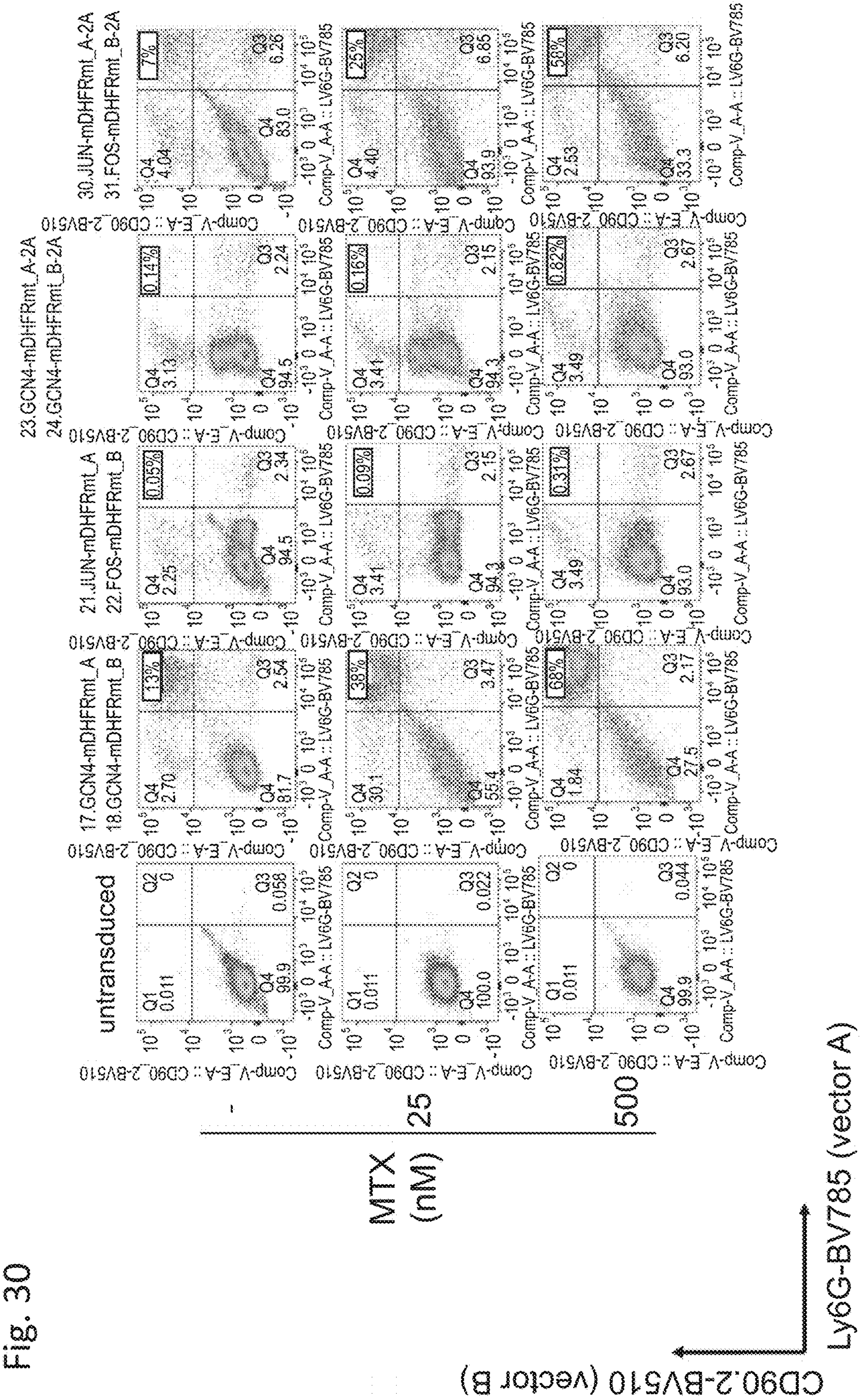
FIG. 30 shows the results of MTX selection of BC 46 cells.

FIG. 30 shows the results of MTX selection of BC 46 cells. BC46 cells from FIG. 28 were left untreated (row 1), or were treated with 25 nM (row 2) or 50 nM (row 3) MTX for 4 days (after determination of transduction efficiency), after which enrichment of double transduced cells was measured by FACS analysis. The data indicated that cells infected with vector pair 17-18 were enriched from 13% to 38% (25 nM MTX; 2.9 fold) and 68% (50 nM MTX; 5.2 fold), that cells infected with vector pair 21-22 were enriched from 0.05% to 0.31% (50 nM MTX; 6.2 fold), that cells infected with vector pair 23-24 were enriched from 0.14% to 0.82% (50 nM MTX; 5.9 fold), and that cells infected with vector pair 30-31 were enriched from 7% to 25% (25 nM MTX; 3.6 fold) and 58% (50 nM MTX; 8.3 fold). Together, these data showed that the split-DHFR strategy can efficiently enrich double engineered T cells, and that this enrichment operates in a MTX dose-dependent manner.

Figure 31:
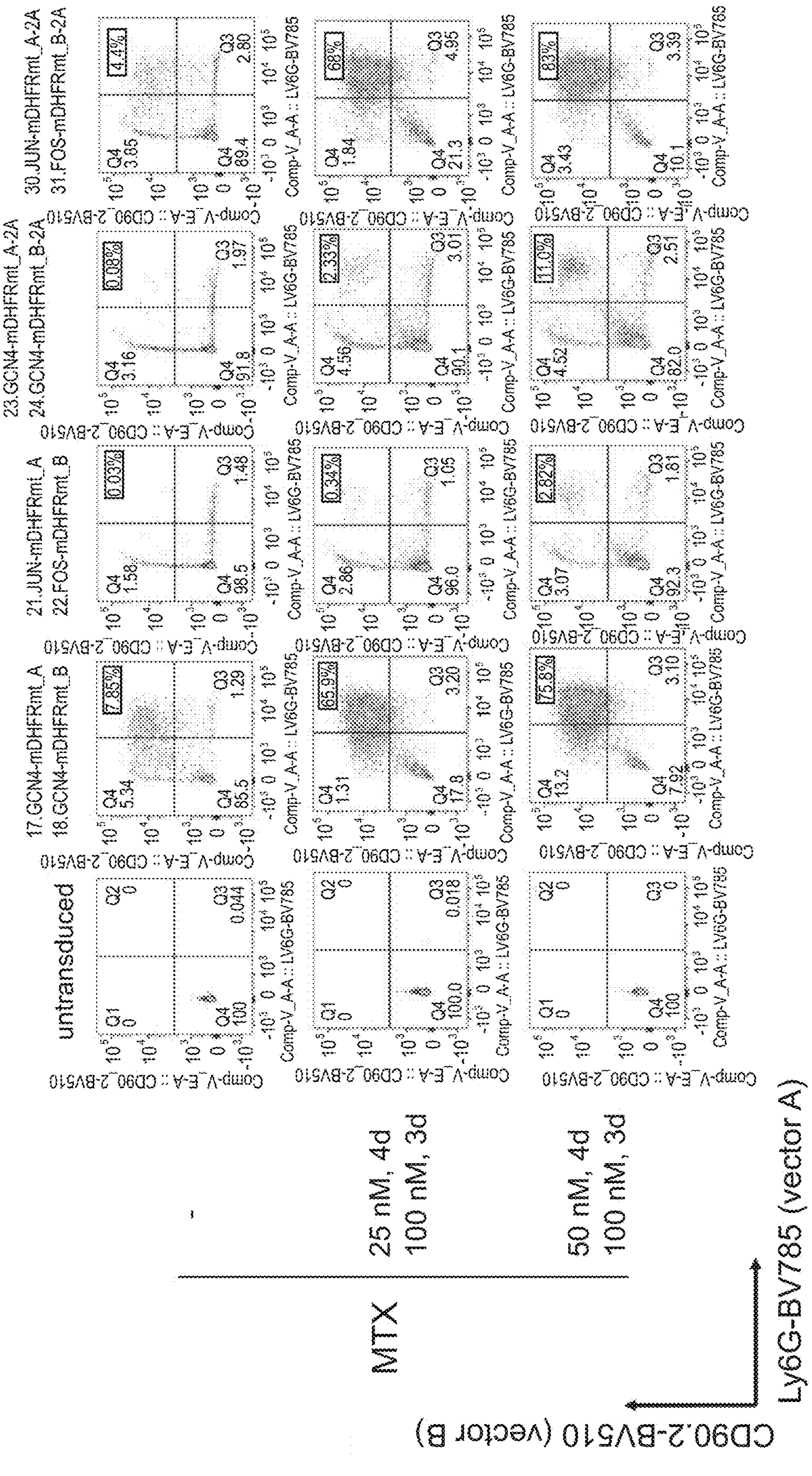
FIG. 31 shows the results of selecting BC 45 cells in higher MTX concentration.

FIG. 31 shows the results of selecting BC 45 cells in higher MTX concentration. BC45 cells from FIG. 29 were continuously treated with 100 nM MTX for another 3 days, after which enrichment of double transduced cells was measured by FACS analysis. The data indicated that cells infected with vector pair 17-18 were enriched from 7.85% to 65.9% (row 2; 8.4 fold) and 75.8% (row 3; 9.7 fold), that cells infected with vector pair 21-22 were enriched from 0.03% to 0.34% (row 2; 11.3 fold) and 2.82% (row 3; 94 fold), that cells infected with vector pair 23-24 were enriched from 0.08% to 2.33% (row 2; 29 fold) and 11% (row 3; 138 fold), and that cells infected with vector pair 30-31 were enriched from 4.4% to 68% (row 2; 15.5 fold) and 83% (row 3; 18.9 fold). Together, these data showed that the split-DHFR strategy can efficiently enrich double engineered T cells, and that this enrichment operates in a MTX dose-dependent manner.

Figure 32:
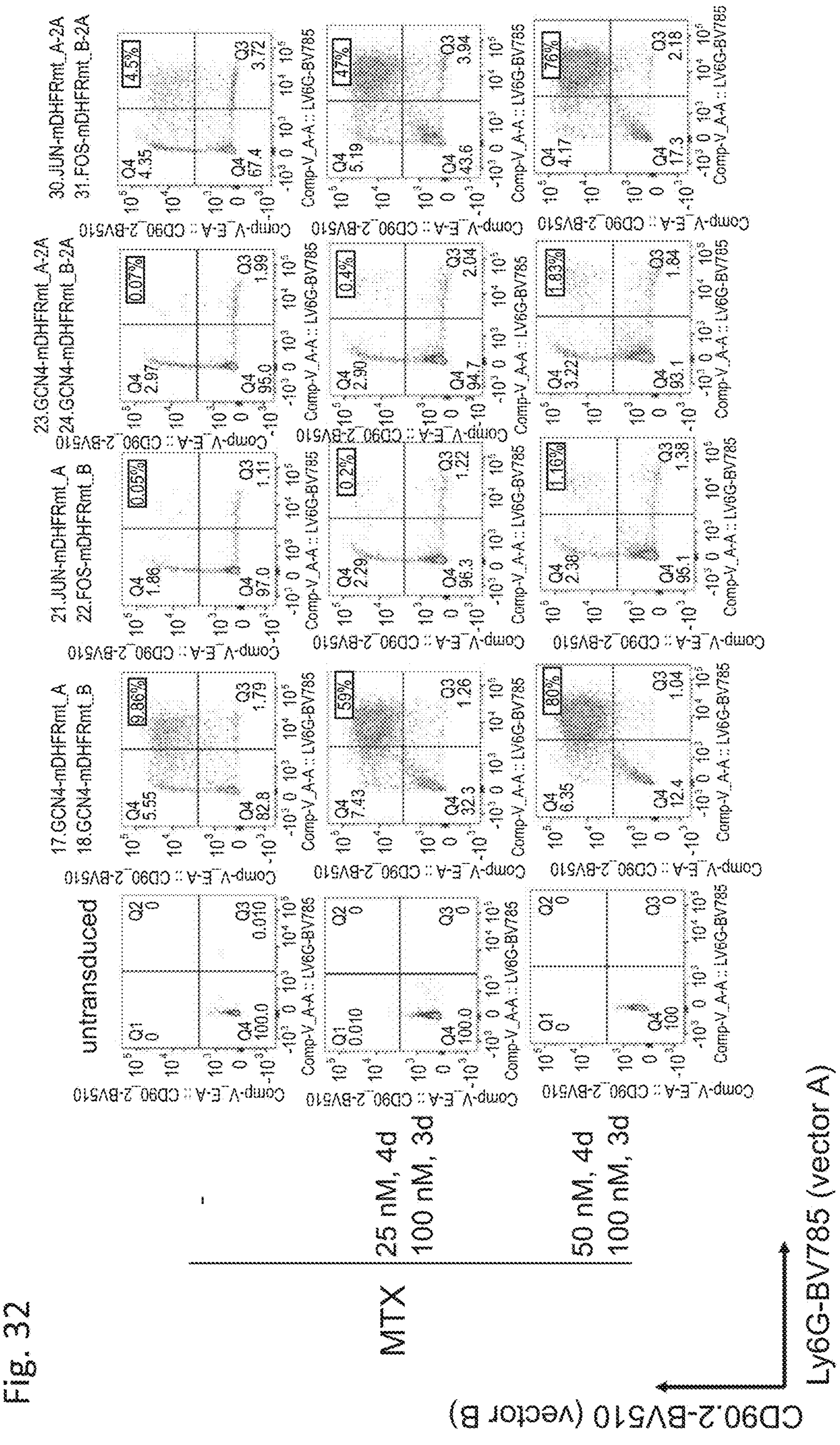
FIG. 32 shows the results of selecting BC 46 cells in higher MTX concentration.

FIG. 32 shows the results of selecting BC 46 cells in higher MTX concentration. BC46 cells from FIG. 30 were continuously treated with 100 nM MTX for another 3 days, after which enrichment of double transduced cells was measured by FACS analysis. The data indicated that cells infected with vector pair 17-18 were enriched from 9.86% to 59% (row 2; 6 fold) and 80% (row 3; 8.1 fold), that cells infected with vector pair 21-22 were enriched from 0.05% to 0.2% (row 2; 4 fold) and 1.16% (row 3; 23.2 fold), that cells infected with vector pair 23-24 were enriched from 0.07% to 0.4% (row 2; 5.7 fold) and 1.83% (row 3; 26.1 fold), and that cells infected with vector pair 30-31 were enriched from 4.5% to 47% (row 2; 10.4 fold) and 76% (row 3; 16.9 fold). Together, these data showed that the split-DHFR strategy can efficiently enrich double engineered T cells, and that this enrichment operates in a MTX dose-dependent manner.

Example 9

This example shows that a split-DHFR system using mutant JUN-FOS leucine zippers can enrich double engineered T cells with comparable efficiency as one using wildtype JUN-FOS leucine zippers.

Figure 43A:
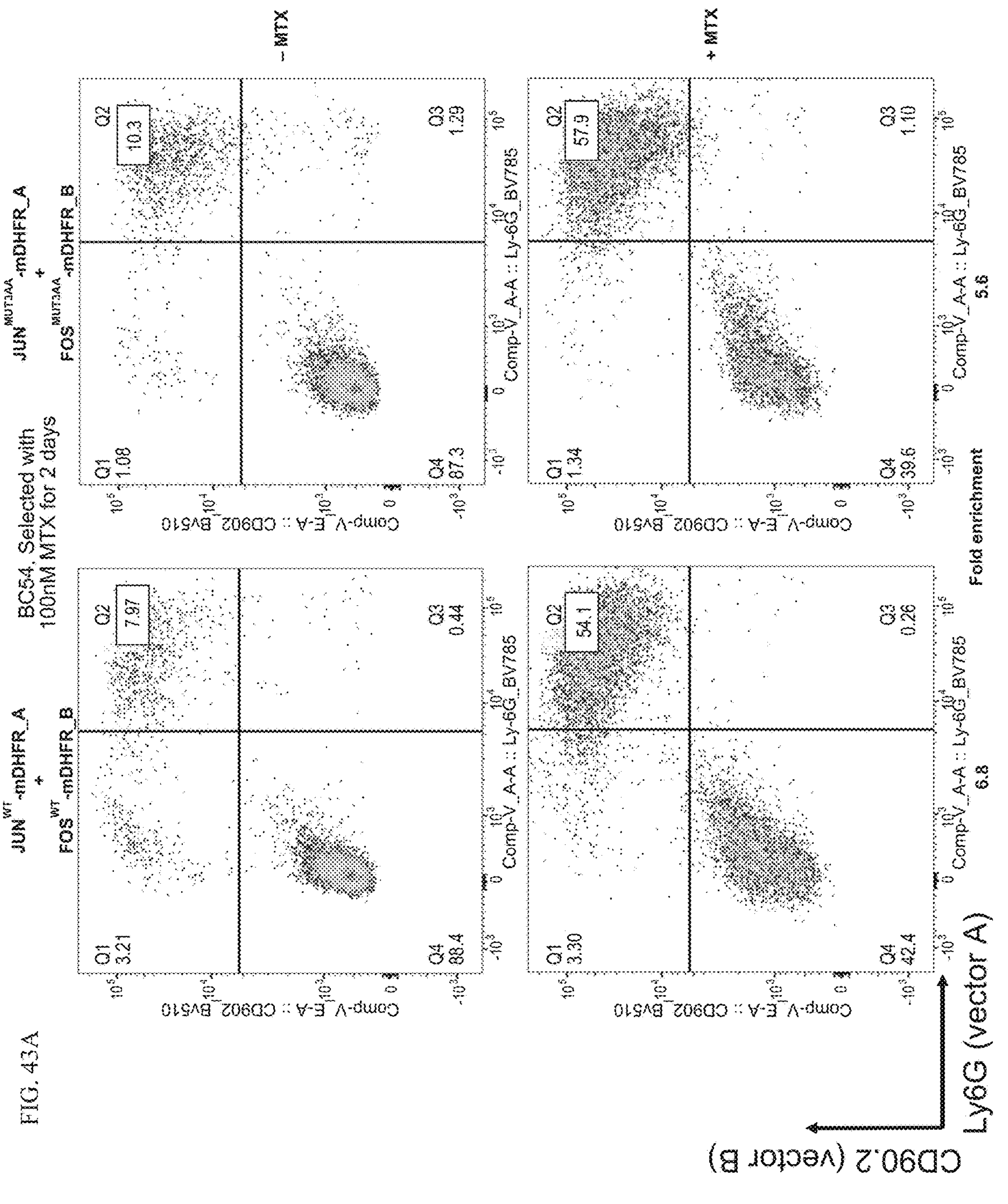
FIG. 43A-43B show the FACS results for $Jun^{MUT3AA}$-$Fos^{MUT3AA}$ based split-DHFR selection after 2 days of methotrexate.
Figure 43B:
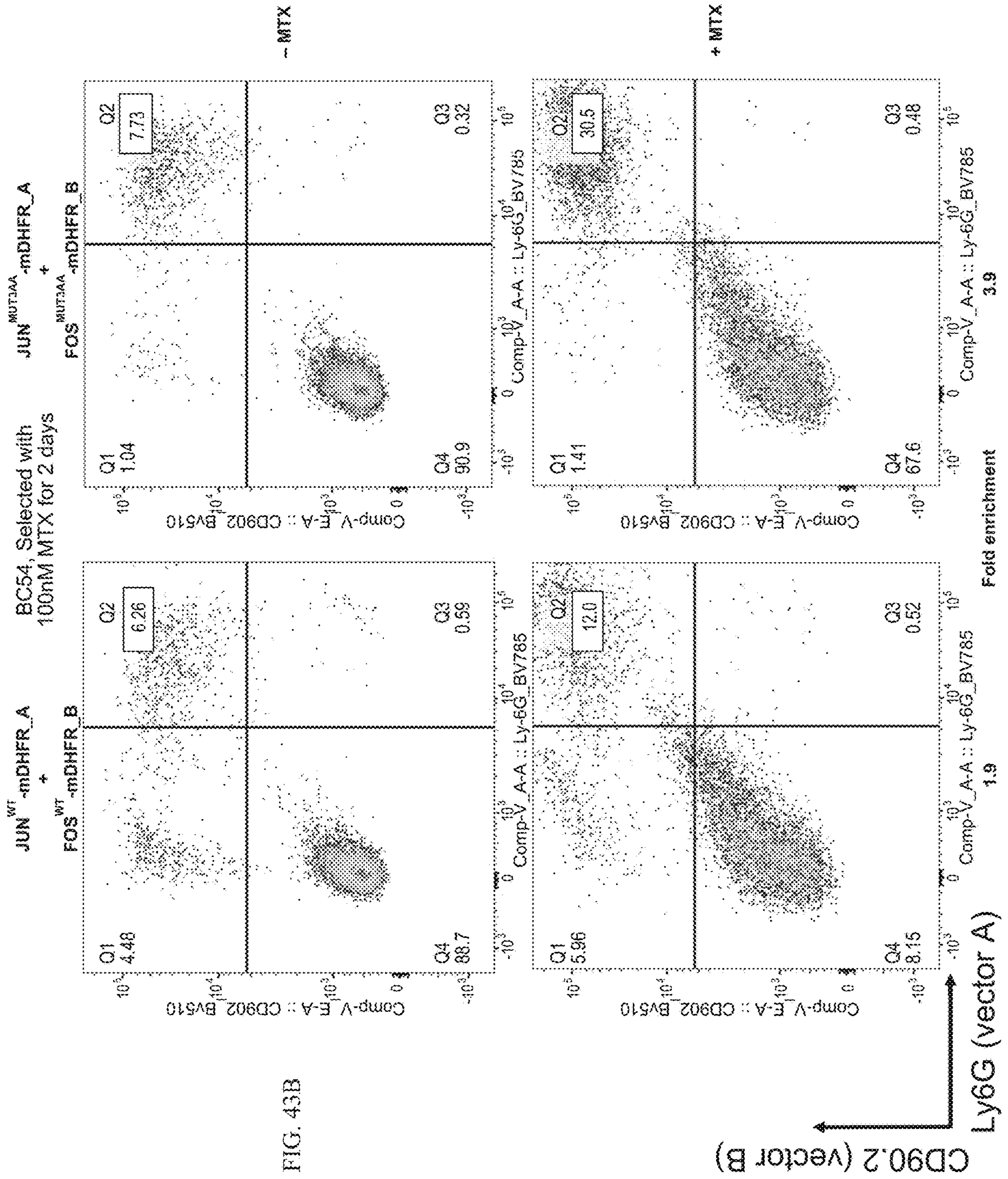
Figure 44A:
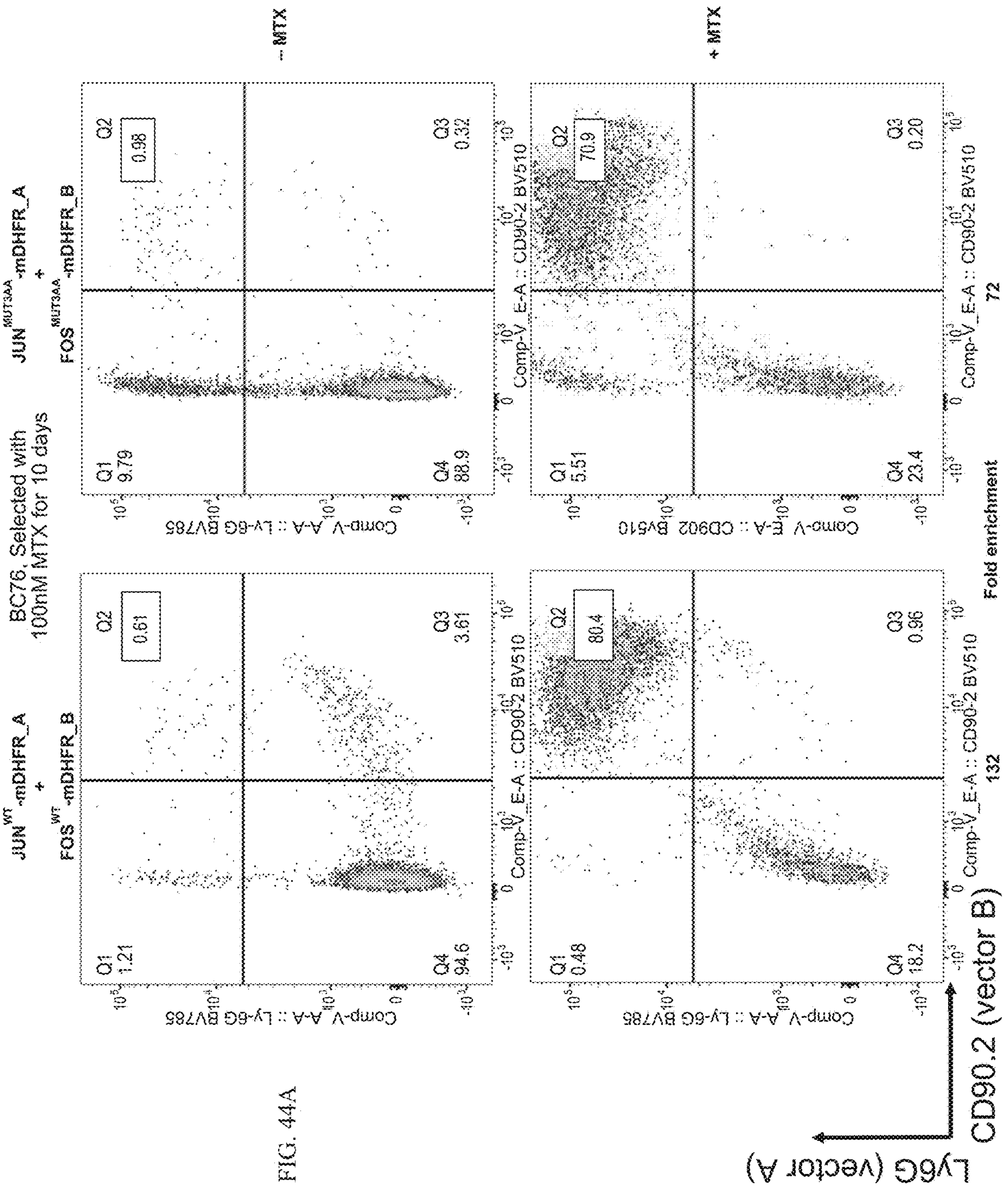
FIGS. 44A-44D show the FACS results for $Jun^{MUT3AA}$-$Fos^{MUT3AA}$ and $Jun^{MUT4AA}$-$Fos^{MUT4AA}$ based split-DHFR selection after 10 days of methotrexate.
Figure 44B:
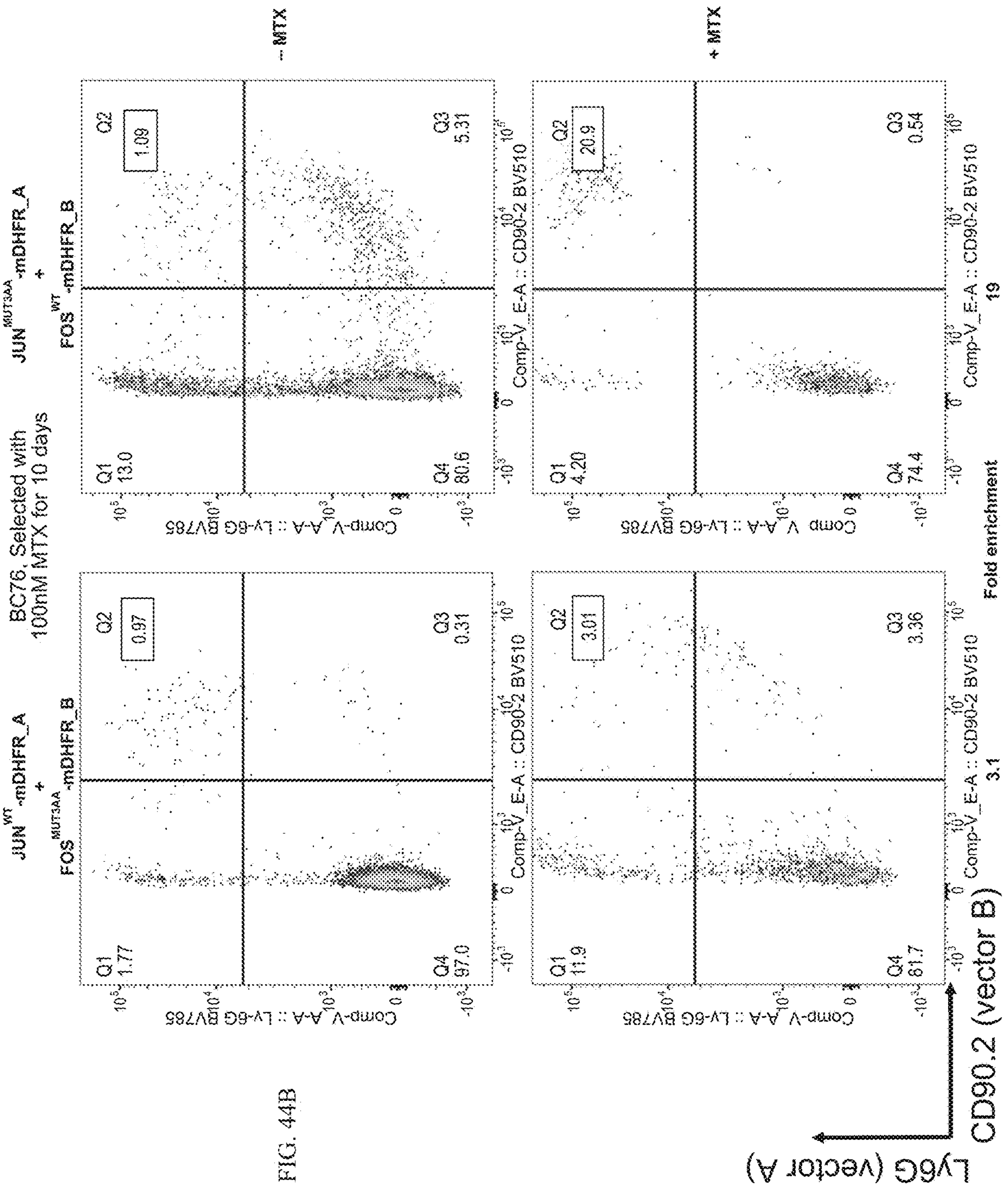
Figure 44C:
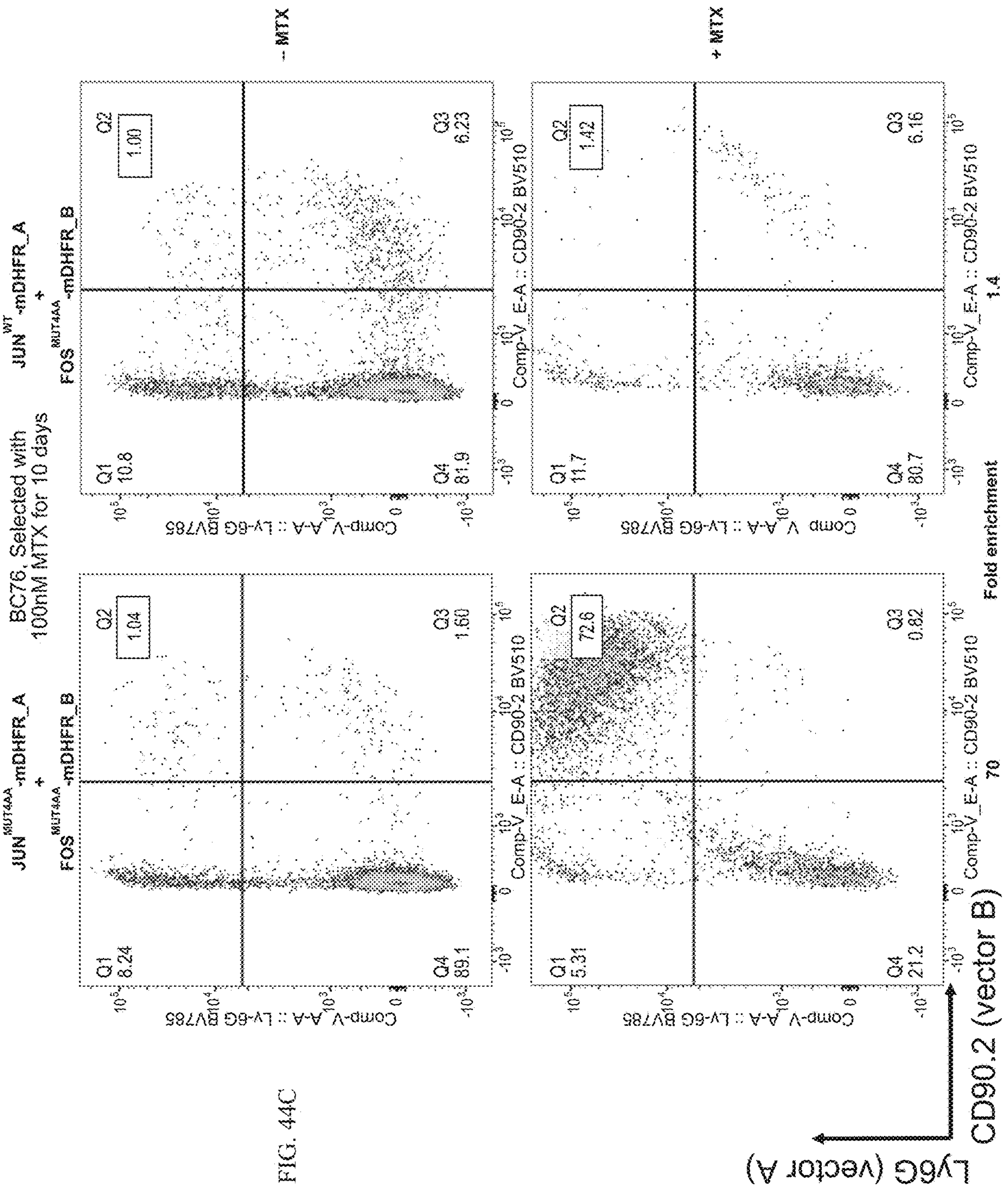
Figure 44D:
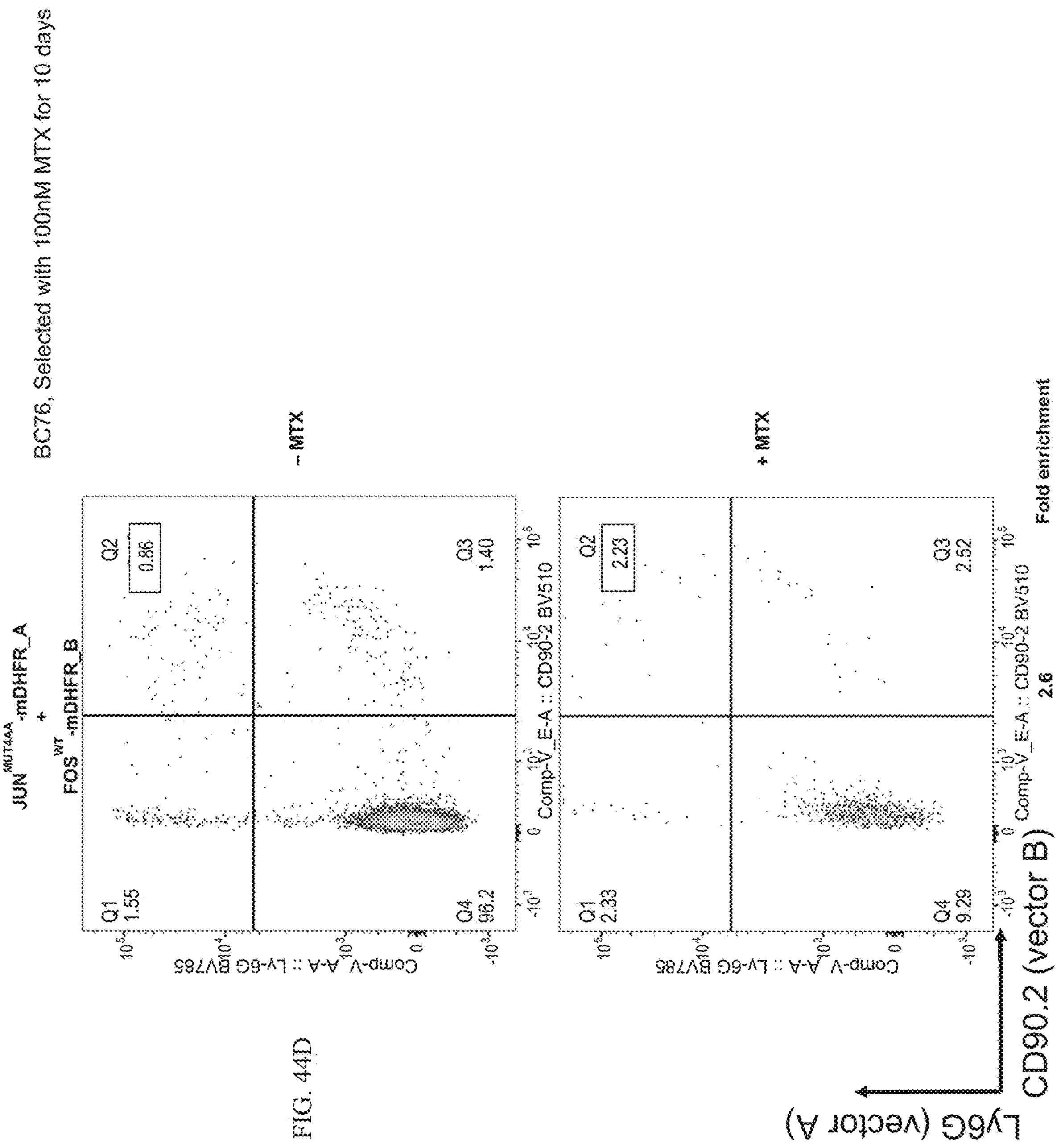

FIGS. 43A and 43B show the results of MTX selection of double engineered BC54 T cells. Activated human primary T cells isolated from a buffy coat, BC54, were double-infected with BEAV retroviral vectors encoding an MTX-resistant murine DHFR$^{FS}$ mutant (mDHFR) split into an N-terminal and C-terminal protein half (vector A and B), fused to heterodimerizing JUN-FOS leucine zippers. JUN$^{WT}$ depicts a wildtype JUN leucine zipper, FOS$^{WT}$ depicts a wildtype FOS leucine zipper, JUN$^{MUT3AA}$ depicts a mutant JUN leucine zipper containing three acidic amino acids from FOS, FOS$^{MUT3AA}$ depicts a mutant FOS leucine zipper containing three basic amino acids from JUN. Vector A and B also encoded a Ly6G and CD90.2 transduction marker, respectively. Starting at 4 days post transduction, cells were either left untreated (row 1), or were treated with 100 nM MTX for 2 days (row 2), after which enrichment of double transduced cells was measured by FACS analysis. The data indicated that cells infected with vector pair JUN$^{WT}$-mDHFR_A+FOS$^{WT}$-mDHFR_B were enriched from 7.97% to 54.1% (6.8 fold), that cells infected with vector pair JUN$^{MUT3AA}$-mDHFR_A+FOS$^{MUT3AA}$-mDHFR_B were enriched from 10.3% to 57.9% (5.6 fold), that cells infected with vector pair JUN$^{WT}$-mDHFR_A+FOS$^{MUT3AA}$-mDHFR_B were enriched from 6.26% to 12.0% (1.9 fold), and that cells infected with vector pair JUN$^{MUT3AA}$-mDHFR_A+FOS$^{WT}$-mDHFR_B were enriched from 7.73% to 30.5% (3.9 fold). Together, these data showed that a split-DHFR system using mutant JUN-FOS leucine zippers with three charge-pair mutations can efficiently enrich double engineered T cells, but that three charge-pair mutations are insufficient to abolish interaction with wildtype JUN and FOS leucine zippers.

FIGS. 44A-44D show the results of MTX selection of double engineered BC76 T cells. Activated human primary T cells isolated from a buffy coat, BC76, were double-infected with retroviral vectors encoding an MTX-resistant murine DHFR$^{FS}$ mutant (mDHFR) split into an N-terminal and C-terminal protein half (vector A and B), fused to heterodimerizing JUN-FOS leucine zippers. JUN$^{WT}$ depicts a wildtype JUN leucine zipper, FOS$^{WT}$ depicts a wildtype FOS leucine zipper, JUN$^{MUT3AA}$ depicts a mutant JUN leucine zipper containing three acidic amino acids from FOS, FOS$^{MUT3AA}$ depicts a mutant FOS leucine zipper containing three basic amino acids from JUN, JUN$^{MUT4AA}$ depicts a mutant JUN leucine zipper containing four acidic amino acids from FOS, FOS$^{MUT4AA}$ depicts a mutant FOS leucine zipper containing four basic amino acids from JUN. Vector A and B also encoded a Ly6G and CD90.2 transduction marker, respectively. Starting at 4 days post transduction, cells were either left untreated (row 1), or were treated with 100 nM MTX for 10 days (row 2), after which enrichment of double transduced cells was measured by FACS analysis. The data indicated that cells infected with vector pair JUN$^{WT}$-mDHFR_A+FOS$^{WT}$-mDHFR_B were enriched from 0.61% to 80.4% (132 fold), that cells infected with vector pair JUN$^{MUT3AA}$-mDHFR_A+FOS$^{MUT3AA}$-mDHFR_B were enriched from 0.98% to 70.9% (72 fold), that cells infected with vector pair JUN$^{WT}$-mDHFR_A+FOS$^{MUT3AA}$-mDHFR_B were enriched from 0.97% to 3.01% (3.1 fold), that cells infected with vector pair JUN$^{MUT3AA}$-mDHFR_A+FOS$^{WT}$-mDHFR_B were enriched from 1.09% to 20.9% (19 fold), that cells infected with vector pair JUN$^{MUT4AA}$-mDHFR_A+FOS$^{MUT4AA}$-mDHFR_B were enriched from 1.04% to 72.6% (70 fold), that cells infected with vector pair JUN$^{WT}$-mDHFR_A+FOS$^{MUT4AA}$-mDHFR_B were enriched from 1.00% to 1.42% (1.4 fold), and that cells infected with vector pair JUN$^{MUT4AA}$-mDHFR_A+FOS$^{WT}$-mDHFR_B were enriched from 0.86% to 2.23% (2.6 fold). Together, these data showed that a split-DHFR system using mutant JUN-FOS leucine zippers with four charge-pair mutations can efficiently enrich double engineered T cells, and that four charge-pair mutations are sufficient to largely abolish interaction with wildtype JUN and FOS leucine zippers.

Example 10

This example shows that a split-DHFR system using mutant FKBP12 dimerization domains can enrich double engineered T cells in the presence of the chemical dimerization inducer AP1903.

Figure 45A:
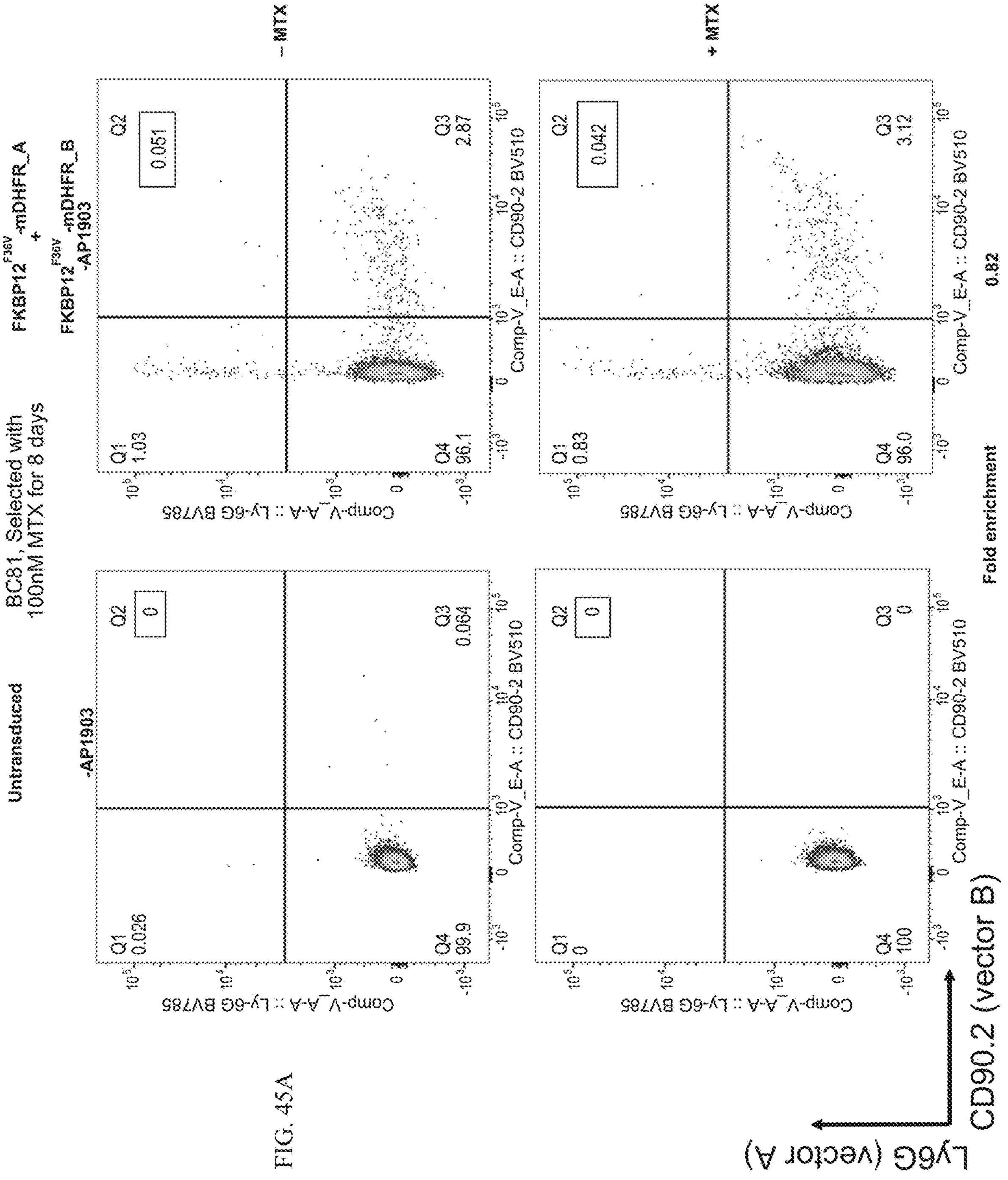
FIGS. 45A-45B show the FACS results for $FKBP12^{F36V}$ based split-DHFR selection after 8 days of methotrexate.
Figure 45B:
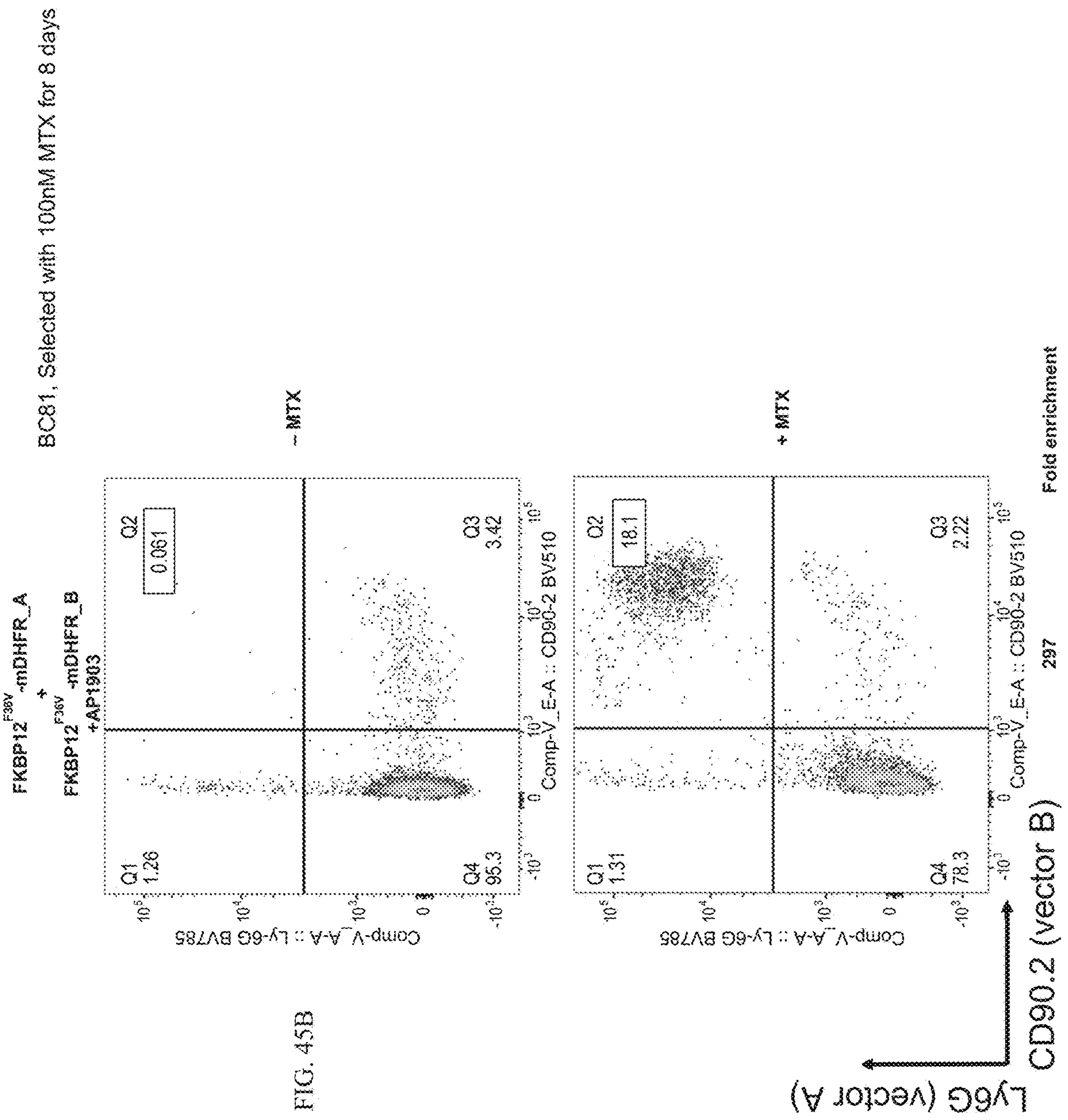

FIGS. 45A-45B show the results of MTX selection of double engineered BC81 T cells. Activated human primary T cells isolated from a buffy coat, BC81, were double-infected with retroviral vectors encoding an MTX-resistant murine DHFR$^{FS}$ mutant (mDHFR) split into an N-terminal and C-terminal protein half (vector A and B), fused to homodimerizing mutant FKBP12 domains. Untransduced depicts non-transduced cells, FKBP12$^{F36V}$ depicts an FKBP12 protein containing an F36V mutation, which enhances binding to the AP1903 dimerizer drug. Vector A and B also encoded a Ly6G and CD90.2 transduction marker, respectively. Starting at 4 days post transduction, cells were either left untreated (columns 1 and 2) or were treated with 10 nM AP1903 for 4 hours (column 3). Subsequently, cells were left untreated (row 1), or were treated with 100 nM MTX for 8 days (row 2), after which enrichment of double transduced cells was measured by FACS analysis. The data indicated that cells infected with vector pair FKBP12$^{F36V}$-mDHFR_A+FKBP12$^{F36V}$-mDHFR_B without AP1903 treatment were enriched from 0.051% to 0.042% (0.82 fold), and that cells infected with vector pair FKBP12$^{F36V}$-mDHFR_A+FKBP12$^{F36V}$-mDHFR_B with AP1903 treatment were enriched from 0.061% to 18.1% (297 fold). Together, these data showed that a split-DHFR system using mutant FKBP12 dimerization domains can efficiently enrich double engineered T cells, and that this enrichment operates in an AP1903-dependent manner.

Example 11

This example shows that a split-DHFR system using mutant FKBP12 dimerization domains or mutant JUN-FOS leucine zippers can enrich double engineered T cells that have knock-in of a first exogenous protein into a first locus and a second exogenous protein into a second locus.

Figure 46A:
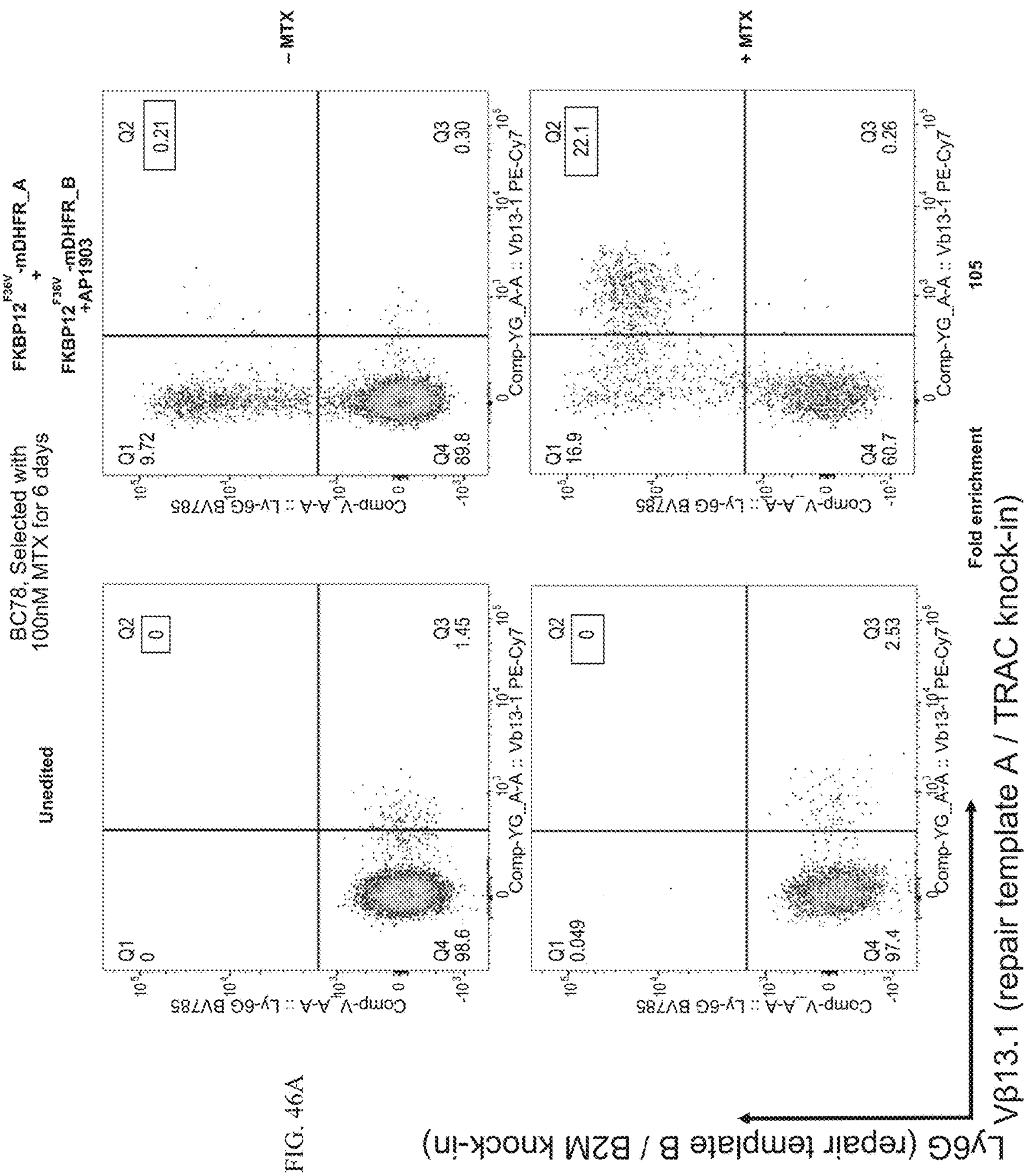
FIGS. 46A-46B show the FACS results comparing $FKBP12^{F36V}$ based split-DHFR selection and $Jun^{MUT4AA}$-$Fos^{MUT4AA}$ based split-DHFR selection after 6 days of methotrexate.
Figure 46B:
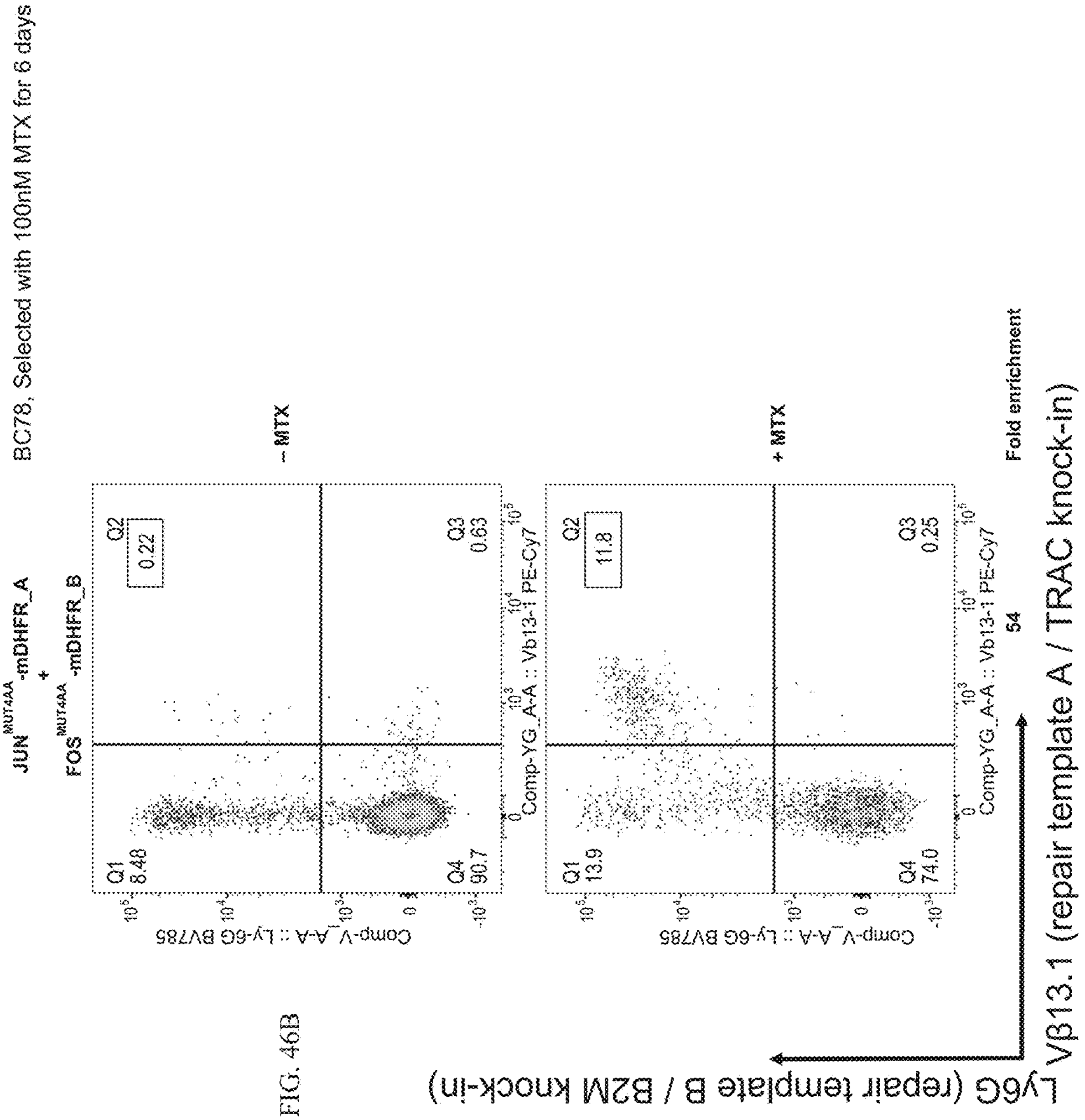

FIG. 46 shows the results of MTX selection of double engineered BC78 T cells. Activated human primary T cells isolated from a buffy coat, BC78, were electroporated with Cas9 RNPs and repair templates encoding an MTX-resistant murine DHFR$^{FS}$ mutant (mDHFR) split into an N-terminal and C-terminal protein half (repair template A and B), fused to homodimerizing mutant FKBP12 domains, or heterodimerizing mutant JUN-FOS leucine zippers. Unedited depicts unelectroporated cells, FKBP12$^{F36V}$-mDHFR_A depicts TRAC locus knock-in of a repair template encoding the NY-ESO-1 1G4 TCR and an FKBP12 protein containing an F36V mutation, FKBP12$^{F36V}$-mDHFR_B depicts B2M locus knock-in of a repair template encoding a dominant-negative TGFBR2, Ly6G and an FKBP12 protein containing an F36V mutation, JUN$^{MUT4AA}$-mDHFR_A depicts TRAC locus knock-in of a repair template encoding the NY-ESO-1 1G4 TCR and a mutant JUN leucine zipper containing four acidic amino acids from FOS, and FOS$^{MUT4AA}$-mDHFR_B depicts B2M locus knock-in of a repair template encoding a dominant-negative TGFBR2, Ly6G and a mutant FOS leucine zipper containing four basic amino acids from JUN. Starting at 4 days post electroporation, cells were either left untreated (columns 1 and 3) or were treated with 10 nM AP1903 for 1 hour (column 2). Subsequently, cells were left untreated (row 1), or were treated with 100 nM MTX for 6 days (row 2), after which enrichment of double engineered cells was measured by FACS analysis. The data indicated that cells edited with repair template pair FKBP12$^{F36V}$-mDHFR_A+FKBP12$^{F36V}$-mDHFR_B were enriched from 0.21% to 22.1% (105 fold), and that cells edited with repair template pair JUN$^{MUT4AA}$-mDHFR_A+FOS$^{MUT4AA}$-mDHFR_B were enriched from 0.22% to 11.8% (54 fold). Together, these data showed that a split-DHFR system using mutant FKBP12 dimerization domains or mutant JUN-FOS leucine zippers with four charge-pair mutations can efficiently enrich double engineered T cells that have knock-in of multiple exogenous proteins into two different loci.

Example 12

This example shows that a split-DHFR system using mutant JUN-FOS leucine zippers can enrich double engineered T cells with comparable efficiency as one using wildtype JUN-FOS leucine zippers.

Figure 47A:
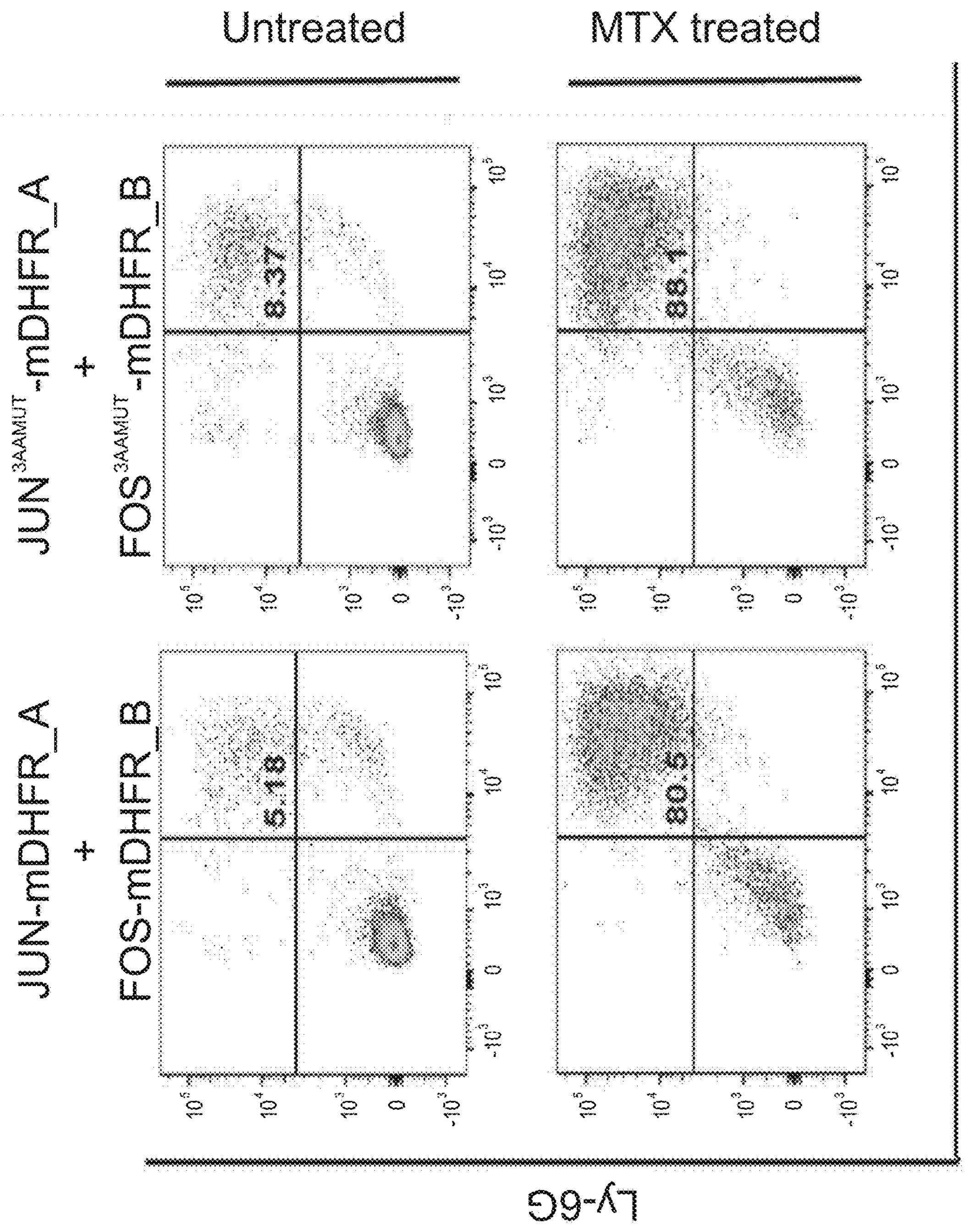
FIG. 47A shows the FACS results comparing $Jun^{MUT3AA}$-$Fos^{MUT3AA}$ and Jun-Fos based CD90.2 and Ly-6G selection after no treatment or 100 nM methotrexate treatment for four days.
Figure 47B:
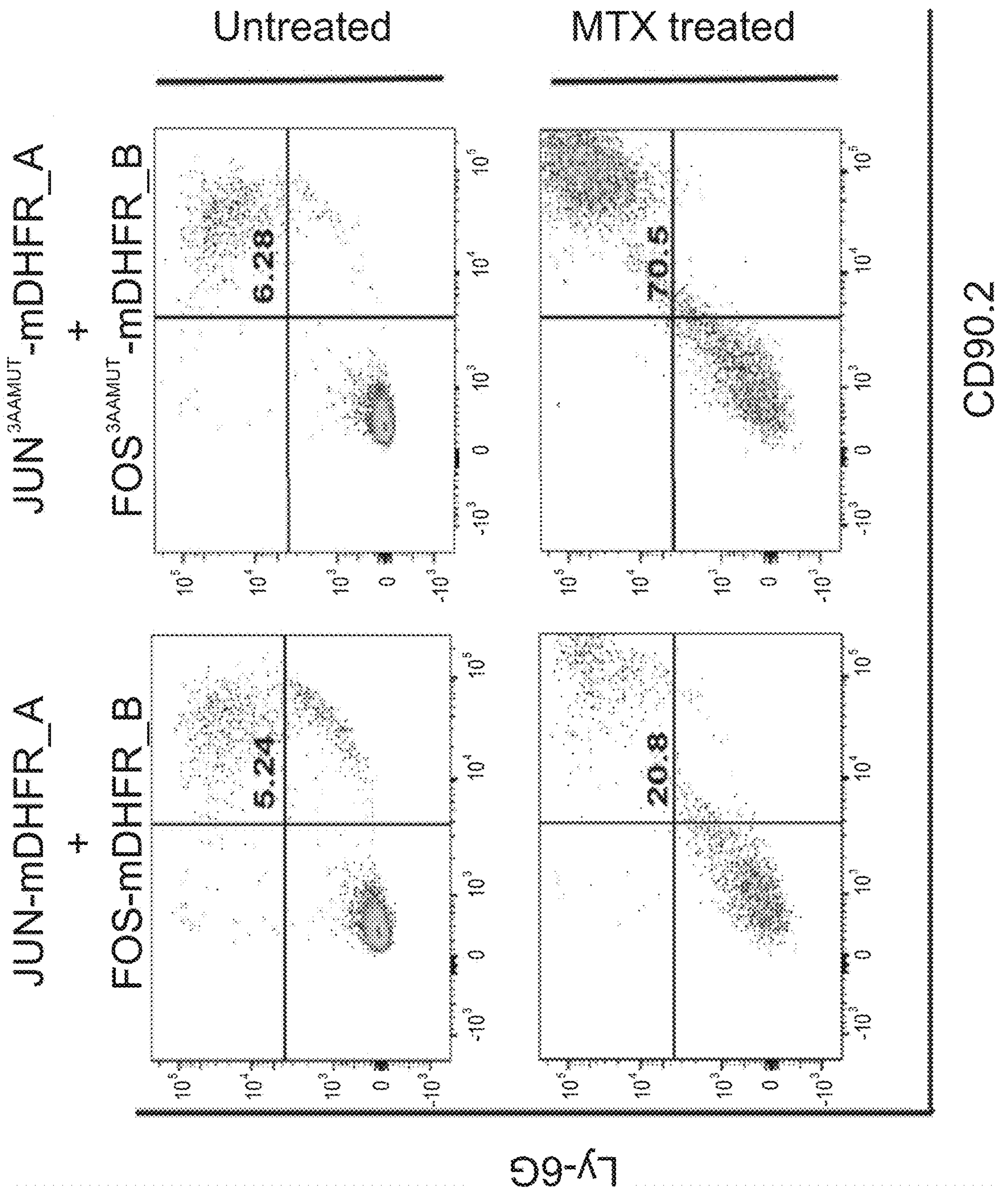
FIG. 47B shows the FACS results comparing Jun-$Fos^{MUT3AA}$ and $Jun^{MUT3AA}$-Fos based CD90.2 and Ly-6G selection after no treatment or 100 nM methotrexate treatment for four days.
Figure 48:
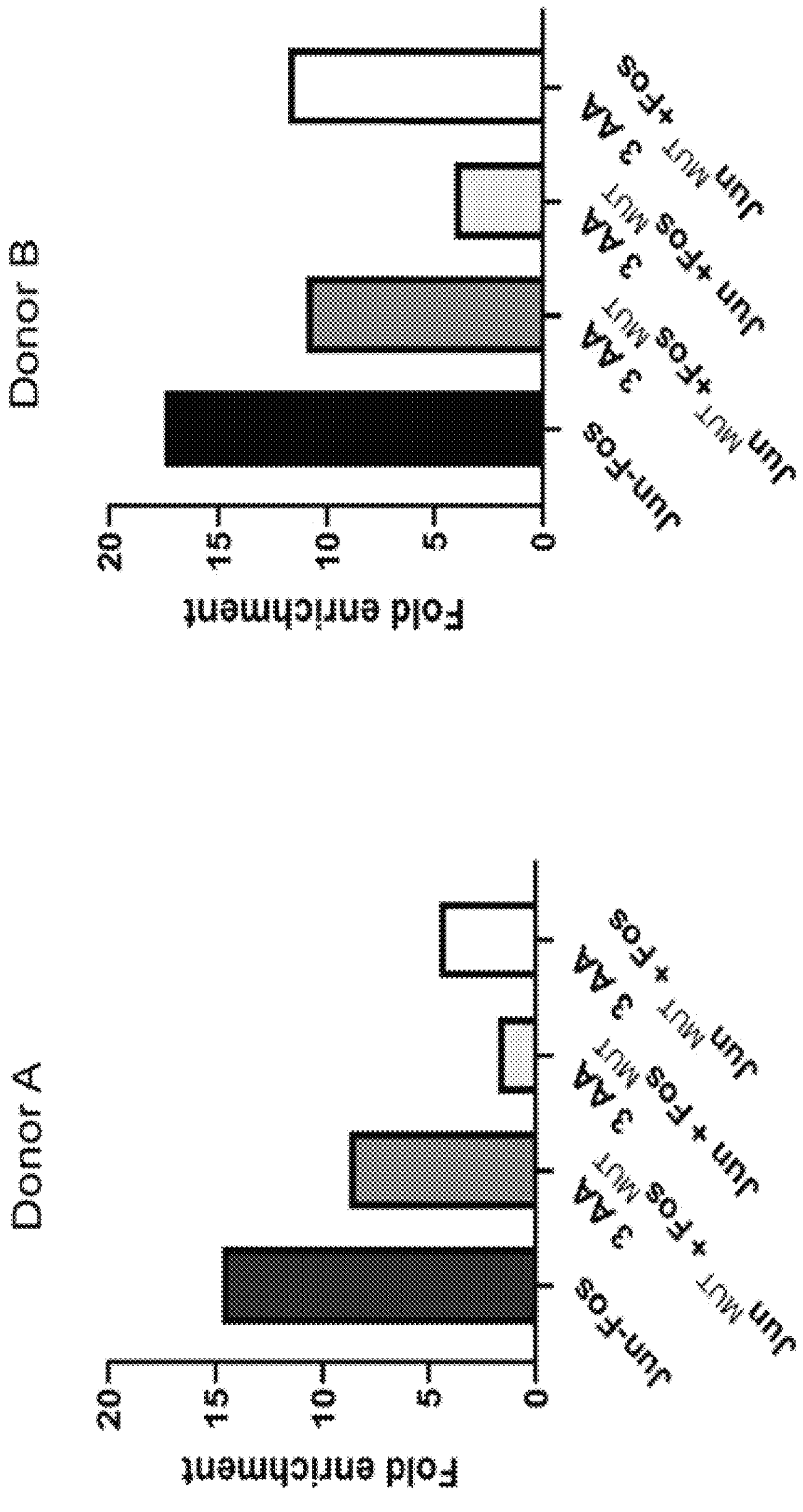
FIG. 48 is a bar chart showing fold-enrichment of engineered T cells in Donor A and Donor B following infection with vector pair $JUN^{WT}$-mDHFR_A+$FOS^{WT}$-mDHFR_B, $JUN^{MUT3AA}$-mDHFR_A+$FOS^{MUT3AA}$-mDHFR_B, $JUN^{WT}$-mDHFR_A+$FOS^{MUT3AA}$-mDHFR_B, or $JUN^{MUT3AA}$-mDHFR_A+$FOS^{WT}$-mDHFR_B.

FIGS. 47A, 47B and 48 show the results of MTX selection of double engineered T cells from donor A and B. Activated human primary T cells isolated from two buffy coats A and B, were double-infected with retroviral vectors encoding an MTX-resistant murine DHFR$^{FS}$ mutant (mDHFR) split into an N-terminal and C-terminal protein half (vector A and B), fused to heterodimerizing JUN-FOS leucine zippers. JUN$^{WT}$ depicts a wildtype JUN leucine zipper, FOS$^{WT}$ depicts a wildtype FOS leucine zipper, JUN$^{MUT3AA}$ depicts a mutant JUN leucine zipper containing three acidic amino acids from FOS, FOS$^{MUT3AA}$ depicts a mutant FOS leucine zipper containing three basic amino acids from JUN. Vector A and B also encoded a Ly6G and CD90.2 transduction marker, respectively. Starting at 4 days post transduction, cells (from donor B) were either left untreated (FIGS. 47A and 47B, row 1), or were treated with 100 nM MTX for 4 days (FIGS. 47A and 47B, row 2), after which enrichment of double transduced cells was measured by FACS analysis. The data indicated that cells (from donor B) infected with vector pair JUN$^{WT}$-mDHFR_A+FOS$^{WT}$-mDHFR_B were enriched from 5.18% to 80.5% (15.5 fold), that cells infected with vector pair JUN$^{MUT3AA}$-mDHFR_A+FOS$^{MUT3AA}$-mDHFR_B were enriched from 8.37% to 88.1% (10.5 fold), that cells infected with vector pair JUN$^{WT}$-mDHFR_A+FOS$^{MUT3AA}$-mDHFR_B were enriched from 5.24% to 20.8% (4 fold), and that cells infected with vector pair JUN$^{MUT3AA}$-mDHFR_A+FOS$^{WT}$-mDHFR_B were enriched from 6.28% to 70.5% (11.2 fold). Together, these data showed that a split-DHFR system using mutant JUN-FOS leucine zippers with three charge-pair mutations can efficiently enrich double engineered T cells, but that three charge-pair mutations are insufficient to abolish interaction with wildtype JUN and FOS leucine zippers. FIG. 48 shows the FACS quantification data of cells from both donor A and donor B.

Figure 49:
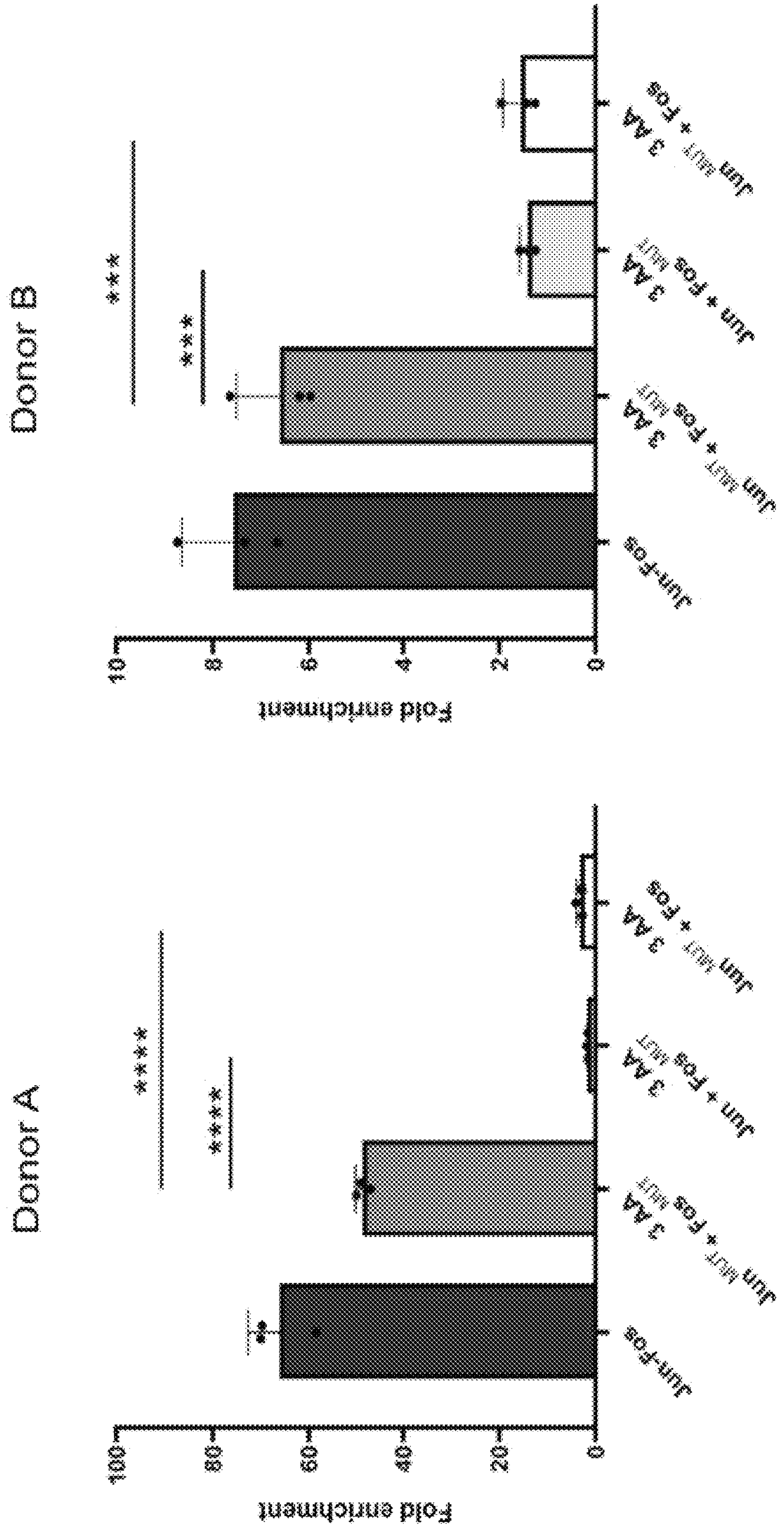
FIG. 49 is a bar chart showing fold-enrichment of engineered T cells in Donor A and Donor B following 100 nM methotrexate treatment for six days, four days after infection with vector pair $JUN^{WT}$-mDHFR_A+$FOS^{WT}$-mDHFR_B, $JUN^{MUT3AA}$-mDHFR_A+$FOS^{MUT3AA}$-mDHFR_B, $JUN^{WT}$-mDHFR_A+$FOS^{MUT3AA}$-mDHFR_B, or $JUN^{MUT3AA}$-mDHFR_A+$FOS^{WT}$-mDHFR_B.
Figure 50:
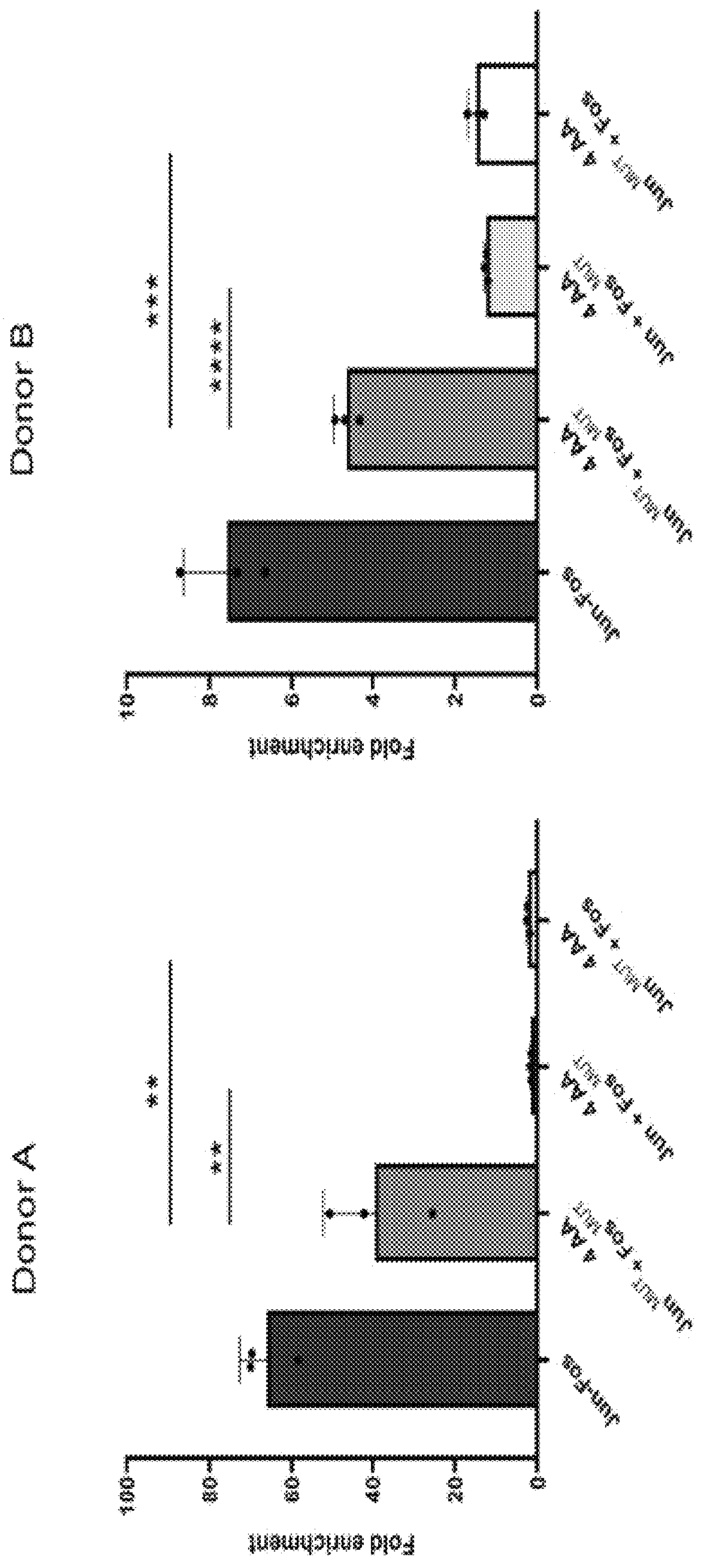
FIG. 50 is a bar chart showing fold-enrichment of engineered T cells in Donor A and Donor B following 100 nM methotrexate treatment for six days, four days after infection with vector pair $JUN^{WT}$-mDHFR_A+$FOS^{WT}$-mDHFR_B, $JUN^{MUT4AA}$-mDHFR_A+$Fos^{MUT4AA}$-mDHFR_B, $JUN^{WT}$-mDHFR_A+$FOS^{MUT4AA}$-mDHFR_B, or $JUN^{MUT4AA}$-mDHFR_A+$FOS^{WT}$-mDHFR_B.

FIGS. 49 and 50 show the results of MTX selection of double engineered T cells from two donors. Activated human primary T cells isolated from buffy coats from two donors (A and B), were double-infected with retroviral vectors encoding an MTX-resistant murine DHFR$^{FS}$ mutant (mDHFR) split into an N-terminal and C-terminal protein half (vector A and B), fused to heterodimerizing JUN-FOS leucine zippers of shorter length (all FOS JUN leucine zippers described in this slides are of shorter length). JUN$^{WT}$ depicts a wildtype JUN leucine zipper, FOS$^{WT}$ depicts a wildtype FOS leucine zipper, JUN$^{MUT3AA}$ depicts a mutant JUN leucine zipper containing three acidic amino acids from FOS, FOS$^{MUT3AA}$ depicts a mutant FOS leucine zipper containing three basic amino acids from JUN, JUN$^{MUT4AA}$ depicts a mutant JUN leucine zipper containing four acidic amino acids from FOS, FOS$^{MUT4AA}$ depicts a mutant FOS leucine zipper containing four basic amino acids from JUN. Vector A and B also encoded a Ly6G and CD90.2 transduction marker, respectively. Starting at 4 days post transduction, cells were either left untreated, or were treated with 100 nM MTX for 6 days, after which enrichment of double transduced cells was measured by FACS analysis. The data (FIG. 49) indicated that cells infected with vector pair JUN$^{WT}$-mDHFR_A+FOS$^{WT}$-mDHFR_B were enriched 66±6.6 (donor A) and 7.6±1.1 (donor B) fold, that cells infected with vector pair JUN$^{MUT3AA}$-mDHFR_A+FOS$^{MUT3AA}$-mDHFR_B were enriched 49±1.5 (donor A), 6.6±0.9 (donor B) fold, that cells infected with vector pair JUN$^{WT}$-mDHFR_A+FOS$^{MUT3AA}$-mDHFR_B were enriched 1.7±0.1 (donor A) and 1.4±0.17 (donor B) fold, that cells infected with vector pair JUN$^{MUT3AA}$-mDHFR_A+FOS$^{WT}$-mDHFR_B were enriched 3.2±0.66 (donor A) and 1.5±0.38 (donor B) fold. The data (FIG. 50) indicated that cells infected with vector pair JUN$^{MUT4AA}$-mDHFR_A+FOS$^{MUT4AA}$-mDHFR_B were enriched from enriched 39±13 (donor A) and 4.7±0.32 (donor B) fold, that cells infected with vector pair JUN$^{WT}$-mDHFR_A+FOS$^{MUT4AA}$-mDHFR_B were enriched 1.5±0.13 (donor A) and 1.2±0.043 (donor B), and that cells infected with vector pair JUN$^{MUT4AA}$-mDHFR_A+FOS$^{WT}$-mDHFR_B were enriched 2.2±0.43 (donor A) and 1.5±0.21 (donor B). Together, these data showed that a split-DHFR system using mutant a shorter JUN-FOS leucine zippers with either three or four charge-pair mutations can efficiently enrich double engineered T cells, and that either three or four charge-pair mutations are sufficient to largely abolish interaction with wildtype JUN and FOS leucine zippers.

Example 13

This example shows that a split-DHFR system using eight charge-pair mutations JUN-FOS leucine zippers cannot enrich double engineered T cells.

Figure 51A:
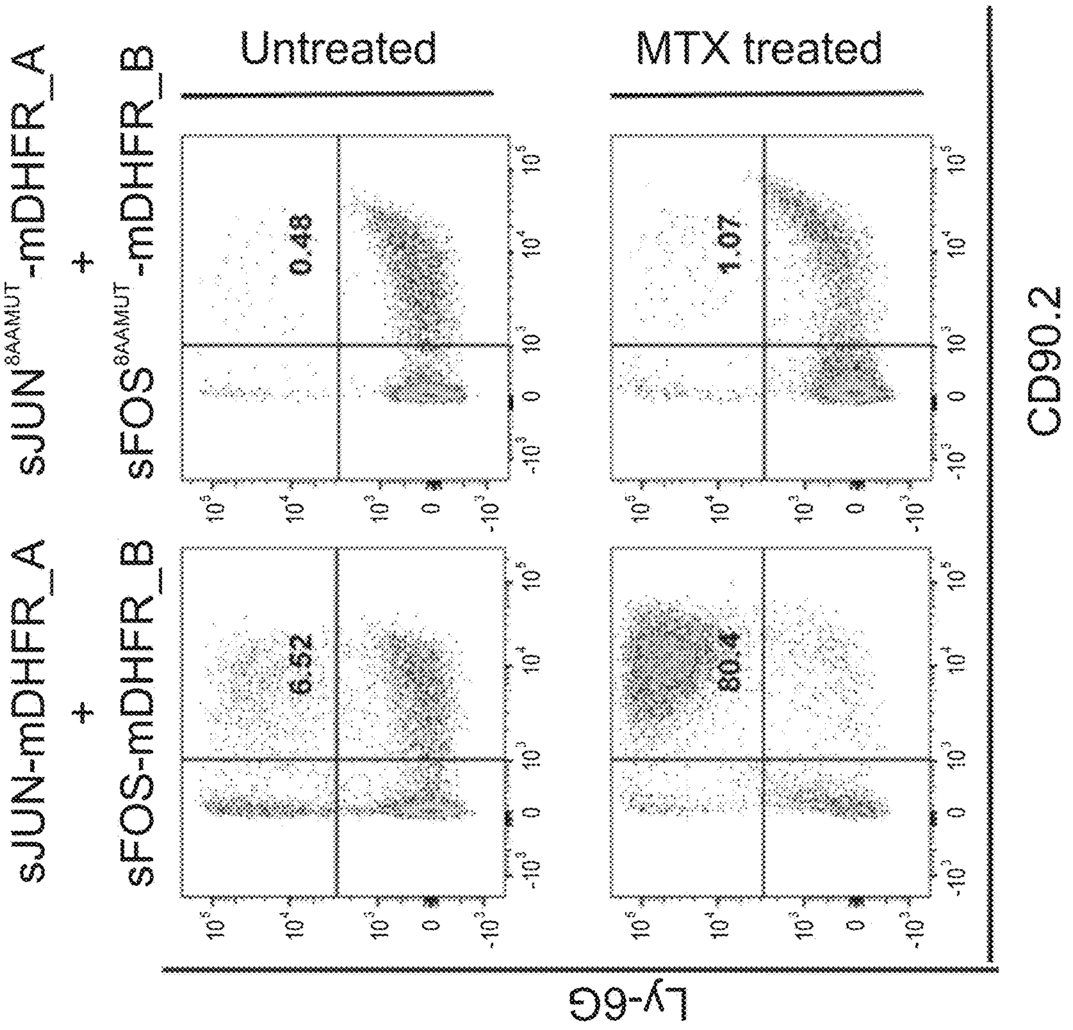
FIGS. 51A and 51B show shows the FACS results of double engineered T cells from donor A and B, using CD90.2 and Ly-6G selection after no treatment or 100 nM methotrexate treatment for six days, four days after infection with either sJUN-mDHFR_A+sFOS-mDHFR_B or pair $sJUN^{MUT8AA}$-mDHFR_A+$sFOS^{MUT8AA}$-mDHFR_B, sJUN-mDHFR_A+sFOS$^{MUT8AA}$-mDHFR_B, or sJUN$^{MUT8AA}$-mDHFR_A+sFOS-mDHFR_B.
Figure 51B:
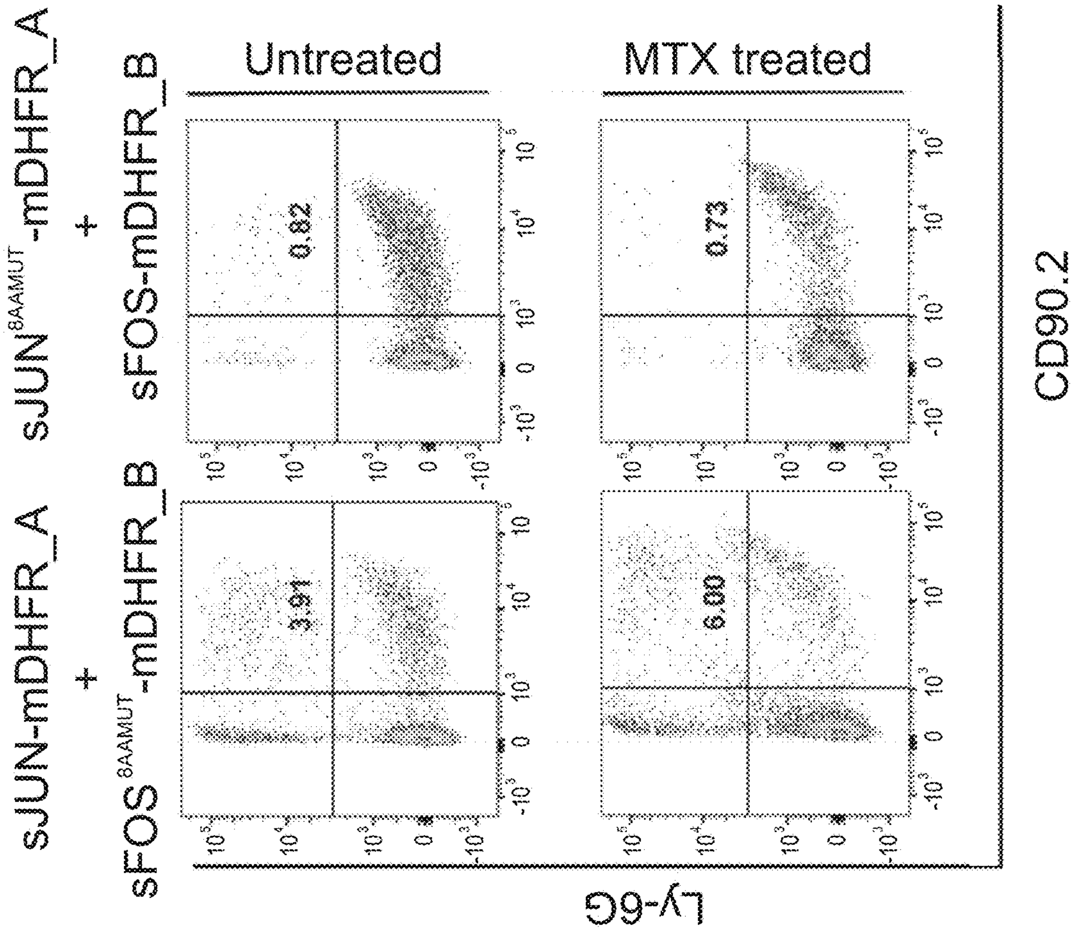
Figure 52:
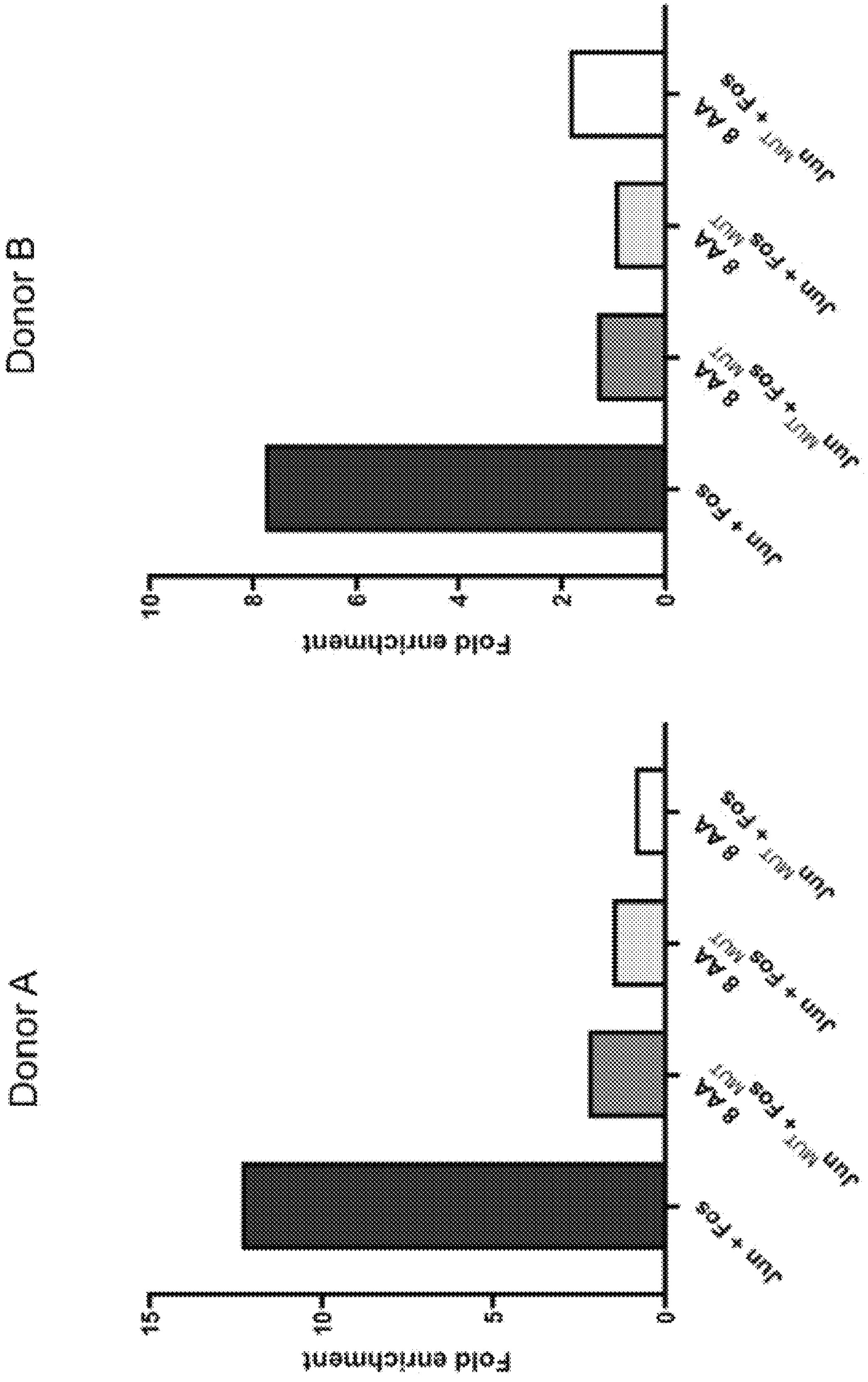
FIG. 52 is a bar chart showing the quantification of fold enrichment of engineered T cells, as generated by the FACS plot from FIGS. 51A-51B.

FIGS. 51A, 51B, and 52 show the results of MTX selection of double engineered T cells from donor A and B. Activated human primary T cells isolated from two buffy coats A and B, were double-infected with retroviral vectors encoding an MTX-resistant murine DHFR$^{FS}$ mutant (mDHFR) split into an N-terminal and C-terminal protein half (vector A and B), fused to heterodimerizing JUN-FOS leucine zippers. sJUN depicts a shorter wildtype JUN leucine zipper, sFOS depicts a wildtype FOS leucine zipper, sJUN$^{MUT8AA}$ depicts a shorter mutant JUN leucine zipper containing eight acidic amino acids from FOS, sFOS$^{MUT8AA}$ depicts a mutant FOS leucine zipper containing eight basic amino acids from JUN. Vector A and B also encoded a Ly6G and CD90.2 transduction marker, respectively. Starting at 4 days post transduction, cells (from donor B) were either left untreated (FIGS. 51A and 51B, row 1), or were treated with 100 nM MTX for 6 days (FIGS. 51A and 51B, row 2), after which enrichment of double transduced cells was measured by FACS analysis. The data (FIGS. 51A and 51B) indicated that cells (from donor A) infected with vector pair sJUN-mDHFR_A+sFOS-mDHFR_B were enriched from 6.52% to 80.4% (12.3 fold), that cells infected with vector pair sJUN$^{MUT8AA}$-mDHFR_A+sFOS$^{MUT8AA}$-mDHFR_B were enriched from 0.48% to 1.07% (2.2 fold), that cells infected with vector pair sJUN-mDHFR_A+sFOS$^{MUT8AA}$-mDHFR_B were enriched from 3.91% to 6% (1.5 fold), and that cells infected with vector pair sJUN$^{MUT8AA}$-mDHFR_A+sFOS-mDHFR_B were enriched from 0.82% to 0.73% (0.9 fold). The data from FIG. 52 shows the quantification of FACS plot from both donor A and B. In conclusion, these data showed that a split-DHFR system using mutant JUN-FOS leucine zippers with eight charge-pair mutations cannot enrich double engineered T cells.

Example 14

This example shows that a split-DHFR system using mutant FKBP12 dimerization domains can enrich double engineered T cells in the presence of the chemical dimerization inducer AP1903.

Figure 53:
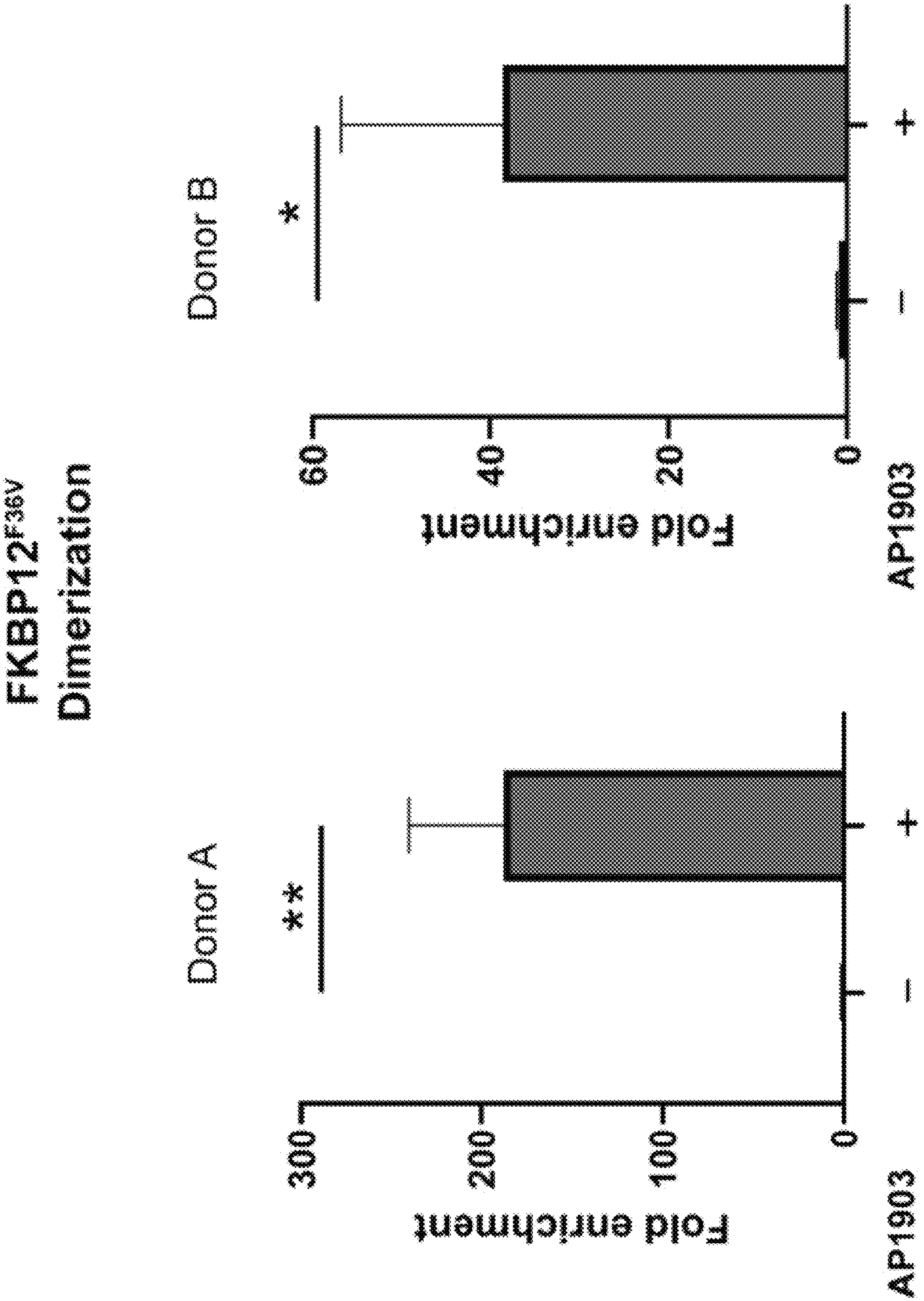
FIG. 53 is a bar chart showing fold-enrichment of engineered T cells in Donor A and Donor B following infection with vector pair FKBP12$^{F36V}$-mDHFR_A+FKBP12$^{F36V}$-mDHFR_B, four hours of either no treatment or 10 nM AP1903, and six days of treatment with 100 nM methotrexate.

FIG. 53 shows the results of MTX selection of double engineered T cells from donor A and B. Activated human primary T cells isolated from two buffy coats donor A and B, were double-infected with retroviral vectors encoding an MTX-resistant murine DHFR$^{FS}$ mutant (mDHFR) split into an N-terminal and C-terminal protein half (vector A and B), fused to homodimerizing mutant FKBP12 domains. Untransduced depicts non-transduced cells, FKBP12$^{F36V}$ depicts an FKBP12 protein containing an F36V mutation, which enhances binding to the AP1903 dimerizer drug. Vector A and B also encoded a Ly6G and CD90.2 transduction marker, respectively. Starting at 4 days post transduction, cells were either left untreated or were treated with 10 nM AP1903 for 4 hours. Subsequently, cells were left untreated, or were treated with 100 nM MTX for 6 days, after which enrichment of double transduced cells was measured by FACS analysis. The data indicated that cells infected with vector pair FKBP12$^{F36V}$-mDHFR_A+FKBP12$^{F36V}$-mDHFR_B with AP1903 treatment were enriched 188±53 (donor A) and 39±18 (donor B), respectively. Together, these data showed that a split-DHFR system using mutant FKBP12 dimerization domains can efficiently enrich double engineered T cells.

Example 15

This example shows that B2M guides can mediate efficient cutting at B2M locus.

Figure 54:
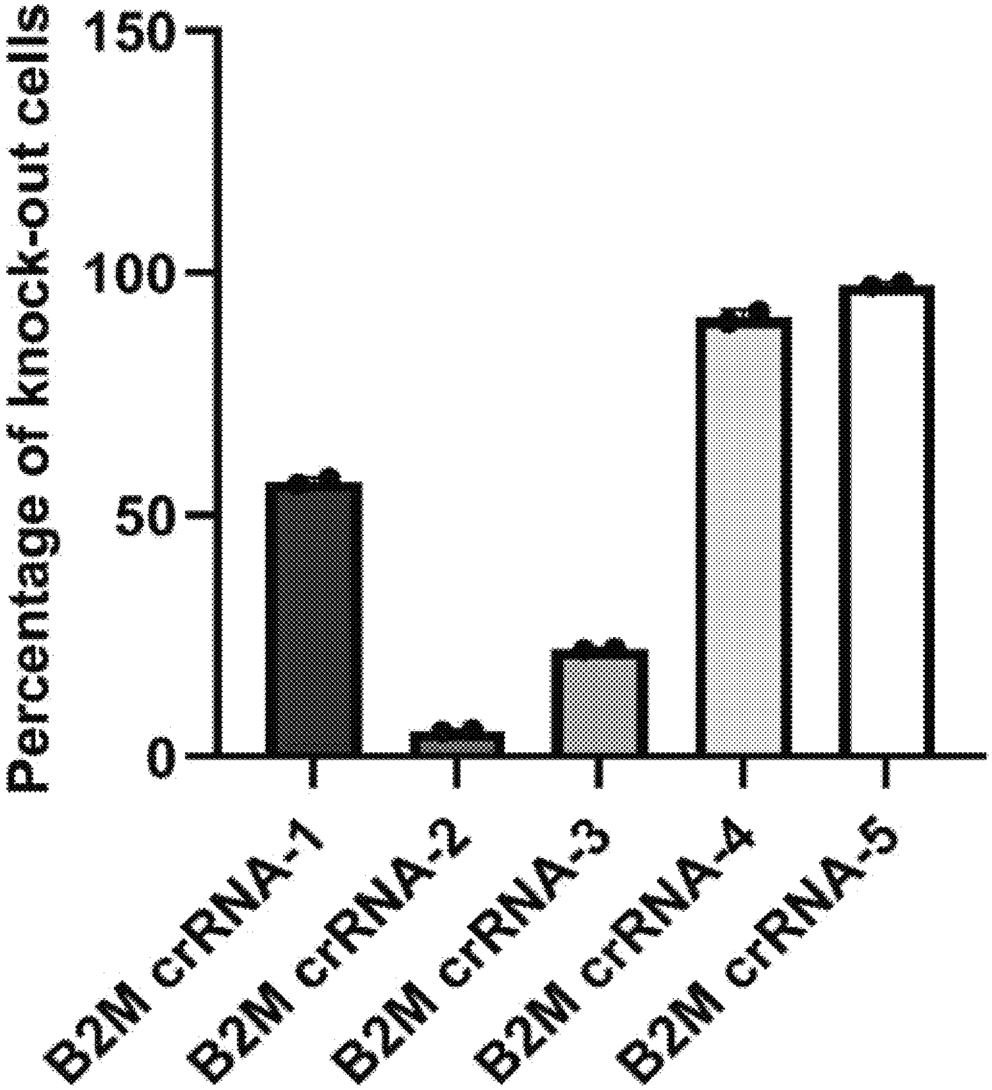
FIG. 54 is a bar chart showing the percentage of knockout cells in human primary T cells treated with one of five Cas9 RNPs targeting the B2M locus.

FIG. 54 shows the results of screening of efficient guides targeting B2M locus. Activated human primary T cells isolated from a buffy coat, were electroporated with five Cas9 RNPs targeting distinct B2M locus. Two days post electroporation, cells were FACS analyzed by measuring HLA-ABC expression. The data indicated that crB2M-4 and crB2M-5 can target B2M locus with knockout efficiency above 80%. Based on this data, crB2M-4 and crB2M-5 were chosen for subsequent knockin experiments.

Exemplary Arrangements (a):

1. A method for selection or enrichment of a genetically engineered cell comprising:
   - i) introducing into a cell at least one two-part nucleotide sequence capable of expressing both the first-part and second-part nucleotide sequences in the cell,
   - wherein the cell has an essential protein for the survival and/or proliferation that is reduced to a level that the cell cannot survive and/or proliferate in a normal cell culture medium,
   - wherein the at least one two-part nucleotide sequence is operable for expression in the cell or becomes operable for expression when inserted into a pre-determined site in the target genome, and
   - wherein the at least one two-part nucleotide sequence comprises a first-part nucleotide sequence encoding the essential protein for the survival and/or proliferation, or a variant thereof, and a second-part nucleotide sequence encoding a protein to be expressed, wherein the second-part nucleotide sequence encodes a protein of interest; and
   - ii) culturing the cell in the normal cell culture medium without a pharmacologic exogenous selection pressure for selection or enrichment of the cell that expresses both the first-part and second-part nucleotide sequences.
2. A method for selection or enrichment of a genetically engineered cell comprising:
   - i) reducing the level of at least a first protein that is essential for the survival and/or proliferation of a cell to the level that the cell cannot survive and/or proliferate under normal in vitro propagation conditions;
   - ii) introducing into the cell at least a two-part nucleotide sequence that is capable of expressing both the first-part and second-part nucleotide sequences in the cell and comprises a first-part nucleotide sequence encoding the first protein, or a variant thereof, and a second-part nucleotide sequence encoding a second protein to be expressed, wherein the at least one two-part nucleotide sequence is operable for expression in the cell or becomes operable for expression when inserted into a pre-determined site in the target genome, and wherein the second-part protein is a protein of interest, and iii) culturing the cell under normal in vitro propagation conditions without a pharmacologic exogenous selection pressure for enrichment of the cell that expresses both the first protein and second protein.

3. The method of any one of arrangements 1 or 2, wherein the reduction in level of the essential protein can be permanent or transient.

4. The method of any one of arrangements 2-3, wherein the reduction in level of the essential protein comprises a knock-out of the gene encoding the essential protein.

5. The method of arrangement 4, wherein the knock-out is mediated by CRISPR Ribonucleoprotein (RNP), TALEN, MegaTAL, or any other nucleases.

6. The method of any one of arrangements 2-3, wherein the reduction in level of the essential protein comprises transient reduction in the level of the essential protein at the RNA level.

7. The method of arrangement 6, wherein the transient suppression is through siRNA, miRNA, or CRISPR interference (CRISPRi).

8. The method of any one of arrangements 1-7, wherein the cell is a T cell, NK cell, NKT cell, iNKT cell, hematopoietic stem cell, mesenchymal stem cell, iPSC, neural precursor cell, a cell type in retinal gene therapy, or any other cell.

9. The method of any one of arrangements 1-8, wherein the first-part nucleotide sequence is altered in nucleotide sequence to achieve nuclease, siRNA, miRNA, or CRISPRi resistance.

10. The method of arrangement 9, wherein the first part nucleotide sequence encodes a protein having an identical amino acid sequence to the essential first protein.

11. The method of any one of the preceding arrangements, wherein the first-part nucleotide sequence is altered to encode an altered protein that does not have an identical amino acid sequence to the first protein.

12. The method of arrangement 11, wherein the altered protein has specific features that the first protein does not have.

13. The method of arrangement 12, wherein specific features include, but are not limited to, one or more of the following: reduced activity, increased activity, and altered half-life.

14. The method of any of the preceding arrangements, wherein both the first-part and the second-part nucleotide sequences can be driven by a same promoter or different promoters.

15. The method of any one of the preceding arrangements, wherein the second-part nucleotide sequence comprises at least a therapeutic gene.

16. The method of any one of the preceding arrangements, wherein the second-part nucleotide sequence encodes a neo-antigen T-cell receptor complex (TCR) containing a TCR alpha chain and a TCR beta chain.

17. The method of any one of the preceding arrangements, wherein the essential or first protein is dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC).

18. The method of any one of the preceding arrangements, wherein the first-part nucleotide sequence comprises a nuclease-resistant or siRNA-resistant DHFR gene, and the second-part nucleotide sequence comprises a TRA gene and a TRB gene.

19. The method of arrangement 18, wherein the TRA, TRB, and DHFR genes are operably configured to be expressed from a single open reading frame.

20. The method of arrangement 19, wherein the TRA, TRB, and DHFR genes are separated by an at least one linker.

21. The method of arrangement 20, wherein the order of the at least one linker, TRA, TRB, and DHFR genes is the following:

TRA-linker-TRB-linker-DHFR,
TRA-linker-DHFR-linker-TRB,
TRB-linker-TRA-linker-DHFR,
TRB-linker-DHFR-linker-TRA,
DHFR-linker-TRA-linker-TRB, or
DHFR-linker-TRB-linker-TRA.

22. The method of arrangement 20 or 21, wherein the at least one linker is an at least one self-cleaving 2A peptide and/or an at least one IRES element.

23. The method of any one of arrangements 18-22, wherein the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1.

24. The method of any one of the preceding arrangements, wherein the two-part nucleotide sequence is integrated into the genome of the cell.

25. The method of any one of the preceding arrangements, wherein the at least one two part nucleotide sequence becomes operable for expression when inserted into the pre-determined site in the target genome and both the first-part and second-part nucleotide sequences are driven by a promoter in the target genome.

26. The method of arrangement 24 or 25, wherein the integration is through nuclease-mediated site-specific integration, transposon-mediated gene delivery, or virus-mediate gene delivery.

27. The method of arrangement 26, wherein the nuclease-mediated site-specific integration is through CRISPR RNP, optionally a CRISPR/Cas9 RNP.

28. The method of arrangement 27, further comprising using the Split intein system.

29. The method of any one of arrangements 1-23, wherein the introduced two-part nucleotide sequence is not integrated into the genome of the cell.

30. The method of any one of arrangements 1-27, wherein a CRISPR RNP that targets an endogenous TCR Constant locus, the first-part nucleotide sequence encoding a nuclease-resistant DHFR gene, and the second-part nucleotide sequence encoding a neo-antigen TCR are delivered to the cell.

31. The method of arrangement 30, wherein the endogenous TCR constant locus can be a TCR alpha Constant (TRAC) locus or a TCR beta Constant (TRBC) locus.

32. The method of arrangement 30 or 31, wherein the delivery is by electroporation, or methods based on mechanical or chemical membrane permeabilization.

33. The method of any one of arrangements 1-5, 8-28, or 30-32, wherein a first CRISPR RNP is used to knock-out endogenous dihydrofolate reductase (DHFR) gene, and a second CRISPR RNP is used to knock-in into an endogenous TCR constant locus the first-part nucleotide sequence comprising the CRISPR nuclease-resistant DHFR gene and the second-part nucleotide sequence encoding a therapeutic TCR gene.

34. The method of arrangement 33, wherein the second CRISPR RNP is a TRAC RNP that cuts the TRAC locus for knock-in.

35. The method of any one of arrangements 5, 27, 30, 33, or 34, wherein the CRISPR RNP is a CRISPR/Cas9 RNP.

36. The method of any one of arrangements 1-35, wherein the normal cell culture medium is one that is suitable for non-modified cell's growth and/or proliferation.

37. The method of any one of arrangements 1-36, wherein the normal cell culture medium is without any exogenous selection pressure.

38. The method of any one of arrangements 5-37 wherein a CRISPR RNP is used to knock-in into a pre-determined site in the target genome a second two-part nucleotide, optionally wherein the pre-determined site in the target genome is the B2M gene.

39. A method for selection or enrichment of a genetically engineered cell comprising:

i) introducing into a cell at least one two-part nucleotide sequence capable of expressing both the first-part and second-part nucleotide sequences in the cell, wherein the cell has the functional activity of an essential protein for the survival and/or proliferation that is reduced such that the cell cannot survive and/or proliferate in a normal cell culture medium, wherein the at least one two-part nucleotide sequence is operable for expression in the cell or becomes operable for expression when inserted into a pre-determined site in the target genome, and wherein the at least one two-part nucleotide sequence comprises a first-part nucleotide sequence encodes a first protein that provides a substantially equivalent function to the essential protein for the survival and/or proliferation and a second-part nucleotide sequence encodes a second protein to be expressed, wherein the second protein that is a protein of interest; and ii) culturing the cell in cell culture medium containing at least one supplement leading to enrichment or selection of the cell that expresses both the first protein and the second protein.

40. A method for selection or enrichment of a genetically engineered cell comprising:

i) reducing the functional activity of at least a first protein that is essential for the survival and/or proliferation of a cell to the level that the cell cannot survive and/or proliferate under normal in vitro propagation conditions;

ii) introducing into the cell at least a two-part nucleotide sequence that is capable of expressing both the first-part and second-part nucleotide sequences in the cell and comprises a first-part nucleotide sequence encodes a first protein that provides a substantially equivalent function to and a second-part nucleotide sequence encoding a second protein to be expressed, wherein the at least one two-part nucleotide sequence is operable for expression in the cell or becomes operable for expression when inserted into a pre-determined site in the target genome, and wherein the second protein is a protein of interest, and iii) culturing the cell in cell culture medium containing at least one supplement leading to selection or enrichment of the cell that expresses both the first protein and the second protein.

41. The method of arrangement 39 or 40, wherein the cell is a T cell, NK cell, NKT cell, iNKT cell, hematopoietic stem cell, mesenchymal stem cell, iPSC, neural precursor cell, a cell type in retinal gene therapy, or any other cell.

42. The method of any one of arrangements 39-41, wherein the first-part nucleotide sequence is altered in nucleotide sequence to achieve nuclease, siRNA, miRNA, or CRISPRi resistance, and either a) encodes a protein having an identical amino acid sequence to the first protein or b) encodes a protein having an adjusted functionality to the first protein.

43. The method of any one of arrangements 39-42, wherein the first-part nucleotide sequence is altered to encode an altered protein that does not have an identical amino acid sequence to the first protein.

44. The method of arrangement 43, wherein the altered protein has specific features that the first protein does not have.

45. The method of arrangement 44, wherein the specific features include, but are not limited to, one or more of the following: reduced activity, increased activity, altered half-life resistance to small molecule inhibition, and increased activity after small molecule binding.

46. The method of any one of arrangements 39-45, wherein both the first-part and second-part nucleotide sequences can be driven by a same promoter or different promoters.

47. The method of any one of arrangements 39-46, wherein the second-part nucleotide sequence comprises at least a therapeutic gene.

48. The method of any one of arrangements 39-47, wherein the second-part nucleotide sequence encodes a neo-antigen T-cell receptor complex (TCR) containing a TCR alpha chain and a TCR beta chain.

49. The method of any one of arrangements 39-48, wherein the essential or first protein is dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC).

50. The method of any one of arrangements 39-49, wherein the first-part nucleotide sequence comprises a protein inhibitor-resistant DHFR gene, and the second-part nucleotide sequence comprises a TRA gene and a TRB gene.

51. The method of arrangement 50, wherein the TRA, TRB, and DHFR genes are operably configured to be expressed from a single open reading frame.

52. The method of arrangement 51, wherein the TRA, TRB, and DHFR genes are separated by an at least one linker.

53. The method of arrangement 52, wherein the order of the at least one linker, TRA, TRB, and DHFR genes is the following:

TRA-linker-TRB-linker-DHFR,
TRA-linker-DHFR-linker-TRB,
TRB-linker-TRA-linker-DHFR,
TRB-linker-DHFR-linker-TRA,
DHFR-linker-TRA-linker-TRB, or
DHFR-linker-TRB-linker-TRA.

54. The method of arrangement 53, wherein the at least one linker is an at least one self-cleaving 2A peptide and/or an at least one IRES element.

55. The method of any one of arrangements 50-54, wherein the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1.

56. The method of any one of arrangements 39-55, wherein the two-part nucleotide sequence is integrated into the genome of the cell.

57. The method of any one of arrangements 39-56, wherein the at least one two part nucleotide sequence becomes operable for expression when inserted into the pre-determined site in the target genome and both the first-part and second-part nucleotide sequences are driven by a promoter in the target genome.

58. The method of arrangement 57, wherein the integration is through nuclease-mediated site-specific integration, transposon-mediated gene delivery, or virus-mediate gene delivery.

59. The method of arrangement 58, wherein the nuclease-mediated site-specific integration is through CRISPR RNP, optionally a CRISPR/Cas9 RNP.

60. The method of arrangement 59, further comprising using the Split intein system.

61. The method of any one of arrangements 39-55, wherein the introduced two-part nucleotide sequence is not integrated into the genome of the cell.

62. The method of any one of arrangements 39-60, wherein a CRISPR RNP that targets an endogenous TCR Constant locus, the first-part nucleotide sequence encoding a protein inhibitor-resistant DHFR gene, and the second-part nucleotide sequence encoding a neo-antigen TCR are delivered to the cell.

63. The method of arrangement 62, wherein the endogenous TCR constant locus can be a TCR alpha Constant (TRAC) locus or a TCR beta Constant (TRBC) locus.

64. The method of arrangement 62 or 63, wherein the delivery is by electroporation, or methods based on mechanical or chemical membrane permeabilization.

65. The method of any one of arrangements 62-64, wherein the CRISPR RNP is a TRAC RNP that cuts the TRAC locus for knock-in.

66. The method of any one of arrangements 59, 62, or 65 wherein the CRISPR RNP is a CRISPR/Cas9 RNP.

67. The method of any one of arrangements 39-66, wherein the supplement leading to enrichment or selection of the cell is an antibody that allows enrichment of the cells by flow cytometry or magnetic bead enrichment.

68. The method of any one of arrangements arrangement 39-67, wherein the supplement impairs survival and/or proliferation of cells without expressing both the first protein and the second protein.

69. The method of arrangement 68, wherein the first protein mediates resistance of the cell to the supplement mediated impairment of survival and/or proliferation of cells.

70. The method of any one of arrangements 39-69, wherein the supplement is methotrexate.

71. The method of any one of arrangements 69 or 70, wherein the first protein is a methotrexate-resistant DHFR mutant protein.

72. A method for selection or enrichment of a genetically engineered cell comprising:

i) introducing into a cell at least two two-part nucleotide sequences capable of expressing both a first-part and a second-part nucleotide sequence in the cell, wherein the cell has an essential protein for the survival and/or proliferation that is suppressed to a level that the cell cannot survive and/or proliferate, wherein the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest, wherein the second two-part nucleotide sequence comprises a first-part nucleotide sequence encoding a second fusion protein comprising a non-functional portion of the essential protein for the survival and/or proliferation fused to a second binding domain and a second-part nucleotide sequence encoding a second protein of interest, wherein, when both the first and second fusion proteins are expressed together in a cell, the function of the essential protein for the survival and/or proliferation is restored; and ii) culturing the cell under conditions leading to the selection of the cell that expresses both the first and second two-part nucleotide sequences.

73. A method for selection or enrichment of a genetically engineered cell comprising:

i) suppressing at least a first protein that is essential for the survival and/or proliferation of a cell to the level that the cell cannot survive and/or proliferate under normal in vitro propagation conditions;

ii) introducing at least two two-part nucleotide sequences that are capable of being expressed in the cell, wherein the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a first protein of interest, wherein the second two-part nucleotide sequence comprises a first-part nucleotide sequence encoding a second fusion protein comprising non-functional portion of the essential protein for the survival and/or proliferation fused to a second binding domain and a second-part nucleotide sequence encoding a second protein protein of interest, wherein, when both the first and second fusion proteins are expressed together in a cell, the function of the essential protein for the survival and/or proliferation is restored, and iii) culturing the cell under in vitro propagation conditions that lead to the enrichment of the cell that expresses both the first fusion protein and second fusion protein.

74. The method of arrangement 72 or 73, wherein the essential protein is a DHFR protein.

75. The method of arrangement 74, wherein the first fusion protein comprises an N-terminal portion of DHFR and the second fusion protein comprises a C-terminal portion of DHFR.

76. The method of arrangement 74, wherein the first fusion protein comprises a C-terminal portion of DHFR and the second fusion protein comprises an N-terminal portion of DHFR.

77. The method of arrangement 74 or 75, wherein the N-terminal portion of DHFR comprises SEQ ID NO: 22.

78. The method of any one of arrangements 74-77, wherein the C-terminal portion of DHFR comprises SEQ ID NO: 23.

79. The method of any one of arrangements 72-78, wherein the second-part nucleotide sequence of either the first or second two-part nucleotide sequences is exogenous to the cell.

80. The method of any one of arrangements 72-79, wherein the second-part nucleotide sequence of either the first or second two-part nucleotide sequence is a TCR.

81. The method of any one of arrangements 72-80, wherein the first and second binding domains are derived from GCN4.

82. The method of any one of arrangements 72-81, wherein the first and/or second binding domains comprise SEQ ID NO: 24.

83. The method of any one of arrangements 72-82, wherein the first fusion protein and second fusion protein comprise SEQ ID NO: 39 or SEQ ID NO: 40.

84. The method of any one of arrangements 72-80, wherein the first and second binding domains are derived from FKBP12.

85. The method of arrangement 84, wherein the FKBP12 has an F36V mutation.

86. The method of any one of arrangements 72-80, 84, or 85, wherein the first and/or second binding domains comprise SEQ ID NO: 31.

87. The method of any one of arrangements 72-80 or 84-86, wherein the first fusion protein and second fusion protein comprise SEQ ID NO: 62 or SEQ ID NO: 63.

88. The method of any one of arrangements 72-80, wherein the first binding domain and the second binding domain are derived from JUN and FOS.

89. The method of arrangement 88, wherein the first binding domain and second binding domain have complementary mutations that preserve binding to each other.

90. The method of arrangement 89, wherein neither the first binding domain nor the second binding domain bind to a native binding partner.

91. The method of any one of arrangements 72-80 or 88-90, wherein each of the first binding domain and second binding domain have between 3 and 7 complementary mutations.

92. The method of arrangement 91 wherein the first binding domain and second binding domain each have 3 complementary mutations.

93. The method of any one of arrangements 72-80, or 88-92, wherein the first binding domain and second binding domain comprise SEQ ID NO: 26 or SEQ ID NO: 29.

94. The method of any one of arrangements 72-80, or 88-93, the first fusion protein and second fusion protein comprise SEQ ID NO: 35 or SEQ ID NO: 36.

95. The method of arrangement 91, wherein the first binding domain and second binding domain each have 4 complementary mutations.

96. The method of any one of arrangements 72-80, 88-91, or 95 wherein the first binding domain and second binding domain comprise SEQ ID NO: 27 and SEQ ID NO: 30.

97. The method of any one of arrangements 72-80, 88-91, 95, or 96 wherein the first fusion protein and second fusion protein comprise SEQ ID NO: 37 and SEQ ID NO: 38.

98. The method of any one of arrangements 72-97, wherein the at least two two-part nucleotide sequences are integrated into the genome of the cell.

99. The method of any one of arrangements 72-98, wherein the at least two two-part nucleotide sequences become operable for expression when inserted into predetermined sites in the target genome and both the first-part and second-part nucleotide sequences are driven by a promoters in the target genome.

100. The method of arrangement 98 or 99, wherein the integration is through nuclease-mediated site-specific integration, transposon-mediated gene delivery, or virus-mediate gene delivery.

101. The method of arrangement 100, wherein the nuclease-mediated site-specific integration is through CRISPR RNP.

102. The method of any one of arrangements 72-101, wherein the first two-part nucleotide sequence is delivered to the cell by a CRISPR RNP that targets an endogenous TCR Constant locus, the first first-part nucleotide sequence encodes a non-functional portion of a DHFR protein, and the first second-part nucleotide sequence encodes a neo-antigen TCR.

103. The method of any one of arrangements 72-102, wherein the second two-part nucleotide sequence is delivered to the cell by a CRISPR RNP that targets an endogenous locus other than a TCR Constant locus, the second first-part nucleotide sequence encodes a non-functional portion of a DHFR protein, and the second second-part nucleotide sequence encodes a protein of interest.

104. The method of arrangement 103, wherein the first first-part nucleotide sequence and the second first-part nucleotide sequences encode fusion proteins comprising non-functional portions of a DHFR protein that have DHFR activity when the fusion proteins are co-expressed.

105. The method of any one of arrangements 102-104, wherein the endogenous TCR Constant locus can be a TCR alpha Constant (TRAC) locus or a TCR beta Constant (TRBC) locus.

106. The method of any one of arrangements 103-105, wherein the endogenous locus other than a TCR Constant locus is a B2M locus.

107. The method of any one of arrangements 102-106, wherein the delivery is by electroporation, or methods based on mechanical or chemical membrane permeabilization.

108. The method of any one of arrangements 101-107, wherein the CRISPR RNP is a CRISPR/Cas9 RNP.

109. The method of any one of arrangements 26-28, 30-38, 58-60, 62-71, or 100-108 in which the nuclease allows for in-frame exonic integration into a gene locus to express at least one part of one of the two-part nucleotides from the endogenous promotor, the endogenous splice sites, and the endogenous termination signal.

110. The method of any one of arrangements 26-28, 30-38, 58-60, 62-71, or 100-108 in which the nuclease allows for in-frame exonic integration into a gene locus to express at least one part of one of the two-part nucleotides from the endogenous promotor, the endogenous splice sites, and an exogenous termination signal.

111. The method of any one of arrangements 26-28, 30-38, 58-60, 62-71, or 100-108 in which the nuclease allows for intronic integration into a gene locus to express at least one part of one of the two-part nucleotides from the endogenous promotor, an exogenous splice acceptor site, and an exogenous termination signal.

112. The method of any one of arrangements 1-80 wherein the essential or first protein is split into at least two individually dysfunctional protein portions, wherein each of the at least two portions is fused to multimerization domain and wherein each of the at least two portions is integrated into distinct two-part nucleotide sequences to allow for selection of cells in which all distinct two-part nucleotide sequences are expressed, optionally wherein the function of the essential or first protein is restored.

113. The method of any one of arrangements 1-80 wherein the essential or first protein is split into a dysfunctional N-terminal and C-terminal protein half, each half fused to a homo- or heterodimerizing protein partner or to a split intein.

114. The method of any one of arrangements 112 or 113, wherein the essential or first protein is a DHFR protein.

115. The method of arrangement 114, wherein a first dysfunctional protein portion comprises an N-terminal portion of DHFR and a second dysfunctional protein portion comprises a C-terminal portion of DHFR.

116. The method of arrangement 115, wherein the N-terminal portion of DHFR comprises SEQ ID NO: 22.

117. The method of arrangement 116, wherein the C-terminal portion of DHFR comprises SEQ ID NO: 23.

118. The method of any one of arrangements 108-110 wherein the homodimerizing protein is GCN4, FKBP12, or a variant thereof.

119. The method of any one of arrangements 108-110, wherein the heterodimerizing proteins are Jun/Fos, or variants thereof.

120. The method of any one of arrangements 72-76, 80-83, or 108-111 wherein restoration of the function of the essential protein is induced, optionally by AP1903.

121. The method of any one of arrangements 72-108, wherein the culturing step is done in the presence of methotrexate.

122. The method any one of arrangements 1-121, wherein the protein of interest is a T cell receptor.

123. The method of arrangement 122, wherein the T cell receptor is specific for a viral or a tumor antigen.

124. The method of arrangement 123, wherein the tumor antigen is a tumor neo-antigen.

125. The method any one of the preceding arrangements, wherein the genetically engineered cell is a primary human T cell.

126. A method for enrichment of a genetically engineered T cell comprising i) introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and ii) culturing the cell in cell culture medium containing methotrexate leading to enrichment of the cell that expresses both the first protein and the second protein.

127. A method for enrichment of a T cell engineered to express an exogenous T cell receptor gene comprising:

i) knocking-out an endogenous TRBC gene from its locus using a first CRISPR/Cas9 RNP;

ii) knocking-in, using a second CRISPR/Cas9 RNP, into the endogenous TRBC locus a first-part nucleotide sequence encoding a methotrexate-resistant DHFR gene and a second-part nucleotide sequence comprising a therapeutic TCR gene, wherein both nucleotide sequences are operably linked allowing for expression from the endogenous TRBC promotor; and iii) culturing the cells in cell culture medium containing methotrexate leading to enrichment of T cells that express both the therapeutic TCR and the methotrexate-resistant DHFR gene.

128. A method for selection of a genetically engineered cell comprising:

i) introducing at least one two-part nucleotide sequence that is operable for expression in a cell, wherein the cell has an essential protein for the survival and/or proliferation that is suppressed to a level that the cell cannot survive and/or proliferate, and wherein the at least one two-part nucleotide sequence comprises a first-part nucleotide sequence encoding the essential protein for the survival and/or proliferation and a second-part nucleotide sequence encoding a protein to be expressed, wherein the second-part nucleotide sequence is encoding a protein that is exogenous to the cell; and ii) culturing the cell under conditions leading to the selection of the cell that expresses both the first-part and second-part nucleotide sequences.

129. A method for enrichment of a genetically engineered cell comprising:

i) decreasing activity of at least a first protein that is essential for the survival and/or proliferation of a cell to the level that the cell cannot survive and/or proliferate under normal in vitro propagation conditions;

ii) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and iii) culturing the cell under in vitro propagation conditions that lead to the enrichment of the cell that expresses both the first protein and second protein.

130. A cell that is made according to any one of the arranged methods above.

131. A T cell comprising:

an endogenous dihydrofolate reductase (DHFR) being suppressed by the presence of methotrexate to a level that the cell cannot survive and/or proliferate, and at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

132. A T cell comprising:

a knock-out of endogenous dihydrofolate reductase (DHFR), and at least one two-part nucleotide sequence comprising:

a first-part nucleotide sequence encoding a DHFR protein, or variant thereof; and a second-part nucleotide sequence encoding a T-cell receptor operably expressed from the endogenous TRA or TRB promotor.

133. A T cell comprising:

an endogenous dihydrofolate reductase (DHFR) configured to be suppressed by a presence of methotrexate to a level that the cell cannot survive and/or proliferate, and at least two two-part nucleotide sequences, wherein the first two-part nucleotide sequence comprises:

i) a first first-part nucleotide sequence encoding a non-functional or dysfunctional portion of a DHFR protein, or variant thereof; and ii) a first second-part nucleotide sequence encoding a T-cell receptor operably expressed from the endogenous TRA or TRB promotor, wherein the second two-part nucleotide sequence comprises:

iii) a second first-part nucleotide sequence encoding a non-functional or dysfunctional portion of a DHFR protein, or variant thereof; and iv) a second second-part nucleotide sequence encoding a protein of interest operably expressed from the endogenous B2M promotor, and wherein the cell is configured to have DHFR activity.

Exemplary Arrangements (b):

1. A method for selection of a genetically engineered cell comprising:

i) introducing at least one two-part nucleotide sequence that is operable for expression in a cell, wherein the cell has an essential protein for the survival and/or proliferation that is suppressed to a level that the cell cannot survive and/or proliferate in a normal cell culture medium, and wherein the at least one two-part nucleotide sequence comprises a first-part nucleotide sequence encoding the essential protein for the survival and/or proliferation and a second-part nucleotide sequence encoding a protein to be expressed, wherein the second-part nucleotide sequence is encoding a protein that is exogenous to the cell; and ii) culturing the cell in the normal cell culture medium for selection of the cell that expresses both the first-part and second-part nucleotide sequences.

2. A method for enrichment of a genetically engineered cell comprising:

i) decreasing activity of at least a first protein that is essential for the survival and/or proliferation of a cell to the level that the cell cannot survive and/or proliferate under normal in vitro propagation conditions;

ii) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and iii) culturing the cell under normal in vitro propagation conditions for enrichment of the cell that expresses both the first protein and second protein.

3. The method of arrangement 2, wherein the decreasing activity can be permanently or transiently.

4. The method of arrangement 2, wherein the decreasing activity comprises knock-out of the gene encoding the essential protein.

5. The method of arrangement 4, wherein the knock-out is mediated by CRISPR/Cas9 Ribonucleoprotein (RNP), TALEN, MegaTAL, or any other nucleases.

6. The method of arrangement 2, wherein the decreasing activity comprises transient suppression of the activity of the essential protein.

7. The method of arrangement 6, wherein the transient suppression is through siRNA, miRNA, CRISPR interference (CRISPRi), or a protein inhibitor.

8. The method of arrangement 1 or 2, wherein the cell is a T cell, hematopoietic stem cell, mesenchymal stem cell, iPSC, neural precursor cell, a cell type in retinal gene therapy, or any other cell.

9. The method of arrangement 1 or 2, wherein the first-part nucleotide sequence is altered in nucleotide sequence to achieve nuclease, siRNA, miRNA, or CRISPRi resistance, but a) encodes a protein having an identical amino acid sequence to the first protein or b) encodes a protein having an adjusted functionality to the first protein.

10. The method of arrangement 1 or 2, wherein the first-part nucleotide sequence is altered to encode an altered protein that does not have an identical amino acid sequence to the first protein.

11. The method of arrangement 10, wherein the altered protein has specific features that the first protein does not have.

12. The method of arrangement 11, wherein the specific features include, but are not limited to, one or more of the following: reduced activity, increased activity, altered half-life, resistance to small molecule inhibition, and increased activity after small molecule binding.

13. The method of arrangement 1 or 2, wherein the at least one nucleotide sequence is operable for expressing both the first-part and second-part nucleotide sequences.

14. The method of arrangement 1 or 2, wherein both the first-part and second-part nucleotide sequences can be driven by a same promoter or different promoters.

15. The method of arrangement 1 or 2, wherein the second-part nucleotide sequence comprises at least a therapeutic gene.

16. The method of arrangement 1 or 2, wherein the second-part nucleotide sequence encodes a neo-antigen T-cell receptor complex (TCR) containing a TCR alpha chain and a TCR beta chain.

17. The method of arrangement 1 or 2, wherein the essential or first protein is dihydrofolate reductase (DHFR), Inosine Monophosphate Dehydrogenase 2 (IMPDH2), O-6-Methylguanine-DNA Methyltransferase (MGMT), Deoxycytidine kinase (DCK), Hypoxanthine Phosphoribosyltransferase 1 (HPRT1), Interleukin 2 Receptor Subunit Gamma (IL2RG), Actin Beta (ACTB), Eukaryotic Translation Elongation Factor 1 Alpha 1 (EEF1A1), Glyceraldehyde-3-Phosphate Dehydrogenase (GAPDH), Phosphoglycerate Kinase 1 (PGK1), or Transferrin Receptor (TFRC).

18. The method of arrangement 1 or 2, wherein the first-part nucleotide sequence comprises a nuclease-resistant, siRNA-resistant, or protein inhibitor-resistant DHFR gene, and the second-part nucleotide sequence comprises a TRA gene and a TRB gene.

19. The method of arrangement 18, wherein the protein inhibitor-resistant DHFR gene is a methotrexate-resistant DHFR gene.

20. The method of arrangement 18, wherein the TRA, TRB, and DHFR genes are operably configured to be expressed from a single open reading frame.

21. The method of arrangement 20, wherein the TRA, TRB, and DHFR genes are separated by linkers.

22. The method of arrangement 21, wherein the order of the linkers, TRA, TRB, and DHFR genes is in the following order:

TRA-linker-TRB-linker-DHFR,
TRA-linker-DHFR-linker-TRB,
TRB-linker-TRA-linker-DHFR,
TRB-linker-DHFR-linker-TRA,
DHFR-linker-TRA-linker-TRB, or
DHFR-linker-TRB-linker-TRA.

23. The method of arrangement 22, wherein the linkers are self-cleaving 2A peptides or IRES elements.

24. The method of arrangement 18, wherein the DHFR, TRA, and TRB genes are driven by an endogenous TCR promoter or any other suitable promoters including, but not limited to the following promoters: TRAC, TRBC1/2, DHFR, EEF1A1, ACTB, B2M, CD52, CD2, CD3G, CD3D, CD3E, LCK, LAT, PTPRC, IL2RG, ITGB2, TGFBR2, PDCD1, CTLA4, FAS, TNFRSF1A (TNFR1), TNFRSF10B (TRAILR2), ADORA2A, BTLA, CD200R1, LAG3, TIGIT, HAVCR2 (TIM3), VSIR (VISTA), IL10RA, IL4RA, EIF4A1, FTH1, FTL, HSPA5, and PGK1.

25. The method of arrangement 1 or 2, wherein the two-part nucleotide sequence is integrated into the genome of the cell.

26. The method of arrangement 25, wherein the integration is through nuclease-mediated site-specific integration, transposon-mediated gene delivery, or virus-mediate gene delivery.

27. The method of arrangement 26, wherein the nuclease-mediated site-specific integration is through CRISPR/Cas9 RNP.

28. The method of arrangement 27, further comprising using the Split intein system.

29. The method of arrangement 1 or 2, wherein the introduced two-part nucleotide sequence is not integrated into the genome of the cell.

30. The method of arrangement 1 or 2, wherein a CRISPR/Cas9 RNP that targets the endogenous TCR Constant locus, the first-part nucleotide sequence encoding a nuclease-resistant DHFR gene, and the second-part nucleotide sequence encoding a neo-antigen TCR are delivered to the cell.

31. The method of arrangement 30, wherein the endogenous TCR constant locus can be a TCR alpha Constant (TRAC) locus or a TCR beta Constant (TRBC) locus.

32. The method of arrangement 30, wherein the delivery is by electroporation, or methods based on mechanical or chemical membrane permeabilization.

33. The method of arrangement 2, wherein a first CRISPR/Cas9 RNP is used to knock-out endogenous dihydrofolate reductase (DHFR) gene, and a second CRISPR/Cas9 RNP is used to knock-in into an endogenous TCR constant locus the first-part nucleotide sequence comprising the CRISPR/Cas9 nuclease-resistant DHFR gene and the second-part nucleotide sequence encoding a therapeutic TCR gene.

34. The method of arrangement 33, wherein methotrexate is used to inhibit the first protein, and a CRISPR/Cas9 RNP is used to knock-in into an endogenous TCR constant locus the first-part nucleotide sequence encoding a methotrexate-resistant DHFR protein and the second-part nucleotide sequence comprising a therapeutic TCR gene.

35. The method of arrangement 33, wherein the second CRISPR/Cas9 RNP is a TRAC RNP that cuts the TRAC locus for knock-in.

36. The method of arrangement 1 or 2, wherein the normal cell culture medium is one that is suitable for non-modified cell's growth and/or proliferation.

37. The method of arrangement 1 or 2, wherein the normal cell culture medium is without an exogenous selection pressure, such as a drug molecule or an antibody that allows enrichment of the cells by flow cytometry or magnetic bead enrichment.

38. A cell that is made according to any of the above methods.

39. A cell comprising:

endogenous dihydrofolate reductase (DHFR) being suppressed to a level that the cell cannot survive and/or proliferate in a normal cell culture medium, and at least a two-part nucleotide sequence comprising a first-part nucleotide sequence encoding DHFR and a second-part nucleotide sequence encoding a neo-antigen T-cell receptor complex.

40. A method for enrichment of a genetically engineered cell comprising:

i) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and
ii) culturing the cell in cell culture medium containing at least one supplement leading to enrichment of the cell that expresses both the first protein and the second protein.

41. The method of arrangement 40, wherein the genetically engineered cell is a primary human T cell.

42. The method of arrangement 40, wherein the supplement impairs survival and/or proliferation of cells without expressing both the first protein and the second protein.

43. The method of arrangement 40, wherein at least one protein mediates resistance of the cell to the supplement mediated impairment of survival and/or proliferation of cells.

44. The method of arrangement 42, wherein the supplement is methotrexate.

45. The method of arrangement 40, wherein the first protein is a methotrexate-resistant DHFR mutant protein.

46. The method of arrangement 40, wherein the second protein is a T cell receptor.

47. The method of arrangement 46, wherein the T cell receptor is specific for a viral or a tumor antigen.

48. The method of arrangement 40, wherein the first-part nucleotide sequence is altered in nucleotide sequence to achieve nuclease, siRNA, miRNA, or CRISPRi resistance.

49. The method of arrangement 40, in which expression of the at least a two-part nucleotide sequence is achieved by site-specific integration into an endogenous gene locus of the cell.

50. The method of arrangement 49, in which site-specific integration into an endogenous gene locus of the cell is achieved by using CRISPR/Cas9, TALEN, MegaTAL or any other nuclease that allows for traceless integration into a gene locus to enable expression from the endogenous promotor of the gene locus.

51. The method of arrangement 50, in which the nuclease allows for in-frame exonic integration into a gene locus to enable expression from the endogenous promotor, the endogenous splice sites, and the endogenous termination signal.

52. The method of arrangement 50, in which the nuclease allows for in-frame exonic integration into a gene locus to enable expression from the endogenous promotor, the endogenous splice sites, and an exogenous termination signal.

53. The method of arrangement 50, in which the nuclease allows for intronic integration into a gene locus to enable expression from the endogenous promotor, an exogenous splice acceptor site, and an exogenous termination signal.

54. The method of arrangement 40, wherein a CRISPR/Cas9 RNP is used to knock-in into an endogenous TCR constant locus the first-part nucleotide sequence encoding a methotrexate-resistant DHFR mutant protein and the second-part nucleotide sequence comprising a therapeutic TCR gene.

55. The method of arrangements 50 and 54, further comprising a second CRISPR/Cas9 RNP that is used to knock-out the endogenous TRAC or TRBC gene.

56. A method for enrichment of a genetically engineered T cell comprising i) introducing a two-part nucleotide sequence comprising a first-part nucleotide sequence encoding a methotrexate-resistant DHFR protein and a second-part nucleotide sequence encoding a T-cell receptor complex or Chimeric antigen receptor in the T cell by integration of the two-part nucleotide sequence downstream of the TRA or TRB promotor, and ii) culturing the cell in cell culture medium containing methotrexate leading to enrichment of the cell that expresses both the first protein and the second protein.

57. A method for enrichment of a T cell engineered to express an exogenous T cell receptor gene comprising:

i) knocking-out an endogenous TRBC gene from its locus using a first CRISPR/Cas9 RNP;

ii) knocking-in, using a second CRISPR/Cas9 RNP, into the endogenous TRBC locus a first-part nucleotide sequence encoding a methotrexate-resistant DHFR gene and a second-part nucleotide sequence comprising a therapeutic TCR gene, wherein both nucleotide sequences are operably linked allowing for expression from the endogenous TRBC promotor; and iii) culturing the cells in cell culture medium containing methotrexate leading to enrichment of T cells that express both the therapeutic TCR and the methotrexate-resistant DHFR gene.

58. A T cell comprising:

an endogenous dihydrofolate reductase (DHFR) being suppressed by the presence of methotrexate to a level that the cell cannot survive and/or proliferate, and at least a two-part nucleotide sequence comprising a first-part nucleotide sequence encoding a methotrexate-resistant DHFR protein and a second-part nucleotide sequence encoding a T-cell receptor operably expressed from the endogenous TRA or TRB promotor.

59. The method of arrangement 1, 2 or 40 wherein the essential or first protein is split into at least two individually dysfunctional protein portions, wherein each of the at least two portions is fused to multimerization domain and wherein each of the at least two portions is integrated into distinct two-part nucleotide sequences to allow for selection of cells in which all distinct two-part nucleotide sequences are expressed.

60. The method of arrangement 59, wherein the essential or first protein is split into a dysfunctional N-terminal and C-terminal protein half, each half fused to a homo- or heterodimerizing protein partner or to a split intein.

61. The method of arrangement 59, wherein the essential or first protein is a DHFR protein.

62. A method for selection of a genetically engineered cell comprising:

i) introducing at least one two-part nucleotide sequence that is operable for expression in a cell, wherein the cell has an essential protein for the survival and/or proliferation that is suppressed to a level that the cell cannot survive and/or proliferate, and wherein the at least one two-part nucleotide sequence comprises a first-part nucleotide sequence encoding the essential protein for the survival and/or proliferation and a second-part nucleotide sequence encoding a protein to be expressed, wherein the second-part nucleotide sequence is encoding a protein that is exogenous to the cell; and ii) culturing the cell under conditions leading to the selection of the cell that expresses both the first-part and second-part nucleotide sequences.

63. A method for enrichment of a genetically engineered cell comprising:

i) decreasing activity of at least a first protein that is essential for the survival and/or proliferation of a cell to the level that the cell cannot survive and/or proliferate under normal in vitro propagation conditions;

ii) introducing at least a two-part nucleotide sequence that is operable for expression in the cell and comprises a first-part nucleotide sequence encoding the first protein and a second-part nucleotide sequence encoding a second protein to be expressed, wherein the second-part protein is exogenous to the cell, and iii) culturing the cell under in vitro propagation conditions that lead to the enrichment of the cell that expresses both the first protein and second protein.

64. A method for selection of a genetically engineered cell comprising:

i) introducing at least two two-part nucleotide sequences that are operable for expression in a cell, wherein the cell has an essential protein for the survival and/or proliferation that is suppressed to a level that the cell cannot survive and/or proliferate, wherein the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed, wherein the second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed, wherein, when both the first and second fusion proteins are expressed together in a cell, the function of the essential protein for the survival and/or proliferation is restored; and ii) culturing the cell under conditions leading to the selection of the cell that expresses both the first and second two-part nucleotide sequences.

65. A method for enrichment of a genetically engineered cell comprising:

i) decreasing activity of at least a first protein that is essential for the survival and/or proliferation of a cell to the level that the cell cannot survive and/or proliferate under normal in vitro propagation conditions;

ii) introducing at least two two-part nucleotide sequences that are operable for expression in a cell, wherein the first two-part nucleotide sequence comprises a first-part nucleotide sequence encoding a first fusion protein comprising a non-functional portion of the essential protein for the survival and/or proliferation fused to a first binding domain and a second-part nucleotide sequence encoding a protein to be expressed, wherein the second two-part nucleotide sequence comprises a first-part nucleotide sequence encoding a second fusion protein comprising non-functional portion of the essential protein for the survival and/or proliferation fused to a second binding domain and a second-part nucleotide sequence encoding a protein to be expressed, wherein, when both the first and second fusion proteins are expressed together in a cell, the function of the essential protein for the survival and/or proliferation is restored, and iii) culturing the cell under in vitro propagation conditions that lead to the enrichment of the cell that expresses both the first fusion protein and second fusion protein.

66. The method of arrangement 64 or 65, wherein the essential protein is a DHFR protein.

67. The method of any one of arrangements 64-66, wherein the second-part nucleotide sequence of either the first or second two-part nucleotide sequences is exogenous to the cell.

68. The method of any one of arrangements 64-67, wherein the second-part nucleotide sequence of either the first or second two-part nucleotide sequence is a TCR.

69. The method of any one of arrangements 64-68, wherein the first and second binding domains are derived from GCN4.

70. The method of any one of arrangements 64-68, wherein the first and second binding domains are derived from FKBP12.

71. The method of arrangement 70, wherein the FKBP12 has an F36V mutation.

72. The method of any one of arrangements 64-68, wherein the first binding domain is derived from JUN and the second binding domains is derived from FOS.

73. The method of arrangement 72, wherein the first binding domain and second binding domain have complementary mutations that preserve binding to each other.

74. The method of arrangement 73, wherein neither the first binding domain nor the second binding domain bind to a native binding partner.

75. The method of any one of arrangements 72-74, wherein each of the first binding domain and second binding domain have between 3 and 7 complementary mutations.

76. The method of arrangement 75 wherein the first binding domain and second binding domain each have 3 complementary mutations.

77. The method of arrangement 75, wherein the first binding domain and second binding domain each have 4 complementary mutations.

78. The method of any of arrangements 64-68, 70, or 71, wherein the restoration of the function of the essential protein is induced, optionally by AP1903.

79. The method of any of arrangements 64-78, wherein the culturing step is done in the presence of methotrexate.

What is claimed is:

1. A method for selection or enrichment of a genetically engineered cell comprising:

i) introducing into a cell a nucleic acid comprising a first-part nucleotide sequence and a second-part nucleotide sequence, wherein the nucleic acid becomes operable for expression of both the first-part and second-part nucleotide sequences when inserted into a pre-determined site in a target genome, wherein the pre-determined site is a TCR Constant locus or B2M locus, and wherein the expression of both the first-part and second-part nucleotide sequences are driven by a promoter in the target genome, and wherein the first-part nucleotide sequence encodes a first protein that provides for the selection or enrichment of the genetically engineered cell, and the second-part nucleotide sequence encodes a second protein to be expressed, wherein the second protein is a protein of interest; and ii) culturing the cell in a cell culture medium under conditions that lead to enrichment or selection of the cell that expresses both the first protein and the second protein.

2. The method of claim 1, wherein the cell is a T cell, NK cell, NKT cell, iNKT cell, hematopoietic stem cell, mesenchymal stem cell, iPSC, neural precursor cell, a cell type in retinal gene therapy, or any other cell.

3. The method of claim 1, wherein the second-part nucleotide sequence comprises at least a therapeutic gene.

4. The method of claim 1, wherein the second-part nucleotide sequence encodes a neo-antigen T-cell receptor complex (TCR) containing a TCR alpha chain and a TCR beta chain.

5. The method of claim 1, wherein the first-part nucleotide sequence comprises a protein inhibitor-resistant DHFR gene, and the second-part nucleotide sequence comprises a TRA gene and a TRB gene.

6. The method of claim 5, wherein the pre-determined site is a TCR Constant locus, and wherein the expression of the DHFR, TRA, and TRB genes are driven by an endogenous TCR promoter.

7. The method of claim 6, wherein the cell culture medium comprises a supplement, wherein the supplement impairs survival and/or proliferation of cells without expressing both the first protein and the second protein and the first protein mediates resistance of the cell to the supplement mediated impairment of survival and/or proliferation of cells.

8. The method of claim 7, wherein the supplement is methotrexate.

9. The method of claim 8, wherein the first protein is a methotrexate-resistant DHFR mutant protein.

10. A cell that is made according to the method of claim 1.

11. The method of claim 1, wherein the first protein provides for the selection or enrichment of the genetically engineered cell by conferring resistance to a supplement in the cell culture medium, and wherein the culturing the cell comprises culturing the cell in a cell culture medium comprising the supplement.

12. The method of claim 1, wherein the first protein is an essential protein or variant thereof that functions in the proliferation of the genetically engineered cell, and wherein the level of endogenous expression of the essential protein in the cell is reduced such that the genetically engineered cell cannot proliferate in the cell culture in the absence of the expression of the first protein.

13. The method of claim 12, wherein the essential protein functions in at least one of: cell growth, replication, cell cycle, gene regulation, stress response, metabolism, apoptosis, nutrient acquisition, protein turnover, cell surface integrity, essential enzyme activity, survival, or any combination thereof.

14. The method of claim 1, wherein the nucleotide sequence of the first-part nucleotide sequence is nuclease, siRNA, miRNA, or CRISPRi resistant.

15. The method of claim 1, wherein the first protein is a variant of an endogenous protein.

16. The method of claim 15, wherein relative to the endogenous protein the variant protein comprises at least one of: reduced activity, increased activity, altered half-life resistance to small molecule inhibition, increased activity after small molecule binding, or any combination thereof.

* * * * *

SEQUENCE LISTING

```
<160> NUMBER OF SEQ ID NOS: 63

<210> SEQ ID NO 1
<211> LENGTH: 187
<212> TYPE: PRT
<213> ORGANISM: Homo sapiens

<400> SEQUENCE: 1

Met Val Gly Ser Leu Asn Cys Ile Val Ala Val Ser Gln Asn Met Gly
1               5                   10                  15

Ile Gly Lys Asn Gly Asp Leu Pro Trp Pro Pro Leu Arg Asn Glu Phe
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
```

```
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185


<210> SEQ ID NO 2
<211> LENGTH: 187
<212> TYPE: PRT
<213> ORGANISM: Homo sapiens

<400> SEQUENCE: 2

Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185


<210> SEQ ID NO 3
<211> LENGTH: 561
<212> TYPE: DNA
<213> ORGANISM: Homo sapiens

<400> SEQUENCE: 3

atggttggtt cgctaaactg catcgtcgct gtgtcccaga acatgggcat cggcaagaac      60

ggggacctgc cctggccacc gctcaggaat gaattcagat atttccagag aatgaccaca     120

acctcttcag tagaaggtaa acagaatctg gtgattatgg gtaagaagac ctggttctcc     180

attcctgaga agaatcgacc tttaaagggt agaattaatt tagttctcag cagagaactc     240

aaggaacctc cacaaggagc tcattttctt tccagaagtc tagatgatgc cttaaaactt     300

actgaacaac cagaattagc aaataaagta gacatggtct ggatagttgg tggcagttct     360

gtttataagg aagccatgaa tcacccaggc catcttaaac tatttgtgac aaggatcatg     420

caagactttg aaagtgacac gtttttttcca gaaattgatt tggagaaata taaacttctg   480

ccagaatacc caggtgttct ctctgatgtc caggaggaga aaggcattaa gtacaaattt     540

gaagtatatg agaagaatga t                                                561
```

<210> SEQ ID NO 4
<211> LENGTH: 561
<212> TYPE: DNA
<213> ORGANISM: Homo sapiens

<400> SEQUENCE: 4
atggtaggct ccctgaactg tatagttgcg gtatcccaaa atatggggat tggaaagaac 60
ggagaccttc cgtggccgcc cctccgaaat gaatttcgat actttcagag aatgacaact 120
acctcatctg tagagggaaa gcaaaatctg gttatcatgg gaaagaaaac gtggttctct 180
atccctgaaa aaaacagacc tctcaaaggc aggataaatt tggtattgtc aagagaattg 240
aaggaaccgc cacaaggagc tcattttctc agcagatctc tggacgatgc actcaaactc 300
accgaacaac cagaacttgc taataaggtt gatatggtct ggatagttgg gggcagcagt 360
gtatataagg aagccatgaa ccatcctggc catctgaagc tgtttgttac gaggataatg 420
caggacttcg agtccgacac tttttccca gagattgact tggaaaagta taaactcttg 480
cctgagtatc ctggggttct ctccgatgtc caagaggaga aaggtattaa atataagttt 540
gaagtttatg aaaaaaacga t 561

<210> SEQ ID NO 5
<211> LENGTH: 561
<212> TYPE: DNA
<213> ORGANISM: Homo sapiens

<400> SEQUENCE: 5
atggtaggct ccctgaactg tatagttgcg gtatcccaaa atatggggat tggaaagaac 60
ggagactttc cgtggccgcc cctccgaaat gaatcccgat actttcagag aatgacaact 120
acctcatctg tagagggaaa gcaaaatctg gttatcatgg gaaagaaaac gtggttctct 180
atccctgaaa aaaacagacc tctcaaaggc aggataaatt tggtattgtc aagagaattg 240
aaggaaccgc cacaaggagc tcattttctc agcagatctc tggacgatgc actcaaactc 300
accgaacaac cagaacttgc taataaggtt gatatggtct ggatagttgg gggcagcagt 360
gtatataagg aagccatgaa ccatcctggc catctgaagc tgtttgttac gaggataatg 420
caggacttcg agtccgacac tttttccca gagattgact tggaaaagta taaactcttg 480
cctgagtatc ctggggttct ctccgatgtc caagaggaga aaggtattaa atataagttt 540
gaagtttatg aaaaaaacga t 561

<210> SEQ ID NO 6
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 6

Thr Ile Ala Arg Leu Glu Glu Glu Val Lys Thr Leu Glu Ala Lys Glu
1 5 10 15

Ser Glu Leu Ala Ser Thr Ala Asn Met Leu Glu Glu Lys Val Ala Gln
20 25 30

Leu Glu Gln Lys Val
35

<210> SEQ ID NO 7
<211> LENGTH: 37

<212> TYPE: PRT
<213> ORGANISM: Artificial Sequence
<220> FEATURE:
<223> OTHER INFORMATION: Synthetic Polypeptide

<400> SEQUENCE: 7

Leu Arg Asp Thr Leu Gln Ala Lys Thr Asp Gln Leu Lys Asp Asn Gln
1               5                   10                  15

Ser Ala Leu Gln Thr Arg Ile Ala Asn Leu Leu Lys Lys Gln Glu Lys
            20                  25                  30

Leu Glu Phe Ile Leu
        35

<210> SEQ ID NO 8
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 8

Thr Ile Ala Arg Leu Glu Glu Glu Val Lys Thr Leu Glu Ala Lys Glu
1               5                   10                  15

Ser Glu Leu Ala Ser Thr Ala Asn Met Leu Glu Glu Lys Val Ala Gln
            20                  25                  30

Leu Glu Gln Lys Val Gly Gly Gly Gly Ser Gly Gly Gly Gly Ser Met
        35                  40                  45

Val Arg Pro Leu Asn Cys Ile Val Ala Val Ser Gln Asn Met Gly Ile
    50                  55                  60

Gly Lys Asn Gly Asp Phe Pro Trp Pro Pro Leu Arg Asn Glu Ser Lys
65                  70                  75                  80

Tyr Phe Gln Arg Met Thr Thr Thr Ser Ser Val Glu Gly Lys Gln Asn
                85                  90                  95

Leu Val Ile Met Gly Arg Lys Thr Trp Phe Ser Ile Pro Glu Lys Asn
            100                 105                 110

Arg Pro Leu Lys Asp Arg Ile Asn Ile Val Leu Ser Arg Glu Leu Lys
        115                 120                 125

Glu Pro Pro Arg Gly Ala His Phe Leu Ala Lys Ser Leu Asp Asp Ala
    130                 135                 140

Leu Arg Leu Ile Glu Gln Pro Glu Leu
145                 150

<210> SEQ ID NO 9
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 9

Leu Arg Asp Thr Leu Gln Ala Lys Thr Asp Gln Leu Lys Asp Asn Gln
1               5                   10                  15

Ser Ala Leu Gln Thr Arg Ile Ala Asn Leu Leu Lys Lys Gln Glu Lys
            20                  25                  30

Leu Glu Phe Ile Leu Gly Gly Gly Gly Ser Gly Gly Gly Gly Ser Ala
        35                  40                  45

Ser Lys Val Asp Met Val Trp Ile Val Gly Gly Ser Ser Val Tyr Gln
    50                  55                  60

Glu Ala Met Asn Gln Pro Gly His Leu Arg Leu Phe Val Thr Arg Ile

```
65                  70                  75                  80

Met Gln Glu Phe Glu Ser Asp Thr Phe Phe Pro Glu Ile Asp Leu Gly
                85                  90                  95

Lys Tyr Lys Leu Leu Pro Glu Tyr Pro Gly Val Leu Ser Glu Val Gln
            100                 105                 110

Glu Glu Lys Gly Ile Lys Tyr Lys Phe Glu Val Tyr Glu Lys Lys Asp
        115                 120                 125
```

<210> SEQ ID NO 10
<211> LENGTH: 20
<212> TYPE: DNA
<213> ORGANISM: Homo sapiens

<400> SEQUENCE: 10
tgattatggg taagaagacc 20

<210> SEQ ID NO 11
<211> LENGTH: 20
<212> TYPE: DNA
<213> ORGANISM: Homo sapiens

<400> SEQUENCE: 11
aaccttaggg aacctccaca 20

<210> SEQ ID NO 12
<211> LENGTH: 20
<212> TYPE: DNA
<213> ORGANISM: Homo sapiens

<400> SEQUENCE: 12
cggcccggca gatacctgag 20

<210> SEQ ID NO 13
<211> LENGTH: 20
<212> TYPE: DNA
<213> ORGANISM: Homo sapiens

<400> SEQUENCE: 13
gacatggtct ggatagttgg 20

<210> SEQ ID NO 14
<211> LENGTH: 20
<212> TYPE: DNA
<213> ORGANISM: Homo sapiens

<400> SEQUENCE: 14
gtcgctgtgt cccagaacat 20

<210> SEQ ID NO 15
<211> LENGTH: 20
<212> TYPE: DNA
<213> ORGANISM: Homo sapiens

<400> SEQUENCE: 15
cagatacctg agcggtggcc 20

<210> SEQ ID NO 16
<211> LENGTH: 20
<212> TYPE: DNA
<213> ORGANISM: Homo sapiens

<400> SEQUENCE: 16
cacattacct tctactgaag 20

<210> SEQ ID NO 17
<211> LENGTH: 20
<212> TYPE: DNA
<213> ORGANISM: Homo sapiens

<400> SEQUENCE: 17
cgtcgctgtg tcccagaaca 20

<210> SEQ ID NO 18
<211> LENGTH: 20
<212> TYPE: DNA
<213> ORGANISM: Homo sapiens

<400> SEQUENCE: 18
accacaacct cttcagtaga 20

<210> SEQ ID NO 19
<211> LENGTH: 20
<212> TYPE: DNA
<213> ORGANISM: Homo sapiens

<400> SEQUENCE: 19
aaattaattc taccctttaa 20

<210> SEQ ID NO 20
<211> LENGTH: 20
<212> TYPE: DNA
<213> ORGANISM: Homo sapiens

<400> SEQUENCE: 20
gagaatcaaa atcggtgaat 20

<210> SEQ ID NO 21
<211> LENGTH: 20
<212> TYPE: DNA
<213> ORGANISM: Homo sapiens

<400> SEQUENCE: 21
gagtagcgcg agcacagcta 20

<210> SEQ ID NO 22
<211> LENGTH: 106
<212> TYPE: PRT
<213> ORGANISM: Artificial Sequence
<220> FEATURE:
<223> OTHER INFORMATION: Synthetic Polypeptide

<400> SEQUENCE: 22

```
Met Val Arg Pro Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Lys Tyr Phe Gln Arg Met Thr Thr Thr Ser Ser Val Glu Gly Lys Gln
        35                  40                  45

Asn Leu Val Ile Met Gly Arg Lys Thr Trp Phe Ser Ile Pro Glu Lys
    50                  55                  60

Asn Arg Pro Leu Lys Asp Arg Ile Asn Ile Val Leu Ser Arg Glu Leu
65                  70                  75                  80

Lys Glu Pro Pro Arg Gly Ala His Phe Leu Ala Lys Ser Leu Asp Asp
                85                  90                  95
```

```
Ala Leu Arg Leu Ile Glu Gln Pro Glu Leu
            100                 105


<210> SEQ ID NO 23
<211> LENGTH: 81
<212> TYPE: PRT
<213> ORGANISM: Artificial Sequence
<220> FEATURE:
<223> OTHER INFORMATION: Synthetic Polypeptide

<400> SEQUENCE: 23

Ala Ser Lys Val Asp Met Val Trp Ile Val Gly Gly Ser Ser Val Tyr
1               5                   10                  15

Gln Glu Ala Met Asn Gln Pro Gly His Leu Arg Leu Phe Val Thr Arg
            20                  25                  30

Ile Met Gln Glu Phe Glu Ser Asp Thr Phe Phe Pro Glu Ile Asp Leu
        35                  40                  45

Gly Lys Tyr Lys Leu Leu Pro Glu Tyr Pro Gly Val Leu Ser Glu Val
    50                  55                  60

Gln Glu Glu Lys Gly Ile Lys Tyr Lys Phe Glu Val Tyr Glu Lys Lys
65                  70                  75                  80

Asp


<210> SEQ ID NO 24
<211> LENGTH: 47
<212> TYPE: PRT
<213> ORGANISM: Artificial Sequence
<220> FEATURE:
<223> OTHER INFORMATION: Synthetic Polypeptide

<400> SEQUENCE: 24

Asn Thr Glu Ala Ala Arg Arg Ser Arg Ala Arg Lys Leu Gln Arg Met
1               5                   10                  15

Lys Gln Leu Glu Asp Lys Val Glu Glu Leu Leu Ser Lys Asn Tyr His
            20                  25                  30

Leu Glu Asn Glu Val Ala Arg Leu Lys Lys Leu Val Gly Glu Arg
        35                  40                  45


<210> SEQ ID NO 25
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 25

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn His
        35                  40


<210> SEQ ID NO 26
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 26
```

```
Arg Ile Ala Arg Leu Glu Glu Glu Val Lys Thr Leu Glu Ala Gln Asn
1               5                   10                  15

Ser Glu Leu Ala Ser Thr Ala Asn Met Leu Glu Glu Gln Val Ala Gln
            20                  25                  30

Leu Lys Gln Lys Val Met Asn His
        35                  40


<210> SEQ ID NO 27
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 27

Arg Ile Ala Arg Leu Glu Glu Glu Val Lys Thr Leu Glu Ala Gln Asn
1               5                   10                  15

Ser Glu Leu Ala Ser Thr Ala Asn Met Leu Glu Glu Gln Val Ala Gln
            20                  25                  30

Leu Glu Gln Lys Val
        35


<210> SEQ ID NO 28
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 28

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
            20                  25                  30

Leu Glu Phe Ile Leu Ala Ala His
        35                  40


<210> SEQ ID NO 29
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 29

Leu Thr Asp Thr Leu Gln Ala Lys Thr Asp Gln Leu Lys Asp Glu Lys
1               5                   10                  15

Ser Ala Leu Gln Thr Arg Ile Ala Asn Leu Leu Lys Glu Lys Glu Lys
            20                  25                  30

Leu Glu Phe Ile Leu Ala Ala His
        35                  40


<210> SEQ ID NO 30
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 30

Leu Thr Asp Thr Leu Gln Ala Lys Thr Asp Gln Leu Lys Asp Glu Lys
1               5                   10                  15
```

```
Ser Ala Leu Gln Thr Arg Ile Ala Asn Leu Leu Lys Lys Lys Glu Lys
            20                  25                  30

Leu Glu Phe Ile Leu
        35


<210> SEQ ID NO 31
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 31

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105


<210> SEQ ID NO 32
<211> LENGTH: 191
<212> TYPE: PRT
<213> ORGANISM: Artificial Sequence
<220> FEATURE:
<223> OTHER INFORMATION: Synthetic Polypeptide

<400> SEQUENCE: 32

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175
```

```
Gly Val Ala Ile Ser Val Ile Ile Ile Phe Tyr Cys Tyr Arg Val
            180                 185                 190


<210> SEQ ID NO 33
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 33

Gly Gly Gly Gly Ser Gly Gly Gly Gly Ser
1               5                   10


<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Ser Gly Gly Gly Ser
1               5


<210> SEQ ID NO 35
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 35

Arg Ile Ala Arg Leu Glu Glu Glu Val Lys Thr Leu Glu Ala Gln Asn
1               5                   10                  15

Ser Glu Leu Ala Ser Thr Ala Asn Met Leu Glu Glu Gln Val Ala Gln
            20                  25                  30

Leu Lys Gln Lys Val Gly Gly Gly Gly Ser Gly Gly Gly Gly Ser Met
        35                  40                  45

Val Arg Pro Leu Asn Cys Ile Val Ala Val Ser Gln Asn Met Gly Ile
    50                  55                  60

Gly Lys Asn Gly Asp Phe Pro Trp Pro Pro Leu Arg Asn Glu Ser Lys
65                  70                  75                  80

Tyr Phe Gln Arg Met Thr Thr Thr Ser Ser Val Glu Gly Lys Gln Asn
                85                  90                  95

Leu Val Ile Met Gly Arg Lys Thr Trp Phe Ser Ile Pro Glu Lys Asn
            100                 105                 110

Arg Pro Leu Lys Asp Arg Ile Asn Ile Val Leu Ser Arg Glu Leu Lys
        115                 120                 125

Glu Pro Pro Arg Gly Ala His Phe Leu Ala Lys Ser Leu Asp Asp Ala
    130                 135                 140

Leu Arg Leu Ile Glu Gln Pro Glu Leu
145                 150


<210> SEQ ID NO 36
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 36
```

```
Leu Thr Asp Thr Leu Gln Ala Lys Thr Asp Gln Leu Lys Asp Glu Lys
1               5                   10                  15

Ser Ala Leu Gln Thr Arg Ile Ala Asn Leu Leu Lys Glu Lys Glu Lys
            20                  25                  30

Leu Glu Phe Ile Leu Gly Gly Gly Gly Ser Gly Gly Gly Gly Ser Ala
        35                  40                  45

Ser Lys Val Asp Met Val Trp Ile Val Gly Gly Ser Ser Val Tyr Gln
    50                  55                  60

Glu Ala Met Asn Gln Pro Gly His Leu Arg Leu Phe Val Thr Arg Ile
65                  70                  75                  80

Met Gln Glu Phe Glu Ser Asp Thr Phe Phe Pro Glu Ile Asp Leu Gly
                85                  90                  95

Lys Tyr Lys Leu Leu Pro Glu Tyr Pro Gly Val Leu Ser Glu Val Gln
            100                 105                 110

Glu Glu Lys Gly Ile Lys Tyr Lys Phe Glu Val Tyr Glu Lys Lys Asp
        115                 120                 125
```

<210> SEQ ID NO 37
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 37

```
Arg Ile Ala Arg Leu Glu Glu Glu Val Lys Thr Leu Glu Ala Gln Asn
1               5                   10                  15

Ser Glu Leu Ala Ser Thr Ala Asn Met Leu Glu Glu Gln Val Ala Gln
            20                  25                  30

Leu Glu Gln Lys Val Gly Gly Gly Gly Ser Gly Gly Gly Gly Ser Met
        35                  40                  45

Val Arg Pro Leu Asn Cys Ile Val Ala Val Ser Gln Asn Met Gly Ile
    50                  55                  60

Gly Lys Asn Gly Asp Phe Pro Trp Pro Pro Leu Arg Asn Glu Ser Lys
65                  70                  75                  80

Tyr Phe Gln Arg Met Thr Thr Thr Ser Ser Val Glu Gly Lys Gln Asn
                85                  90                  95

Leu Val Ile Met Gly Arg Lys Thr Trp Phe Ser Ile Pro Glu Lys Asn
            100                 105                 110

Arg Pro Leu Lys Asp Arg Ile Asn Ile Val Leu Ser Arg Glu Leu Lys
        115                 120                 125

Glu Pro Pro Arg Gly Ala His Phe Leu Ala Lys Ser Leu Asp Asp Ala
    130                 135                 140

Leu Arg Leu Ile Glu Gln Pro Glu Leu
145                 150
```

<210> SEQ ID NO 38
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 38

```
Leu Thr Asp Thr Leu Gln Ala Lys Thr Asp Gln Leu Lys Asp Glu Lys
1               5                   10                  15

Ser Ala Leu Gln Thr Arg Ile Ala Asn Leu Leu Lys Lys Lys Glu Lys
```

```
            20                  25                  30

Leu Glu Phe Ile Leu Gly Gly Gly Gly Ser Gly Gly Gly Gly Ser Ala
        35                  40                  45

Ser Lys Val Asp Met Val Trp Ile Val Gly Gly Ser Ser Val Tyr Gln
    50                  55                  60

Glu Ala Met Asn Gln Pro Gly His Leu Arg Leu Phe Val Thr Arg Ile
65                  70                  75                  80

Met Gln Glu Phe Glu Ser Asp Thr Phe Phe Pro Glu Ile Asp Leu Gly
                85                  90                  95

Lys Tyr Lys Leu Leu Pro Glu Tyr Pro Gly Val Leu Ser Glu Val Gln
            100                 105                 110

Glu Glu Lys Gly Ile Lys Tyr Lys Phe Glu Val Tyr Glu Lys Lys Asp
        115                 120                 125


<210> SEQ ID NO 39
<211> LENGTH: 163
<212> TYPE: PRT
<213> ORGANISM: Artificial Sequence
<220> FEATURE:
<223> OTHER INFORMATION: Synthetic Polypeptide

<400> SEQUENCE: 39

Asn Thr Glu Ala Ala Arg Arg Ser Arg Ala Arg Lys Leu Gln Arg Met
1               5                   10                  15

Lys Gln Leu Glu Asp Lys Val Glu Glu Leu Leu Ser Lys Asn Tyr His
            20                  25                  30

Leu Glu Asn Glu Val Ala Arg Leu Lys Lys Leu Val Gly Glu Arg Gly
        35                  40                  45

Gly Gly Gly Ser Gly Gly Gly Gly Ser Met Val Arg Pro Leu Asn Cys
    50                  55                  60

Ile Val Ala Val Ser Gln Asn Met Gly Ile Gly Lys Asn Gly Asp Phe
65                  70                  75                  80

Pro Trp Pro Pro Leu Arg Asn Glu Ser Lys Tyr Phe Gln Arg Met Thr
                85                  90                  95

Thr Thr Ser Ser Val Glu Gly Lys Gln Asn Leu Val Ile Met Gly Arg
            100                 105                 110

Lys Thr Trp Phe Ser Ile Pro Glu Lys Asn Arg Pro Leu Lys Asp Arg
        115                 120                 125

Ile Asn Ile Val Leu Ser Arg Glu Leu Lys Glu Pro Pro Arg Gly Ala
    130                 135                 140

His Phe Leu Ala Lys Ser Leu Asp Asp Ala Leu Arg Leu Ile Glu Gln
145                 150                 155                 160

Pro Glu Leu


<210> SEQ ID NO 40
<211> LENGTH: 138
<212> TYPE: PRT
<213> ORGANISM: Artificial Sequence
<220> FEATURE:
<223> OTHER INFORMATION: Synthetic Polypeptide

<400> SEQUENCE: 40

Asn Thr Glu Ala Ala Arg Arg Ser Arg Ala Arg Lys Leu Gln Arg Met
1               5                   10                  15

Lys Gln Leu Glu Asp Lys Val Glu Glu Leu Leu Ser Lys Asn Tyr His
            20                  25                  30

Leu Glu Asn Glu Val Ala Arg Leu Lys Lys Leu Val Gly Glu Arg Gly
```

```
        35                  40                  45

Gly Gly Gly Ser Gly Gly Gly Gly Ser Ala Ser Lys Val Asp Met Val
    50                  55                  60

Trp Ile Val Gly Gly Ser Ser Val Tyr Gln Glu Ala Met Asn Gln Pro
65                  70                  75                  80

Gly His Leu Arg Leu Phe Val Thr Arg Ile Met Gln Glu Phe Glu Ser
                85                  90                  95

Asp Thr Phe Phe Pro Glu Ile Asp Leu Gly Lys Tyr Lys Leu Leu Pro
            100                 105                 110

Glu Tyr Pro Gly Val Leu Ser Glu Val Gln Glu Glu Lys Gly Ile Lys
        115                 120                 125

Tyr Lys Phe Glu Val Tyr Glu Lys Lys Asp
    130                 135


<210> SEQ ID NO 41
<211> LENGTH: 178
<212> TYPE: PRT
<213> ORGANISM: Artificial Sequence
<220> FEATURE:
<223> OTHER INFORMATION: Synthetic Polypeptide

<400> SEQUENCE: 41

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn His Gly Gly Gly Gly Ser Gly Gly Gly
        35                  40                  45

Gly Ser Met Val Arg Pro Leu Asn Cys Ile Val Ala Val Ser Gln Asn
    50                  55                  60

Met Gly Ile Gly Lys Asn Gly Asp Phe Pro Trp Pro Pro Leu Arg Asn
65                  70                  75                  80

Glu Ser Lys Tyr Phe Gln Arg Met Thr Thr Thr Ser Ser Val Glu Gly
                85                  90                  95

Lys Gln Asn Leu Val Ile Met Gly Arg Lys Thr Trp Phe Ser Ile Pro
            100                 105                 110

Glu Lys Asn Arg Pro Leu Lys Asp Arg Ile Asn Ile Val Leu Ser Arg
        115                 120                 125

Glu Leu Lys Glu Pro Pro Arg Gly Ala His Phe Leu Ala Lys Ser Leu
    130                 135                 140

Asp Asp Ala Leu Arg Leu Ile Glu Gln Pro Glu Leu Gly Ser Gly Ala
145                 150                 155                 160

Thr Asn Phe Ser Leu Leu Lys Gln Ala Gly Asp Val Glu Glu Asn Pro
                165                 170                 175

Gly Pro


<210> SEQ ID NO 42
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 42

Leu Thr Asp Thr Leu Gln Ala Glu Thr Asp Gln Leu Glu Asp Glu Lys
1               5                   10                  15

Ser Ala Leu Gln Thr Glu Ile Ala Asn Leu Leu Lys Glu Lys Glu Lys
```

```
            20                  25                  30

Leu Glu Phe Ile Leu Ala Ala His Gly Gly Gly Gly Ser Gly Gly Gly
        35                  40                  45

Gly Ser Ala Ser Lys Val Asp Met Val Trp Ile Val Gly Gly Ser Ser
    50                  55                  60

Val Tyr Gln Glu Ala Met Asn Gln Pro Gly His Leu Arg Leu Phe Val
65                  70                  75                  80

Thr Arg Ile Met Gln Glu Phe Glu Ser Asp Thr Phe Phe Pro Glu Ile
                85                  90                  95

Asp Leu Gly Lys Tyr Lys Leu Leu Pro Glu Tyr Pro Gly Val Leu Ser
            100                 105                 110

Glu Val Gln Glu Glu Lys Gly Ile Lys Tyr Lys Phe Glu Val Tyr Glu
        115                 120                 125

Lys Lys Asp Gly Ser Gly Ala Thr Asn Phe Ser Leu Leu Lys Gln Ala
    130                 135                 140

Gly Asp Val Glu Glu Asn Pro Gly Pro
145                 150


<210> SEQ ID NO 43
<211> LENGTH: 156
<212> TYPE: PRT
<213> ORGANISM: Artificial Sequence
<220> FEATURE:
<223> OTHER INFORMATION: Synthetic Polypeptide

<400> SEQUENCE: 43

Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn His Gly Gly Gly Gly Ser Gly Gly Gly
        35                  40                  45

Gly Ser Met Val Arg Pro Leu Asn Cys Ile Val Ala Val Ser Gln Asn
    50                  55                  60

Met Gly Ile Gly Lys Asn Gly Asp Phe Pro Trp Pro Pro Leu Arg Asn
65                  70                  75                  80

Glu Ser Lys Tyr Phe Gln Arg Met Thr Thr Thr Ser Ser Val Glu Gly
                85                  90                  95

Lys Gln Asn Leu Val Ile Met Gly Arg Lys Thr Trp Phe Ser Ile Pro
            100                 105                 110

Glu Lys Asn Arg Pro Leu Lys Asp Arg Ile Asn Ile Val Leu Ser Arg
        115                 120                 125

Glu Leu Lys Glu Pro Pro Arg Gly Ala His Phe Leu Ala Lys Ser Leu
    130                 135                 140

Asp Asp Ala Leu Arg Leu Ile Glu Gln Pro Glu Leu
145                 150                 155


<210> SEQ ID NO 44
<211> LENGTH: 131
<212> TYPE: PRT
<213> ORGANISM: Artificial Sequence
<220> FEATURE:
<223> OTHER INFORMATION: Synthetic Polypeptide

<400> SEQUENCE: 44

Leu Thr Asp Thr Leu Gln Ala Glu Thr Asp Gln Leu Glu Asp Glu Lys
1               5                   10                  15
```

```
Ser Ala Leu Gln Thr Glu Ile Ala Asn Leu Leu Lys Glu Lys Glu Lys
            20                  25                  30

Leu Glu Phe Ile Leu Ala Ala His Gly Gly Gly Gly Ser Gly Gly Gly
        35                  40                  45

Gly Ser Ala Ser Lys Val Asp Met Val Trp Ile Val Gly Gly Ser Ser
    50                  55                  60

Val Tyr Gln Glu Ala Met Asn Gln Pro Gly His Leu Arg Leu Phe Val
65                  70                  75                  80

Thr Arg Ile Met Gln Glu Phe Glu Ser Asp Thr Phe Phe Pro Glu Ile
                85                  90                  95

Asp Leu Gly Lys Tyr Lys Leu Leu Pro Glu Tyr Pro Gly Val Leu Ser
            100                 105                 110

Glu Val Gln Glu Glu Lys Gly Ile Lys Tyr Lys Phe Glu Val Tyr Glu
        115                 120                 125

Lys Lys Asp
    130


<210> SEQ ID NO 45
<211> LENGTH: 185
<212> TYPE: PRT
<213> ORGANISM: Artificial Sequence
<220> FEATURE:
<223> OTHER INFORMATION: Synthetic Polypeptide

<400> SEQUENCE: 45

Asn Thr Glu Ala Ala Arg Arg Ser Arg Ala Arg Lys Leu Gln Arg Met
1               5                   10                  15

Lys Gln Leu Glu Asp Lys Val Glu Glu Leu Leu Ser Lys Asn Tyr His
            20                  25                  30

Leu Glu Asn Glu Val Ala Arg Leu Lys Lys Leu Val Gly Glu Arg Gly
        35                  40                  45

Gly Gly Gly Ser Gly Gly Gly Gly Ser Met Val Arg Pro Leu Asn Cys
    50                  55                  60

Ile Val Ala Val Ser Gln Asn Met Gly Ile Gly Lys Asn Gly Asp Phe
65                  70                  75                  80

Pro Trp Pro Pro Leu Arg Asn Glu Ser Lys Tyr Phe Gln Arg Met Thr
                85                  90                  95

Thr Thr Ser Ser Val Glu Gly Lys Gln Asn Leu Val Ile Met Gly Arg
            100                 105                 110

Lys Thr Trp Phe Ser Ile Pro Glu Lys Asn Arg Pro Leu Lys Asp Arg
        115                 120                 125

Ile Asn Ile Val Leu Ser Arg Glu Leu Lys Glu Pro Pro Arg Gly Ala
    130                 135                 140

His Phe Leu Ala Lys Ser Leu Asp Asp Ala Leu Arg Leu Ile Glu Gln
145                 150                 155                 160

Pro Glu Leu Gly Ser Gly Ala Thr Asn Phe Ser Leu Leu Lys Gln Ala
                165                 170                 175

Gly Asp Val Glu Glu Asn Pro Gly Pro
            180                 185


<210> SEQ ID NO 46
<211> LENGTH: 160
<212> TYPE: PRT
<213> ORGANISM: Artificial Sequence
<220> FEATURE:
<223> OTHER INFORMATION: Synthetic Polypeptide

<400> SEQUENCE: 46
```

```
Asn Thr Glu Ala Ala Arg Arg Ser Arg Ala Arg Lys Leu Gln Arg Met
1               5                   10                  15

Lys Gln Leu Glu Asp Lys Val Glu Glu Leu Leu Ser Lys Asn Tyr His
            20                  25                  30

Leu Glu Asn Glu Val Ala Arg Leu Lys Lys Leu Val Gly Glu Arg Gly
        35                  40                  45

Gly Gly Gly Ser Gly Gly Gly Gly Ser Ala Ser Lys Val Asp Met Val
    50                  55                  60

Trp Ile Val Gly Gly Ser Ser Val Tyr Gln Glu Ala Met Asn Gln Pro
65                  70                  75                  80

Gly His Leu Arg Leu Phe Val Thr Arg Ile Met Gln Glu Phe Glu Ser
                85                  90                  95

Asp Thr Phe Phe Pro Glu Ile Asp Leu Gly Lys Tyr Lys Leu Leu Pro
            100                 105                 110

Glu Tyr Pro Gly Val Leu Ser Glu Val Gln Glu Glu Lys Gly Ile Lys
        115                 120                 125

Tyr Lys Phe Glu Val Tyr Glu Lys Lys Asp Gly Ser Gly Ala Thr Asn
    130                 135                 140

Phe Ser Leu Leu Lys Gln Ala Gly Asp Val Glu Glu Asn Pro Gly Pro
145                 150                 155                 160
```

<210> SEQ ID NO 47
<211> LENGTH: 2284
<212> TYPE: DNA
<213> ORGANISM: Artificial Sequence
<220> FEATURE:
<223> OTHER INFORMATION: Synthetic Oligonucleotide

<400> SEQUENCE: 47

```
gccagagtta tattgctggg gttttgaaga agatcctatt aaataaaaga ataagcagta     60

ttattaagta gccctgcatt tcaggtttcc ttgagtggca ggccaggcct ggccgtgaac    120

gttcactgaa atcatggcct cttggccaag attgatagct tgtgcctgtc cctgagtccc    180

agtccatcac gagcagctgg tttctaagat gctatttccc gtataaagca tgagaccgtg    240

acttgccagc cccacagagc cccgcccttg tccatcactg gcatctggac tccagcctgg    300

gttggggcaa agagggaaat gagatcatgt cctaaccctg atcctcttgt cccacagata    360

tccagaaccc tgaccctgcc gtgtaccagc tgagagactc taaatccagt gacaagtctg    420

tctgcctatt cggatctggc gccaccaatt tcagcctgct gaaacaggct ggcgacgtgg    480

aagagaaccc cggacctatg tctatcggcc tgctgtgttg tgccgctctg tctctgcttt    540

gggccggacc tgttaatgcc ggcgtgaccc agacacctaa gttccaggtg ctgaaaaccg    600

gccagagcat gaccctgcag tgcgcccagg atatgaacca cgagtacatg agctggtaca    660

gacaggaccc tggcatgggc ctgagactga tccactattc tgtcggagcc ggcatcaccg    720

accagggcga agttcctaat ggctacaacg tgtccagaag caccaccgag gacttcccac    780

tgagactgct gtctgccgct cctagccaga ccagcgtgta cttttgtgcc agcagctacg    840

tgggcaacac cggcgagctg ttttttggcg agggcagcag actgaccgtg ctggaggacc    900

tgaagaacgt gttccctcca aaggtggccg tgttcgagcc ttctgaggcc gagatcagcc    960

acacacagaa agccacactc gtgtgtctgg ccaccggctt ctaccccgat cacgtggaac   1020

tgtcttggtg ggtcaacggc aaagaggtgc acagcggcgt cagcacagat ccccagcctc   1080

tgaaagaaca gcccgctctg aacgacagcc ggtactgtct gagcagcaga ctgagagtgt   1140
```

```
ccgccacctt ctggcagaac cccagaaacc acttcagatg ccaggtgcag ttctacggcc   1200
tgagcgaaaa cgacgagtgg acccaggaca gggccaagcc tgtgacacag atcgtgtctg   1260
ccgaagcctg ggcagagcc gattgtggct ttaccagcga gagctaccag cagggcgtgc   1320
tgtctgccac aatcctgtac gagatcctgc tgggcaaagc cactctgtac gccgtgctgg   1380
tgtctgccct ggtgctgatg gccatggtca agcggaagga tagcagaggc ggcagcggcg   1440
aaggcagagg ctctcttctt acatgcggcg acgtcgaaga aaatcctggg cctatgaagt   1500
ccctgcgggt gctgctggtt atcctgtggc tgcagctgag ctgggtctgg tcccagaaac   1560
aagaagtgac tcagatccca gccgctctga gtgtgcctga gggcgaaaac ctggtcctga   1620
actgcagctt caccgacagc gccatctaca acctgcagtg gttcaggcag gatcccggca   1680
agggactgac aagcctgctg ctgattcaga gcagccagag agagcagacc tccggcagac   1740
tgaatgccag cctggataag agcagcggcc gcagcacact gtatatcgcc gcttctcagc   1800
ctggcgatag cgccacatat ctgtgtgccg tgcgacctct gtacggcggc agctacatcc   1860
ctacatttgg cagaggcacc agcctgatcg tgcacccta cattcagaac cccgatcctg   1920
ccgtgtatca gctgagagac agcaagtcca gcgacaagag cgtgtgtttg ttcaccgatt   1980
ttgattctca aacaaatgtg tcacaaagta aggattctga tgtgtatatc acagacaaaa   2040
ctgtgctaga catgaggtct atggacttca agagcaacag tgctgtggcc tggagcaaca   2100
aatctgactt tgcatgtgca aacgccttca acaacagcat tattccagaa gacaccttct   2160
tccccagccc aggtaagggc agctttggtg ccttcgcagg ctgtttcctt gcttcaggaa   2220
tggccaggtt ctgcccagag ctctggtcaa tgatgtctaa aactcctctg attggtggtc   2280
tcgg                                                                2284
```

<210> SEQ ID NO 48
<211> LENGTH: 2905
<212> TYPE: DNA
<213> ORGANISM: Artificial Sequence
<220> FEATURE:
<223> OTHER INFORMATION: Synthetic Oligonucleotide

<400> SEQUENCE: 48

```
gccagagtta tattgctggg gttttgaaga agatcctatt aaataaaaga ataagcagta     60
ttattaagta gccctgcatt tcaggtttcc ttgagtggca ggccaggcct ggccgtgaac    120
gttcactgaa atcatggcct cttggccaag attgatagct tgtgcctgtc cctgagtccc    180
agtccatcac gagcagctgg tttctaagat gctatttccc gtataaagca tgagaccgtg    240
acttgccagc cccacagagc cccgcccttg tccatcactg gcatctggac tccagcctgg    300
gttggggcaa agagggaaat gagatcatgt cctaaccctg atcctcttgt cccacagata    360
tccagaaccc tgaccctgcc gtgtaccagc tgagagactc taaatccagt gacaagtctg    420
tctgcctatt cggatctggc gccaccaatt tcagcctgct gaaacaggct ggcgacgtgg    480
aagagaaccc cggacctatg tctatcggcc tgctgtgttg tgccgctctg tctctgcttt    540
gggccggacc tgttaatgcc ggcgtgaccc agacacctaa gttccaggtg ctgaaaaccg    600
gccagagcat gaccctgcag tgcgcccagg atatgaacca cgagtacatg agctggtaca    660
gacaggaccc tggcatgggc ctgagactga tccactattc tgtcggagcc ggcatcaccg    720
accagggcga agttcctaat ggctacaacg tgtccagaag caccaccgag gacttcccac    780
tgagactgct gtctgccgct cctagccaga ccagcgtgta cttttgtgcc agcagctacg    840
tgggcaacac cggcgagctg ttttttggcg agggcagcag actgaccgtg ctggaagatc    900
```

tgaacaaggt gttccctcca gaggtggccg tgttcgagcc ttctgaggcc gagatcagcc 960
acacacagaa agccacactc gtgtgcctgg ccaccggctt ttttcccgat cacgtggaac 1020
tgtcttggtg ggtcaacggc aaagaggtgc acagcggcgt cagcacagat ccccagcctc 1080
tgaaagaaca gcccgctctg aacgacagcc ggtactgtct gtcctccaga ctgagagtgt 1140
ccgccacctt ctggcagaac cccagaaacc acttcagatg ccaggtgcag ttctacggcc 1200
tgagcgagaa cgatgagtgg acccaggata gagccaagcc tgtgacacag atcgtgtctg 1260
ccgaagcctg gggcagagcc gattgtggct ttacctccgt gtcctatcag cagggcgtgc 1320
tgagcgccac aatcctgtat gagatcctgc tgggcaaagc cactctgtac gccgtgctgg 1380
tgtctgccct ggtgctgatg gccatggtca agagaaagga cttcggcagc ggcgaaggca 1440
gaggctctct tcttacatgc ggcgacgtcg aagaaaatcc tgggcctatg gtaggctccc 1500
tgaactgtat agttgcggta tcccaaaata tggggattgg aaagaacgga gaccttccgt 1560
ggccgcccct ccgaaatgaa tttcgatact ttcagagaat gacaactacc tcatctgtag 1620
agggaaagca aaatctggtt atcatgggaa agaaaacgtg gttctctatc cctgaaaaaa 1680
acagacctct caaaggcagg ataaatttgg tattgtcaag agaattgaag gaaccgccac 1740
aaggagctca ttttctcagc agatctctgg acgatgcact caaactcacc gaacaaccag 1800
aacttgctaa taaggttgat atggtctgga tagttggggg cagcagtgta tataaggaag 1860
ccatgaacca tcctggccat ctgaagctgt ttgttacgag gataatgcag gacttcgagt 1920
ccgacacttt tttcccagag attgacttgg aaaagtataa actcttgcct gagtatcctg 1980
gggttctctc cgatgtccaa gaggagaaag gtattaaata taagtttgaa gtttatgaaa 2040
aaaacgatgg atctggcgcc accaatttca gcctgctgaa acaggctggc gacgtggaag 2100
agaaccccgg acctatgaag tccctgcggg tgctgctggt tatcctgtgg ctgcagctga 2160
gctgggtctg gtcccagaaa caagaagtga ctcagatccc agccgctctg agtgtgcctg 2220
agggcgaaaa cctggtcctg aactgcagct tcaccgacag cgccatctac aacctgcagt 2280
ggttcaggca ggatcccggc aagggactga caagcctgct gctgattcag agcagccaga 2340
gagagcagac ctccggcaga ctgaatgcca gcctggataa gagcagcggc cgcagcacac 2400
tgtatatcgc cgcttctcag cctggcgata gcgccacata tctgtgtgcc gtgcgacctc 2460
tgtacggcgg cagctacatc cctacatttg gcagaggcac cagcctgatc gtgcacccct 2520
acattcagaa ccccgatcct gccgtgtatc agctgagaga cagcaagtcc agcgacaaga 2580
gcgtgtgttt gttcaccgat tttgattctc aaacaaatgt gtcacaaagt aaggattctg 2640
atgtgtatat cacagacaaa actgtgctag acatgaggtc tatggacttc aagagcaaca 2700
gtgctgtggc ctggagcaac aaatctgact ttgcatgtgc aaacgccttc aacaacagca 2760
ttattccaga agacaccttc ttccccagcc caggtaaggg cagctttggt gccttcgcag 2820
gctgtttcct tgcttcagga atggccaggt tctgcccaga gctctggtca atgatgtcta 2880
aaactcctct gattggtggt ctcgg 2905

<210> SEQ ID NO 49
<211> LENGTH: 2905
<212> TYPE: DNA
<213> ORGANISM: Artificial Sequence
<220> FEATURE:
<223> OTHER INFORMATION: Synthetic Oligonucleotide

<400> SEQUENCE: 49

-continued

```
gccagagtta tattgctggg gttttgaaga agatcctatt aaataaaaga ataagcagta     60
ttattaagta gccctgcatt tcaggtttcc ttgagtggca ggccaggcct ggccgtgaac    120
gttcactgaa atcatggcct cttggccaag attgatagct tgtgcctgtc cctgagtccc    180
agtccatcac gagcagctgg tttctaagat gctatttccc gtataaagca tgagaccgtg    240
acttgccagc cccacagagc cccgcccttg tccatcactg gcatctggac tccagcctgg    300
gttggggcaa agagggaaat gagatcatgt cctaaccctg atcctcttgt cccacagata    360
tccagaaccc tgaccctgcc gtgtaccagc tgagagactc taaatccagt gacaagtctg    420
tctgcctatt cggatctggc gccaccaatt tcagcctgct gaaacaggct ggcgacgtgg    480
aagagaaccc cggacctatg tctatcggcc tgctgtgttg tgccgctctg tctctgcttt    540
gggccggacc tgttaatgcc ggcgtgaccc agacacctaa gttccaggtg ctgaaaaccg    600
gccagagcat gaccctgcag tgcgcccagg atatgaacca cgagtacatg agctggtaca    660
gacaggaccc tggcatgggc ctgagactga tccactattc tgtcggagcc ggcatcaccg    720
accagggcga agttcctaat ggctacaacg tgtccagaag caccaccgag gacttcccac    780
tgagactgct gtctgccgct cctagccaga ccagcgtgta cttttgtgcc agcagctacg    840
tgggcaacac cggcgagctg ttttttggcg agggcagcag actgaccgtg ctggaagatc    900
tgaacaaggt gttccctcca gaggtggccg tgttcgagcc ttctgaggcc gagatcagcc    960
acacacagaa agccacactc gtgtgcctgg ccaccggctt ttttcccgat cacgtggaac   1020
tgtcttggtg ggtcaacggc aaagaggtgc acagcggcgt cagcacagat ccccagcctc   1080
tgaaagaaca gcccgctctg aacgacagcc ggtactgtct gtcctccaga ctgagagtgt   1140
ccgccacctt ctggcagaac cccagaaacc acttcagatg ccaggtgcag ttctacggcc   1200
tgagcgagaa cgatgagtgg acccaggata gagccaagcc tgtgacacag atcgtgtctg   1260
ccgaagcctg gggcagagcc gattgtggct ttacctccgt gtcctatcag cagggcgtgc   1320
tgagcgccac aatcctgtat gagatcctgc tgggcaaagc cactctgtac gccgtgctgg   1380
tgtctgccct ggtgctgatg gccatggtca agagaaagga cttcggcagc ggcgaaggca   1440
gaggctctct tcttacatgc ggcgacgtcg aagaaaatcc tgggcctatg gtaggctccc   1500
tgaactgtat agttgcggta tcccaaaata tggggattgg aaagaacgga gactttccgt   1560
ggccgcccct ccgaaatgaa tcccgatact ttcagagaat gacaactacc tcatctgtag   1620
agggaaagca aaatctggtt atcatgggaa agaaaacgtg gttctctatc cctgaaaaaa   1680
acagacctct caaaggcagg ataaatttgg tattgtcaag agaattgaag gaaccgccac   1740
aaggagctca ttttctcagc agatctctgg acgatgcact caaactcacc gaacaaccag   1800
aacttgctaa taaggttgat atggtctgga tagttggggg cagcagtgta tataaggaag   1860
ccatgaacca tcctggccat ctgaagctgt ttgttacgag gataatgcag gacttcgagt   1920
ccgacacttt tttcccagag attgacttgg aaaagtataa actcttgcct gagtatcctg   1980
gggttctctc cgatgtccaa gaggagaaag gtattaaata taagtttgaa gtttatgaaa   2040
aaaacgatgg atctggcgcc accaatttca gcctgctgaa acaggctggc gacgtggaag   2100
agaaccccgg acctatgaag tccctgcggg tgctgctggt tatcctgtgg ctgcagctga   2160
gctgggtctg gtcccagaaa caagaagtga ctcagatccc agccgctctg agtgtgcctg   2220
agggcgaaaa cctggtcctg aactgcagct tcaccgacag cgccatctac aacctgcagt   2280
ggttcaggca ggatcccggc aagggactga caagcctgct gctgattcag agcagccaga   2340
gagagcagac ctccggcaga ctgaatgcca gcctggataa gagcagcggc cgcagcacac   2400
```

tgtatatcgc cgcttctcag cctggcgata gcgccacata tctgtgtgcc gtgcgacctc 2460
tgtacggcgg cagctacatc cctacatttg gcagaggcac cagcctgatc gtgcacccct 2520
acattcagaa ccccgatcct gccgtgtatc agctgagaga cagcaagtcc agcgacaaga 2580
gcgtgtgttt gttcaccgat tttgattctc aaacaaatgt gtcacaaagt aaggattctg 2640
atgtgtatat cacagacaaa actgtgctag acatgaggtc tatggacttc aagagcaaca 2700
gtgctgtggc ctggagcaac aaatctgact ttgcatgtgc aaacgccttc aacaacagca 2760
ttattccaga agacaccttc ttccccagcc caggtaaggg cagctttggt gccttcgcag 2820
gctgtttcct tgcttcagga atggccaggt tctgcccaga gctctggtca atgatgtcta 2880
aaactcctct gattggtggt ctcgg 2905

<210> SEQ ID NO 50
<211> LENGTH: 2809
<212> TYPE: DNA
<213> ORGANISM: Artificial Sequence
<220> FEATURE:
<223> OTHER INFORMATION: Synthetic Oligonucleotide

<400> SEQUENCE: 50
gccagagtta tattgctggg gttttgaaga agatcctatt aaataaaaga ataagcagta 60
ttattaagta gccctgcatt tcaggtttcc ttgagtggca ggccaggcct ggccgtgaac 120
gttcactgaa atcatggcct cttggccaag attgatagct tgtgcctgtc cctgagtccc 180
agtccatcac gagcagctgg tttctaagat gctatttccc gtataaagca tgagaccgtg 240
acttgccagc cccacagagc cccgcccttg tccatcactg gcatctggac tccagcctgg 300
gttggggcaa agagggaaat gagatcatgt cctaaccctg atcctcttgt cccacagata 360
tccagaaccc tgaccctgcc gtgtaccagc tgagagactc taaatccagt gacaagtctg 420
tctgcctatt cggatctggc gccaccaatt tcagcctgct gaaacaggct ggcgacgtgg 480
aagagaaccc cggacctatg tctatcggcc tgctgtgttg tgccgctctg tctctgcttt 540
gggccggacc tgttaatgcc ggcgtgaccc agacacctaa gttccaggtg ctgaaaaccg 600
gccagagcat gaccctgcag tgcgcccagg atatgaacca cgagtacatg agctggtaca 660
gacaggaccc tggcatgggc ctgagactga tccactattc tgtcggagcc ggcatcaccg 720
accagggcga agttcctaat ggctacaacg tgtccagaag caccaccgag gacttcccac 780
tgagactgct gtctgccgct cctagccaga ccagcgtgta cttttgtgcc agcagctacg 840
tgggcaacac cggcgagctg ttttttggcg agggcagcag actgaccgtg ctggaagatc 900
tgcggaacgt gttccctcca aaggtggccg tgtttgagcc tagcgaggcc gagatcagcc 960
acacacagaa agccacactc gtgtgtctgg ccaccggctt ctatcccgat cacgtggaac 1020
tgtcttggtg ggtcaacggc aaagaggtgc acagcggcgt cagcacagat ccccagcctc 1080
tgaaagaaca gcccgctctg aacgacagcc ggtactgtct gtcctccaga ctgagagtgt 1140
ccgccacctt ctggcagaac cccagaaacc acttcagatg ccaggtgcag ttctacggcc 1200
tgagcgagaa cgacaagtgg cctgagggat ctgccaagcc tgtgacacag atcgtgtctg 1260
ccgaagcttg ggcagagcc gattgtggct ttaccagcga gagctaccag cagggcgttc 1320
tgtctgccac catcctgtac gagatcctgc tgggcaaagc cactctgtac gccgtgctgg 1380
tgtctgccct ggtgctgatg gccatggtca agcggaagga tagcagaggc ggaagcggag 1440
aaggcagagg ctctctgctt acatgcggag atgtggaaga aaatcctgga ccaagaatcg 1500
cccgcctgga agaagaggtc aagaccctgg aggcccagaa cagcgagctg gcctctaccg 1560
ccaacatgct ggaagaacag gtcgcccagc tggagcagaa agtcggcggc ggaggatctg 1620
gcggaggcgg atctatggtt cgacccctga attgcatcgt ggccgtgtct cagaacatgg 1680
gcatcggcaa gaacggcgac ttcccttggc ctcctctgcg gaacgagagc aagtacttcc 1740
agagaatgac caccaccagc agcgtggaag gcaagcagaa cctggtcatc atgggcagaa 1800
agacctggtt cagcatcccc gagaagaaca ggcccctgaa ggaccggatc aacatcgtgc 1860
tgagcagaga gctgaaagag cctcctagag gcgcccactt tctggccaag tctctggacg 1920
atgccctgcg gctgattgag cagcctgaac ttggcagcgg cgccacaaac ttttcactgc 1980
tgaagcaagc cggggatgtc gaagagaatc cagggcctat gaagtccctg cgggtgctgc 2040
tggttatcct gtggctgcag ctgagctggg tctggtccca gaaacaagaa gtgactcaga 2100
tcccagccgc tctgagtgtg cctgagggcg aaaacctggt cctgaactgc agcttcaccg 2160
acagcgccat ctacaacctg cagtggttca ggcaggatcc cggcaaggga ctgacaagcc 2220
tgctgctgat tcagagcagc cagagagagc agacctccgg cagactgaat gccagcctgg 2280
ataagagcag cggccgcagc acactgtata tcgccgcttc tcagcctggc gatagcgcca 2340
catatctgtg tgccgtgcga cctctgtacg gcggcagcta catccctaca tttggcagag 2400
gcaccagcct gatcgtgcac ccctacattc agaaccccga tcctgccgtg tatcagctga 2460
gagacagcaa gtccagcgac aagagcgtgt gtttgttcac cgattttgat tctcaaacaa 2520
atgtgtcaca aagtaaggat tctgatgtgt atatcacaga caaaactgtg ctagacatga 2580
ggtctatgga cttcaagagc aacagtgctg tggcctggag caacaaatct gactttgcat 2640
gtgcaaacgc cttcaacaac agcattattc cagaagacac cttcttcccc agcccaggta 2700
agggcagctt tggtgccttc gcaggctgtt tccttgcttc aggaatggcc aggttctgcc 2760
cagagctctg gtcaatgatg tctaaaactc ctctgattgg tggtctcgg 2809

<210> SEQ ID NO 51
<211> LENGTH: 2617
<212> TYPE: DNA
<213> ORGANISM: Artificial Sequence
<220> FEATURE:
<223> OTHER INFORMATION: Synthetic Oligonucleotide

<400> SEQUENCE: 51
gaagttctcc ttctgctagg tagcattcaa agatcttaat cttctgggtt tccgttttct 60
cgaatgaaaa atgcaggtcc gagcagttaa ctggctgggg caccattagc aagtcactta 120
gcatctctgg ggccagtctg caaagcgagg gggcagcctt aatgtgcctc cagcctgaag 180
tcctagaatg agcgcccggt gtcccaagct ggggcgcgca ccccagatcg gagggcgccg 240
atgtacagac agcaaactca cccagtctag tgcatgcctt cttaaacatc acgagactct 300
aagaaaagga aactgaaaac gggaaagtcc ctctctctaa cctggcactg cgtcgctggc 360
ttggagacag gtgacggtcc ctgcgggcct tgtcctgatt ggctgggcac gcgtttaata 420
taagtggagg cgtcgcgctg gcgggcattc ctgaagctga cagcattcgg gccgagatgt 480
ctcgctccgt ggccttagct ggatctggag aaggcagagg cagcctgctt acatgcggag 540
atgtggaaga aaatcctgga ccaatgggaa gaggcctgct gagaggactg tggcctctgc 600
acattgtgct gtggaccaga atcgccagca caatccctcc acacgtgcag aaaagcgtga 660
acaacgacat gatcgtgacc gacaacaatg gcgccgtgaa gttccctcag ctgtgcaagt 720
tctgcgacgt gcggttcagc acctgtgaca accagaaaag ctgcatgagc aactgcagca 780
tcaccagcat ctgcgagaag ccccaagaag tgtgcgtcgc cgtctggcgg aagaacgacg 840
agaacatcac cctggaaacc gtgtgtcacg accccaagct gccctaccac gacttcatcc 900
tggaagatgc cgcctctcct aagtgcatca tgaaggaaaa gaagaagccc ggcgagacat 960
tcttcatgtg cagctgctcc agcgacgagt gcaacgacaa catcatcttc agcgaagagt 1020
acaacaccag caatcccgac ctgctgctgg tcatcttcca ggtgaccggc atcagcctgc 1080
tgcctccact gggagttgcc atcagcgtga tcatcatctt ttactgctac cgcgtgggat 1140
ctggcgccac caatttcagc ctgctgaaac aggctggcga cgtggaagag aaccccggac 1200
ctctgaccga cacactgcag gccaagacag accaactgaa agatgagaag tctgccctgc 1260
agaccaggat cgctaacctg ctgaaaaaga aagagaagct cgagttcatc ctgggtggcg 1320
gaggatctgg cggaggcgga tctgccagca aggtggacat ggtctggatc gtcggcggct 1380
cctctgtgta ccaagaggcc atgaatcagc ccggacacct gaggctgttc gtgaccagaa 1440
tcatgcaaga gttcgagagc gacacattct tcccagagat cgacctgggc aagtacaagc 1500
tgctgcctga gtatcccggc gtgctgtctg aggtgcaaga ggaaaagggc atcaagtata 1560
agttcgaggt gtacgagaaa aaggatggat ccggcgaagg cagaggatct ctgctgacat 1620
gtggcgacgt ggaagagaac cctggaccta tggatacctg ccacattgcc aagagctgcg 1680
tgctgatcct gctggtcgtt ctgctgtgtg ccgagcgagc acagggcctc gagtgctaca 1740
attgcattgg cgtgccacct gagacaagct gcaacaccac cacctgtcct ttcagcgacg 1800
gcttctgtgt ggccctggaa atcgaagtga tcgtggacag ccaccggtcc aaagtgaagt 1860
ccaacctgtg cctgcctatc tgccccacca cactggacaa caccgagatc acaggcaacg 1920
ccgtgaacgt gaaaacctac tgctgcaaag aggacctctg caacgccgct gttccaacag 1980
gtggaagctc ttggactatg gccggcgtgc tgctgtttag cctggtgtct gttctgctgc 2040
agaccttcct gggatcaggc gccacgaatt ttagcctgct caaacaggcg ggcgacgtag 2100
aagagaaccc aggacctgtg ctcgcgctac tctctctttc tggcctggag gctatccagc 2160
gtgagtctct cctaccctcc cgctctggtc cttcctctcc cgctctgcac cctctgtggc 2220
cctcgctgtg ctctctcgct ccgtgacttc ccttctccaa gttctccttg gtggcccgcc 2280
gtggggctag tccagggctg gatctcgggg aagcggcggg gtggcctggg agtggggaag 2340
ggggtgcgca cccgggacgc gcgctacttg ccccctttcgg cggggagcag gggagacctt 2400
tggcctacgg cgacgggagg gtcgggacaa agtttagggc gtcgataagc gtcagagcgc 2460
cgaggttggg ggagggtttc tcttccgctc tttcgcgggg cctctggctc ccccagcgca 2520
gctggagtgg gggacgggta ggctcgtccc aaaggcgcgg cgctgaggtt tgtgaacgcg 2580
tggaggggcg cttggggtct gggggaggcg tcgcccg 2617

<210> SEQ ID NO 52
<211> LENGTH: 2617
<212> TYPE: DNA
<213> ORGANISM: Artificial Sequence
<220> FEATURE:
<223> OTHER INFORMATION: Synthetic Oligonucleotide

<400> SEQUENCE: 52
agtatcttgg ggccaaatca tgtagactct tgagtgatgt gttaaggaat gctatgagtg 60
ctgagagggc atcagaagtc cttgagagcc tccagagaaa ggctcttaaa aatgcagcgc 120
aatctccagt gacagaagat actgctagaa atctgctaga aaaaaaacaa aaaaggcatg 180

```
tatagaggaa ttatgaggga aagataccaa gtcacggttt attcttcaaa atggaggtgg    240
cttgttggga aggtggaagc tcatttggcc agagtggaaa tggaattggg agaaatcgat    300
gaccaaatgt aaacacttgg tgcctgatat agcttgacac caagttagcc ccaagtgaaa    360
taccctggca atattaatgt gtcttttccc gatattcctc aggtactcca aagattcagg    420
tttactcacg tcatccagca gagaatggaa agtcaaattt cctgaattgc tatgtgtctg    480
ggtttcatcc atccgacatt ggatctggag aaggcagagg cagcctgctt acatgcggag    540
atgtggaaga aaatcctgga ccaatgggaa gaggcctgct gagaggactg tggcctctgc    600
acattgtgct gtggaccaga atcgccagca caatccctcc acacgtgcag aaaagcgtga    660
acaacgacat gatcgtgacc gacaacaatg gcgccgtgaa gttccctcag ctgtgcaagt    720
tctgcgacgt gcggttcagc acctgtgaca accagaaaag ctgcatgagc aactgcagca    780
tcaccagcat ctgcgagaag ccccaagaag tgtgcgtcgc cgtctggcgg aagaacgacg    840
agaacatcac cctggaaacc gtgtgtcacg accccaagct gccctaccac gacttcatcc    900
tggaagatgc cgcctctcct aagtgcatca tgaaggaaaa gaagaagccc ggcgagacat    960
tcttcatgtg cagctgctcc agcgacgagt gcaacgacaa catcatcttc agcgaagagt   1020
acaacaccag caatcccgac ctgctgctgg tcatcttcca ggtgaccggc atcagcctgc   1080
tgcctccact gggagttgcc atcagcgtga tcatcatctt ttactgctac cgcgtgggat   1140
ctggcgccac caatttcagc ctgctgaaac aggctggcga cgtggaagag aaccccggac   1200
ctctgaccga cacactgcag gccaagacag accaactgaa agatgagaag tctgccctgc   1260
agaccaggat cgctaacctg ctgaaaaaga aagagaagct cgagttcatc ctgggtggcg   1320
gaggatctgg cggaggcgga tctgccagca aggtggacat ggtctggatc gtcggcggct   1380
cctctgtgta ccaagaggcc atgaatcagc ccggacacct gaggctgttc gtgaccagaa   1440
tcatgcaaga gttcgagagc gacacattct tcccagagat cgacctgggc aagtacaagc   1500
tgctgcctga gtatcccggc gtgctgtctg aggtgcaaga ggaaaagggc atcaagtata   1560
agttcgaggt gtacgagaaa aaggatggat ccggcgaagg cagaggatct ctgctgacat   1620
gtggcgacgt ggaagagaac cctggaccta tggatacctg ccacattgcc aagagctgcg   1680
tgctgatcct gctggtcgtt ctgctgtgtg ccgagcgagc acagggcctc gagtgctaca   1740
attgcattgg cgtgccacct gagacaagct gcaacaccac cacctgtcct ttcagcgacg   1800
gcttctgtgt ggccctggaa atcgaagtga tcgtggacag ccaccggtcc aaagtgaagt   1860
ccaacctgtg cctgcctatc tgccccacca cactggacaa caccgagatc acaggcaacg   1920
ccgtgaacgt gaaaacctac tgctgcaaag aggacctctg caacgccgct gttccaacag   1980
gtggaagctc ttggactatg gccggcgtgc tgctgtttag cctggtgtct gttctgctgc   2040
agaccttcct gggatcaggc gccacgaatt ttagcctgct caaacaggcg ggcgacgtag   2100
aagagaaccc aggacctgaa gttgacttac tgaagaatgg agagagaatt gaaaaagtgg   2160
agcattcaga cttgtctttc agcaaggact ggtctttcta tctcttgtac tacactgaat   2220
tcacccccac tgaaaaagat gagtatgcct gccgtgtgaa ccatgtgact ttgtcacagc   2280
ccaagatagt taagtggggt aagtcttaca ttcttttgta agctgctgaa agttgtgtat   2340
gagtagtcat atcataaagc tgctttgata taaaaaaggt ctatggccat actaccctga   2400
atgagtccca tcccatctga tataaacaat ctgcatattg ggattgtcag ggaatgttct   2460
taaagatcag attagtggca cctgctgaga tactgatgca cagcatggtt tctgaaccag   2520
tagtttccct gcagttgagc agggagcagc agcagcactt gcacaaatac atatacactc   2580
```

ttaacacttc ttacctactg gcttcctcta gcttttg 2617

<210> SEQ ID NO 53
<211> LENGTH: 3007
<212> TYPE: DNA
<213> ORGANISM: Artificial Sequence
<220> FEATURE:
<223> OTHER INFORMATION: Synthetic Oligonucleotide

<400> SEQUENCE: 53
gccagagtta tattgctggg gttttgaaga agatcctatt aaataaaaga ataagcagta 60
ttattaagta gccctgcatt tcaggtttcc ttgagtggca ggccaggcct ggccgtgaac 120
gttcactgaa atcatggcct cttggccaag attgatagct tgtgcctgtc cctgagtccc 180
agtccatcac gagcagctgg tttctaagat gctatttccc gtataaagca tgagaccgtg 240
acttgccagc cccacagagc cccgcccttg tccatcactg gcatctggac tccagcctgg 300
gttggggcaa agagggaaat gagatcatgt cctaaccctg atcctcttgt cccacagata 360
tccagaaccc tgaccctgcc gtgtaccagc tgagagactc taaatccagt gacaagtctg 420
tctgcctatt cggatctggc gccaccaatt tcagcctgct gaaacaggct ggcgacgtgg 480
aagagaaccc cggacctatg tctatcggcc tgctgtgttg tgccgctctg tctctgcttt 540
gggccggacc tgttaatgcc ggcgtgaccc agacacctaa gttccaggtg ctgaaaaccg 600
gccagagcat gaccctgcag tgcgcccagg atatgaacca cgagtacatg agctggtaca 660
gacaggaccc tggcatgggc ctgagactga tccactattc tgtcggagcc ggcatcaccg 720
accagggcga agttcctaat ggctacaacg tgtccagaag caccaccgag gacttcccac 780
tgagactgct gtctgccgct cctagccaga ccagcgtgta cttttgtgcc agcagctacg 840
tgggcaacac cggcgagctg ttttttggcg agggcagcag actgaccgtg ctggaagatc 900
tgcggaacgt gttccctcca aaggtggccg tgtttgagcc tagcgaggcc gagatcagcc 960
acacacagaa agccacactc gtgtgtctgg ccaccggctt ctatcccgat cacgtggaac 1020
tgtcttggtg ggtcaacggc aaagaggtgc acagcggcgt cagcacagat ccccagcctc 1080
tgaaagaaca gcccgctctg aacgacagcc ggtactgtct gtcctccaga ctgagagtgt 1140
ccgccacctt ctggcagaac cccagaaacc acttcagatg ccaggtgcag ttctacggcc 1200
tgagcgagaa cgacaagtgg cctgagggat ctgccaagcc tgtgacacag atcgtgtctg 1260
ccgaagcttg ggcagagcc gattgtggct ttaccagcga gagctaccag cagggcgttc 1320
tgtctgccac catcctgtac gagatcctgc tgggcaaagc cactctgtac gccgtgctgg 1380
tgtctgccct ggtgctgatg gccatggtca agcggaagga tagcagaggc ggaagcggag 1440
aaggcagagg ctctctgctt acatgcggag atgtggaaga aaatcctgga ccaatgggag 1500
ttcaagtgga gacaatatca ccaggcgatg gaaggacatt ccccaagcga gggcaaacgt 1560
gtgtggtaca ctacactggc atgttggagg acggaaagaa agtcgacagt tcccgcgacc 1620
ggaataagcc tttcaaattc atgctcggca agcaggaggt cattcggggt tgggaggaag 1680
gggtcgcgca aatgagtgtc ggacaacgcg caaaacttac tatttcccca gattacgcct 1740
acggagccac aggtcaccct ggtatcatac caccccacgc gactctggtt tttgatgtcg 1800
aattgctgaa attggaatct ggcggaggct ctatggttcg acccctgaat tgcatcgtgg 1860
ccgtgtctca gaacatgggc atcggcaaga acggcgactt cccttggcct cctctgcgga 1920
acgagagcaa gtacttccag agaatgacca ccaccagcag cgtggaaggc aagcagaacc 1980
tggtcatcat gggcagaaag acctggttca gcatccccga gaagaacagg cccctgaagg 2040
accggatcaa catcgtgctg agcagagagc tgaaagagcc tcctagaggc gcccactttc 2100
tggccaagtc tctggacgat gccctgcggc tgattgagca gcctgaactt ggcagcggcg 2160
ccacaaactt ttcactgctg aagcaagccg gggatgtcga agagaatcca gggcctatga 2220
agtccctgcg ggtgctgctg gttatcctgt ggctgcagct gagctgggtc tggtcccaga 2280
aacaagaagt gactcagatc ccagccgctc tgagtgtgcc tgagggcgaa aacctggtcc 2340
tgaactgcag cttcaccgac agcgccatct acaacctgca gtggttcagg caggatcccg 2400
gcaagggact gacaagcctg ctgctgattc agagcagcca gagagagcag acctccggca 2460
gactgaatgc cagcctggat aagagcagcg gccgcagcac actgtatatc gccgcttctc 2520
agcctggcga tagcgccaca tatctgtgtg ccgtgcgacc tctgtacggc ggcagctaca 2580
tccctacatt tggcagaggc accagcctga tcgtgcaccc ctacattcag aaccccgatc 2640
ctgccgtgta tcagctgaga gacagcaagt ccagcgacaa gagcgtgtgt ttgttcaccg 2700
attttgattc tcaaacaaat gtgtcacaaa gtaaggattc tgatgtgtat atcacagaca 2760
aaactgtgct agacatgagg tctatggact tcaagagcaa cagtgctgtg gcctggagca 2820
acaaatctga ctttgcatgt gcaaacgcct tcaacaacag cattattcca gaagacacct 2880
tcttccccag cccaggtaag ggcagctttg gtgccttcgc aggctgtttc cttgcttcag 2940
gaatggccag gttctgccca gagctctggt caatgatgtc taaaactcct ctgattggtg 3000
gtctcgg 3007

<210> SEQ ID NO 54
<211> LENGTH: 2815
<212> TYPE: DNA
<213> ORGANISM: Artificial Sequence
<220> FEATURE:
<223> OTHER INFORMATION: Synthetic Oligonucleotide

<400> SEQUENCE: 54
gaagttctcc ttctgctagg tagcattcaa agatcttaat cttctgggtt tccgttttct 60
cgaatgaaaa atgcaggtcc gagcagttaa ctggctgggg caccattagc aagtcactta 120
gcatctctgg ggccagtctg caaagcgagg gggcagcctt aatgtgcctc cagcctgaag 180
tcctagaatg agcgcccggt gtcccaagct ggggcgcgca ccccagatcg gagggcgccg 240
atgtacagac agcaaactca cccagtctag tgcatgcctt cttaaacatc acgagactct 300
aagaaaagga aactgaaaac gggaaagtcc ctctctctaa cctggcactg cgtcgctggc 360
ttggagacag gtgacggtcc ctgcgggcct tgtcctgatt ggctgggcac gcgtttaata 420
taagtggagg cgtcgcgctg gcgggcattc ctgaagctga cagcattcgg gccgagatgt 480
ctcgctccgt ggccttagct ggatctggag aaggcagagg cagcctgctt acatgcggag 540
atgtggaaga aaatcctgga ccaatgggaa gaggcctgct gagaggactg tggcctctgc 600
acattgtgct gtggaccaga atcgccagca caatccctcc acacgtgcag aaaagcgtga 660
acaacgacat gatcgtgacc gacaacaatg gcgccgtgaa gttccctcag ctgtgcaagt 720
tctgcgacgt gcggttcagc acctgtgaca accagaaaag ctgcatgagc aactgcagca 780
tcaccagcat ctgcgagaag ccccaagaag tgtgcgtcgc cgtctggcgg aagaacgacg 840
agaacatcac cctggaaacc gtgtgtcacg accccaagct gccctaccac gacttcatcc 900
tggaagatgc cgcctctcct aagtgcatca tgaaggaaaa gaagaagccc ggcgagacat 960
tcttcatgtg cagctgctcc agcgacgagt gcaacgacaa catcatcttc agcgaagagt 1020
acaacaccag caatcccgac ctgctgctgg tcatcttcca ggtgaccggc atcagcctgc 1080
tgcctccact gggagttgcc atcagcgtga tcatcatctt ttactgctac cgcgtgggat 1140
ctggcgccac caatttcagc ctgctgaaac aggctggcga cgtggaagag aaccccggac 1200
ctatgggtgt gcaggtggaa acaatctctc cgggagacgg tcgcactttc ccgaagcgcg 1260
ggcaaacctg tgtcgtacat tacactggca tgttggaaga tggaaaaaag gtcgatagtt 1320
ctcgcgaccg caataagcca ttcaaattca tgctggggaa gcaggaggtt attcgcggat 1380
gggaggaagg agttgcccaa atgtctgtgg gacaaagggc caagttgact attagtcccg 1440
actacgcata cggggcgacc ggacaccccg gtataatacc ccctcacgcc actctggtct 1500
tcgacgtaga gcttttgaaa ctcgagtcag gggcggatc tgccagcaag gtggacatgg 1560
tctggatcgt cggcggctcc tctgtgtacc aagaggccat gaatcagccc ggacacctga 1620
ggctgttcgt gaccagaatc atgcaagagt tcgagagcga cacattcttc ccagagatcg 1680
acctgggcaa gtacaagctg ctgcctgagt atcccggcgt gctgtctgag gtgcaagagg 1740
aaaagggcat caagtataag ttcgaggtgt acgagaaaaa ggatggatcc ggcgaaggca 1800
gaggatctct gctgacatgt ggcgacgtgg aagagaaccc tggacctatg gatacctgcc 1860
acattgccaa gagctgcgtg ctgatcctgc tggtcgttct gctgtgtgcc gagcgagcac 1920
agggcctcga gtgctacaat tgcattggcg tgccacctga gacaagctgc aacaccacca 1980
cctgtccttt cagcgacggc ttctgtgtgg ccctggaaat cgaagtgatc gtggacagcc 2040
accggtccaa agtgaagtcc aacctgtgcc tgcctatctg ccccaccaca ctggacaaca 2100
ccgagatcac aggcaacgcc gtgaacgtga aaacctactg ctgcaaagag gacctctgca 2160
acgccgctgt tccaacaggt ggaagctctt ggactatggc cggcgtgctg ctgtttagcc 2220
tggtgtctgt tctgctgcag accttcctgg gatcaggcgc cacgaatttt agcctgctca 2280
aacaggcggg cgacgtagaa gagaacccag gacctgtgct cgcgctactc tctctttctg 2340
gcctggaggc tatccagcgt gagtctctcc taccctcccg ctctggtcct tcctctcccg 2400
ctctgcaccc tctgtggccc tcgctgtgct ctctcgctcc gtgacttccc ttctccaagt 2460
tctccttggt ggcccgccgt ggggctagtc cagggctgga tctcggggaa gcggcggggt 2520
ggcctgggag tggggaaggg ggtgcgcacc cgggacgcgc gctacttgcc cctttcggcg 2580
gggagcaggg gagacctttg gcctacggcg acgggagggt cgggacaaag tttagggcgt 2640
cgataagcgt cagagcgccg aggttggggg agggtttctc ttccgctctt tcgcggggcc 2700
tctggctccc ccagcgcagc tggagtgggg gacgggtagg ctcgtcccaa aggcgcggcg 2760
ctgaggtttg tgaacgcgtg gaggggcgct tggggtctgg gggaggcgtc gcccg 2815

<210> SEQ ID NO 55
<211> LENGTH: 2815
<212> TYPE: DNA
<213> ORGANISM: Artificial Sequence
<220> FEATURE:
<223> OTHER INFORMATION: Synthetic Oligonucleotide

<400> SEQUENCE: 55
agtatcttgg ggccaaatca tgtagactct tgagtgatgt gttaaggaat gctatgagtg 60
ctgagagggc atcagaagtc cttgagagcc tccagagaaa ggctcttaaa aatgcagcgc 120
aatctccagt gacagaagat actgctagaa atctgctaga aaaaaaacaa aaaaggcatg 180
tatagaggaa ttatgaggga aagataccaa gtcacggttt attcttcaaa atggaggtgg 240

```
cttgttggga aggtggaagc tcatttggcc agagtggaaa tggaattggg agaaatcgat    300
gaccaaatgt aaacacttgg tgcctgatat agcttgacac caagttagcc ccaagtgaaa    360
taccctggca atattaatgt gtcttttccc gatattcctc aggtactcca aagattcagg    420
tttactcacg tcatccagca gagaatggaa agtcaaattt cctgaattgc tatgtgtctg    480
ggtttcatcc atccgacatt ggatctggag aaggcagagg cagcctgctt acatgcggag    540
atgtggaaga aaatcctgga ccaatgggaa gaggcctgct gagaggactg tggcctctgc    600
acattgtgct gtggaccaga atcgccagca caatccctcc acacgtgcag aaaagcgtga    660
acaacgacat gatcgtgacc gacaacaatg gcgccgtgaa gttccctcag ctgtgcaagt    720
tctgcgacgt gcggttcagc acctgtgaca accagaaaag ctgcatgagc aactgcagca    780
tcaccagcat ctgcgagaag ccccaagaag tgtgcgtcgc cgtctggcgg aagaacgacg    840
agaacatcac cctggaaacc gtgtgtcacg accccaagct gccctaccac gacttcatcc    900
tggaagatgc cgcctctcct aagtgcatca tgaaggaaaa gaagaagccc ggcgagacat    960
tcttcatgtg cagctgctcc agcgacgagt gcaacgacaa catcatcttc agcgaagagt   1020
acaacaccag caatcccgac ctgctgctgg tcatcttcca ggtgaccggc atcagcctgc   1080
tgcctccact gggagttgcc atcagcgtga tcatcatctt ttactgctac cgcgtgggat   1140
ctggcgccac caatttcagc ctgctgaaac aggctggcga cgtggaagag aaccccggac   1200
ctatgggtgt gcaggtggaa acaatctctc cgggagacgg tcgcactttc ccgaagcgcg   1260
ggcaaacctg tgtcgtacat tacactggca tgttggaaga tggaaaaaag gtcgatagtt   1320
ctcgcgaccg caataagcca ttcaaattca tgctggggaa gcaggaggtt attcgcggat   1380
gggaggaagg agttgcccaa atgtctgtgg gacaaagggc caagttgact attagtcccg   1440
actacgcata cggggcgacc ggacaccccg gtataatacc ccctcacgcc actctggtct   1500
tcgacgtaga gcttttgaaa ctcgagtcag gggggcggatc tgccagcaag gtggacatgg  1560
tctggatcgt cggcggctcc tctgtgtacc aagaggccat gaatcagccc ggacacctga   1620
ggctgttcgt gaccagaatc atgcaagagt tcgagagcga cacattcttc ccagagatcg   1680
acctgggcaa gtacaagctg ctgcctgagt atcccggcgt gctgtctgag gtgcaagagg   1740
aaaagggcat caagtataag ttcgaggtgt acgagaaaaa ggatggatcc ggcgaaggca   1800
gaggatctct gctgacatgt ggcgacgtgg aagagaaccc tggacctatg gatacctgcc   1860
acattgccaa gagctgcgtg ctgatcctgc tggtcgttct gctgtgtgcc gagcgagcac   1920
agggcctcga gtgctacaat tgcattggcg tgccacctga gacaagctgc aacaccacca   1980
cctgtccttt cagcgacggc ttctgtgtgg ccctggaaat cgaagtgatc gtggacagcc   2040
accggtccaa agtgaagtcc aacctgtgcc tgcctatctg ccccaccaca ctggacaaca   2100
ccgagatcac aggcaacgcc gtgaacgtga aaacctactg ctgcaaagag gacctctgca   2160
acgccgctgt tccaacaggt ggaagctctt ggactatggc cggcgtgctg ctgtttagcc   2220
tggtgtctgt tctgctgcag accttcctgg gatcaggcgc cacgaatttt agcctgctca   2280
aacaggcggg cgacgtagaa gagaacccag gacctgaagt tgacttactg aagaatggag   2340
agagaattga aaaagtggag cattcagact tgtctttcag caaggactgg tctttctatc   2400
tcttgtacta cactgaattc acccccactg aaaaagatga gtatgcctgc cgtgtgaacc   2460
atgtgacttt gtcacagccc aagatagtta agtggggtaa gtcttacatt cttttgtaag   2520
ctgctgaaag ttgtgtatga gtagtcatat cataaagctg ctttgatata aaaaaggtct   2580
atggccatac taccctgaat gagtcccatc ccatctgata taaacaatct gcatattggg   2640
```

```
attgtcaggg aatgttctta aagatcagat tagtggcacc tgctgagata ctgatgcaca   2700

gcatggtttc tgaaccagta gtttccctgc agttgagcag ggagcagcag cagcacttgc   2760

acaaatacat atacactctt aacacttctt acctactggc ttcctctagc ttttg        2815


<210> SEQ ID NO 56
<211> LENGTH: 25
<212> TYPE: DNA
<213> ORGANISM: Homo sapiens

<400> SEQUENCE: 56

gagcaggttc tcattgataa caagc                                           25


<210> SEQ ID NO 57
<211> LENGTH: 25
<212> TYPE: DNA
<213> ORGANISM: Homo sapiens

<400> SEQUENCE: 57

atcaattgag gtacggagaa actga                                           25


<210> SEQ ID NO 58
<211> LENGTH: 25
<212> TYPE: DNA
<213> ORGANISM: Homo sapiens

<400> SEQUENCE: 58

gtcatggttg gttcgctaaa ctgca                                           25


<210> SEQ ID NO 59
<211> LENGTH: 25
<212> TYPE: DNA
<213> ORGANISM: Homo sapiens

<400> SEQUENCE: 59

gcaggttctc attgataaca agctc                                           25


<210> SEQ ID NO 60
<211> LENGTH: 25
<212> TYPE: DNA
<213> ORGANISM: Homo sapiens

<400> SEQUENCE: 60

gttgacttta gatctataat tattt                                           25


<210> SEQ ID NO 61
<211> LENGTH: 25
<212> TYPE: DNA
<213> ORGANISM: Homo sapiens

<400> SEQUENCE: 61

aaatcatcaa ttgaggtacg gagaa                                           25


<210> SEQ ID NO 62
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 62

Gly Val Gln Val Glu Thr Ile Ser Pro Gly Asp Gly Arg Thr Phe Pro
1               5                   10                  15
```

```
Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Ser Gly Gly Gly Ser
            100                 105                 110

Met Val Arg Pro Leu Asn Cys Ile Val Ala Val Ser Gln Asn Met Gly
        115                 120                 125

Ile Gly Lys Asn Gly Asp Phe Pro Trp Pro Pro Leu Arg Asn Glu Ser
    130                 135                 140

Lys Tyr Phe Gln Arg Met Thr Thr Thr Ser Ser Val Glu Gly Lys Gln
145                 150                 155                 160

Asn Leu Val Ile Met Gly Arg Lys Thr Trp Phe Ser Ile Pro Glu Lys
                165                 170                 175

Asn Arg Pro Leu Lys Asp Arg Ile Asn Ile Val Leu Ser Arg Glu Leu
            180                 185                 190

Lys Glu Pro Pro Arg Gly Ala His Phe Leu Ala Lys Ser Leu Asp Asp
        195                 200                 205

Ala Leu Arg Leu Ile Glu Gln Pro Glu Leu
    210                 215
```

<210> SEQ ID NO 63
<211> LENGTH: 193
<212> TYPE: PRT
<213> ORGANISM: Artificial Sequence
<220> FEATURE:
<223> OTHER INFORMATION: Synthetic Polypeptide

<400> SEQUENCE: 63

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Ser Gly Gly Gly Ser
            100                 105                 110

Ala Ser Lys Val Asp Met Val Trp Ile Val Gly Gly Ser Ser Val Tyr
        115                 120                 125

Gln Glu Ala Met Asn Gln Pro Gly His Leu Arg Leu Phe Val Thr Arg
    130                 135                 140

Ile Met Gln Glu Phe Glu Ser Asp Thr Phe Phe Pro Glu Ile Asp Leu
145                 150                 155                 160
```

-continued

```
Gly Lys Tyr Lys Leu Leu Pro Glu Tyr Pro Gly Val Leu Ser Glu Val
                165                 170                 175

Gln Glu Glu Lys Gly Ile Lys Tyr Lys Phe Glu Val Tyr Glu Lys Lys
            180                 185                 190

Asp
```